US007060504B2

(12) United States Patent
Tracey et al.

(10) Patent No.: US 7,060,504 B2
(45) Date of Patent: *Jun. 13, 2006

(54) ANTAGONISTS OF HMG1 FOR TREATING INFLAMMATORY CONDITIONS

(75) Inventors: Kevin J. Tracey, Old Greenwich, CT (US); Haichao Wang, Avenel, NJ (US)

(73) Assignee: North Shore-Long Island Jewish Research Institute, Mnahasset, NY (US)

( * ) Notice: Subject to any disclaimer, the term of this patent is extended or adjusted under 35 U.S.C. 154(b) by 548 days.

This patent is subject to a terminal disclaimer.

(21) Appl. No.: 10/242,056

(22) Filed: Sep. 11, 2002

(65) Prior Publication Data

US 2003/0113323 A1    Jun. 19, 2003

Related U.S. Application Data

(60) Continuation of application No. 10/210,747, filed on Jul. 31, 2002, which is a continuation of application No. 09/503,632, filed on Feb. 14, 2000, now Pat. No. 6,468,533, which is a division of application No. 09/248,574, filed on Feb. 11, 1999, now Pat. No. 6,303,321.

(51) Int. Cl.
| | |
|---|---|
| G01N 33/53 | (2006.01) |
| G01N 33/566 | (2006.01) |
| A01N 1/02 | (2006.01) |
| C12Q 1/00 | (2006.01) |
| A16K 39/395 | (2006.01) |

(52) U.S. Cl. .......................... 436/501; 435/6; 435/7.1; 435/7.21; 424/130.1; 424/145.1; 530/351; 530/387.1; 530/388.22; 530/350; 514/2; 536/23.5

(58) Field of Classification Search ................ 436/501; 435/6, 7.1, 7.21; 424/130.1, 145.1; 530/351, 530/387.1, 388.22, 350; 514/2; 536/23.5
See application file for complete search history.

(56) References Cited

U.S. PATENT DOCUMENTS

| | | | |
|---|---|---|---|
| 5,594,114 A | 1/1997 | Goodearl et al. | |
| 6,303,321 B1 | 10/2001 | Tracey et al. | 435/7.1 |
| 6,448,223 B1 | 9/2002 | Tracey et al. | |
| 6,468,533 B1 | 10/2002 | Tracey et al. | |

FOREIGN PATENT DOCUMENTS

| | | |
|---|---|---|
| EP | 1 079 849 B1 | 1/2002 |
| JP | 362166897 A | 1/1986 |
| WO | WO 99/59609 | 11/1999 |
| WO | WO 02/074337 A1 | 9/2002 |
| WO | WO 02/092004 A2 | 11/2002 |
| WO | WO 2004/004763 A2 | 1/2004 |

OTHER PUBLICATIONS

Immunology, Janis Kuby, W.H. Freeman and Company, 1992, p. 1.*

Zhang, M. et al., "Tumor Necrosis Factor", in *The Cytokine Handbook*, (Academic Press Limited), Third Edition, pp. 517-547 (1998).

Johns, E.W., et al. "History, Definitions and Problems", in *The HMG Chromosomal Problems*, (Academic Press), London: Chapter 1, pp. 1-7 (1982).

Landsman, D., et al., "A Signature for the HMG-1 Box DNA-Binding Proteins", *BioEssays*, 15(8): 539-546 (1993).

Baxevanis, A.D., et al., "The HMG-1 Box Protein Family: Classification and Functional Relationships", *Nucleic Acids Res.*, 23(9):1604-1613 (1995).

Merenmies, J., et al., "30-kDa Heparin-Binding Protein of Brain (Amphoterin) Involved in Neurite Outgrowth" *J. Biol. Chem.*, 266 (25): 16722-16729 (1991).

Milev, P., et al., "High Affinity Binding and Overlapping Localization of Neurocan and Phosphacan/Protein-Tyrosine Phosphatase —ζ/β with Tenascine -4, Amphoterine, and the Heparin-Binding Growth-Associated Molecule", *J. Biol. Chem.*, 273 (12): 6998-7005 (1998).

Salmivirta, M., et al., "Neurite Growth-Promoting Protein (Amphoterin, p. 30) Binds Syndecan ", *Exp. Cell Res.*, 200: 444-451 (1992).

Melloni, E.,et al., "Identity in Molecular Structure Between "Differentiation Enhanceing Factor" of Murine Erithroleukemia Cells and the 30 kD Heparin-Binding Protein of Developing Rat Brain", *Biochemical and Biophysical Research Communications*, 210(1) : (1995).

Melloni, E., et al., "Extracellular Release of the 'Differentiation Enhancing Factor', and a HMG1 Protein Type, is an Early Step in mUrine Erythroluekemia Cell Differentiation", *FEBS Lett.*, 368: 466-470 (1995).

Mohan, P.S., et al., "Sulfoglycolipids Bind to Adhesive Protein Amphoterin (p. 30) in the Nervous System", *Biochemical and Biophysical Research Communications*, 182(2) (1992).

Yamawaki, M., et al., "Generation and Characterization of Anti-Sulfoglucuronosyl Paragloboside Monoclonal Antibody NGR50 and its Immunoreactivity with Peripheral Nerve", *J. Neurosi. Res.*, 44: 586-593 (1996).

(Continued)

Primary Examiner—Elizabeth Kemmerer
Assistant Examiner—Michael Brannock
(74) Attorney, Agent, or Firm—Hamilton, Brook, Smith & Reynolds, P.C.

(57) ABSTRACT

There is disclosed a pharmaceutical composition and method for treating sepsis, including septic shock and ARDS (acute respiratory distress syndrome), comprising administering an effective amount of a HMG1 antagonist. There is further disclosed a diagnostic method for monitoring the severity or potential lethality of sepsis or septic shock, comprising measuring the serum concentration of HMG1 in a patient exhibiting or at risk or exhibit sepsis or septic shock symptoms. Lastly, there is disclosed a pharmaceutical composition and method for effecting weight loss or treating obesity, comprising administering an effective amount of HMG1 or a therapeutically active HMG1 fragment.

24 Claims, 10 Drawing Sheets

OTHER PUBLICATIONS

Vassalli, J., et al., "The Plasminogen Activator/Plasmin System", *J. Clin. Invest.*, 88: 1067-1072 (1991).

Parkkinen, J., et al., "Interactions of Plasminogen and Tissue Plasminogen Activator (t-PA) with Amphoterin", *J. Biol. Chem.*, 266(25): 16730-16735 (1991).

Radlitz, A., et al., "Receptors for Plasminogen and t-PA: An Update", *Baillière's Clinical Haemtology*, 8(2): 313-327 (1995).

Sobajima, J., et al., "Novel autoantigens of perinuclear anti-neutrophil cytoplasmic antibodies (P-ANCA) in ulcerative colitia: non-histone chromosomal proteins, HMG1 and HMG2" *Clin. Exp. Immunol.*, 107:135-140 (1997).

Sobajima, J., et al., "Anti-neutrophil cytopasmic antibodies (ANCA) in ulcerative colitis: anti-cathepsin G and a novel antibody correlate with a refractory type," *Clin. Exp. Immunol.*, 105:120-124 (1996).

Sparatore, B., et al., "Extracellular high-mobility group 1 protein is essential for murine erythroleukaemia cell differentiation," *Biochem. J.*, 320:253-256 (1996).

Tomita, N., et al., "Direct In Vivo Gene Introduction Into Rat Kidney," *Biochemical and Biophysical Research Communications* 186(1) :129-134 (1992).

Wang, H., et al., "HMG-1 as a Late Mediator of Endotoxin Lethality in Mice," *Science* 285:248-251 (1999).

Faciola, L., et al., "High Mobility Group 1 Protein is Not Stably Associated with the Chromosomes of Somatic Cells," *J. Cell Biol.*, 137(1):19-26 (1997).

Vanderbilt, J.N., et al., "Monoclonal Antibodies as Probes for the Complexity, Phylogeny, and Chromatin Distribution of High Mobility Group Chromosomal Proteins 1 and 2," *J. Biol. Chem.*, 260(16):9336-9345 (1985).

Bustin, M., et al., "Antigenic Determinants of High Mobility Group Chrosomal Proteins 1 and 2," *Biochemistry*, 21:6773-6777 (1982).

Tsuneoka, M., et al., "Monoclonal Antibody Against Non-Histone Chromosomal Protein High Mobility Group 1 Co-Migrates With High Mobility Group 1 Into the Nucleus," *J. Biol Chem.*, 261(4):1829-1834 (1986).

Bianchi, M.E., et al., "The DNA Binding Site of HMG1 Protein is Composed of Two Similar Segments (HMG Boxes), Both of Which Have Counterparts in Other Eukaryotic Regulatory Proteins," *EMBO J.*, 11(3): 1055-1063 (1992).

Abraham, E., et al., "Cutting Edge: HMG-1 as a Mediator of Acute Lung Inflammation," *J. Immunol.*, 165:2950-2954 (2000).

Andersson, U., et al., "High Mobility Group 1 Protein (HMG-1) Stimulates Proinflammatory Cytokine Synthesis in Human Monocytes," *J. Exp. Med.*, 192:565-570 (2000).

Bustin, M. "Revised Nomenclature for High Mobility Group (HMG) Chromosomal Proteins," *Trends Biochem. Sci.*, 26:152-153 (2001).

Degryse, B., et al., "The High Mobility Group (HMG) Boxes of the Nuclear Protein HMG1 Induce Chemotaxis and Cytoskeleton Reorganization in Rat Smooth Muscle Cells," *J. Cell Biol.*, 152:1197-1206 (2001)

Wang, H., et al., "Proinflammatory Cytokine (Tumor Necrosis Factor and Interleukin 1) Stimulate Release of High Mobility Group Protein-1 by Pituicytes," *Surgery*, 126:389-392(1999).

Passalacqua, M., et al., "Stimulated Astrocytes Release High-Mobility Group 1 Protein, an Inducer of Lan-5 Neuroblastoma Cell Differentiation," *Neuroscience*, 82(4):1021-1028 (1998).

Chou, D. K. H., et al., "Identity of Nuclear High-Mobility-Group Protein, HMG-1, and Sulfoglucuronyl Carbohydrate-Binding Protein, SBP-1, in Brain," *J. Neurochem.*, 77:120-131 (2001).

Imamura, T., et al., "Interaction with p53 Enhances Binding of Cisplatin-Modified DNA by High Mobility Group 1 Protein," *J. Biol. Chem.*, 276(10):7534-7540 (2001).

Ise, T., et al., "Transcription Factor Y-Box Binding Protein 1 Binds Preferentially to Cisplatin-Modified DNA and Interacts With Proliferating Cell Nuclear Antigen," *Cancer Res.*, 59:342-346 (1999).

Jung, F., et al., "Antibodies Against a Peptide Sequence Located in the Linker Region of the HMG-1/2 Box Domains in Sera From Patients With Juvenile Rheumatoid Arthritis," *Arthiritis Rheum.*, 40(10):1803-1809 (1997).

Bianchi, M.E., et al., "Specific Recognition of Cruciform DNA by Nuclear Protein HMG1," *Science*, 243:1056-1059 (1989).

Suda, T., et al., "A Novel Activity of HMG Domains: Promotion of the Triple-Stranded Complex Formation Between DNA Containing $(GGA/TCC)_{11}$ and $d(GGA)_{11}$ Oligonucleotides," *Nucleic Acids Res.*, 24(23):4733-4740 (1996).

Ayer, L. M., et al., "Antibodies to HMG Proteins Patients With Drug Induced Autoimmunity," *Arthritis Rheum.*, 37(1):98-103 (1994).

Rauvala, H., et al., "The Adhesive and Neurite-Promoting Molecule p30: Analysis of the Amino-Terminal Sequence and Production of Antipeptide Antibodies That Detect p30 at the Surface of Neuroblastoma Cells and of Brain Neurons," *J. Cell Biol.*, 107(6):2293-2305 (1988).

Sobajima, J., et al., "Prevalence and Characterization of Perinuclear Anti-Neutrophil Cytoplasmic Antibodies (P-ANCA) Directed Against HMG1 and HMG2 in Ulcerative Colitis (UC)," *Clin. Exp. Immunol.*, 111:402-407 (1998).

Yamada, S., et al., "High Mobility Group Protein 1 (HMGB1) Quantified by ELISA With a Monoclonal Antibody That Does Not Cross-React With HMGB2," *Clin. Chem.*, 49(9):1535-1537 (2003).

Uesugi, H., et al., "Prevalence and Characterization of Novel pANCA, Antibodies to the High Mobility Group Non-Histone Chromosomal Proteins HMG1 and HMG2, in Systemic Rheumatic Diseases," *J. Rheumatol.*, 25(4):703-709 (1998).

Bustin, M., et al., "Immunological Relatedness of High Mobility Group Chromosomal Proteins from Calf Thymus," *J. Biol. Chem.*, 253(5):1694-1699 (1978).

Rauvala, H. and Pihlaskari, R., "Isolation and Some Characteristics of an Adhesive Factor of Brain That Enhances Neurite Outgrowth in Central Neurons," *J. Biol. Chem.*, 262(34):16625-16635 (1987).

Daston, M. M., and Ratner, N., "Expression of P30, a Protein with Adhesive Properties, in Schwann Cells and Neurons of the Developing and Regenerating Peripheral Nerve," *J. Cell Biol.*, 112(6):1229-1239 (1991).

Parkinnen, J., et al. "Amphoterin, the 30-kDa Protein in a Family of HMG1-type Polypeptides," *J. Biol. Chem.*, 268(26):19726-19738 (1993).

Sobajima, J., et al. "High Mobility Group (HMG) Non-histone Chromosomal Proteins HMG1 and HMG2 are Significant Target Antigens of Perinuclear Anti-Neutrophil Cytoplasmic Antibodies in Autoimmune Hepatitis," *Gut*, 44:867-873 (1999).

Ma, W., et al. "Detection of Anti-Neutrophil Cytoplasmic Antibodies in MRL/Mp-*Ipr/Ipr* Mice and Analysis of Their Target Antigen," *Autoimmunity*, 32(4):281-291 (2000).

Banks, G. C., et al., "The HMG-I(Y) A•T-hook Peptide Motif Confers DNA-binding Specificity to a Structured Chimeric Protein," *J. Biol. Chem.*, 274(23):16536-16544 (1999).

Scaffidi, P., et al., "Release of chromatin protein HMGB1 by Necrotic Cells Triggers Inflammation," *Nature*, 418:191-95 (2002).

Abaza, M.-S. I. and Atassi, M. Z., "Effects of Amino Acid Substitutions Outside an Antigenic Site on Protein Binding to Monoclonal Antibodies of Predetermined Specificity Obtained by Peptide Immunization: Demonstration with Region 94-100 (Antigenic Site 3) of Myoglobin," *J. Protein Chem.*, 11(5):433-444 (1992).

Colman, P. M., "Effects of Amino Acid Sequence Changes on Antibody-Antigen Interactions," *Res. Immunol.*, 145(1):33-36 (1994).

Freeman, B. D., et al., "The Role of Inflammation in Sepsis and Septic Shock: A Meta-Analysis of Both Clinical and Preclinical Trials of Anti-Inflammatory Therapies," in *Inflammation:Basic Principals and Clinical Correlates* (John I. Gallin and Ralph Snyderman eds:, Lippincott, Williams & Wilkins, Philadelphia, 3rd ed. 1999), pp. 965-975.

Lederman, S, et al., "A Single Amino Acid Substitution in a Common African Allele of the CD4 Molecule Ablates Binding of the Monoclonal Antibody OKT," *Mol. Immunol.*, 28(11):1171-1181 (1991).

Czura, C., et al., "Dual Roles of HMGB1: DNA Binding and Cytokine," *J. Endotoxin Res.*, 7(4):315-321 (2001).

Wen, L., et al., "A Human Placental cDNA Clone that Encodes Nonhiston Chromosomal Protein HMG-1," *Nucleic Acids Res.*, 17(3):1197-1213 (1989).

Romani, M., et al., "Serological Analysis of Species Specificity in the High Mobility Group Chromosomal Proteins," *J. Biol. Chem.*, 254(8):2918-2922 (1979).

Ombrellino, M., et al., "Increased Serum Concentrations of High-Mobility-Group Protien 1 in Haemorrhagic Shock," *Lancet*, 354(9188):1446-47 (1999).

Kokkola, R., et al., "High Mobility Group Box Chromosomal Protein 1," *Arthritis Rheum.*, 46(10):2598-2603 (2002).

Taniguchi, N., et al., "High Mobility Group Box Chromosomal Protein 1 Plays a Role in the Pathogenesis of Rheumatoid Arthritis as a Novel Cytokine," *Arthritis Rheum.*, 48(4):971-981 (2003).

Andersson, U and Erlandsson-Harris, H., "HMGB1 is a Potent Trigger of Arthritis," *J. Intern. Med.* 255:344-350 (2004).

Alleva, L. M., et al., "High Mobility Group Box 1 (HMGB1) Protein: Possible Amplification Signal in the Pathogenesis of Falciparum Malaria," *Trans. R. Soc. Trop. Med. Hyg.*, 99:171-174 (2005).

Fei, J., et al., "Study on High Mobility Group-1 Protein in Patients with Multiple Trauma," *Zhongguo Wei Zhong Bing Ji Jiu Yi Xue*, 17(5):273-275 (2005) (Abstract only).

* cited by examiner

```
                          SEQUENCE LISTING (1) GENERAL INFORMATION:

(iii) NUMBER OF SEQUENCES:   88

(2) INFORMATION FOR SEQ ID NO:1:

(i) SEQUENCE CHARACTERISTICS:
         (A) LENGTH: 11 amino acids
         (B) TYPE: amino acid
         (C) STRANDEDNESS:
         (D) TOPOLOGY: linear (ii) MOLECULE TYPE: protein (v) FRAGMENT TYPE: N-terminal (xi) SEQUENCE DESCRIPTION: SEQ ID NO:1 (TCBAII N-TERMINUS):

Phe Ile Gln Gly Tyr Ser Asp Leu Phe Gly Asn
1               5                   10

(2) INFORMATION FOR SEQ ID NO:2:

(i) SEQUENCE CHARACTERISTICS:
         (A) LENGTH: 12 amino acids
         (B) TYPE: amino acid
         (C) STRANDEDNESS:
         (D) TOPOLOGY: linear (ii) MOLECULE TYPE: protein (v) FRAGMENT TYPE: N-terminal (xi) SEQUENCE DESCRIPTION: SEQ ID NO:2 (TCAC N-TERMINUS):

Met Gln Asp Ser Pro Glu Val Ser Ile Thr Thr Trp
1               5                   10

(2) INFORMATION FOR SEQ ID NO:3:

(i) SEQUENCE CHARACTERISTICS:
         (A) LENGTH: 19 amino acids
         (B) TYPE: amino acid
         (C) STRANDEDNESS:
         (D) TOPOLOGY: linear (ii) MOLECULE TYPE: protein
```

(v) FRAGMENT TYPE: N-terminal (xi) SEQUENCE DESCRIPTION: SEQ ID NO:3 (TCABI N-TERMINUS):

Ser Glu Ser Leu Phe Thr Gln Thr Leu Lys Glu Ala Arg Arg Asp Ala
1               5                   10                  15

Leu Val Ala (2) INFORMATION FOR SEQ ID NO:4:

(i) SEQUENCE CHARACTERISTICS:
            (A) LENGTH: 14 amino acids
            (B) TYPE: amino acid
            (C) STRANDEDNESS:
            (D) TOPOLOGY: linear (ii) MOLECULE TYPE: protein (v) FRAGMENT TYPE: N-terminal (xi) SEQUENCE DESCRIPTION: SEQ ID NO:4 (TCAAIII N-TERMINUS):

Ala Ser Pro Leu Ser Thr Ser Glu Leu Thr Ser Lys Leu Asn
1               5                   10

(2) INFORMATION FOR SEQ ID NO:5:

(i) SEQUENCE CHARACTERISTICS:
            (A) LENGTH: 9 amino acids
            (B) TYPE: amino acid
            (C) STRANDEDNESS:
            (D) TOPOLOGY: linear (ii) MOLECULE TYPE: protein (v) FRAGMENT TYPE: N-terminal (xi) SEQUENCE DESCRIPTION: SEQ ID NO:5 (TCABII N-TERMINUS):

Ala Gly Asp Thr Ala Asn Ile Gly Asp
1               5

(2) INFORMATION FOR SEQ ID NO:6:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: protein (v) FRAGMENT TYPE: N-terminal (xi) SEQUENCE DESCRIPTION: SEQ ID NO:6:

Leu Gly Gly Ala Ala Thr Leu Leu Asp Leu Leu Leu Pro Gln Ile
1               5                   10                  15

(2) INFORMATION FOR SEQ ID NO:7:

(i) SEQUENCE CHARACTERISTICS:
            (A) LENGTH: 11 amino acids
            (B) TYPE: amino acid
            (C) STRANDEDNESS:
            (D) TOPOLOGY: linear (ii) MOLECULE TYPE: protein (v) FRAGMENT TYPE: N-terminal (xi) SEQUENCE DESCRIPTION: SEQ ID NO:7 (TCCB N-TERMINUS):

```
Met Leu Ser Thr Met Glu Lys Gln Leu Asn Glu
1               5                   10
```

(2) INFORMATION FOR SEQ ID NO:8:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: protein (v) FRAGMENT TYPE: N-terminal (xi) SEQUENCE DESCRIPTION: SEQ ID NO:8 (TCCA N-TERMINUS):

```
Met Asn Leu Ala Ser Pro Leu Ile Ser
1               5
```

(2) INFORMATION FOR SEQ ID NO:9:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: protein (v) FRAGMENT TYPE: N-terminal (xi) SEQUENCE DESCRIPTION: SEQ ID NO:9:

```
Met Ile Asn Leu Asp Ile Asn Glu Gln Asn Lys Ile Met Val Val Ser
1               5                   10                  15
```

(2) INFORMATION FOR SEQ ID NO:10:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: protein (v) FRAGMENT TYPE: N-terminal (xi) SEQUENCE DESCRIPTION: SEQ ID NO:10:

```
Ala Ala Lys Asp Val Lys Phe Gly Ser Asp Ala Arg Val Lys Met Leu
1               5                   10                  15
Arg Gly Val Asn
            20
```

(2) INFORMATION FOR SEQ ID NO:11:

(i) SEQUENCE CHARACTERISTICS:
        (A) LENGTH: 7515 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..7515

(xi) SEQUENCE DESCRIPTION: SEQ ID NO:11 (TCBA GENE):

```
ATG CAA AAC TCA TTA TCA AGC ACT ATC GAT ACT ATT TGT CAG AAA CTG    48
Met Gln Asn Ser Leu Ser Ser Thr Ile Asp Thr Ile Cys Gln Lys Leu
```

```
  1               5                  10                 15
CAA TTA ACT TGT CCG GCG GAA ATT GCT TTG TAT CCC TTT GAT ACT TTC     96
Gln Leu Thr Cys Pro Ala Glu Ile Ala Leu Tyr Pro Phe Asp Thr Phe
            20                  25                  30

CGG GAA AAA ACT CGG GGA ATG GTT AAT TGG GGG GAA GCA AAA CGG ATT    144
Arg Glu Lys Thr Arg Gly Met Val Asn Trp Gly Glu Ala Lys Arg Ile
        35                  40                  45

TAT GAA ATT GCA CAA GCG GAA CAG GAT AGA AAC CTA CTT CAT GAA AAA    192
Tyr Glu Ile Ala Gln Ala Glu Gln Asp Arg Asn Leu Leu His Glu Lys
    50                  55                  60

CGT ATT TTT GCC TAT GCT AAT CCG CTG CTG AAA AAC GCT GTT CGG TTG    240
Arg Ile Phe Ala Tyr Ala Asn Pro Leu Leu Lys Asn Ala Val Arg Leu
65                  70                  75                  80

GGT ACC CGG CAA ATG TTG GGT TTT ATA CAA GGT TAT AGT GAT CTG TTT    288
Gly Thr Arg Gln Met Leu Gly Phe Ile Gln Gly Tyr Ser Asp Leu Phe
                85                  90                  95

GGT AAT CGT GCT GAT AAC TAT GCC GCG CCG GGC TCG GTT GCA TCG ATG    336
Gly Asn Arg Ala Asp Asn Tyr Ala Ala Pro Gly Ser Val Ala Ser Met
            100                 105                 110

TTC TCA CCG GCG GCT TAT TTG ACG GAA TTG TAC CGT GAA GCC AAA AAC    384
Phe Ser Pro Ala Ala Tyr Leu Thr Glu Leu Tyr Arg Glu Ala Lys Asn
        115                 120                 125

TTG CAT GAC AGC AGC TCA ATT TAT TAC CTA GAT AAA CGT CGC CCG GAT    432
Leu His Asp Ser Ser Ser Ile Tyr Tyr Leu Asp Lys Arg Arg Pro Asp
    130                 135                 140

TTA GCA AGC TTA ATG CTC AGC CAG AAA AAT ATG GAT GAG GAA ATT TCA    480
Leu Ala Ser Leu Met Leu Ser Gln Lys Asn Met Asp Glu Glu Ile Ser
145                 150                 155                 160

ACG CTG GCT CTC TCT AAT GAA TTG TGC CTT GCC GGG ATC GAA ACA AAA    528
Thr Leu Ala Leu Ser Asn Glu Leu Cys Leu Ala Gly Ile Glu Thr Lys
                165                 170                 175

ACA GGA AAA TCA CAA GAT GAA GTG ATG GAT ATG TTG TCA ACT TAT CGT    576
Thr Gly Lys Ser Gln Asp Glu Val Met Asp Met Leu Ser Thr Tyr Arg
            180                 185                 190

TTA AGT GGA GAG ACA CCT TAT CAT CAC GCT TAT GAA ACT GTT CGT GAA    624
Leu Ser Gly Glu Thr Pro Tyr His His Ala Tyr Glu Thr Val Arg Glu
        195                 200                 205

ATC GTT CAT GAA CGT GAT CCA GGA TTT CGT CAT TTG TCA CAG GCA CCC    672
Ile Val His Glu Arg Asp Pro Gly Phe Arg His Leu Ser Gln Ala Pro
    210                 215                 220

ATT GTT GCT GCT AAG CTC GAT CCT GTG ACT TTG TTG GGT ATT AGC TCC    720
Ile Val Ala Ala Lys Leu Asp Pro Val Thr Leu Leu Gly Ile Ser Ser
225                 230                 235                 240

CAT ATT TCG CCA GAA CTG TAT AAC TTG CTG ATT GAG GAG ATC CCG GAA    768
His Ile Ser Pro Glu Leu Tyr Asn Leu Leu Ile Glu Glu Ile Pro Glu
                245                 250                 255

AAA GAT GAA GCC GCG CTT GAT ACG CTT TAT AAA ACA AAC TTT GGC GAT    816
Lys Asp Glu Ala Ala Leu Asp Thr Leu Tyr Lys Thr Asn Phe Gly Asp
            260                 265                 270

ATT ACT ACT GCT CAG TTA ATG TCC CCA AGT TAT CTG GCC CGG TAT TAT    864
Ile Thr Thr Ala Gln Leu Met Ser Pro Ser Tyr Leu Ala Arg Tyr Tyr
        275                 280                 285

GGC GTC TCA CCG GAA GAT ATT GCC TAC GTG ACG ACT TCA TTA TCA CAT    912
Gly Val Ser Pro Glu Asp Ile Ala Tyr Val Thr Thr Ser Leu Ser His
    290                 295                 300

GTT GGA TAT AGC AGT GAT ATT CTG GTT ATT CCG TTG GTC GAT GGT GTG    960
Val Gly Tyr Ser Ser Asp Ile Leu Val Ile Pro Leu Val Asp Gly Val
305                 310                 315                 320

GGT AAG ATG GAA GTA GTT CGT GTT ACC CGA ACA CCA TCG GAT AAT TAT   1008
```

```
                Gly Lys Met Glu Val Val Arg Val Thr Arg Thr Pro Ser Asp Asn Tyr
                                325                 330                 335

ACC AGT CAG ACG AAT TAT ATT GAG CTG TAT CCA CAG GGT GGC GAC AAT        1056
Thr Ser Gln Thr Asn Tyr Ile Glu Leu Tyr Pro Gln Gly Gly Asp Asn
                340                 345                 350

TAT TTG ATC AAA TAC AAT CTA AGC AAT AGT TTT GGT TTG GAT GAT TTT        1104
Tyr Leu Ile Lys Tyr Asn Leu Ser Asn Ser Phe Gly Leu Asp Asp Phe
            355                 360                 365

TAT CTG CAA TAT AAA GAT GGT TCC GCT GAT TGG ACT GAG ATT GCC CAT        1152
Tyr Leu Gln Tyr Lys Asp Gly Ser Ala Asp Trp Thr Glu Ile Ala His
        370                 375                 380

AAT CCC TAT CCT GAT ATG GTC ATA AAT CAA AAG TAT GAA TCA CAG GCG        1200
Asn Pro Tyr Pro Asp Met Val Ile Asn Gln Lys Tyr Glu Ser Gln Ala
385                 390                 395                 400

ACA ATC AAA CGT AGT GAC TCT GAC AAT ATA CTC AGT ATA GGG TTA CAA        1248
Thr Ile Lys Arg Ser Asp Ser Asp Asn Ile Leu Ser Ile Gly Leu Gln
                405                 410                 415

AGA TGG CAT AGC GGT AGT TAT AAT TTT GCC GCC GCC AAT TTT AAA ATT        1296
Arg Trp His Ser Gly Ser Tyr Asn Phe Ala Ala Ala Asn Phe Lys Ile
                420                 425                 430

GAC CAA TAC TCC CCG AAA GCT TTC CTG CTT AAA ATG AAT AAG GCT ATT        1344
Asp Gln Tyr Ser Pro Lys Ala Phe Leu Leu Lys Met Asn Lys Ala Ile
            435                 440                 445

CGG TTG CTC AAA GCT ACC GGC CTC TCT TTT GCT ACG TTG GAG CGT ATT        1392
Arg Leu Leu Lys Ala Thr Gly Leu Ser Phe Ala Thr Leu Glu Arg Ile
        450                 455                 460

GTT GAT AGT GTT AAT AGC ACC AAA TCC ATC ACG GTT GAG GTA TTA AAC        1440
Val Asp Ser Val Asn Ser Thr Lys Ser Ile Thr Val Glu Val Leu Asn
465                 470                 475                 480

AAG GTT TAT CGG GTA AAA TTC TAT ATT GAT CGT TAT GGC ATC AGT GAA        1488
Lys Val Tyr Arg Val Lys Phe Tyr Ile Asp Arg Tyr Gly Ile Ser Glu
                485                 490                 495

GAG ACA GCC GCT ATT TTG GCT AAT ATT AAT ATC TCT CAG CAA GCT GTT        1536
Glu Thr Ala Ala Ile Leu Ala Asn Ile Asn Ile Ser Gln Gln Ala Val
                500                 505                 510

GGC AAT CAG CTT AGC CAG TTT GAG CAA CTA TTT AAT CAC CCG CCG CTC        1584
Gly Asn Gln Leu Ser Gln Phe Glu Gln Leu Phe Asn His Pro Pro Leu
            515                 520                 525

AAT GGT ATT CGC TAT GAA ATC AGT GAG GAC AAC TCC AAA CAT CTT CCT        1632
Asn Gly Ile Arg Tyr Glu Ile Ser Glu Asp Asn Ser Lys His Leu Pro
        530                 535                 540

AAT CCT GAT CTG AAC CTT AAA CCA GAC AGT ACC GGT GAT GAT CAA CGC        1680
Asn Pro Asp Leu Asn Leu Lys Pro Asp Ser Thr Gly Asp Asp Gln Arg
545                 550                 555                 560

AAG GCG GTT TTA AAA CGC GCG TTT CAG GTT AAC GCC AGT GAG TTG TAT        1728
Lys Ala Val Leu Lys Arg Ala Phe Gln Val Asn Ala Ser Glu Leu Tyr
                565                 570                 575

CAG ATG TTA TTG ATC ACT GAT CGT AAA GAA GAC GGT GTT ATC AAA AAT        1776
Gln Met Leu Leu Ile Thr Asp Arg Lys Glu Asp Gly Val Ile Lys Asn
                580                 585                 590

AAC TTA GAG AAT TTG TCT GAT CTG TAT TTG GTT AGT TTG CTG GCC CAG        1824
Asn Leu Glu Asn Leu Ser Asp Leu Tyr Leu Val Ser Leu Leu Ala Gln
            595                 600                 605

ATT CAT AAC CTG ACT ATT GCT GAA TTG AAC ATT TTG TTG GTG ATT TGT        1872
Ile His Asn Leu Thr Ile Ala Glu Leu Asn Ile Leu Leu Val Ile Cys
        610                 615                 620

GGC TAT GGC GAC ACC AAC ATT TAT CAG ATT ACC GAC GAT AAT TTA GCC        1920
Gly Tyr Gly Asp Thr Asn Ile Tyr Gln Ile Thr Asp Asp Asn Leu Ala
625                 630                 635                 640
```

```
                                            -continued
AAA ATA GTG GAA ACA TTG TTG TGG ATC ACT CAA TGG TTG AAG ACC CAA       1968
Lys Ile Val Glu Thr Leu Leu Trp Ile Thr Gln Trp Leu Lys Thr Gln
            645                 650                 655

AAA TGG ACA GTT ACC GAC CTG TTT CTG ATG ACC ACG GCC ACT TAC AGC       2016
Lys Trp Thr Val Thr Asp Leu Phe Leu Met Thr Thr Ala Thr Tyr Ser
                660                 665                 670

ACC ACT TTA ACG CCA GAA ATT AGC AAT CTG ACG GCT ACG TTG TCT TCA       2064
Thr Thr Leu Thr Pro Glu Ile Ser Asn Leu Thr Ala Thr Leu Ser Ser
                    675                 680                 685

ACT TTG CAT GGC AAA GAG AGT CTG ATT GGG GAA GAT CTG AAA AGA GCA       2112
Thr Leu His Gly Lys Glu Ser Leu Ile Gly Glu Asp Leu Lys Arg Ala
        690                 695                 700

ATG GCG CCT TGC TTC ACT TCG GCT TTG CAT TTG ACT TCT CAA GAA GTT       2160
Met Ala Pro Cys Phe Thr Ser Ala Leu His Leu Thr Ser Gln Glu Val
705                 710                 715                 720

GCG TAT GAC CTG CTG TTG TGG ATA GAC CAG ATT CAA CCG GCA CAA ATA       2208
Ala Tyr Asp Leu Leu Leu Trp Ile Asp Gln Ile Gln Pro Ala Gln Ile
                725                 730                 735

ACT GTT GAT GGG TTT TGG GAA GAA GTG CAA ACA ACA CCA ACC AGC TTG       2256
Thr Val Asp Gly Phe Trp Glu Glu Val Gln Thr Thr Pro Thr Ser Leu
                    740                 745                 750

AAG GTG ATT ACC TTT GCT CAG GTG CTG GCA CAA TTG AGC CTG ATC TAT       2304
Lys Val Ile Thr Phe Ala Gln Val Leu Ala Gln Leu Ser Leu Ile Tyr
        755                 760                 765

CGT CGT ATT GGG TTA AGT GAA ACG GAA CTG TCA CTG ATC GTG ACT CAA       2352
Arg Arg Ile Gly Leu Ser Glu Thr Glu Leu Ser Leu Ile Val Thr Gln
770                 775                 780

TCT TCT CTG CTA GTG GCA GGC AAA AGC ATA CTG GAT CAC GGT CTG TTA       2400
Ser Ser Leu Leu Val Ala Gly Lys Ser Ile Leu Asp His Gly Leu Leu
785                 790                 795                 800

ACC CTG ATG GCC TTG GAA GGT TTT CAT ACC TGG GTT AAT GGC TTG GGG       2448
Thr Leu Met Ala Leu Glu Gly Phe His Thr Trp Val Asn Gly Leu Gly
                805                 810                 815

CAA CAT GCC TCC TTG ATA TTG GCG GCG TTG AAA GAC GGA GCC TTG ACA       2496
Gln His Ala Ser Leu Ile Leu Ala Ala Leu Lys Asp Gly Ala Leu Thr
                    820                 825                 830

GTT ACC GAT GTA GCA CAA GCT ATG AAT AAG GAG GAA TCT CTC CTA CAA       2544
Val Thr Asp Val Ala Gln Ala Met Asn Lys Glu Glu Ser Leu Leu Gln
        835                 840                 845

ATG GCA GCT AAT CAG GTG GAG AAG GAT CTA ACA AAA CTG ACC AGT TGG       2592
Met Ala Ala Asn Gln Val Glu Lys Asp Leu Thr Lys Leu Thr Ser Trp
850                 855                 860

ACA CAG ATT GAC GCT ATT CTG CAA TGG TTA CAG ATG TCT TCG GCC TTG       2640
Thr Gln Ile Asp Ala Ile Leu Gln Trp Leu Gln Met Ser Ser Ala Leu
865                 870                 875                 880

GCG GTT TCT CCA CTG GAT CTG GCA GGG ATG ATG GCC CTG AAA TAT GGG       2688
Ala Val Ser Pro Leu Asp Leu Ala Gly Met Met Ala Leu Lys Tyr Gly
                885                 890                 895

ATA GAT CAT AAC TAT GCT GCC TGG CAA GCT GCG GCG GCT GCG CTG ATG       2736
Ile Asp His Asn Tyr Ala Ala Trp Gln Ala Ala Ala Ala Ala Leu Met
                    900                 905                 910

GCT GAT CAT GCT AAT CAG GCA CAG AAA AAA CTG GAT GAG ACG TTC AGT       2784
Ala Asp His Ala Asn Gln Ala Gln Lys Lys Leu Asp Glu Thr Phe Ser
        915                 920                 925

AAG GCA TTA TGT AAC TAT TAT ATT AAT GCT GTT GTC GAT AGT GCT GCT       2832
Lys Ala Leu Cys Asn Tyr Tyr Ile Asn Ala Val Val Asp Ser Ala Ala
930                 935                 940

GGA GTA CGT GAT CGT AAC GGT TTA TAT ACC TAT TTG CTG ATT GAT AAT       2880
Gly Val Arg Asp Arg Asn Gly Leu Tyr Thr Tyr Leu Leu Ile Asp Asn
                945                 950                 955                 960
```

```
CAG GTT TCT GCC GAT GTG ATC ACT TCA CGT ATT GCA GAA GCT ATC GCC        2928
Gln Val Ser Ala Asp Val Ile Thr Ser Arg Ile Ala Glu Ala Ile Ala
            965                 970                 975

GGT ATT CAA CTG TAC GTT AAC CGG GCT TTA AAC CGA GAT GAA GGT CAG        2976
Gly Ile Gln Leu Tyr Val Asn Arg Ala Leu Asn Arg Asp Glu Gly Gln
        980                 985                 990

CTT GCA TCG GAC GTT AGT ACC CGT CAG TTC TTC ACT GAC TGG GAA CGT        3024
Leu Ala Ser Asp Val Ser Thr Arg Gln Phe Phe Thr Asp Trp Glu Arg
            995                1000                1005

TAC AAT AAA CGT TAC AGT ACT TGG GCT GGT GTC TCT GAA CTG GTC TAT        3072
Tyr Asn Lys Arg Tyr Ser Thr Trp Ala Gly Val Ser Glu Leu Val Tyr
        1010                1015                1020

TAT CCA GAA AAC TAT GTT GAT CCC ACT CAG CGC ATT GGG CAA ACC AAA        3120
Tyr Pro Glu Asn Tyr Val Asp Pro Thr Gln Arg Ile Gly Gln Thr Lys
1025                1030                1035                1040

ATG ATG GAT GCG CTG TTG CAA TCC ATC AAC CAG AGC CAG CTA AAT GCG        3168
Met Met Asp Ala Leu Leu Gln Ser Ile Asn Gln Ser Gln Leu Asn Ala
            1045                1050                1055

GAT ACG GTG GAA GAT GCT TTC AAA ACT TAT TTG ACC AGC TTT GAG CAG        3216
Asp Thr Val Glu Asp Ala Phe Lys Thr Tyr Leu Thr Ser Phe Glu Gln
        1060                1065                1070

GTA GCA AAT CTG AAA GTA ATT AGT GCT TAC CAC GAT AAT GTG AAT GTG        3264
Val Ala Asn Leu Lys Val Ile Ser Ala Tyr His Asp Asn Val Asn Val
            1075                1080                1085

GAT CAA GGA TTA ACT TAT TTT ATC GGT ATC GAC CAA GCA GCT CCG GGT        3312
Asp Gln Gly Leu Thr Tyr Phe Ile Gly Ile Asp Gln Ala Ala Pro Gly
        1090                1095                1100

ACG TAT TAC TGG CGT AGT GTT GAT CAC AGC AAA TGT GAA AAT GGC AAG        3360
Thr Tyr Tyr Trp Arg Ser Val Asp His Ser Lys Cys Glu Asn Gly Lys
1105                1110                1115                1120

TTT GCC GCT AAT GCT TGG GGT GAG TGG AAT AAA ATT ACC TGT GCT GTC        3408
Phe Ala Ala Asn Ala Trp Gly Glu Trp Asn Lys Ile Thr Cys Ala Val
            1125                1130                1135

AAT CCT TGG AAA AAT ATC ATC CGT CCG GTT GTT TAT ATG TCC CGC TTA        3456
Asn Pro Trp Lys Asn Ile Ile Arg Pro Val Val Tyr Met Ser Arg Leu
        1140                1145                1150

TAT CTG CTA TGG CTG GAG CAG CAA TCA AAG AAA AGT GAT GAT GGT AAA        3504
Tyr Leu Leu Trp Leu Glu Gln Gln Ser Lys Lys Ser Asp Asp Gly Lys
            1155                1160                1165

ACC ACG ATT TAT CAA TAT AAC TTA AAA CTG GCT CAT ATT CGT TAC GAC        3552
Thr Thr Ile Tyr Gln Tyr Asn Leu Lys Leu Ala His Ile Arg Tyr Asp
        1170                1175                1180

GGT AGT TGG AAT ACA CCA TTT ACT TTT GAT GTG ACA GAA AAG GTA AAA        3600
Gly Ser Trp Asn Thr Pro Phe Thr Phe Asp Val Thr Glu Lys Val Lys
1185                1190                1195                1200

AAT TAC ACG TCG AGT ACT GAT GCT GCT GAA TCT TTA GGG TTG TAT TGT        3648
Asn Tyr Thr Ser Ser Thr Asp Ala Ala Glu Ser Leu Gly Leu Tyr Cys
            1205                1210                1215

ACT GGT TAT CAA GGG GAA GAC ACT CTA TTA GTT ATG TTC TAT TCG ATG        3696
Thr Gly Tyr Gln Gly Glu Asp Thr Leu Leu Val Met Phe Tyr Ser Met
        1220                1225                1230

CAG AGT AGT TAT AGC TCC TAT ACC GAT AAT AAT GCG CCG GTC ACT GGG        3744
Gln Ser Ser Tyr Ser Ser Tyr Thr Asp Asn Asn Ala Pro Val Thr Gly
            1235                1240                1245

CTA TAT ATT TTC GCT GAT ATG TCA TCA GAC AAT ATG ACG AAT GCA CAA        3792
Leu Tyr Ile Phe Ala Asp Met Ser Ser Asp Asn Met Thr Asn Ala Gln
        1250                1255                1260

GCA ACT AAC TAT TGG AAT AAC AGT TAT CCG CAA TTT GAT ACT GTG ATG        3840
Ala Thr Asn Tyr Trp Asn Asn Ser Tyr Pro Gln Phe Asp Thr Val Met
```

-continued

| | |
|---|---|
| GCA GAT CCG GAT AGC GAC AAT AAA AAA GTC ATA ACC AGA AGA GTT AAT<br>Ala Asp Pro Asp Ser Asp Asn Lys Lys Val Ile Thr Arg Arg Val Asn<br>                           1285                    1290                  1295 | 3888 |
| AAC CGT TAT GCG GAG GAT TAT GAA ATT CCT TCC TCT GTG ACA AGT AAC<br>Asn Arg Tyr Ala Glu Asp Tyr Glu Ile Pro Ser Ser Val Thr Ser Asn<br>     1300                  1305                1310 | 3936 |
| AGT AAT TAT TCT TGG GGT GAT CAC AGT TTA ACC ATG CTT TAT GGT GGT<br>Ser Asn Tyr Ser Trp Gly Asp His Ser Leu Thr Met Leu Tyr Gly Gly<br>              1315                1320                1325 | 3984 |
| AGT GTT CCT AAT ATT ACT TTT GAA TCG GCG GCA GAA GAT TTA AGG CTA<br>Ser Val Pro Asn Ile Thr Phe Glu Ser Ala Ala Glu Asp Leu Arg Leu<br>         1330                1335                1340 | 4032 |
| TCT ACC AAT ATG GCA TTG AGT ATT ATT CAT AAT GGA TAT GCG GGA ACC<br>Ser Thr Asn Met Ala Leu Ser Ile Ile His Asn Gly Tyr Ala Gly Thr<br>1345                1350                1355                1360 | 4080 |
| CGC CGT ATA CAA TGT AAT CTT ATG AAA CAA TAC GCT TCA TTA GGT GAT<br>Arg Arg Ile Gln Cys Asn Leu Met Lys Gln Tyr Ala Ser Leu Gly Asp<br>              1365                1370                1375 | 4128 |
| AAA TTT ATA ATT TAT GAT TCA TCA TTT GAT GAT GCA AAC CGT TTT AAT<br>Lys Phe Ile Ile Tyr Asp Ser Ser Phe Asp Asp Ala Asn Arg Phe Asn<br>         1380                1385                1390 | 4176 |
| CTG GTG CCA TTG TTT AAA TTC GGA AAA GAC GAG AAC TCA GAT GAT AGT<br>Leu Val Pro Leu Phe Lys Phe Gly Lys Asp Glu Asn Ser Asp Asp Ser<br>              1395                1400                1405 | 4224 |
| ATT TGT ATA TAT AAT GAA AAC CCT TCC TCT GAA GAT AAG AAG TGG TAT<br>Ile Cys Ile Tyr Asn Glu Asn Pro Ser Ser Glu Asp Lys Lys Trp Tyr<br>     1410                1415                1420 | 4272 |
| TTT TCT TCG AAA GAT GAC AAT AAA ACA GCG GAT TAT AAT GGT GGA ACT<br>Phe Ser Ser Lys Asp Asp Asn Lys Thr Ala Asp Tyr Asn Gly Gly Thr<br>1425                1430                1435                1440 | 4320 |
| CAA TGT ATA GAT GCT GGA ACC AGT AAC AAA GAT TTT TAT TAT AAT CTC<br>Gln Cys Ile Asp Ala Gly Thr Ser Asn Lys Asp Phe Tyr Tyr Asn Leu<br>              1445                1450                1455 | 4368 |
| CAG GAG ATT GAA GTA ATT AGT GTT ACT GGT GGG TAT TGG TCG AGT TAT<br>Gln Glu Ile Glu Val Ile Ser Val Thr Gly Gly Tyr Trp Ser Ser Tyr<br>                1460                1465                1470 | 4416 |
| AAA ATA TCC AAC CCG ATT AAT ATC AAT ACG GGC ATT GAT AGT GCT AAA<br>Lys Ile Ser Asn Pro Ile Asn Ile Asn Thr Gly Ile Asp Ser Ala Lys<br>     1475                1480                1485 | 4464 |
| GTA AAA GTC ACC GTA AAA GCG GGT GGT GAC GAT CAA ATC TTT ACT GCT<br>Val Lys Val Thr Val Lys Ala Gly Gly Asp Asp Gln Ile Phe Thr Ala<br>         1490                1495                1500 | 4512 |
| GAT AAT AGT ACC TAT GTT CCT CAG CAA CCG GCA CCC AGT TTT GAG GAG<br>Asp Asn Ser Thr Tyr Val Pro Gln Gln Pro Ala Pro Ser Phe Glu Glu<br>1505                1510                1515                1520 | 4560 |
| ATG ATT TAT CAG TTC AAT AAC CTG ACA ATA GAT TGT AAG AAT TTA AAT<br>Met Ile Tyr Gln Phe Asn Asn Leu Thr Ile Asp Cys Lys Asn Leu Asn<br>              1525                1530                1535 | 4608 |
| TTC ATC GAC AAT CAG GCA CAT ATT GAG ATT GAT TTC ACC GCT ACG GCA<br>Phe Ile Asp Asn Gln Ala His Ile Glu Ile Asp Phe Thr Ala Thr Ala<br>         1540                1545                1550 | 4656 |
| CAA GAT GGC CGA TTC TTG GGT GCA GAA ACT TTT ATT ATC CCG GTA ACT<br>Gln Asp Gly Arg Phe Leu Gly Ala Glu Thr Phe Ile Ile Pro Val Thr<br>1555                1560                1565 | 4704 |
| AAA AAA GTT CTC GGT ACT GAG AAC GTG ATT GCG TTA TAT AGC GAA AAT<br>Lys Lys Val Leu Gly Thr Glu Asn Val Ile Ala Leu Tyr Ser Glu Asn<br>     1570                1575                1580 | 4752 |
| AAC GGT GTT CAA TAT ATG CAA ATT GGC GCA TAT CGT ACC CGT TTG AAT | 4800 |

-continued

```
Asn Gly Val Gln Tyr Met Gln Ile Gly Ala Tyr Arg Thr Arg Leu Asn
1585                1590                1595                1600

ACG TTA TTC GCT CAA CAG TTG GTT AGC CGT GCT AAT CGT GGC ATT GAT       4848
Thr Leu Phe Ala Gln Gln Leu Val Ser Arg Ala Asn Arg Gly Ile Asp
                1605                1610                1615

GCA GTG CTC AGT ATG GAA ACT CAG AAT ATT CAG GAA CCG CAA TTA GGA       4896
Ala Val Leu Ser Met Glu Thr Gln Asn Ile Gln Glu Pro Gln Leu Gly
            1620                1625                1630

GCG GGC ACA TAT GTG CAG CTT GTG TTG GAT AAA TAT GAT GAG TCT ATT       4944
Ala Gly Thr Tyr Val Gln Leu Val Leu Asp Lys Tyr Asp Glu Ser Ile
        1635                1640                1645

CAT GGC ACT AAT AAA AGC TTT GCT ATT GAA TAT GTT GAT ATA TTT AAA       4992
His Gly Thr Asn Lys Ser Phe Ala Ile Glu Tyr Val Asp Ile Phe Lys
    1650                1655                1660

GAG AAC GAT AGT TTT GTG ATT TAT CAA GGA GAA CTT AGC GAA ACA AGT       5040
Glu Asn Asp Ser Phe Val Ile Tyr Gln Gly Glu Leu Ser Glu Thr Ser
1665                1670                1675                1680

CAA ACT GTT GTG AAA GTT TTC TTA TCC TAT TTT ATA GAG GCG ACT GGA       5088
Gln Thr Val Val Lys Val Phe Leu Ser Tyr Phe Ile Glu Ala Thr Gly
                1685                1690                1695

AAT AAG AAC CAC TTA TGG GTA CGT GCT AAA TAC CAA AAG GAA ACG ACT       5136
Asn Lys Asn His Leu Trp Val Arg Ala Lys Tyr Gln Lys Glu Thr Thr
            1700                1705                1710

GAT AAG ATC TTG TTC GAC CGT ACT GAT GAG AAA GAT CCG CAC GGT TGG       5184
Asp Lys Ile Leu Phe Asp Arg Thr Asp Glu Lys Asp Pro His Gly Trp
        1715                1720                1725

TTT CTC AGC GAC GAT CAC AAG ACC TTT AGT GGT CTC TCT TCC GCA CAG       5232
Phe Leu Ser Asp Asp His Lys Thr Phe Ser Gly Leu Ser Ser Ala Gln
    1730                1735                1740

GCA TTA AAG AAC GAC AGT GAA CCG ATG GAT TTC TCT GGC GCC AAT GCT       5280
Ala Leu Lys Asn Asp Ser Glu Pro Met Asp Phe Ser Gly Ala Asn Ala
1745                1750                1755                1760

CTC TAT TTC TGG GAA CTG TTC TAT TAC ACG CCG ATG ATG ATG GCT CAT       5328
Leu Tyr Phe Trp Glu Leu Phe Tyr Tyr Thr Pro Met Met Met Ala His
                1765                1770                1775

CGT TTG TTG CAG GAA CAG AAT TTT GAT GCG GCG AAC CAT TGG TTC CGT       5376
Arg Leu Leu Gln Glu Gln Asn Phe Asp Ala Ala Asn His Trp Phe Arg
            1780                1785                1790

TAT GTC TGG AGT CCA TCC GGT TAT ATC GTT GAT GGT AAA ATT GCT ATC       5424
Tyr Val Trp Ser Pro Ser Gly Tyr Ile Val Asp Gly Lys Ile Ala Ile
        1795                1800                1805

TAC CAC TGG AAC GTG CGA CCG CTG GAA GAA GAC ACC AGT TGG AAT GCA       5472
Tyr His Trp Asn Val Arg Pro Leu Glu Glu Asp Thr Ser Trp Asn Ala
    1810                1815                1820

CAA CAA CTG GAC TCC ACC GAT CCA GAT GCT GTA GCC CAA GAT GAT CCG       5520
Gln Gln Leu Asp Ser Thr Asp Pro Asp Ala Val Ala Gln Asp Asp Pro
1825                1830                1835                1840

ATG CAC TAC AAG GTG GCT ACC TTT ATG GCG ACG TTG GAT CTG CTA ATG       5568
Met His Tyr Lys Val Ala Thr Phe Met Ala Thr Leu Asp Leu Leu Met
                1845                1850                1855

GCC CGT GGT GAT GCT GCT TAC CGC CAG TTA GAG CGT GAT ACG TTG GCT       5616
Ala Arg Gly Asp Ala Ala Tyr Arg Gln Leu Glu Arg Asp Thr Leu Ala
            1860                1865                1870

GAA GCT AAA ATG TGG TAT ACA CAG GCG CTT AAT CTG TTG GGT GAT GAG       5664
Glu Ala Lys Met Trp Tyr Thr Gln Ala Leu Asn Leu Leu Gly Asp Glu
        1875                1880                1885

CCA CAA GTG ATG CTG AGT ACG ACT TGG GCT AAT CCA ACA TTG GGT AAT       5712
Pro Gln Val Met Leu Ser Thr Thr Trp Ala Asn Pro Thr Leu Gly Asn
    1890                1895                1900
```

```
GCT GCT TCA AAA ACC ACA CAG CAG GTT CGT CAG CAA GTG CTT ACC CAG          5760
Ala Ala Ser Lys Thr Thr Gln Gln Val Arg Gln Gln Val Leu Thr Gln
1905                1910                1915                1920

TTG CGT CTC AAT AGC AGG GTA AAA ACC CCG TTG CTA GGA ACA GCC AAT          5808
Leu Arg Leu Asn Ser Arg Val Lys Thr Pro Leu Leu Gly Thr Ala Asn
                1925                1930                1935

TCC CTG ACC GCT TTA TTC CTG CCG CAG GAA AAT AGC AAG CTC AAA GGC          5856
Ser Leu Thr Ala Leu Phe Leu Pro Gln Glu Asn Ser Lys Leu Lys Gly
            1940                1945                1950

TAC TGG CGG ACA CTG GCG CAG CGT ATG TTT AAT TTA CGT CAT AAT CTG          5904
Tyr Trp Arg Thr Leu Ala Gln Arg Met Phe Asn Leu Arg His Asn Leu
        1955                1960                1965

TCG ATT GAC GGC CAG CCG CTC TCC TTG CCG CTG TAT GCT AAA CCG GCT          5952
Ser Ile Asp Gly Gln Pro Leu Ser Leu Pro Leu Tyr Ala Lys Pro Ala
    1970                1975                1980

GAT CCA AAA GCT TTA CTG AGT GCG GCG GTT TCA GCT TCT CAA GGG GGA          6000
Asp Pro Lys Ala Leu Leu Ser Ala Ala Val Ser Ala Ser Gln Gly Gly
1985                1990                1995                2000

GCC GAC TTG CCG AAG GCG CCG CTG ACT ATT CAC CGC TTC CCT CAA ATG          6048
Ala Asp Leu Pro Lys Ala Pro Leu Thr Ile His Arg Phe Pro Gln Met
                2005                2010                2015

CTA GAA GGG GCA CGG GGC TTG GTT AAC CAG CTT ATA CAG TTC GGT AGT          6096
Leu Glu Gly Ala Arg Gly Leu Val Asn Gln Leu Ile Gln Phe Gly Ser
            2020                2025                2030

TCA CTA TTG GGG TAC AGT GAG CGT CAG GAT GCG GAA GCT ATG AGT CAA          6144
Ser Leu Leu Gly Tyr Ser Glu Arg Gln Asp Ala Glu Ala Met Ser Gln
        2035                2040                2045

CTA CTG CAA ACC CAA GCC AGC GAG TTA ATA CTG ACC AGT ATT CGT ATG          6192
Leu Leu Gln Thr Gln Ala Ser Glu Leu Ile Leu Thr Ser Ile Arg Met
    2050                2055                2060

CAG GAT AAC CAA TTG GCA GAG CTG GAT TCG GAA AAA ACC GCC TTG CAA          6240
Gln Asp Asn Gln Leu Ala Glu Leu Asp Ser Glu Lys Thr Ala Leu Gln
2065                2070                2075                2080

GTC TCT TTA GCT GGA GTG CAA CAA CGG TTT GAC AGC TAT AGC CAA CTG          6288
Val Ser Leu Ala Gly Val Gln Gln Arg Phe Asp Ser Tyr Ser Gln Leu
                2085                2090                2095

TAT GAG GAG AAC ATC AAC GCA GGT GAG CAG CGA GCG CTG GCG TTA CGC          6336
Tyr Glu Glu Asn Ile Asn Ala Gly Glu Gln Arg Ala Leu Ala Leu Arg
            2100                2105                2110

TCA GAA TCT GCT ATT GAG TCT CAG GGA GCG CAG ATT TCC CGT ATG GCA          6384
Ser Glu Ser Ala Ile Glu Ser Gln Gly Ala Gln Ile Ser Arg Met Ala
        2115                2120                2125

GGC GCG GGT GTT GAT ATG GCA CCA AAT ATC TTC GGC CTG GCT GAT GGC          6432
Gly Ala Gly Val Asp Met Ala Pro Asn Ile Phe Gly Leu Ala Asp Gly
    2130                2135                2140

GGC ATG CAT TAT GGT GCT ATT GCC TAT GCC ATC GCT GAC GGT ATT GAG          6480
Gly Met His Tyr Gly Ala Ile Ala Tyr Ala Ile Ala Asp Gly Ile Glu
2145                2150                2155                2160

TTG AGT GCT TCT GCC AAG ATG GTT GAT GCG GAG AAA GTT GCT CAG TCG          6528
Leu Ser Ala Ser Ala Lys Met Val Asp Ala Glu Lys Val Ala Gln Ser
                2165                2170                2175

GAA ATA TAT CGC CGT CGC CGT CAA GAA TGG AAA ATT CAG CGT GAC AAC          6576
Glu Ile Tyr Arg Arg Arg Arg Gln Glu Trp Lys Ile Gln Arg Asp Asn
            2180                2185                2190

GCA CAA GCG GAG ATT AAC CAG TTA AAC GCG CAA CTG GAA TCA CTG TCT          6624
Ala Gln Ala Glu Ile Asn Gln Leu Asn Ala Gln Leu Glu Ser Leu Ser
        2195                2200                2205

ATT CGC CGT GAA GCC GCT GAA ATG CAA AAA GAG TAC CTG AAA ACC CAG          6672
Ile Arg Arg Glu Ala Ala Glu Met Gln Lys Glu Tyr Leu Lys Thr Gln
    2210                2215                2220
```

```
CAA GCT CAG GCG CAG GCA CAA CTT ACT TTC TTA AGA AGC AAA TTC AGT       6720
Gln Ala Gln Ala Gln Ala Gln Leu Thr Phe Leu Arg Ser Lys Phe Ser
2225                2230                2235                2240

AAT CAA GCG TTA TAT AGT TGG TTA CGA GGG CGT TTG TCA GGT ATT TAT       6768
Asn Gln Ala Leu Tyr Ser Trp Leu Arg Gly Arg Leu Ser Gly Ile Tyr
                2245                2250                2255

TTC CAG TTC TAT GAC TTG GCC GTA TCA CGT TGC CTG ATG GCA GAG CAA       6816
Phe Gln Phe Tyr Asp Leu Ala Val Ser Arg Cys Leu Met Ala Glu Gln
            2260                2265                2270

TCC TAT CAA TGG GAA GCT AAT GAT AAT TCC ATT AGC TTT GTC AAA CCG       6864
Ser Tyr Gln Trp Glu Ala Asn Asp Asn Ser Ile Ser Phe Val Lys Pro
        2275                2280                2285

GGT GCA TGG CAA GGA ACT TAC GCC GGC TTA TTG TGT GGA GAA GCT TTG       6912
Gly Ala Trp Gln Gly Thr Tyr Ala Gly Leu Leu Cys Gly Glu Ala Leu
    2290                2295                2300

ATA CAA AAT CTG GCA CAA ATG GAA GAG GCA TAT CTG AAA TGG GAA TCT       6960
Ile Gln Asn Leu Ala Gln Met Glu Glu Ala Tyr Leu Lys Trp Glu Ser
2305                2310                2315                2320

CGC GCT TTG GAA GTA GAA CGC ACG GTT TCA TTG GCA GTG GTT TAT GAT       7008
Arg Ala Leu Glu Val Glu Arg Thr Val Ser Leu Ala Val Val Tyr Asp
                2325                2330                2335

TCA CTG GAA GGT AAT GAT CGT TTT AAT TTA GCG GAA CAA ATA CCT GCA       7056
Ser Leu Glu Gly Asn Asp Arg Phe Asn Leu Ala Glu Gln Ile Pro Ala
            2340                2345                2350

TTA TTG GAT AAG GGG GAG GGA ACA GCA GGA ACT AAA GAA AAT GGG TTA       7104
Leu Leu Asp Lys Gly Glu Gly Thr Ala Gly Thr Lys Glu Asn Gly Leu
        2355                2360                2365

TCA TTG GCT AAT GCT ATC CTG TCA GCT TCG GTC AAA TTG TCC GAC TTG       7152
Ser Leu Ala Asn Ala Ile Leu Ser Ala Ser Val Lys Leu Ser Asp Leu
    2370                2375                2380

AAA CTG GGA ACG GAT TAT CCA GAC AGT ATC GTT GGT AGC AAC AAG GTT       7200
Lys Leu Gly Thr Asp Tyr Pro Asp Ser Ile Val Gly Ser Asn Lys Val
2385                2390                2395                2400

CGT CGT ATT AAG CAA ATC AGT GTT TCG CTA CCT GCA TTG GTT GGG CCT       7248
Arg Arg Ile Lys Gln Ile Ser Val Ser Leu Pro Ala Leu Val Gly Pro
                2405                2410                2415

TAT CAG GAT GTT CAG GCT ATG CTC AGC TAT GGT GGC AGT ACT CAA TTG       7296
Tyr Gln Asp Val Gln Ala Met Leu Ser Tyr Gly Gly Ser Thr Gln Leu
            2420                2425                2430

CCG AAA GGT TGT TCA GCG TTG GCT GTG TCT CAT GGT ACC AAT GAT AGT       7344
Pro Lys Gly Cys Ser Ala Leu Ala Val Ser His Gly Thr Asn Asp Ser
        2435                2440                2445

GGT CAG TTC CAG TTG GAT TTC AAT GAC GGC AAA TAC CTG CCA TTT GAA       7392
Gly Gln Phe Gln Leu Asp Phe Asn Asp Gly Lys Tyr Leu Pro Phe Glu
    2450                2455                2460

GGT ATT GCT CTT GAT GAT CAG GGT ACA CTG AAT CTT CAA TTT CCG AAT       7440
Gly Ile Ala Leu Asp Asp Gln Gly Thr Leu Asn Leu Gln Phe Pro Asn
2465                2470                2475                2480

GCT ACC GAC AAG CAG AAA GCA ATA TTG CAA ACT ATG AGC GAT ATT ATT       7488
Ala Thr Asp Lys Gln Lys Ala Ile Leu Gln Thr Met Ser Asp Ile Ile
                2485                2490                2495

TTG CAT ATT CGT TAT ACC ATC CGT TAA                                   7515
Leu His Ile Arg Tyr Thr Ile Arg *
        2500                2505

(2) INFORMATION FOR SEQ ID NO:12:

(i) SEQUENCE CHARACTERISTICS:
        (A) LENGTH: 2503 amino acids
        (B) TYPE: amino acid
```

-continued (D) TOPOLOGY: linear (ii) MOLECULE TYPE: protein (xi) SEQUENCE DESCRIPTION: SEQ ID NO:12 (TCBA PROTEIN):

```
Met Gln Asn Ser Leu Ser Ser Thr Ile Asp Thr Ile Cys Gln Lys Leu
 1               5                  10                  15

Gln Leu Thr Cys Pro Ala Glu Ile Ala Leu Tyr Pro Phe Asp Thr Phe
            20                  25                  30

Arg Glu Lys Thr Arg Gly Met Val Asn Trp Gly Glu Ala Lys Arg Ile
        35                  40                  45

Tyr Glu Ile Ala Gln Ala Glu Gln Asp Arg Asn Leu Leu His Glu Lys
    50                  55                  60

Arg Ile Phe Ala Tyr Ala Asn Pro Leu Leu Lys Asn Ala Val Arg Leu
65                  70                  75                  80

Gly Thr Arg Gln Met Leu Gly Phe Ile Gln Gly Tyr Ser Asp Leu Phe
                85                  90                  95

Gly Asn Arg Ala Asp Asn Tyr Ala Ala Pro Gly Ser Val Ala Ser Met
            100                 105                 110

Phe Ser Pro Ala Ala Tyr Leu Thr Glu Leu Tyr Arg Glu Ala Lys Asn
        115                 120                 125

Leu His Asp Ser Ser Ser Ile Tyr Tyr Leu Asp Lys Arg Arg Pro Asp
    130                 135                 140

Leu Ala Ser Leu Met Leu Ser Gln Lys Asn Met Asp Glu Glu Ile Ser
145                 150                 155                 160

Thr Leu Ala Leu Ser Asn Glu Leu Cys Leu Ala Gly Ile Glu Thr Lys
                165                 170                 175

Thr Gly Lys Ser Gln Asp Glu Val Met Asp Met Leu Ser Thr Tyr Arg
            180                 185                 190

Leu Ser Gly Glu Thr Pro Tyr His His Ala Tyr Glu Thr Val Arg Glu
        195                 200                 205

Ile Val His Glu Arg Asp Pro Gly Phe Arg His Leu Ser Gln Ala Pro
    210                 215                 220

Ile Val Ala Ala Lys Leu Asp Pro Val Thr Leu Leu Gly Ile Ser Ser
225                 230                 235                 240

His Ile Ser Pro Glu Leu Tyr Asn Leu Leu Ile Glu Glu Ile Pro Glu
                245                 250                 255

Lys Asp Glu Ala Ala Leu Asp Thr Leu Tyr Lys Thr Asn Phe Gly Asp
            260                 265                 270

Ile Thr Thr Ala Gln Leu Met Ser Pro Ser Tyr Leu Ala Arg Tyr Tyr
        275                 280                 285

Gly Val Ser Pro Glu Asp Ile Ala Tyr Val Thr Thr Ser Leu Ser His
    290                 295                 300

Val Gly Tyr Ser Ser Asp Ile Leu Val Ile Pro Leu Val Asp Gly Val
305                 310                 315                 320

Gly Lys Met Glu Val Val Arg Val Thr Arg Thr Pro Ser Asp Asn Tyr
                325                 330                 335

Thr Ser Gln Thr Asn Tyr Ile Glu Leu Tyr Pro Gln Gly Gly Asp Asn
            340                 345                 350

Tyr Leu Ile Lys Tyr Asn Leu Ser Asn Ser Phe Gly Leu Asp Asp Phe
        355                 360                 365

Tyr Leu Gln Tyr Lys Asp Gly Ser Ala Asp Trp Thr Glu Ile Ala His
    370                 375                 380

Asn Pro Tyr Pro Asp Met Val Ile Asn Gln Lys Tyr Glu Ser Gln Ala
```

-continued

```
385                 390                 395                 400
Thr Ile Lys Arg Ser Asp Ser Asp Asn Ile Leu Ser Ile Gly Leu Gln
                405                 410                 415
Arg Trp His Ser Gly Ser Tyr Asn Phe Ala Ala Asn Phe Lys Ile
            420                 425                 430
Asp Gln Tyr Ser Pro Lys Ala Phe Leu Leu Lys Met Asn Lys Ala Ile
                435                 440                 445
Arg Leu Leu Lys Ala Thr Gly Leu Ser Phe Ala Thr Leu Glu Arg Ile
            450                 455                 460
Val Asp Ser Val Asn Ser Thr Lys Ser Ile Thr Val Glu Val Leu Asn
465                 470                 475                 480
Lys Val Tyr Arg Val Lys Phe Tyr Ile Asp Arg Tyr Gly Ile Ser Glu
                485                 490                 495
Glu Thr Ala Ala Ile Leu Ala Asn Ile Asn Ile Ser Gln Gln Ala Val
                500                 505                 510
Gly Asn Gln Leu Ser Gln Phe Glu Gln Leu Phe Asn His Pro Pro Leu
            515                 520                 525
Asn Gly Ile Arg Tyr Glu Ile Ser Glu Asp Asn Ser Lys His Leu Pro
            530                 535                 540
Asn Pro Asp Leu Asn Leu Lys Pro Asp Ser Thr Gly Asp Asp Gln Arg
545                 550                 555                 560
Lys Ala Val Leu Lys Arg Ala Phe Gln Val Asn Ala Ser Glu Leu Tyr
                565                 570                 575
Gln Met Leu Leu Ile Thr Asp Arg Lys Glu Asp Gly Val Ile Lys Asn
                580                 585                 590
Asn Leu Glu Asn Leu Ser Asp Leu Tyr Leu Val Ser Leu Leu Ala Gln
            595                 600                 605
Ile His Asn Leu Thr Ile Ala Glu Leu Asn Ile Leu Leu Val Ile Cys
            610                 615                 620
Gly Tyr Gly Asp Thr Asn Ile Tyr Gln Ile Thr Asp Asp Asn Leu Ala
625                 630                 635                 640
Lys Ile Val Glu Thr Leu Leu Trp Ile Thr Gln Trp Leu Lys Thr Gln
                645                 650                 655
Lys Trp Thr Val Thr Asp Leu Phe Leu Met Thr Thr Ala Thr Tyr Ser
                660                 665                 670
Thr Thr Leu Thr Pro Glu Ile Ser Asn Leu Thr Ala Thr Leu Ser Ser
            675                 680                 685
Thr Leu His Gly Lys Glu Ser Leu Ile Gly Glu Asp Leu Lys Arg Ala
            690                 695                 700
Met Ala Pro Cys Phe Thr Ser Ala Leu His Leu Thr Ser Gln Glu Val
705                 710                 715                 720
Ala Tyr Asp Leu Leu Leu Trp Ile Asp Gln Ile Gln Pro Ala Gln Ile
                725                 730                 735
Thr Val Asp Gly Phe Trp Glu Glu Val Gln Thr Thr Pro Thr Ser Leu
                740                 745                 750
Lys Val Ile Thr Phe Ala Gln Val Leu Ala Gln Leu Ser Leu Ile Tyr
            755                 760                 765
Arg Arg Ile Gly Leu Ser Glu Thr Glu Leu Ser Leu Ile Val Thr Gln
            770                 775                 780
Ser Ser Leu Leu Val Ala Gly Lys Ser Ile Leu Asp His Gly Leu Leu
785                 790                 795                 800
Thr Leu Met Ala Leu Glu Gly Phe His Thr Trp Val Asn Gly Leu Gly
                805                 810                 815
```

-continued

Gln His Ala Ser Leu Ile Leu Ala Ala Leu Lys Asp Gly Ala Leu Thr
          820                 825                 830

Val Thr Asp Val Ala Gln Ala Met Asn Lys Glu Glu Ser Leu Leu Gln
          835                 840                 845

Met Ala Ala Asn Gln Val Glu Lys Asp Leu Thr Lys Leu Thr Ser Trp
          850                 855                 860

Thr Gln Ile Asp Ala Ile Leu Gln Trp Leu Gln Met Ser Ser Ala Leu
865                 870                 875                 880

Ala Val Ser Pro Leu Asp Leu Ala Gly Met Met Ala Leu Lys Tyr Gly
              885                 890                 895

Ile Asp His Asn Tyr Ala Ala Trp Gln Ala Ala Ala Ala Leu Met
          900                 905                 910

Ala Asp His Ala Asn Gln Ala Gln Lys Lys Leu Asp Glu Thr Phe Ser
          915                 920                 925

Lys Ala Leu Cys Asn Tyr Tyr Ile Asn Ala Val Asp Ser Ala Ala
          930                 935                 940

Gly Val Arg Asp Arg Asn Gly Leu Tyr Thr Tyr Leu Leu Ile Asp Asn
945                 950                 955                 960

Gln Val Ser Ala Asp Val Ile Thr Ser Arg Ile Ala Glu Ala Ile Ala
              965                 970                 975

Gly Ile Gln Leu Tyr Val Asn Arg Ala Leu Asn Arg Asp Glu Gly Gln
              980                 985                 990

Leu Ala Ser Asp Val Ser Thr Arg Gln Phe Phe Thr Asp Trp Glu Arg
              995                 1000                1005

Tyr Asn Lys Arg Tyr Ser Thr Trp Ala Gly Val Ser Glu Leu Val Tyr
          1010                1015                1020

Tyr Pro Glu Asn Tyr Val Asp Pro Thr Gln Arg Ile Gly Gln Thr Lys
1025                1030                1035                1040

Met Met Asp Ala Leu Leu Gln Ser Ile Asn Gln Ser Gln Leu Asn Ala
              1045                1050                1055

Asp Thr Val Glu Asp Ala Phe Lys Thr Tyr Leu Thr Ser Phe Glu Gln
              1060                1065                1070

Val Ala Asn Leu Lys Val Ile Ser Ala Tyr His Asp Asn Val Asn Val
              1075                1080                1085

Asp Gln Gly Leu Thr Tyr Phe Ile Gly Ile Asp Gln Ala Ala Pro Gly
              1090                1095                1100

Thr Tyr Tyr Trp Arg Ser Val Asp His Ser Lys Cys Glu Asn Gly Lys
1105                1110                1115                1120

Phe Ala Ala Asn Ala Trp Gly Glu Trp Asn Lys Ile Thr Cys Ala Val
              1125                1130                1135

Asn Pro Trp Lys Asn Ile Ile Arg Pro Val Val Tyr Met Ser Arg Leu
          1140                1145                1150

Tyr Leu Leu Trp Leu Glu Gln Gln Ser Lys Lys Ser Asp Asp Gly Lys
          1155                1160                1165

Thr Thr Ile Tyr Gln Tyr Asn Leu Lys Leu Ala His Ile Arg Tyr Asp
          1170                1175                1180

Gly Ser Trp Asn Thr Pro Phe Thr Phe Asp Val Thr Glu Lys Val Lys
1185                1190                1195                1200

Asn Tyr Thr Ser Ser Thr Asp Ala Ala Glu Ser Leu Gly Leu Tyr Cys
          1205                1210                1215

Thr Gly Tyr Gln Gly Glu Asp Thr Leu Leu Val Met Phe Tyr Ser Met
          1220                1225                1230

-continued

```
Gln Ser Ser Tyr Ser Ser Tyr Thr Asp Asn Asn Ala Pro Val Thr Gly
    1235                1240                1245

Leu Tyr Ile Phe Ala Asp Met Ser Asp Asn Met Thr Asn Ala Gln
    1250                1255                1260

Ala Thr Asn Tyr Trp Asn Ser Tyr Pro Gln Phe Asp Thr Val Met
1265                1270                1275                1280

Ala Asp Pro Asp Ser Asp Asn Lys Lys Val Ile Thr Arg Arg Val Asn
                1285                1290                1295

Asn Arg Tyr Ala Glu Asp Tyr Glu Ile Pro Ser Ser Val Thr Ser Asn
            1300                1305                1310

Ser Asn Tyr Ser Trp Gly Asp His Ser Leu Thr Met Leu Tyr Gly Gly
        1315                1320                1325

Ser Val Pro Asn Ile Thr Phe Glu Ser Ala Ala Glu Asp Leu Arg Leu
    1330                1335                1340

Ser Thr Asn Met Ala Leu Ser Ile Ile His Asn Gly Tyr Ala Gly Thr
1345                1350                1355                1360

Arg Arg Ile Gln Cys Asn Leu Met Lys Gln Tyr Ala Ser Leu Gly Asp
                1365                1370                1375

Lys Phe Ile Ile Tyr Asp Ser Ser Phe Asp Ala Asn Arg Phe Asn
            1380                1385                1390

Leu Val Pro Leu Phe Lys Phe Gly Lys Asp Glu Asn Ser Asp Asp Ser
        1395                1400                1405

Ile Cys Ile Tyr Asn Glu Asn Pro Ser Ser Glu Asp Lys Lys Trp Tyr
    1410                1415                1420

Phe Ser Ser Lys Asp Asp Asn Lys Thr Ala Asp Tyr Asn Gly Gly Thr
1425                1430                1435                1440

Gln Cys Ile Asp Ala Gly Thr Ser Asn Lys Asp Phe Tyr Tyr Asn Leu
                1445                1450                1455

Gln Glu Ile Glu Val Ile Ser Val Thr Gly Gly Tyr Trp Ser Ser Tyr
            1460                1465                1470

Lys Ile Ser Asn Pro Ile Asn Ile Asn Thr Gly Ile Asp Ser Ala Lys
        1475                1480                1485

Val Lys Val Thr Val Lys Ala Gly Gly Asp Asp Gln Ile Phe Thr Ala
    1490                1495                1500

Asp Asn Ser Thr Tyr Val Pro Gln Gln Pro Ala Pro Ser Phe Glu Glu
1505                1510                1515                1520

Met Ile Tyr Gln Phe Asn Asn Leu Thr Ile Asp Cys Lys Asn Leu Asn
                1525                1530                1535

Phe Ile Asp Asn Gln Ala His Ile Glu Ile Asp Phe Thr Ala Thr Ala
            1540                1545                1550

Gln Asp Gly Arg Phe Leu Gly Ala Glu Thr Phe Ile Ile Pro Val Thr
        1555                1560                1565

Lys Lys Val Leu Gly Thr Glu Asn Val Ile Ala Leu Tyr Ser Glu Asn
    1570                1575                1580

Asn Gly Val Gln Tyr Met Gln Ile Gly Ala Tyr Arg Thr Arg Leu Asn
1585                1590                1595                1600

Thr Leu Phe Ala Gln Gln Leu Val Ser Arg Ala Asn Arg Gly Ile Asp
                1605                1610                1615

Ala Val Leu Ser Met Glu Thr Gln Asn Ile Gln Glu Pro Gln Leu Gly
            1620                1625                1630

Ala Gly Thr Tyr Val Gln Leu Val Leu Asp Lys Tyr Asp Glu Ser Ile
        1635                1640                1645

His Gly Thr Asn Lys Ser Phe Ala Ile Glu Tyr Val Asp Ile Phe Lys
```

-continued

```
            1650                1655                1660
Glu Asn Asp Ser Phe Val Ile Tyr Gln Gly Glu Leu Ser Glu Thr Ser
1665                1670                1675                1680

Gln Thr Val Val Lys Val Phe Leu Ser Tyr Phe Ile Glu Ala Thr Gly
                1685                1690                1695

Asn Lys Asn His Leu Trp Val Arg Ala Lys Tyr Gln Lys Glu Thr Thr
            1700                1705                1710

Asp Lys Ile Leu Phe Asp Arg Thr Asp Glu Lys Asp Pro His Gly Trp
            1715                1720                1725

Phe Leu Ser Asp Asp His Lys Thr Phe Ser Gly Leu Ser Ser Ala Gln
            1730                1735                1740

Ala Leu Lys Asn Asp Ser Glu Pro Met Asp Phe Ser Gly Ala Asn Ala
1745                1750                1755                1760

Leu Tyr Phe Trp Glu Leu Phe Tyr Tyr Thr Pro Met Met Met Ala His
                1765                1770                1775

Arg Leu Leu Gln Glu Gln Asn Phe Asp Ala Ala Asn His Trp Phe Arg
            1780                1785                1790

Tyr Val Trp Ser Pro Ser Gly Tyr Ile Val Asp Gly Lys Ile Ala Ile
            1795                1800                1805

Tyr His Trp Asn Val Arg Pro Leu Glu Glu Asp Thr Ser Trp Asn Ala
            1810                1815                1820

Gln Gln Leu Asp Ser Thr Asp Pro Asp Ala Val Ala Gln Asp Asp Pro
1825                1830                1835                1840

Met His Tyr Lys Val Ala Thr Phe Met Ala Thr Leu Asp Leu Leu Met
                1845                1850                1855

Ala Arg Gly Asp Ala Ala Tyr Arg Gln Leu Glu Arg Asp Thr Leu Ala
            1860                1865                1870

Glu Ala Lys Met Trp Tyr Thr Gln Ala Leu Asn Leu Leu Gly Asp Glu
            1875                1880                1885

Pro Gln Val Met Leu Ser Thr Thr Trp Ala Asn Pro Thr Leu Gly Asn
            1890                1895                1900

Ala Ala Ser Lys Thr Thr Gln Gln Val Arg Gln Gln Val Leu Thr Gln
1905                1910                1915                1920

Leu Arg Leu Asn Ser Arg Val Lys Thr Pro Leu Leu Gly Thr Ala Asn
                1925                1930                1935

Ser Leu Thr Ala Leu Phe Leu Pro Gln Glu Asn Ser Lys Leu Lys Gly
            1940                1945                1950

Tyr Trp Arg Thr Leu Ala Gln Arg Met Phe Asn Leu Arg His Asn Leu
            1955                1960                1965

Ser Ile Asp Gly Gln Pro Leu Ser Leu Pro Leu Tyr Ala Lys Pro Ala
            1970                1975                1980

Asp Pro Lys Ala Leu Leu Ser Ala Val Ser Ala Ser Gln Gly Gly
1985                1990                1995                2000

Ala Asp Leu Pro Lys Ala Pro Leu Thr Ile His Arg Phe Pro Gln Met
                2005                2010                2015

Leu Glu Gly Ala Arg Gly Leu Val Asn Gln Leu Ile Gln Phe Gly Ser
            2020                2025                2030

Ser Leu Leu Gly Tyr Ser Glu Arg Gln Asp Ala Glu Ala Met Ser Gln
            2035                2040                2045

Leu Leu Gln Thr Gln Ala Ser Glu Leu Ile Leu Thr Ser Ile Arg Met
            2050                2055                2060

Gln Asp Asn Gln Leu Ala Glu Leu Asp Ser Glu Lys Thr Ala Leu Gln
2065                2070                2075                2080
```

-continued

Val Ser Leu Ala Gly Val Gln Gln Arg Phe Asp Ser Tyr Ser Gln Leu
            2085                2090                2095

Tyr Glu Glu Asn Ile Asn Ala Gly Glu Gln Arg Ala Leu Ala Leu Arg
        2100                2105                2110

Ser Glu Ser Ala Ile Glu Ser Gln Gly Ala Gln Ile Ser Arg Met Ala
        2115                2120                2125

Gly Ala Gly Val Asp Met Ala Pro Asn Ile Phe Gly Leu Ala Asp Gly
        2130                2135                2140

Gly Met His Tyr Gly Ala Ile Ala Tyr Ala Ile Ala Asp Gly Ile Glu
2145                2150                2155                2160

Leu Ser Ala Ser Ala Lys Met Val Asp Ala Glu Lys Val Ala Gln Ser
            2165                2170                2175

Glu Ile Tyr Arg Arg Arg Gln Glu Trp Lys Ile Gln Arg Asp Asn
        2180                2185                2190

Ala Gln Ala Glu Ile Asn Gln Leu Asn Ala Gln Leu Glu Ser Leu Ser
        2195                2200                2205

Ile Arg Arg Glu Ala Ala Glu Met Gln Lys Glu Tyr Leu Lys Thr Gln
    2210                2215                2220

Gln Ala Gln Ala Gln Ala Gln Leu Thr Phe Leu Arg Ser Lys Phe Ser
2225                2230                2235                2240

Asn Gln Ala Leu Tyr Ser Trp Leu Arg Gly Arg Leu Ser Gly Ile Tyr
            2245                2250                2255

Phe Gln Phe Tyr Asp Leu Ala Val Ser Arg Cys Leu Met Ala Glu Gln
        2260                2265                2270

Ser Tyr Gln Trp Glu Ala Asn Asp Asn Ser Ile Ser Phe Val Lys Pro
        2275                2280                2285

Gly Ala Trp Gln Gly Thr Tyr Ala Gly Leu Leu Cys Gly Glu Ala Leu
    2290                2295                2300

Ile Gln Asn Leu Ala Gln Met Glu Glu Ala Tyr Leu Lys Trp Glu Ser
2305                2310                2315                2320

Arg Ala Leu Glu Val Glu Arg Thr Val Ser Leu Ala Val Val Tyr Asp
            2325                2330                2335

Ser Leu Glu Gly Asn Asp Arg Phe Asn Leu Ala Glu Gln Ile Pro Ala
        2340                2345                2350

Leu Leu Asp Lys Gly Glu Gly Thr Ala Gly Thr Lys Glu Asn Gly Leu
    2355                2360                2365

Ser Leu Ala Asn Ala Ile Leu Ser Ala Ser Val Lys Leu Ser Asp Leu
    2370                2375                2380

Lys Leu Gly Thr Asp Tyr Pro Asp Ser Ile Val Gly Ser Asn Lys Val
2385                2390                2395                2400

Arg Arg Ile Lys Gln Ile Ser Val Ser Leu Pro Ala Leu Val Gly Pro
            2405                2410                2415

Tyr Gln Asp Val Gln Ala Met Leu Ser Tyr Gly Gly Ser Thr Gln Leu
        2420                2425                2430

Pro Lys Gly Cys Ser Ala Leu Ala Val Ser His Gly Thr Asn Asp Ser
        2435                2440                2445

Gly Gln Phe Gln Leu Asp Phe Asn Asp Gly Lys Tyr Leu Pro Phe Glu
    2450                2455                2460

Gly Ile Ala Leu Asp Asp Gln Gly Thr Leu Asn Leu Gln Phe Pro Asn
2465                2470                2475                2480

Ala Thr Asp Lys Gln Lys Ala Ile Leu Gln Thr Met Ser Asp Ile Ile
            2485                2490                2495

```
Leu His Ile Arg Tyr Thr Ile Arg
            2500                2505

(2) INFORMATION FOR SEQ ID NO:13:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13 (TCDAII N-TERMINUS):

Leu Ile Gly Tyr Asn Asn Gln Phe Ser Gly Xaa Ala
1               5                   10

(2) INFORMATION FOR SEQ ID NO:14:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14 (TCDB N-TERMINUS):

Met Gln Asn Ser Gln Thr Phe Ser Val Gly Glu Leu
1               5                   10

(2) INFORMATION FOR SEQ ID NO:15:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15 (TCAAII N-TERMINUS):

Ala Gln Asp Gly Asn Gln Asp Thr Phe Phe Ser Gly Asn Thr
1               5                   10

(2) INFORMATION FOR SEQ ID NO:16:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16 (TCBA N-TERMINUS):

Met Gln Asn Ser Leu
1               5

(2) INFORMATION FOR SEQ ID NO:17:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17 (TCDAII-PTLLL INTERNAL:
```

```
        peptide):

Ala Phe Asn Ile Asp Asp Val Ser Leu Phe
1               5                   10

(2) INFORMATION FOR SEQ ID NO:18:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:18 (TCDAII- PT79 INTERNAL:
         peptide):

Phe Ile Val Tyr Thr Ser Leu Gly Val Asn Pro Asn Asn Ser Ser Asn
1               5                   10                  15

(2) INFORMATION FOR SEQ ID NO:19:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:19 (TCABI- PT158 INTERNAL:
         peptide):

Ile Ser Asp Leu Val Thr Thr Ser Pro Leu Ser Glu Ala Ile Gly Ser
1               5                   10                  15

Leu Gln Leu Phe Ile
            20

(2) INFORMATION FOR SEQ ID NO:20:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:20 (TCABI- PT 108:
         internal peptide):

Met Tyr Tyr Ile Gln Ala Gln Gln Leu Leu Gly Pro
1               5                   10

(2) INFORMATION FOR SEQ ID NO:21:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:21 (TCBAII- PT103:
         internal peptide):

Gly Ile Asp Ala Val Leu Ser Met Glu Thr Gln Asn Ile Gln Glu Pro
1               5                   10                  15

Gln Leu Gly Ala Gly Thr Tyr Val Gln Leu
            20                  25
```

(2) INFORMATION FOR SEQ ID NO:22:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:22 (TCBAII- PT56 INTERNAL:
        peptide):

```
Ile Ser Asn Pro Ile Asn Ile Asn Thr Gly Ile Asp Ser Ala Lys
1               5                   10                  15
```

(2) INFORMATION FOR SEQ ID NO:23:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:23 (TCBA- PT81 (A):
        internal peptide):

```
Thr Tyr Leu Thr Ser Phe Glu Gln Val Ala Asn Leu Lys
1               5                   10
```

(2) INFORMATION FOR SEQ ID NO:24:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:24 (TCBAII- PT81 (B):
        internal peptide):

```
Val Leu Gly Thr Glu Asn Val Ile Ala Leu Tyr Ser Glu Asn Asn Gly
1               5                   10                  15

Val Gln Tyr Met Gln Ile
                20
```

(2) INFORMATION FOR SEQ ID NO:25:

(i) SEQUENCE CHARACTERISTICS:
        (A) LENGTH: 6054 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..43
        (D) OTHER INFORMATION: /product= "end of TcaAiii"

(ix) FEATURE:
        (A) NAME/KEY: RBS
        (B) LOCATION: 51  58

(ix) FEATURE:
        (A) NAME/KEY: CDS
        (B) LOCATION: 65  3634
        (D) OTHER INFORMATION: /product= "TcaBi"

(xi) SEQUENCE DESCRIPTION: SEQ ID NO:25:

```
A GTA GCC CAA AAC TTA AGT GCC GCA ATC AGC AAT CGT CAG TAACCGGATA        50
  Val Ala Gln Asn Leu Ser Ala Ala Ile Ser Asn Arg Gln

AAGAAGGAAT TGATT ATG TCT GAA TCT TTA TTT ACA CAA ACG TTG AAA GAA       100
             Met Ser Glu Ser Leu Phe Thr Gln Thr Leu Lys Glu
             1               5                   10

GCG CGC CGT GAT GCA TTG GTT GCT CAT TAT ATT GCT ACT CAG GTG CCC        148
Ala Arg Arg Asp Ala Leu Val Ala His Tyr Ile Ala Thr Gln Val Pro
        15                  20                  25

GCA GAT TTA AAA GAG AGT ATC CAG ACC GCG GAT GAT CTG TAC GAA TAT        196
Ala Asp Leu Lys Glu Ser Ile Gln Thr Ala Asp Asp Leu Tyr Glu Tyr
    30                  35                  40

CTG TTG CTG GAT ACC AAA ATT AGC GAT CTG GTT ACT ACT TCA CCG CTG        244
Leu Leu Leu Asp Thr Lys Ile Ser Asp Leu Val Thr Thr Ser Pro Leu
45                  50                  55                  60

TCC GAA GCG ATT GGC AGT CTG CAA TTG TTT ATT CAT CGT GCG ATA GAG        292
Ser Glu Ala Ile Gly Ser Leu Gln Leu Phe Ile His Arg Ala Ile Glu
                65                  70                  75

GGC TAT GAC GGC ACG CTG GCA GAC TCA GCA AAA CCC TAT TTT GCC GAT        340
Gly Tyr Asp Gly Thr Leu Ala Asp Ser Ala Lys Pro Tyr Phe Ala Asp
            80                  85                  90

GAA CAG TTT TTA TAT AAC TGG GAT AGT TTT AAC CAC CGT TAT AGC ACT        388
Glu Gln Phe Leu Tyr Asn Trp Asp Ser Phe Asn His Arg Tyr Ser Thr
        95                  100                 105

TGG GCT GGC AAG GAA CGG TTG AAA TTC TAT GCC GGG GAT TAT ATT GAT        436
Trp Ala Gly Lys Glu Arg Leu Lys Phe Tyr Ala Gly Asp Tyr Ile Asp
    110                 115                 120

CCA ACA TTG CGA TTG AAT AAG ACC GAG ATA TTT ACC GCA TTT GAA CAA        484
Pro Thr Leu Arg Leu Asn Lys Thr Glu Ile Phe Thr Ala Phe Glu Gln
125                 130                 135                 140

GGT ATT TCT CAA GGG AAA TTA AAA AGT GAA TTA GTC GAA TCT AAA TTA        532
Gly Ile Ser Gln Gly Lys Leu Lys Ser Glu Leu Val Glu Ser Lys Leu
                145                 150                 155

CGT GAT TAT CTA ATT AGT TAT GAC ACT TTA GCC ACC CTT GAT TAT ATT        580
Arg Asp Tyr Leu Ile Ser Tyr Asp Thr Leu Ala Thr Leu Asp Tyr Ile
            160                 165                 170

ACT GCC TGC CAA GGC AAA GAT AAT AAA ACC ATC TTC TTT ATT GGC CGT        628
Thr Ala Cys Gln Gly Lys Asp Asn Lys Thr Ile Phe Phe Ile Gly Arg
        175                 180                 185

ACA CAG AAT GCA CCC TAT GCA TTT TAT TGG CGA AAA TTA ACT TTA GTC        676
Thr Gln Asn Ala Pro Tyr Ala Phe Tyr Trp Arg Lys Leu Thr Leu Val
    190                 195                 200

ACT GAT GGC GGT AAG TTG AAA CCA GAT CAA TGG TCA GAG TGG CGA GCA        724
Thr Asp Gly Gly Lys Leu Lys Pro Asp Gln Trp Ser Glu Trp Arg Ala
205                 210                 215                 220

ATT AAT GCC GGG ATT AGT GAG GCA TAT TCA GGG CAT GTC GAG CCT TTC        772
Ile Asn Ala Gly Ile Ser Glu Ala Tyr Ser Gly His Val Glu Pro Phe
                225                 230                 235

TGG GAA AAT AAC AAG CTG CAC ATC CGT TGG TTT ACT ATC TCG AAA GAA        820
Trp Glu Asn Asn Lys Leu His Ile Arg Trp Phe Thr Ile Ser Lys Glu
            240                 245                 250

GAT AAA ATA GAT TTT GTT TAT AAA AAC ATC TGG GTG ATG AGT AGC GAT        868
Asp Lys Ile Asp Phe Val Tyr Lys Asn Ile Trp Val Met Ser Ser Asp
        255                 260                 265

TAT AGC TGG GCA TCA AAG AAA AAA ATC TTG GAA CTT TCT TTT ACT GAC        916
Tyr Ser Trp Ala Ser Lys Lys Lys Ile Leu Glu Leu Ser Phe Thr Asp
    270                 275                 280

TAC AAT AGA GTT GGA GCA ACA GGA TCA TCA AGC CCG ACT GAA GTA GCT        964
Tyr Asn Arg Val Gly Ala Thr Gly Ser Ser Ser Pro Thr Glu Val Ala
```

```
TCA CAA TAT GGT TCT GAT GCT CAG ATG AAT ATT TCT GAT GAT GGG ACT      1012
Ser Gln Tyr Gly Ser Asp Ala Gln Met Asn Ile Ser Asp Asp Gly Thr
            305                 310                 315

GTA CTT ATT TTT CAG AAT GCC GGC GGA GCT ACT CCC AGT ACT GGA GTG      1060
Val Leu Ile Phe Gln Asn Ala Gly Gly Ala Thr Pro Ser Thr Gly Val
        320                 325                 330

ACG TTA TGT TAT GAC TCT GGC AAC GTG ATT AAG AAC CTA TCT AGT ACA      1108
Thr Leu Cys Tyr Asp Ser Gly Asn Val Ile Lys Asn Leu Ser Ser Thr
            335                 340                 345

GGA AGT GCA AAT TTA TCG TCA AAG GAT TAT GCC ACA ACT AAA TTA CGC      1156
Gly Ser Ala Asn Leu Ser Ser Lys Asp Tyr Ala Thr Thr Lys Leu Arg
        350                 355                 360

ATG TGT CAT GGA CAA AGT TAC AAT GAT AAT AAC TAC TGC AAT TTT ACA      1204
Met Cys His Gly Gln Ser Tyr Asn Asp Asn Asn Tyr Cys Asn Phe Thr
365                 370                 375                 380

CTC TCT ATT AAT ACA ATA GAA TTC ACC TCC TAC GGC ACA TTC TCA TCA      1252
Leu Ser Ile Asn Thr Ile Glu Phe Thr Ser Tyr Gly Thr Phe Ser Ser
            385                 390                 395

GAT GGA AAA CAA TTT ACA CCA CCT TCT GGT TCT GCC ATT GAT TTA CAC      1300
Asp Gly Lys Gln Phe Thr Pro Pro Ser Gly Ser Ala Ile Asp Leu His
        400                 405                 410

CTC CCT AAT TAT GTA GAT CTC AAC GCG CTA TTA GAT ATT AGC CTC GAT      1348
Leu Pro Asn Tyr Val Asp Leu Asn Ala Leu Leu Asp Ile Ser Leu Asp
            415                 420                 425

TCA CTA CTT AAT TAT GAC GTT CAG GGG CAG TTT GGC GGA TCT AAT CCG      1396
Ser Leu Leu Asn Tyr Asp Val Gln Gly Gln Phe Gly Gly Ser Asn Pro
        430                 435                 440

GTT GAT AAT TTC AGT GGT CCC TAT GGT ATT TAT CTA TGG GAA ATC TTC      1444
Val Asp Asn Phe Ser Gly Pro Tyr Gly Ile Tyr Leu Trp Glu Ile Phe
445                 450                 455                 460

TTC CAT ATT CCG TTC CTT GTT ACG GTC CGT ATG CAA ACC GAA CAA CGT      1492
Phe His Ile Pro Phe Leu Val Thr Val Arg Met Gln Thr Glu Gln Arg
            465                 470                 475

TAC GAA GAC GCG GAC ACT TGG TAC AAA TAT ATT TTC CGC AGC GCC GGT      1540
Tyr Glu Asp Ala Asp Thr Trp Tyr Lys Tyr Ile Phe Arg Ser Ala Gly
        480                 485                 490

TAT CGC GAT GCT AAT GGC CAG CTC ATT ATG GAT GGC AGT AAA CCA CGT      1588
Tyr Arg Asp Ala Asn Gly Gln Leu Ile Met Asp Gly Ser Lys Pro Arg
            495                 500                 505

TAT TGG AAT GTG ATG CCA TTG CAA CTG GAT ACC GCA TGG GAT ACC ACA      1636
Tyr Trp Asn Val Met Pro Leu Gln Leu Asp Thr Ala Trp Asp Thr Thr
510                 515                 520

CAG CCC GCC ACC ACT GAT CCA GAT GTG ATC GCT ATG GCG GAC CCG ATG      1684
Gln Pro Ala Thr Thr Asp Pro Asp Val Ile Ala Met Ala Asp Pro Met
525                 530                 535                 540

CAT TAC AAG CTG GCG ATA TTC CTG CAT ACC CTT GAT CTA TTG ATT GCC      1732
His Tyr Lys Leu Ala Ile Phe Leu His Thr Leu Asp Leu Leu Ile Ala
            545                 550                 555

CGA GGC GAC AGC GCT TAC CGT CAA CTT GAA CGC GAT ACT CTA GTC GAA      1780
Arg Gly Asp Ser Ala Tyr Arg Gln Leu Glu Arg Asp Thr Leu Val Glu
        560                 565                 570

GCC AAA ATG TAC TAC ATT CAG GCA CAA CAG CTA CTG GGA CCG CGC CCT      1828
Ala Lys Met Tyr Tyr Ile Gln Ala Gln Gln Leu Leu Gly Pro Arg Pro
            575                 580                 585

GAT ATC CAT ACC ACC AAT ACT TGG CCA AAT CCC ACC TTG AGT AAA GAA      1876
Asp Ile His Thr Thr Asn Thr Trp Pro Asn Pro Thr Leu Ser Lys Glu
        590                 595                 600

GCT GGC GCT ATT GCC ACA CCG ACA TTC CTC AGT TCA CCG GAG GTG ATG      1924
```

-continued

| | | | | | | | | | | | | |
|---|---|---|---|---|---|---|---|---|---|---|---|---|
| Ala | Gly | Ala | Ile | Ala | Thr | Pro | Thr | Phe | Leu | Ser | Ser | Pro | Glu | Val | Met |
| 605 | | | | 610 | | | | | 615 | | | | | 620 | |

```
ACG TTC GCT GCC TGG CTA AGC GCA GGC GAT ACC GCA AAT ATT GGC GAC      1972
Thr Phe Ala Ala Trp Leu Ser Ala Gly Asp Thr Ala Asn Ile Gly Asp
            625             630             635

GGT GAT TTC TTG CCA CCG TAC AAC GAT GTA CTA CTC GGT TAC TGG GAT      2020
Gly Asp Phe Leu Pro Pro Tyr Asn Asp Val Leu Leu Gly Tyr Trp Asp
            640             645             650

AAA CTT GAG TTA CGC CTA TAC AAC CTG CGC CAC AAT CTG AGT CTG GAT      2068
Lys Leu Glu Leu Arg Leu Tyr Asn Leu Arg His Asn Leu Ser Leu Asp
            655             660             665

GGT CAA CCG CTA AAT CTG CCA CTG TAT GCC ACG CCG GTA GAC CCG AAA      2116
Gly Gln Pro Leu Asn Leu Pro Leu Tyr Ala Thr Pro Val Asp Pro Lys
            670             675             680

ACC CTG CAA CGC CAG CAA GCC GGA GGG GAC GGT ACA GGC AGT AGT CCG      2164
Thr Leu Gln Arg Gln Gln Ala Gly Gly Asp Gly Thr Gly Ser Ser Pro
685             690             695             700

GCT GGT GGT CAA GGC AGT GTT CAG GGC TGG CGC TAT CCG TTA TTG GTA      2212
Ala Gly Gly Gln Gly Ser Val Gln Gly Trp Arg Tyr Pro Leu Leu Val
            705             710             715

GAA CGC GCC CGC TCT GCC GTG AGT TTG TTG ACT CAG TTC GGC AAC AGC      2260
Glu Arg Ala Arg Ser Ala Val Ser Leu Leu Thr Gln Phe Gly Asn Ser
            720             725             730

TTA CAA ACA ACG TTA GAA CAT CAG GAT AAT GAA AAA ATG ACG ATA CTG      2308
Leu Gln Thr Thr Leu Glu His Gln Asp Asn Glu Lys Met Thr Ile Leu
            735             740             745

TTG CAG ACT CAA CAG GAA GCC ATC CTG AAA CAT CAG CAC GAT ATA CAA      2356
Leu Gln Thr Gln Gln Glu Ala Ile Leu Lys His Gln His Asp Ile Gln
    750             755             760

CAA AAT AAT CTA AAA GGA TTA CAA CAC AGC CTG ACC GCA TTA CAG GCT      2404
Gln Asn Asn Leu Lys Gly Leu Gln His Ser Leu Thr Ala Leu Gln Ala
765             770             775             780

AGC CGT GAT GGC GAC ACA TTG CGG CAA AAA CAT TAC AGC GAC CTG ATT      2452
Ser Arg Asp Gly Asp Thr Leu Arg Gln Lys His Tyr Ser Asp Leu Ile
            785             790             795

AAC GGT GGT CTA TCT GCG GCA GAA ATC GCC GGT CTG ACA CTA CGC AGC      2500
Asn Gly Gly Leu Ser Ala Ala Glu Ile Ala Gly Leu Thr Leu Arg Ser
            800             805             810

ACC GCC ATG ATT ACC AAT GGC GTT GCA ACG GGA TTG CTG ATT GCC GGC      2548
Thr Ala Met Ile Thr Asn Gly Val Ala Thr Gly Leu Leu Ile Ala Gly
            815             820             825

GGA ATC GCC AAC GCG GTA CCT AAC GTC TTC GGG CTG GCT AAC GGT GGA      2596
Gly Ile Ala Asn Ala Val Pro Asn Val Phe Gly Leu Ala Asn Gly Gly
            830             835             840

TCG GAA TGG GGA GCG CCA TTA ATT GGC TCC GGG CAA GCA ACC CAA GTT      2644
Ser Glu Trp Gly Ala Pro Leu Ile Gly Ser Gly Gln Ala Thr Gln Val
845             850             855             860

GGC GCC GGC ATC CAG GAT CAG AGC GCG GGC ATT TCA GAA GTG ACA GCA      2692
Gly Ala Gly Ile Gln Asp Gln Ser Ala Gly Ile Ser Glu Val Thr Ala
            865             870             875

GGC TAT CAG CGT CGT CAG GAA GAA TGG GCA TTG CAA CGG GAT ATT GCT      2740
Gly Tyr Gln Arg Arg Gln Glu Glu Trp Ala Leu Gln Arg Asp Ile Ala
            880             885             890

GAT AAC GAA ATA ACC CAA CTG GAT GCC CAG ATA CAA AGC CTG CAA GAG      2788
Asp Asn Glu Ile Thr Gln Leu Asp Ala Gln Ile Gln Ser Leu Gln Glu
            895             900             905

CAA ATC ACG ATG GCA CAA AAA CAG ATC ACG CTC TCT GAA ACC GAA CAA      2836
Gln Ile Thr Met Ala Gln Lys Gln Ile Thr Leu Ser Glu Thr Glu Gln
            910             915             920
```

-continued

| | | |
|---|---|---|
| GCG AAT GCC CAA GCG ATT TAT GAC CTG CAA ACC ACT CGT TTT ACC GGG<br>Ala Asn Ala Gln Ala Ile Tyr Asp Leu Gln Thr Thr Arg Phe Thr Gly<br>925               930                     935               940 | | 2884 |
| CAG GCA CTG TAT AAC TGG ATG GCC GGT CGT CTC TCC GCG CTC TAT TAC<br>Gln Ala Leu Tyr Asn Trp Met Ala Gly Arg Leu Ser Ala Leu Tyr Tyr<br>                 945                     950                     955 | | 2932 |
| CAA ATG TAT GAT TCC ACT CTG CCA ATC TGT CTC CAG CCA AAA GCC GCA<br>Gln Met Tyr Asp Ser Thr Leu Pro Ile Cys Leu Gln Pro Lys Ala Ala<br>                 960                     965                     970 | | 2980 |
| TTA GTA CAG GAA TTA GGC GAG AAA GAG AGC GAC AGT CTT TTC CAG GTT<br>Leu Val Gln Glu Leu Gly Glu Lys Glu Ser Asp Ser Leu Phe Gln Val<br>     975                     980                     985 | | 3028 |
| CCG GTG TGG AAT GAT CTG TGG CAA GGG CTG TTA GCA GGA GAA GGT TTA<br>Pro Val Trp Asn Asp Leu Trp Gln Gly Leu Leu Ala Gly Glu Gly Leu<br>990                              995                     1000 | | 3076 |
| AGT TCA GAG CTA CAG AAA CTG GAT GCC ATC TGG CTT GCA CGT GGT GGT<br>Ser Ser Glu Leu Gln Lys Leu Asp Ala Ile Trp Leu Ala Arg Gly Gly<br>1005                 1010               1015               1020 | | 3124 |
| ATT GGG CTA GAA GCC ATC CGC ACC GTG TCG CTG GAT ACC CTG TTT GGC<br>Ile Gly Leu Glu Ala Ile Arg Thr Val Ser Leu Asp Thr Leu Phe Gly<br>                 1025               1030               1035 | | 3172 |
| ACA GGG ACG TTA AGT GAA AAT ATC AAT AAA GTG CTT AAC GGG GAA ACG<br>Thr Gly Thr Leu Ser Glu Asn Ile Asn Lys Val Leu Asn Gly Glu Thr<br>                 1040               1045               1050 | | 3220 |
| GTA TCT CCA TCC GGT GGC GTC ACT CTG GCG CTG ACA GGG GAT ATC TTC<br>Val Ser Pro Ser Gly Gly Val Thr Leu Ala Leu Thr Gly Asp Ile Phe<br>1055                 1060               1065 | | 3268 |
| CAA GCA ACA CTG GAT TTG AGT CAG CTA GGT TTG GAT AAC TCT TAC AAC<br>Gln Ala Thr Leu Asp Leu Ser Gln Leu Gly Leu Asp Asn Ser Tyr Asn<br>     1070                     1075               1080 | | 3316 |
| TTG GGT AAC GAG AAG AAA CGT CGT ATT AAA CGT ATC GCC GTC ACC CTG<br>Leu Gly Asn Glu Lys Lys Arg Arg Ile Lys Arg Ile Ala Val Thr Leu<br>1085                 1090               1095               1100 | | 3364 |
| CCA ACA CTT CTG GGG CCA TAT CAA GAT CTT GAA GCC ACA CTG GTA ATG<br>Pro Thr Leu Leu Gly Pro Tyr Gln Asp Leu Glu Ala Thr Leu Val Met<br>                 1105               1110               1115 | | 3412 |
| GGT GCG GAA ATC GCC GCC TTA TCA CAC GGT GTG AAT GAC GGA GGC CGG<br>Gly Ala Glu Ile Ala Ala Leu Ser His Gly Val Asn Asp Gly Gly Arg<br>                 1120               1125               1130 | | 3460 |
| TTT GTT ACC GAC TTT AAC GAC AGC CGT TTT CTG CCT TTT GAA GGT CGA<br>Phe Val Thr Asp Phe Asn Asp Ser Arg Phe Leu Pro Phe Glu Gly Arg<br>     1135                     1140               1145 | | 3508 |
| GAT GCA ACA ACC GGC ACA CTG GAG CTC AAT ATT TTC CAT GCG GGT AAA<br>Asp Ala Thr Thr Gly Thr Leu Glu Leu Asn Ile Phe His Ala Gly Lys<br>     1150                     1155               1160 | | 3556 |
| GAG GGA ACG CAA CAC GAG TTG GTC GCG AAT CTG AGT GAC ATC ATT GTG<br>Glu Gly Thr Gln His Glu Leu Val Ala Asn Leu Ser Asp Ile Ile Val<br>1165                 1170               1175               1180 | | 3604 |
| CAT CTG AAT TAC ATC ATT CGA GAC GCG TAA ATTTCTTTTC TTTGTCGATT<br>His Leu Asn Tyr Ile Ile Arg Asp Ala *<br>                 1185                     1190 | | 3654 |
| ACAGGTCCCT ATCAGGGGCC TGTTATTAAG GAGTACTTTA TGCAGGATTC ACCAGAAGTA | | 3714 |
| TCGATTACAA CGCTGTCACT TCCCAAAGGT GGCGGTGCTA TCAATGGCAT GGGAGAAGCA | | 3774 |
| CTGAATGCTG CCGGCCCTGA TGGAATGGCC TCCCTATCTC TGCCATTACC CCTTTCGACC | | 3834 |
| GGCAGAGGGA CGGCTCCTGG ATTATCGCTG ATTTACAGCA ACAGTGCAGG TAATGGGCCT | | 3894 |
| TTCGGCATCG GCTGGCAATG CGGTGTTATG TCCATTAGCC GACGCACCCA ACATGGCATT | | 3954 |
| CCACAATACG GTAATGACGA CACGTTCCTA TCCCCACAAG GCGAGGTCAT GAATATCGCC | | 4014 |

```
CTGAATGACC AAGGGCAACC TGATATCCGT CAAGACGTTA AAACGCTGCA AGGCGTTACC    4074

TTGCCAATTT CCTATACCGT GACCCGCTAT CAAGCCCGCC AGATCCTGGA TTTCAGTAAA    4134

ATCGAATACT GGCAACCTGC CTCCGGTCAA GAAGGACGCG CTTTCTGGCT GATATCGACA    4194

CCGGACGGGC ATCTACACAT CTTAGGGAAA ACCGCGCAGG CTTGTCTGGC AAATCCGCAA    4254

AATGACCAAC AAATCGCCCA GTGGTTGCTG AAGAAACTG TGACGCCAGC CGGTGAACAT     4314

GTCAGCTATC AATATCGAGC CGAAGATGAA GCCCATTGTG ACGACAATGA AAAAACCGCT    4374

CATCCCAATG TTACCGCACA GCGCTATCTG GTACAGGTGA ACTACAGGCA ACATCAAACC    4434

ACAAGCCAGC CTGTTCGTAC TGGATAACGC ACCTCCCGCA CCGGAAGAGT GGCTGTTTCA    4494

TCTGGTCTTT GACCACGGTG AGCGCGTACC TCACTTCATA CCGTGCCAAC ATGGGATGCA    4554

GGTACAGCGC AATGGTCTGT ACGCCCGGAT ATCTTCTCTC GCTATGAATA TGGTTTTGAA    4614

GTGCGTACTC GCCGCTTATG TCAACAAGTG CTGATGTTTC ACCGCACCGC GCTCATGGCC    4674

GGAGAAGCCA GTACCAATGA CGCCCCGGAA CTGGTTGGAC GCTTAATACT GGAATATGAC    4634

AAAAACGCCA GCGTCACCAC GTTGATTACC ATCCGTCAAT TAAGCCATGA ATCGGACGGG    4794

AGGCCAGTCA CCCAGCCACC ACTAGAACTA GCCTGGCAAC GGTTTGATCT GGAGAAAATC    4854

CCGACATGGC AACGCTTTGA CGCACTAGAT AATTTTAACT CGCAGCAACG TTATCAACTG    4865

GTTGATCTGC GGGGAGAAGG GTTGCCAGGT ATGCTGTATC AAGATCGAGG CGCTTGGTGG    4914

TATAAAGCTC CGCAACGTCA GGAAGACGGA GACAGCAATG CCGTCACTTA CGACAAAATC    4974

GCCCCACTGC CTACCCTACC CAATTTGCAG GATAATGCCT CATTGATGGA TATCAACGGA    5034

GACGGCCAAC TGGATTGGGT TGTTACCGCC TCCGGTATTC GCGGATACCA TAGTCAGCAA    5094

CCCGATGGAA AGTGGACGCA CTTTACGCCA ATCAATGCCT TGCCCGTGGA ATATTTTCAT    5214

CCAAGCATCC AGTTCGCTGA CCTTACCGGG GCAGGCTTAT CTGATTTAGT GTTGATCGGG    5274

CCGAAAAGCG TGCGTCTATA TGCCAACCAG CGAAACGGCT GGCGTAAAGG AGAAGATGTC    5334

CCCCAATCCA CAGGTATCAC CCTGCCTGTC ACAGGGACCG ATGCCCGCAA ACTGGTGGCT    5394

TTCAGTGATA TGCTCGGTTC CGGTCAACAA CATCTGGTGG AAATCAAGGG TAATCGCGTC    5454

ACCTGTTGGC CGAATCTAGG GCATGGCCGT TTCGGTCAAC CACTAACTCT GTCAGGATTT    5514

AGCCAGCCCG AAAATAGCTT CAATCCCGAA CGGCTGTTTC TGGCGGATAT CGACGGCTCC    5574

GGCACCACCG ACCTTATCTA TGCGCAATCC GGCTCTTTGC TCATTTATCT CAACCAAAGT    5634

GGTAATCAGT TTGATGCCCC GTTGACATTA GCGTTGCCAG AAGGCGTACA ATTTGACAAC    5694

ACTTGCCAAC TTCAAGTCGC CGATATTCAG GGATTAGGGA TAGCCAGCTT GATTCTGACT    5754

GTGCCACATA TCGCGCCACA TCACTGGCGT TGTGACCTGT CACTGACCAA ACCCTGGTTG    5814

TTGAATGTAA TGAACAATAA CCGGGGCGCA CATCACACGC TACATTATCG TAGTTCCGCG    5874

CAATTCTGGT TGGATGAAAA ATTACAGCTC ACCAAAGCAG GCAAATCTCC GGCTTGTTAT    5934

CTGCCGTTTC CAATGCATTT GCTATGGTAT ACCGAAATTC AGGATGAAAT CAGCGGCAAC    5994

CGGCTCACCA GTGAAGTCAA CTACAGCCAC GGCGTCTGGG ATGGTAAAGA GCGGGAATTC    6054
```

(2) INFORMATION FOR SEQ ID NO:26:

(i) SEQUENCE CHARACTERISTICS:
        (A) LENGTH: 1188 amino acids
        (B) TYPE: amino acid
        (D) TOPOLOGY: linear (ii) MOLECULE TYPE: protein -continued (xi) SEQUENCE DESCRIPTION: SEQ ID NO:26 (TCAB PROTEIN):

```
Met Ser Glu Ser Leu Phe Thr Gln Thr Leu Lys Glu Ala Arg Arg Asp
 1               5                  10                  15

Ala Leu Val Ala His Tyr Ile Ala Thr Gln Val Pro Ala Asp Leu Lys
            20                  25                  30

Glu Ser Ile Gln Thr Ala Asp Asp Leu Tyr Glu Tyr Leu Leu Leu Asp
            35                  40                  45

Thr Lys Ile Ser Asp Leu Val Thr Thr Ser Pro Leu Ser Glu Ala Ile
        50                  55                  60

Gly Ser Leu Gln Leu Phe Ile His Arg Ala Ile Glu Gly Tyr Asp Gly
 65              70                  75                  80

Thr Leu Ala Asp Ser Ala Lys Pro Tyr Phe Ala Asp Glu Gln Phe Leu
                85                  90                  95

Tyr Asn Trp Asp Ser Phe Asn His Arg Tyr Ser Thr Trp Ala Gly Lys
            100                 105                 110

Glu Arg Leu Lys Phe Tyr Ala Gly Asp Tyr Ile Asp Pro Thr Leu Arg
            115                 120                 125

Leu Asn Lys Thr Glu Ile Phe Thr Ala Phe Glu Gln Gly Ile Ser Gln
        130                 135                 140

Gly Lys Leu Lys Ser Glu Leu Val Glu Ser Lys Leu Arg Asp Tyr Leu
145                 150                 155                 160

Ile Ser Tyr Asp Thr Leu Ala Thr Leu Asp Tyr Ile Thr Ala Cys Gln
                165                 170                 175

Gly Lys Asp Asn Lys Thr Ile Phe Phe Ile Gly Arg Thr Gln Asn Ala
            180                 185                 190

Pro Tyr Ala Phe Tyr Trp Arg Lys Leu Thr Leu Val Thr Asp Gly Gly
            195                 200                 205

Lys Leu Lys Pro Asp Gln Trp Ser Glu Trp Arg Ala Ile Asn Ala Gly
        210                 215                 220

Ile Ser Glu Ala Tyr Ser Gly His Val Glu Pro Phe Trp Glu Asn Asn
225                 230                 235                 240

Lys Leu His Ile Arg Trp Phe Thr Ile Ser Lys Glu Asp Lys Ile Asp
                245                 250                 255

Phe Val Tyr Lys Asn Ile Trp Val Met Ser Ser Asp Tyr Ser Trp Ala
            260                 265                 270

Ser Lys Lys Lys Ile Leu Glu Leu Ser Phe Thr Asp Tyr Asn Arg Val
        275                 280                 285

Gly Ala Thr Gly Ser Ser Pro Thr Glu Val Ala Ser Gln Tyr Gly
290                 295                 300

Ser Asp Ala Gln Met Asn Ile Ser Asp Asp Gly Thr Val Leu Ile Phe
305                 310                 315                 320

Gln Asn Ala Gly Gly Ala Thr Pro Ser Thr Gly Val Thr Leu Cys Tyr
                325                 330                 335

Asp Ser Gly Asn Val Ile Lys Asn Leu Ser Ser Thr Gly Ser Ala Asn
            340                 345                 350

Leu Ser Ser Lys Asp Tyr Ala Thr Thr Lys Leu Arg Met Cys His Gly
            355                 360                 365

Gln Ser Tyr Asn Asp Asn Tyr Cys Asn Phe Thr Leu Ser Ile Asn
        370                 375                 380

Thr Ile Glu Phe Thr Ser Tyr Gly Thr Phe Ser Ser Asp Gly Lys Gln
385                 390                 395                 400

Phe Thr Pro Pro Ser Gly Ser Ala Ile Asp Leu His Leu Pro Asn Tyr
                405                 410                 415
```

```
Val Asp Leu Asn Ala Leu Leu Asp Ile Ser Leu Asp Ser Leu Leu Asn
            420                 425                 430

Tyr Asp Val Gln Gly Gln Phe Gly Gly Ser Asn Pro Val Asp Asn Phe
            435                 440                 445

Ser Gly Pro Tyr Gly Ile Tyr Leu Trp Glu Ile Phe Phe His Ile Pro
            450                 455                 460

Phe Leu Val Thr Val Arg Met Gln Thr Glu Gln Arg Tyr Glu Asp Ala
465                 470                 475                 480

Asp Thr Trp Tyr Lys Tyr Ile Phe Arg Ser Ala Gly Tyr Arg Asp Ala
                    485                 490                 495

Asn Gly Gln Leu Ile Met Asp Gly Ser Lys Pro Arg Tyr Trp Asn Val
            500                 505                 510

Met Pro Leu Gln Leu Asp Thr Ala Trp Asp Thr Thr Gln Pro Ala Thr
            515                 520                 525

Thr Asp Pro Asp Val Ile Ala Met Ala Asp Pro Met His Tyr Lys Leu
            530                 535                 540

Ala Ile Phe Leu His Thr Leu Asp Leu Leu Ile Ala Arg Gly Asp Ser
545                 550                 555                 560

Ala Tyr Arg Gln Leu Glu Arg Asp Thr Leu Val Ala Lys Met Tyr
                    565                 570                 575

Tyr Ile Gln Ala Gln Gln Leu Leu Gly Pro Arg Pro Asp Ile His Thr
            580                 585                 590

Thr Asn Thr Trp Pro Asn Pro Thr Leu Ser Lys Glu Ala Gly Ala Ile
            595                 600                 605

Ala Thr Pro Thr Phe Leu Ser Ser Pro Glu Val Met Thr Phe Ala Ala
            610                 615                 620

Trp Leu Ser Ala Gly Asp Thr Ala Asn Ile Gly Asp Gly Asp Phe Leu
625                 630                 635                 640

Pro Pro Tyr Asn Asp Val Leu Leu Gly Tyr Trp Asp Lys Leu Glu Leu
                    645                 650                 655

Arg Leu Tyr Asn Leu Arg His Asn Leu Ser Leu Asp Gly Gln Pro Leu
            660                 665                 670

Asn Leu Pro Leu Tyr Ala Thr Pro Val Asp Pro Lys Thr Leu Gln Arg
            675                 680                 685

Gln Gln Ala Gly Gly Asp Gly Thr Gly Ser Ser Pro Ala Gly Gly Gln
            690                 695                 700

Gly Ser Val Gln Gly Trp Arg Tyr Pro Leu Leu Val Glu Arg Ala Arg
705                 710                 715                 720

Ser Ala Val Ser Leu Leu Thr Gln Phe Gly Asn Ser Leu Gln Thr Thr
                    725                 730                 735

Leu Glu His Gln Asp Asn Glu Lys Met Thr Ile Leu Leu Gln Thr Gln
            740                 745                 750

Gln Glu Ala Ile Leu Lys His Gln His Asp Ile Gln Gln Asn Asn Leu
            755                 760                 765

Lys Gly Leu Gln His Ser Leu Thr Ala Leu Gln Ala Ser Arg Asp Gly
            770                 775                 780

Asp Thr Leu Arg Gln Lys His Tyr Ser Asp Leu Ile Asn Gly Gly Leu
785                 790                 795                 800

Ser Ala Ala Glu Ile Ala Gly Leu Thr Leu Arg Ser Thr Ala Met Ile
                    805                 810                 815

Thr Asn Gly Val Ala Thr Gly Leu Leu Ile Ala Gly Gly Ile Ala Asn
            820                 825                 830
```

```
Ala Val Pro Asn Val Phe Gly Leu Ala Asn Gly Gly Ser Glu Trp Gly
        835                 840                 845

Ala Pro Leu Ile Gly Ser Gly Gln Ala Thr Gln Val Gly Ala Gly Ile
850                 855                 860

Gln Asp Gln Ser Ala Gly Ile Ser Glu Val Thr Ala Gly Tyr Gln Arg
865                 870                 875                 880

Arg Gln Glu Glu Trp Ala Leu Gln Arg Asp Ile Ala Asp Asn Glu Ile
                885                 890                 895

Thr Gln Leu Asp Ala Gln Ile Gln Ser Leu Gln Glu Gln Ile Thr Met
            900                 905                 910

Ala Gln Lys Gln Ile Thr Leu Ser Glu Thr Glu Gln Ala Asn Ala Gln
        915                 920                 925

Ala Ile Tyr Asp Leu Gln Thr Thr Arg Phe Thr Gly Gln Ala Leu Tyr
    930                 935                 940

Asn Trp Met Ala Gly Arg Leu Ser Ala Leu Tyr Tyr Gln Met Tyr Asp
945                 950                 955                 960

Ser Thr Leu Pro Ile Cys Leu Gln Pro Lys Ala Ala Leu Val Gln Glu
                965                 970                 975

Leu Gly Glu Lys Glu Ser Asp Ser Leu Phe Gln Val Pro Val Trp Asn
            980                 985                 990

Asp Leu Trp Gln Gly Leu Leu Ala Gly Glu Gly Leu Ser Ser Glu Leu
        995                 1000                1005

Gln Lys Leu Asp Ala Ile Trp Leu Ala Arg Gly Ile Gly Leu Glu
    1010                1015                1020

Ala Ile Arg Thr Val Ser Leu Asp Thr Leu Phe Gly Thr Gly Thr Leu
1025                1030                1035                1040

Ser Glu Asn Ile Asn Lys Val Leu Asn Gly Glu Thr Val Ser Pro Ser
                1045                1050                1055

Gly Gly Val Thr Leu Ala Leu Thr Gly Asp Ile Phe Gln Ala Thr Leu
            1060                1065                1070

Asp Leu Ser Gln Leu Gly Leu Asp Asn Ser Tyr Asn Leu Gly Asn Glu
        1075                1080                1085

Lys Lys Arg Arg Ile Lys Arg Ile Ala Val Thr Leu Pro Thr Leu Leu
    1090                1095                1100

Gly Pro Tyr Gln Asp Leu Glu Ala Thr Leu Val Met Gly Ala Glu Ile
1105                1110                1115                1120

Ala Ala Leu Ser His Gly Val Asn Asp Gly Gly Arg Phe Val Thr Asp
                1125                1130                1135

Phe Asn Asp Ser Arg Phe Leu Pro Phe Glu Gly Arg Asp Ala Thr Thr
            1140                1145                1150

Gly Thr Leu Glu Leu Asn Ile Phe His Ala Gly Lys Glu Gly Thr Gln
        1155                1160                1165

His Glu Leu Val Ala Asn Leu Ser Asp Ile Ile Val His Leu Asn Tyr
    1170                1175                1180

Ile Ile Arg Asp Ala
1185            1190

(2) INFORMATION FOR SEQ ID NO:27:

(i) SEQUENCE CHARACTERISTICS:
        (A) LENGTH: 1880 amino acids
        (B) TYPE: nucleic acid
        (C) STRANDEDNESS: double
        (D) TOPOLOGY: linear (ii) MOLECULE TYPE: DNA (genomic)
```

(ix) FEATURE:
    (A) NAME/KEY: CDS
    (B) LOCATION: 1..1881
    (D) OTHER INFORMATION: tcaBi (xi) SEQUENCE DESCRIPTION: SEQ ID NO:27 (TCABI CODING REGION):

| | | | | | | | | | | | | | | | | |
|---|---|---|---|---|---|---|---|---|---|---|---|---|---|---|---|---|
| ATG | TCT | GAA | TCT | TTA | TTT | ACA | CAA | ACG | TTG | AAA | GAA | GCG | CGC | CGT | GAT | 48 |
| Met | Ser | Glu | Ser | Leu | Phe | Thr | Gln | Thr | Leu | Lys | Glu | Ala | Arg | Arg | Asp | |
| 1 | | | | 5 | | | | | 10 | | | | | 15 | | |
| GCA | TTG | GTT | GCT | CAT | TAT | ATT | GCT | ACT | CAG | GTG | CCC | GCA | GAT | TTA | AAA | 96 |
| Ala | Leu | Val | Ala | His | Tyr | Ile | Ala | Thr | Gln | Val | Pro | Ala | Asp | Leu | Lys | |
| | | | 20 | | | | | 25 | | | | | 30 | | | |
| GAG | AGT | ATC | CAG | ACC | GCG | GAT | GAT | CTG | TAC | GAA | TAT | CTG | TTG | CTG | GAT | 144 |
| Glu | Ser | Ile | Gln | Thr | Ala | Asp | Asp | Leu | Tyr | Glu | Tyr | Leu | Leu | Leu | Asp | |
| | | 35 | | | | | 40 | | | | | 45 | | | | |
| ACC | AAA | ATT | AGC | GAT | CTG | GTT | ACT | ACT | TCA | CCG | CTG | TCC | GAA | GCG | ATT | 192 |
| Thr | Lys | Ile | Ser | Asp | Leu | Val | Thr | Thr | Ser | Pro | Leu | Ser | Glu | Ala | Ile | |
| | 50 | | | | | 55 | | | | | 60 | | | | | |
| GGC | AGT | CTG | CAA | TTG | TTT | ATT | CAT | CGT | GCG | ATA | GAG | GGC | TAT | GAC | GGC | 240 |
| Gly | Ser | Leu | Gln | Leu | Phe | Ile | His | Arg | Ala | Ile | Glu | Gly | Tyr | Asp | Gly | |
| 65 | | | | | 70 | | | | | 75 | | | | | 80 | |
| ACG | CTG | GCA | GAC | TCA | GCA | AAA | CCC | TAT | TTT | GCC | GAT | GAA | CAG | TTT | TTA | 288 |
| Thr | Leu | Ala | Asp | Ser | Ala | Lys | Pro | Tyr | Phe | Ala | Asp | Glu | Gln | Phe | Leu | |
| | | | | 85 | | | | | 90 | | | | | 95 | | |
| TAT | AAC | TGG | GAT | AGT | TTT | AAC | CAC | CGT | TAT | AGC | ACT | TGG | GCT | GGC | AAG | 336 |
| Tyr | Asn | Trp | Asp | Ser | Phe | Asn | His | Arg | Tyr | Ser | Thr | Trp | Ala | Gly | Lys | |
| | | | 100 | | | | | 105 | | | | | 110 | | | |
| GAA | CGG | TTG | AAA | TTC | TAT | GCC | GGG | GAT | TAT | ATT | GAT | CCA | ACA | TTG | CGA | 384 |
| Glu | Arg | Leu | Lys | Phe | Tyr | Ala | Gly | Asp | Tyr | Ile | Asp | Pro | Thr | Leu | Arg | |
| | | 115 | | | | | 120 | | | | | 125 | | | | |
| TTG | AAT | AAG | ACC | GAG | ATA | TTT | ACC | GCA | TTT | GAA | CAA | GGT | ATT | TCT | CAA | 432 |
| Leu | Asn | Lys | Thr | Glu | Ile | Phe | Thr | Ala | Phe | Glu | Gln | Gly | Ile | Ser | Gln | |
| | 130 | | | | | 135 | | | | | 140 | | | | | |
| GGG | AAA | TTA | AAA | AGT | GAA | TTA | GTC | GAA | TCT | AAA | TTA | CGT | GAT | TAT | CTA | 480 |
| Gly | Lys | Leu | Lys | Ser | Glu | Leu | Val | Glu | Ser | Lys | Leu | Arg | Asp | Tyr | Leu | |
| 145 | | | | | 150 | | | | | 155 | | | | | 160 | |
| ATT | AGT | TAT | GAC | ACT | TTA | GCC | ACC | CTT | GAT | TAT | ATT | ACT | GCC | TGC | CAA | 528 |
| Ile | Ser | Tyr | Asp | Thr | Leu | Ala | Thr | Leu | Asp | Tyr | Ile | Thr | Ala | Cys | Gln | |
| | | | | 165 | | | | | 170 | | | | | 175 | | |
| GGC | AAA | GAT | AAT | AAA | ACC | ATC | TTC | TTT | ATT | GGC | CGT | ACA | CAG | AAT | GCA | 576 |
| Gly | Lys | Asp | Asn | Lys | Thr | Ile | Phe | Phe | Ile | Gly | Arg | Thr | Gln | Asn | Ala | |
| | | | 180 | | | | | 185 | | | | | 190 | | | |
| CCC | TAT | GCA | TTT | TAT | TGG | CGA | AAA | TTA | ACT | TTA | GTC | ACT | GAT | GGC | GGT | 624 |
| Pro | Tyr | Ala | Phe | Tyr | Trp | Arg | Lys | Leu | Thr | Leu | Val | Thr | Asp | Gly | Gly | |
| | | 195 | | | | | 200 | | | | | 205 | | | | |
| AAG | TTG | AAA | CCA | GAT | CAA | TGG | TCA | GAG | TGG | CGA | GCA | ATT | AAT | GCC | GGG | 672 |
| Lys | Leu | Lys | Pro | Asp | Gln | Trp | Ser | Glu | Trp | Arg | Ala | Ile | Asn | Ala | Gly | |
| | 210 | | | | | 215 | | | | | 220 | | | | | |
| ATT | AGT | GAG | GCA | TAT | TCA | GGG | CAT | GTC | GAG | CCT | TTC | TGG | GAA | AAT | AAC | 720 |
| Ile | Ser | Glu | Ala | Tyr | Ser | Gly | His | Val | Glu | Pro | Phe | Trp | Glu | Asn | Asn | |
| 225 | | | | | 230 | | | | | 235 | | | | | 240 | |
| AAG | CTG | CAC | ATC | CGT | TGG | TTT | ACT | ATC | TCG | AAA | GAA | GAT | AAA | ATA | GAT | 768 |
| Lys | Leu | His | Ile | Arg | Trp | Phe | Thr | Ile | Ser | Lys | Glu | Asp | Lys | Ile | Asp | |
| | | | | 245 | | | | | 250 | | | | | 255 | | |
| TTT | GTT | TAT | AAA | AAC | ATC | TGG | GTG | ATG | AGT | AGC | GAT | TAT | AGC | TGG | GCA | 816 |
| Phe | Val | Tyr | Lys | Asn | Ile | Trp | Val | Met | Ser | Ser | Asp | Tyr | Ser | Trp | Ala | |
| | | | 260 | | | | | 265 | | | | | 270 | | | |
| TCA | AAG | AAA | AAA | ATC | TTG | GAA | CTT | TCT | TTT | ACT | GAC | TAC | AAT | AGA | GTT | 864 |
| Ser | Lys | Lys | Lys | Ile | Leu | Glu | Leu | Ser | Phe | Thr | Asp | Tyr | Asn | Arg | Val | |
| | | 275 | | | | | 280 | | | | | 285 | | | | |

```
GGA GCA ACA GGA TCA TCA AGC CCG ACT GAA GTA GCT TCA CAA TAT GGT        912
Gly Ala Thr Gly Ser Ser Ser Pro Thr Glu Val Ala Ser Gln Tyr Gly
        290                 295                 300

TCT GAT GCT CAG ATG AAT ATT TCT GAT GAT GGG ACT GTA CTT ATT TTT        960
Ser Asp Ala Gln Met Asn Ile Ser Asp Asp Gly Thr Val Leu Ile Phe
305                 310                 315                 320

CAG AAT GCC GGC GGA GCT ACT CCC AGT ACT GGA GTG ACG TTA TGT TAT       1008
Gln Asn Ala Gly Gly Ala Thr Pro Ser Thr Gly Val Thr Leu Cys Tyr
                325                 330                 335

GAC TCT GGC AAC GTG ATT AAG AAC CTA TCT AGT ACA GGA AGT GCA AAT       1056
Asp Ser Gly Asn Val Ile Lys Asn Leu Ser Ser Thr Gly Ser Ala Asn
        340                 345                 350

TTA TCG TCA AAG GAT TAT GCC ACA ACT AAA TTA CGC ATG TGT CAT GGA       1104
Leu Ser Ser Lys Asp Tyr Ala Thr Thr Lys Leu Arg Met Cys His Gly
                355                 360                 365

CAA AGT TAC AAT GAT AAT AAC TAC TGC AAT TTT ACA CTC TCT ATT AAT       1152
Gln Ser Tyr Asn Asp Asn Asn Tyr Cys Asn Phe Thr Leu Ser Ile Asn
        370                 375                 380

ACA ATA GAA TTC ACC TCC TAC GGC ACA TTC TCA TCA GAT GGA AAA CAA       1200
Thr Ile Glu Phe Thr Ser Tyr Gly Thr Phe Ser Ser Asp Gly Lys Gln
385                 390                 395                 400

TTT ACA CCA CCT TCT GGT TCT GCC ATT GAT TTA CAC CTC CCT AAT TAT       1248
Phe Thr Pro Pro Ser Gly Ser Ala Ile Asp Leu His Leu Pro Asn Tyr
                405                 410                 415

GTA GAT CTC AAC GCG CTA TTA GAT ATT AGC CTC GAT TCA CTA CTT AAT       1296
Val Asp Leu Asn Ala Leu Leu Asp Ile Ser Leu Asp Ser Leu Leu Asn
        420                 425                 430

TAT GAC GTT CAG GGG CAG TTT GGC GGA TCT AAT CCG GTT GAT AAT TTC       1344
Tyr Asp Val Gln Gly Gln Phe Gly Gly Ser Asn Pro Val Asp Asn Phe
                435                 440                 445

AGT GGT CCC TAT GGT ATT TAT CTA TGG GAA ATC TTC TTC CAT ATT CCG       1392
Ser Gly Pro Tyr Gly Ile Tyr Leu Trp Glu Ile Phe Phe His Ile Pro
450                 455                 460

TTC CTT GTT ACG GTC CGT ATG CAA ACC GAA CAA CGT TAC GAA GAC GCG       1440
Phe Leu Val Thr Val Arg Met Gln Thr Glu Gln Arg Tyr Glu Asp Ala
465                 470                 475                 480

GAC ACT TGG TAC AAA TAT ATT TTC CGC AGC GCC GGT TAT CGC GAT GCT       1488
Asp Thr Trp Tyr Lys Tyr Ile Phe Arg Ser Ala Gly Tyr Arg Asp Ala
                485                 490                 495

AAT GGC CAG CTC ATT ATG GAT GGC AGT AAA CCA CGT TAT TGG AAT GTG       1536
Asn Gly Gln Leu Ile Met Asp Gly Ser Lys Pro Arg Tyr Trp Asn Val
        500                 505                 510

ATG CCA TTG CAA CTG GAT ACC GCA TGG GAT ACC ACA CAG CCC GCC ACC       1584
Met Pro Leu Gln Leu Asp Thr Ala Trp Asp Thr Thr Gln Pro Ala Thr
                515                 520                 525

ACT GAT CCA GAT GTG ATC GCT ATG GCG GAC CCG ATG CAT TAC AAG CTG       1632
Thr Asp Pro Asp Val Ile Ala Met Ala Asp Pro Met His Tyr Lys Leu
        530                 535                 540

GCG ATA TTC CTG CAT ACC CTT GAT CTA TTG ATT GCC CGA GGC GAC AGC       1680
Ala Ile Phe Leu His Thr Leu Asp Leu Leu Ile Ala Arg Gly Asp Ser
545                 550                 555                 560

GCT TAC CGT CAA CTT GAA CGC GAT ACT CTA GTC GAA GCC AAA ATG TAC       1728
Ala Tyr Arg Gln Leu Glu Arg Asp Thr Leu Val Glu Ala Lys Met Tyr
                565                 570                 575

TAC ATT CAG GCA CAA CAG CTA CTG GGA CCG CGC CCT GAT ATC CAT ACC       1776
Tyr Ile Gln Ala Gln Gln Leu Leu Gly Pro Arg Pro Asp Ile His Thr
        580                 585                 590

ACC AAT ACT TGG CCA AAT CCC ACC TTG AGT AAA GAA GCT GGC GCT ATT       1824
Thr Asn Thr Trp Pro Asn Pro Thr Leu Ser Lys Glu Ala Gly Ala Ile
```

```
                    595                 600                 605
GCC ACA CCG ACA TTC CTC AGT TCA CCG GAG GTG ATG ACG TTC GCT GCC    1872
Ala Thr Pro Thr Phe Leu Ser Ser Pro Glu Val Met Thr Phe Ala Ala
    610                 615                 620

TGG CTA AGC                                                        1881
Trp Leu Ser
625

(2) INFORMATION FOR SEQ ID NO:28:

(i) SEQUENCE CHARACTERISTICS:
        (A) LENGTH: 627 amino acids
        (B) TYPE: amino acid
        (D) TOPOLOGY: linear (ii) MOLECULE TYPE: protein (xi) SEQUENCE DESCRIPTION: SEQ ID NO:28 (TCABI PROTEIN):

Met Ser Glu Ser Leu Phe Thr Gln Thr Leu Lys Glu Ala Arg Arg Asp
1               5                   10                  15

Ala Leu Val Ala His Tyr Ile Ala Thr Gln Val Pro Ala Asp Leu Lys
            20                  25                  30

Glu Ser Ile Gln Thr Ala Asp Asp Leu Tyr Glu Tyr Leu Leu Leu Asp
        35                  40                  45

Thr Lys Ile Ser Asp Leu Val Thr Thr Ser Pro Leu Ser Glu Ala Ile
    50                  55                  60

Gly Ser Leu Gln Leu Phe Ile His Arg Ala Ile Glu Gly Tyr Asp Gly
65                  70                  75                  80

Thr Leu Ala Asp Ser Ala Lys Pro Tyr Phe Ala Asp Glu Gln Phe Leu
                85                  90                  95

Tyr Asn Trp Asp Ser Phe Asn His Arg Tyr Ser Thr Trp Ala Gly Lys
            100                 105                 110

Glu Arg Leu Lys Phe Tyr Ala Gly Asp Tyr Ile Asp Pro Thr Leu Arg
        115                 120                 125

Leu Asn Lys Thr Glu Ile Phe Thr Ala Phe Glu Gln Gly Ile Ser Gln
    130                 135                 140

Gly Lys Leu Lys Ser Glu Leu Val Glu Ser Lys Leu Arg Asp Tyr Leu
145                 150                 155                 160

Ile Ser Tyr Asp Thr Leu Ala Thr Leu Asp Tyr Ile Thr Ala Cys Gln
                165                 170                 175

Gly Lys Asp Asn Lys Thr Ile Phe Phe Ile Gly Arg Thr Gln Asn Ala
            180                 185                 190

Pro Tyr Ala Phe Tyr Trp Arg Lys Leu Thr Leu Val Thr Asp Gly Gly
        195                 200                 205

Lys Leu Lys Pro Asp Gln Trp Ser Glu Trp Arg Ala Ile Asn Ala Gly
    210                 215                 220

Ile Ser Glu Ala Tyr Ser Gly His Val Glu Pro Phe Trp Glu Asn Asn
225                 230                 235                 240

Lys Leu His Ile Arg Trp Phe Thr Ile Ser Lys Glu Asp Lys Ile Asp
                245                 250                 255

Phe Val Tyr Lys Asn Ile Trp Val Met Ser Ser Asp Tyr Ser Trp Ala
            260                 265                 270

Ser Lys Lys Lys Ile Leu Glu Leu Ser Phe Thr Asp Tyr Asn Arg Val
        275                 280                 285

Gly Ala Thr Gly Ser Ser Pro Thr Glu Val Ala Ser Gln Tyr Gly
    290                 295                 300
```

```
Ser Asp Ala Gln Met Asn Ile Ser Asp Asp Gly Thr Val Leu Ile Phe
305                 310                 315                 320

Gln Asn Ala Gly Gly Ala Thr Pro Ser Thr Gly Val Thr Leu Cys Tyr
                325                 330                 335

Asp Ser Gly Asn Val Ile Lys Asn Leu Ser Ser Thr Gly Ser Ala Asn
            340                 345                 350

Leu Ser Ser Lys Asp Tyr Ala Thr Thr Lys Leu Arg Met Cys His Gly
        355                 360                 365

Gln Ser Tyr Asn Asp Asn Asn Tyr Cys Asn Phe Thr Leu Ser Ile Asn
    370                 375                 380

Thr Ile Glu Phe Thr Ser Tyr Gly Thr Phe Ser Ser Asp Gly Lys Gln
385                 390                 395                 400

Phe Thr Pro Pro Ser Gly Ser Ala Ile Asp Leu His Leu Pro Asn Tyr
                405                 410                 415

Val Asp Leu Asn Ala Leu Leu Asp Ile Ser Leu Asp Ser Leu Leu Asn
            420                 425                 430

Tyr Asp Val Gln Gly Gln Phe Gly Gly Ser Asn Pro Val Asp Asn Phe
        435                 440                 445

Ser Gly Pro Tyr Gly Ile Tyr Leu Trp Glu Ile Phe Phe His Ile Pro
    450                 455                 460

Phe Leu Val Thr Val Arg Met Gln Thr Glu Gln Arg Tyr Glu Asp Ala
465                 470                 475                 480

Asp Thr Trp Tyr Lys Tyr Ile Phe Arg Ser Ala Gly Tyr Arg Asp Ala
                485                 490                 495

Asn Gly Gln Leu Ile Met Asp Gly Ser Lys Pro Arg Tyr Trp Asn Val
            500                 505                 510

Met Pro Leu Gln Leu Asp Thr Ala Trp Asp Thr Thr Gln Pro Ala Thr
        515                 520                 525

Thr Asp Pro Asp Val Ile Ala Met Ala Asp Pro Met His Tyr Lys Leu
    530                 535                 540

Ala Ile Phe Leu His Thr Leu Asp Leu Leu Ile Ala Arg Gly Asp Ser
545                 550                 555                 560

Ala Tyr Arg Gln Leu Glu Arg Asp Thr Leu Val Glu Ala Lys Met Tyr
                565                 570                 575

Tyr Ile Gln Ala Gln Gln Leu Leu Gly Pro Arg Pro Asp Ile His Thr
            580                 585                 590

Thr Asn Thr Trp Pro Asn Pro Thr Leu Ser Lys Glu Ala Gly Ala Ile
        595                 600                 605

Ala Thr Pro Thr Phe Leu Ser Ser Pro Glu Val Met Thr Phe Ala Ala
    610                 615                 620

Trp Leu Ser
625

(2) INFORMATION FOR SEQ ID NO:29:

(i) SEQUENCE CHARACTERISTICS:
        (A) LENGTH: 1689 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..1689
        (D) OTHER INFORMATION: tcaBii
```

(xi) SEQUENCE DESCRIPTION: SEQ ID NO:29 (TCABII CODING: regaion):

| | | | | | | | | | | | | | | | | |
|---|---|---|---|---|---|---|---|---|---|---|---|---|---|---|---|---|
| GCA | GGC | GAT | ACC | GCA | AAT | ATT | GGC | GAC | GGT | GAT | TTC | TTG | CCA | CCG | TAC | 48 |
| Ala | Gly | Asp | Thr | Ala | Asn | Ile | Gly | Asp | Gly | Asp | Phe | Leu | Pro | Pro | Tyr | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| AAC | GAT | GTA | CTA | CTC | GGT | TAC | TGG | GAT | AAA | CTT | GAG | TTA | CGC | CTA | TAC | 96 |
| Asn | Asp | Val | Leu | Leu | Gly | Tyr | Trp | Asp | Lys | Leu | Glu | Leu | Arg | Leu | Tyr | |
| | | | 20 | | | | | 25 | | | | | 30 | | | |

| | | | | | | | | | | | | | | | | |
|---|---|---|---|---|---|---|---|---|---|---|---|---|---|---|---|---|
| AAC | CTG | CGC | CAC | AAT | CTG | AGT | CTG | GAT | GGT | CAA | CCG | CTA | AAT | CTG | CCA | 144 |
| Asn | Leu | Arg | His | Asn | Leu | Ser | Leu | Asp | Gly | Gln | Pro | Leu | Asn | Leu | Pro | |
| | | 35 | | | | | 40 | | | | | 45 | | | | |

| | | | | | | | | | | | | | | | | |
|---|---|---|---|---|---|---|---|---|---|---|---|---|---|---|---|---|
| CTG | TAT | GCC | ACG | CCG | GTA | GAC | CCG | AAA | ACC | CTG | CAA | CGC | CAG | CAA | GCC | 192 |
| Leu | Tyr | Ala | Thr | Pro | Val | Asp | Pro | Lys | Thr | Leu | Gln | Arg | Gln | Gln | Ala | |
| | 50 | | | | | 55 | | | | | 60 | | | | | |

| | | | | | | | | | | | | | | | | |
|---|---|---|---|---|---|---|---|---|---|---|---|---|---|---|---|---|
| GGA | GGG | GAC | GGT | ACA | GGC | AGT | AGT | CCG | GCT | GGT | GGT | CAA | GGC | AGT | GTT | 240 |
| Gly | Gly | Asp | Gly | Thr | Gly | Ser | Ser | Pro | Ala | Gly | Gly | Gln | Gly | Ser | Val | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| CAG | GGC | TGG | CGC | TAT | CCG | TTA | TTG | GTA | GAA | CGC | GCC | CGC | TCT | GCC | GTG | 288 |
| Gln | Gly | Trp | Arg | Tyr | Pro | Leu | Leu | Val | Glu | Arg | Ala | Arg | Ser | Ala | Val | |
| | | | | 85 | | | | | 90 | | | | | 95 | | |

| | | | | | | | | | | | | | | | | |
|---|---|---|---|---|---|---|---|---|---|---|---|---|---|---|---|---|
| AGT | TTG | TTG | ACT | CAG | TTC | GGC | AAC | AGC | TTA | CAA | ACA | ACG | TTA | GAA | CAT | 336 |
| Ser | Leu | Leu | Thr | Gln | Phe | Gly | Asn | Ser | Leu | Gln | Thr | Thr | Leu | Glu | His | |
| | | | | 100 | | | | | 105 | | | | | 110 | | |

| | | | | | | | | | | | | | | | | |
|---|---|---|---|---|---|---|---|---|---|---|---|---|---|---|---|---|
| CAG | GAT | AAT | GAA | AAA | ATG | ACG | ATA | CTG | TTG | CAG | ACT | CAA | CAG | GAA | GCC | 384 |
| Gln | Asp | Asn | Glu | Lys | Met | Thr | Ile | Leu | Leu | Gln | Thr | Gln | Gln | Glu | Ala | |
| | | | 115 | | | | | 120 | | | | | 125 | | | |

| | | | | | | | | | | | | | | | | |
|---|---|---|---|---|---|---|---|---|---|---|---|---|---|---|---|---|
| ATC | CTG | AAA | CAT | CAG | CAC | GAT | ATA | CAA | CAA | AAT | AAT | CTA | AAA | GGA | TTA | 432 |
| Ile | Leu | Lys | His | Gln | His | Asp | Ile | Gln | Gln | Asn | Asn | Leu | Lys | Gly | Leu | |
| | 130 | | | | | 135 | | | | | 140 | | | | | |

| | | | | | | | | | | | | | | | | |
|---|---|---|---|---|---|---|---|---|---|---|---|---|---|---|---|---|
| CAA | CAC | AGC | CTG | ACC | GCA | TTA | CAG | GCT | AGC | CGT | GAT | GGC | GAC | ACA | TTG | 480 |
| Gln | His | Ser | Leu | Thr | Ala | Leu | Gln | Ala | Ser | Arg | Asp | Gly | Asp | Thr | Leu | |
| 145 | | | | 150 | | | | | 155 | | | | | 160 | | |

| | | | | | | | | | | | | | | | | |
|---|---|---|---|---|---|---|---|---|---|---|---|---|---|---|---|---|
| CGG | CAA | AAA | CAT | TAC | AGC | GAC | CTG | ATT | AAC | GGT | GGT | CTA | TCT | GCG | GCA | 528 |
| Arg | Gln | Lys | His | Tyr | Ser | Asp | Leu | Ile | Asn | Gly | Gly | Leu | Ser | Ala | Ala | |
| | | | | 165 | | | | | 170 | | | | | 175 | | |

| | | | | | | | | | | | | | | | | |
|---|---|---|---|---|---|---|---|---|---|---|---|---|---|---|---|---|
| GAA | ATC | GCC | GGT | CTG | ACA | CTA | CGC | AGC | ACC | GCC | ATG | ATT | ACC | AAT | GGC | 576 |
| Glu | Ile | Ala | Gly | Leu | Thr | Leu | Arg | Ser | Thr | Ala | Met | Ile | Thr | Asn | Gly | |
| | | | 180 | | | | | 185 | | | | | 190 | | | |

| | | | | | | | | | | | | | | | | |
|---|---|---|---|---|---|---|---|---|---|---|---|---|---|---|---|---|
| GTT | GCA | ACG | GGA | TTG | CTG | ATT | GCC | GGC | GGA | ATC | GCC | AAC | GCG | TAC | CCT | 624 |
| Val | Ala | Thr | Gly | Leu | Leu | Ile | Ala | Gly | Gly | Ile | Ala | Asn | Ala | Val | Pro | |
| | | 195 | | | | | 200 | | | | | 205 | | | | |

| | | | | | | | | | | | | | | | | |
|---|---|---|---|---|---|---|---|---|---|---|---|---|---|---|---|---|
| AAC | GTC | TTC | GGG | CTG | GCT | AAC | GGT | GGA | TCG | GAA | TGG | GGA | GCG | CCA | TTA | 672 |
| Asn | Val | Phe | Gly | Leu | Ala | Asn | Gly | Gly | Ser | Glu | Trp | Gly | Ala | Pro | Leu | |
| | 210 | | | | | 215 | | | | | 220 | | | | | |

| | | | | | | | | | | | | | | | | |
|---|---|---|---|---|---|---|---|---|---|---|---|---|---|---|---|---|
| ATT | GGC | TCC | GGG | CAA | GCA | ACC | CAA | GTT | GGC | GCC | GGC | ATC | CAG | GAT | CAG | 720 |
| Ile | Gly | Ser | Gly | Gln | Ala | Thr | Gln | Val | Gly | Ala | Gly | Ile | Gln | Asp | Gln | |
| 225 | | | | 230 | | | | | 235 | | | | | 240 | | |

| | | | | | | | | | | | | | | | | |
|---|---|---|---|---|---|---|---|---|---|---|---|---|---|---|---|---|
| AGC | GCG | GGC | ATT | TCA | GAA | GTG | ACA | GCA | GGC | TAT | CAG | CGT | CGT | CAG | GAA | 768 |
| Ser | Ala | Gly | Ile | Ser | Glu | Val | Thr | Ala | Gly | Tyr | Gln | Arg | Arg | Gln | Glu | |
| | | | | 245 | | | | | 250 | | | | | 255 | | |

| | | | | | | | | | | | | | | | | |
|---|---|---|---|---|---|---|---|---|---|---|---|---|---|---|---|---|
| GAA | TGG | GCA | TTG | CAA | CGG | GAT | ATT | GCT | GAT | AAC | GAA | ATA | ACC | CAA | CTG | 816 |
| Glu | Trp | Ala | Leu | Gln | Arg | Asp | Ile | Ala | Asp | Asn | Glu | Ile | Thr | Gln | Leu | |
| | | | | 260 | | | | | 265 | | | | | 270 | | |

| | | | | | | | | | | | | | | | | |
|---|---|---|---|---|---|---|---|---|---|---|---|---|---|---|---|---|
| GAT | GCC | CAG | ATA | CAA | AGC | CTG | CAA | GAG | CAA | ATC | ACG | ATG | GCA | CAA | AAA | 864 |
| Asp | Ala | Gln | Ile | Gln | Ser | Leu | Gln | Glu | Gln | Ile | Thr | Met | Ala | Gln | Lys | |
| | | | 275 | | | | | 280 | | | | | 285 | | | |

| | | | | | | | | | | | | | | | | |
|---|---|---|---|---|---|---|---|---|---|---|---|---|---|---|---|---|
| CAG | ATC | ACG | CTC | TCT | GAA | ACC | GAA | CAA | GCG | AAT | GCC | CAA | GCG | ATT | TAT | 912 |
| Gln | Ile | Thr | Leu | Ser | Glu | Thr | Glu | Gln | Ala | Asn | Ala | Gln | Ala | Ile | Tyr | |
| | | 290 | | | | | 295 | | | | | 300 | | | | |

```
GAC CTG CAA ACC ACT CGT TTT ACC GGG CAG GCA CTG TAT AAC TGG ATG      960
Asp Leu Gln Thr Thr Arg Phe Thr Gly Gln Ala Leu Tyr Asn Trp Met
305                 310                 315                 320

GCC GGT CGT CTC TCC GCG CTC TAT TAC CAA ATG TAT GAT TCC ACT CTG     1008
Ala Gly Arg Leu Ser Ala Leu Tyr Tyr Gln Met Tyr Asp Ser Thr Leu
                325                 330                 335

CCA ATC TGT CTC CAG CCA AAA GCC GCA TTA GTA CAG GAA TTA GGC GAG     1056
Pro Ile Cys Leu Gln Pro Lys Ala Ala Leu Val Gln Glu Leu Gly Glu
            340                 345                 350

AAA GAG AGC GAC AGT CTT TTC CAG GTT CCG GTG TGG AAT GAT CTG TGG     1104
Lys Glu Ser Asp Ser Leu Phe Gln Val Pro Val Trp Asn Asp Leu Trp
        355                 360                 365

CAA GGG CTG TTA GCA GGA GAA GGT TTA AGT TCA GAG CTA CAG AAA CTG     1152
Gln Gly Leu Leu Ala Gly Glu Gly Leu Ser Ser Glu Leu Gln Lys Leu
    370                 375                 380

GAT GCC ATC TGG CTT GCA CGT GGT GGT ATT GGG CTA GAA GCC ATC CGC     1200
Asp Ala Ile Trp Leu Ala Arg Gly Gly Ile Gly Leu Glu Ala Ile Arg
385                 390                 395                 400

ACC GTG TCG CTG GAT ACC CTG TTT GGC ACA GGG ACG TTA AGT GAA AAT     1248
Thr Val Ser Leu Asp Thr Leu Phe Gly Thr Gly Thr Leu Ser Glu Asn
                405                 410                 415

ATC AAT AAA GTG CTT AAC GGG GAA ACG GTA TCT CCA TCC GGT GGC GTC     1296
Ile Asn Lys Val Leu Asn Gly Glu Thr Val Ser Pro Ser Gly Gly Val
            420                 425                 430

ACT CTG GCG CTG ACA GGG GAT ATC TTC CAA GCA ACA CTG GAT TTG AGT     1344
Thr Leu Ala Leu Thr Gly Asp Ile Phe Gln Ala Thr Leu Asp Leu Ser
        435                 440                 445

CAG CTA GGT TTG GAT AAC TCT TAC AAC TTG GGT AAC GAG AAG AAA CGT     1392
Gln Leu Gly Leu Asp Asn Ser Tyr Asn Leu Gly Asn Glu Lys Lys Arg
    450                 455                 460

CGT ATT AAA CGT ATC GCC GTC ACC CTG CCA ACA CTT CTG GGG CCA TAT     1440
Arg Ile Lys Arg Ile Ala Val Thr Leu Pro Thr Leu Leu Gly Pro Tyr
465                 470                 475                 480

CAA GAT CTT GAA GCC ACA CTG GTA ATG GGT GCG GAA ATC GCC GCC TTA     1488
Gln Asp Leu Glu Ala Thr Leu Val Met Gly Ala Glu Ile Ala Ala Leu
                485                 490                 495

TCA CAC GGT GTG AAT GAC GGA GGC CGG TTT GTT ACC GAC TTT AAC GAC     1536
Ser His Gly Val Asn Asp Gly Gly Arg Phe Val Thr Asp Phe Asn Asp
            500                 505                 510

AGC CGT TTT CTG CCT TTT GAA GGT CGA GAT GCA ACA ACC GGC ACA CTG     1584
Ser Arg Phe Leu Pro Phe Glu Gly Arg Asp Ala Thr Thr Gly Thr Leu
        515                 520                 525

GAG CTC AAT ATT TTC CAT GCG GGT AAA GAG GGA ACG CAA CAC GAG TTG     1632
Glu Leu Asn Ile Phe His Ala Gly Lys Glu Gly Thr Gln His Glu Leu
    530                 535                 540

GTC GCG AAT CTG AGT GAC ATC ATT GTG CAT CTG AAT TAC ATC ATT CGA     1680
Val Ala Asn Leu Ser Asp Ile Ile Val His Leu Asn Tyr Ile Ile Arg
545                 550                 555                 560

GAC GCG TAA                                                         1689
Asp Ala *
```

(2) INFORMATION FOR SEQ ID NO:30:

(i) SEQUENCE CHARACTERISTICS:
        (A) LENGTH: 561 amino acids
        (B) TYPE: amino acid
        (D) TOPOLOGY: linear (ii) MOLECULE TYPE: protein (xi) SEQUENCE DESCRIPTION: SEQ ID NO:30 (TCABII PROTEIN):

-continued

```
Ala Gly Asp Thr Ala Asn Ile Gly Asp Gly Asp Phe Leu Pro Pro Tyr
 1               5                  10                  15

Asn Asp Val Leu Leu Gly Tyr Trp Asp Lys Leu Glu Leu Arg Leu Tyr
            20                  25                  30

Asn Leu Arg His Asn Leu Ser Leu Asp Gly Gln Pro Leu Asn Leu Pro
            35                  40                  45

Leu Tyr Ala Thr Pro Val Asp Pro Lys Thr Leu Gln Arg Gln Gln Ala
    50                  55                  60

Gly Gly Asp Gly Thr Gly Ser Ser Pro Ala Gly Gly Gln Gly Ser Val
 65                  70                  75                  80

Gln Gly Trp Arg Tyr Pro Leu Leu Val Glu Arg Ala Arg Ser Ala Val
                85                  90                  95

Ser Leu Leu Thr Gln Phe Gly Asn Ser Leu Gln Thr Thr Leu Glu His
            100                 105                 110

Gln Asp Asn Glu Lys Met Thr Ile Leu Leu Gln Thr Gln Gln Glu Ala
        115                 120                 125

Ile Leu Lys His Gln His Asp Ile Gln Gln Asn Asn Leu Lys Gly Leu
    130                 135                 140

Gln His Ser Leu Thr Ala Leu Gln Ala Ser Arg Asp Gly Asp Thr Leu
145                 150                 155                 160

Arg Gln Lys His Tyr Ser Asp Leu Ile Asn Gly Gly Leu Ser Ala Ala
                165                 170                 175

Glu Ile Ala Gly Leu Thr Leu Arg Ser Thr Ala Met Ile Thr Asn Gly
            180                 185                 190

Val Ala Thr Gly Leu Leu Ile Ala Gly Gly Ile Ala Asn Ala Val Pro
        195                 200                 205

Asn Val Phe Gly Leu Ala Asn Gly Gly Ser Glu Trp Gly Ala Pro Leu
    210                 215                 220

Ile Gly Ser Gly Gln Ala Thr Gln Val Gly Ala Gly Ile Gln Asp Gln
225                 230                 235                 240

Ser Ala Gly Ile Ser Glu Val Thr Ala Gly Tyr Gln Arg Arg Gln Glu
                245                 250                 255

Glu Trp Ala Leu Gln Arg Asp Ile Ala Asp Asn Glu Ile Thr Gln Leu
            260                 265                 270

Asp Ala Gln Ile Gln Ser Leu Gln Glu Gln Ile Thr Met Ala Gln Lys
        275                 280                 285

Gln Ile Thr Leu Ser Glu Thr Glu Gln Ala Asn Ala Gln Ala Ile Tyr
    290                 295                 300

Asp Leu Gln Thr Thr Arg Phe Thr Gly Gln Ala Leu Tyr Asn Trp Met
305                 310                 315                 320

Ala Gly Arg Leu Ser Ala Leu Tyr Tyr Gln Met Tyr Asp Ser Thr Leu
                325                 330                 335

Pro Ile Cys Leu Gln Pro Lys Ala Ala Leu Val Gln Glu Leu Gly Glu
            340                 345                 350

Lys Glu Ser Asp Ser Leu Phe Gln Val Pro Val Trp Asn Asp Leu Trp
        355                 360                 365

Gln Gly Leu Leu Ala Gly Glu Gly Leu Ser Ser Leu Gln Lys Leu
    370                 375                 380

Asp Ala Ile Trp Leu Ala Arg Gly Gly Ile Gly Leu Glu Ala Ile Arg
385                 390                 395                 400

Thr Val Ser Leu Asp Thr Leu Phe Gly Thr Gly Thr Leu Ser Glu Asn
                405                 410                 415

Ile Asn Lys Val Leu Asn Gly Glu Thr Val Ser Pro Ser Gly Gly Val
```

-continued

```
                   420                 425                 430
Thr Leu Ala Leu Thr Gly Asp Ile Phe Gln Ala Thr Leu Asp Leu Ser
                435                 440                 445

Gln Leu Gly Leu Asp Asn Ser Tyr Asn Leu Gly Asn Glu Lys Lys Arg
    450                 455                 460

Arg Ile Lys Arg Ile Ala Val Thr Leu Pro Thr Leu Gly Pro Tyr
465                 470                 475                 480

Gln Asp Leu Glu Ala Thr Leu Val Met Gly Ala Glu Ile Ala Ala Leu
                485                 490                 495

Ser His Gly Val Asn Asp Gly Gly Arg Phe Val Thr Asp Phe Asn Asp
                500                 505                 510

Ser Arg Phe Leu Pro Phe Glu Gly Arg Asp Ala Thr Gly Thr Leu
            515                 520                 525

Glu Leu Asn Ile Phe His Ala Gly Lys Glu Gly Thr Gln His Glu Leu
530                 535                 540

Val Ala Asn Leu Ser Asp Ile Ile Val His Leu Asn Tyr Ile Ile Arg
545                 550                 555                 560

Asp Ala
```

(2) INFORMATION FOR SEQ ID NO:31:

(i) SEQUENCE CHARACTERISTICS:
        (A) LENGTH: 4457 amino acids
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..4458

(xi) SEQUENCE DESCRIPTION: SEQ ID NO:31 (TCAC GENE):

```
ATG CAG GAT TCA CCA GAA GTA TCG ATT ACA ACG CTG TCA CTT CCC AAA      48
Met Gln Asp Ser Pro Glu Val Ser Ile Thr Thr Leu Ser Leu Pro Lys
1               5                   10                  15

GGT GGC GGT GCT ATC AAT GGC ATG GGA GAA GCA CTG AAT GCT GCC GGC      96
Gly Gly Gly Ala Ile Asn Gly Met Gly Glu Ala Leu Asn Ala Ala Gly
            20                  25                  30

CCT GAT GGA ATG GCC TCC CTA TCT CTG CCA TTA CCC CTT TCG ACC GGC     144
Pro Asp Gly Met Ala Ser Leu Ser Leu Pro Leu Pro Leu Ser Thr Gly
        35                  40                  45

AGA GGG ACG GCT CCT GGA TTA TCG CTG ATT TAC AGC AAC AGT GCA GGT     192
Arg Gly Thr Ala Pro Gly Leu Ser Leu Ile Tyr Ser Asn Ser Ala Gly
    50                  55                  60

AAT GGG CCT TTC GGC ATC GGC TGG CAA TGC GGT GTT ATG TCC ATT AGC     240
Asn Gly Pro Phe Gly Ile Gly Trp Gln Cys Gly Val Met Ser Ile Ser
65                  70                  75                  80

CGA CGC ACC CAA CAT GGC ATT CCA CAA TAC GGT AAT GAC GAC ACG TTC     288
Arg Arg Thr Gln His Gly Ile Pro Gln Tyr Gly Asn Asp Asp Thr Phe
                85                  90                  95

CTA TCC CCA CAA GGC GAG GTC ATG AAT ATC GCC CTG AAT GAC CAA GGG     336
Leu Ser Pro Gln Gly Glu Val Met Asn Ile Ala Leu Asn Asp Gln Gly
            100                 105                 110

CAA CCT GAT ATC CGT CAA GAC GTT AAA ACG CTG CAA GGC GTT ACC TTG     384
Gln Pro Asp Ile Arg Gln Asp Val Lys Thr Leu Gln Gly Val Thr Leu
        115                 120                 125

CCA ATT TCC TAT ACC GTG ACC CGC TAT CAA GCC CGC CAG ATC CTG GAT     432
Pro Ile Ser Tyr Thr Val Thr Arg Tyr Gln Ala Arg Gln Ile Leu Asp
```

```
                                                              -continued 130                  135                  140
TTC AGT AAA ATC GAA TAC TGG CAA CCT GCC TCC GGT CAA GAA GGA CGC         480
Phe Ser Lys Ile Glu Tyr Trp Gln Pro Ala Ser Gly Gln Glu Gly Arg
145                 150                 155                 160

GCT TTC TGG CTG ATA TCG ACA CCG GAC GGG CAT CTA CAC ATC TTA GGG         528
Ala Phe Trp Leu Ile Ser Thr Pro Asp Gly His Leu His Ile Leu Gly
                    165                 170                 175

AAA ACC GCG CAG GCT TGT CTG GCA AAT CCG CAA AAT GAC CAA CAA ATC         576
Lys Thr Ala Gln Ala Cys Leu Ala Asn Pro Gln Asn Asp Gln Gln Ile
                180                 185                 190

GCC CAG TGG TTG CTG GAA GAA ACT GTG ACG CCA GCC GGT GAA CAT GTC         624
Ala Gln Trp Leu Leu Glu Glu Thr Val Thr Pro Ala Gly Glu His Val
            195                 200                 205

AGC TAT CAA TAT CGA GCC GAA GAT GAA GCC CAT TGT GAC GAC AAT GAA         672
Ser Tyr Gln Tyr Arg Ala Glu Asp Glu Ala His Cys Asp Asp Asn Glu
        210                 215                 220

AAA ACC GCT CAT CCC AAT GTT ACC GCA CAG CGC TAT CTG GTA CAG GTG         720
Lys Thr Ala His Pro Asn Val Thr Ala Gln Arg Tyr Leu Val Gln Val
225                 230                 235                 240

AAC TAC GGC AAC ATC AAA CCA CAA GCC AGC CTG TTC GTA CTG GAT AAC         768
Asn Tyr Gly Asn Ile Lys Pro Gln Ala Ser Leu Phe Val Leu Asp Asn
                    245                 250                 255

GCA CCT CCC GCA CCG GAA GAG TGG CTG TTT CAT CTG GTC TTT GAC CAC         816
Ala Pro Pro Ala Pro Glu Glu Trp Leu Phe His Leu Val Phe Asp His
                260                 265                 270

GGT GAG CGC GAT ACC TCA CTT CAT ACC GTG CCA ACA TGG GAT GCA GGT         864
Gly Glu Arg Asp Thr Ser Leu His Thr Val Pro Thr Trp Asp Ala Gly
            275                 280                 285

ACA GCG CAA TGG TCT GTA CGC CCG GAT ATC TTC TCT CGC TAT GAA TAT         912
Thr Ala Gln Trp Ser Val Arg Pro Asp Ile Phe Ser Arg Tyr Glu Tyr
        290                 295                 300

GGT TTT GAA GTG CGT ACT CGC CGC TTA TGT CAA CAA GTG CTG ATG TTT         960
Gly Phe Glu Val Arg Thr Arg Arg Leu Cys Gln Gln Val Leu Met Phe
305                 310                 315                 320

CAC CGC ACC GCG CTC ATG GCC GGA GAA GCC AGT ACC AAT GAC GCC CCG        1008
His Arg Thr Ala Leu Met Ala Gly Glu Ala Ser Thr Asn Asp Ala Pro
                    325                 330                 335

GAA CTG GTT GGA CGC TTA ATA CTG GAA TAT GAC AAA AAC GCC AGC GTC        1056
Glu Leu Val Gly Arg Leu Ile Leu Glu Tyr Asp Lys Asn Ala Ser Val
                340                 345                 350

ACC ACG TTG ATT ACC ATC CGT CAA TTA AGC CAT GAA TCG GAC GGG AGG        1104
Thr Thr Leu Ile Thr Ile Arg Gln Leu Ser His Glu Ser Asp Gly Arg
            355                 360                 365

CCA GTC ACC CAG CCA CCA CTA GAA CTA GCC TGG CAA CGG TTT GAT CTG        1152
Pro Val Thr Gln Pro Pro Leu Glu Leu Ala Trp Gln Arg Phe Asp Leu
        370                 375                 380

GAG AAA ATC CCG ACA TGG CAA CGC TTT GAC GCA CTA GAT AAT TTT AAC        1200
Glu Lys Ile Pro Thr Trp Gln Arg Phe Asp Ala Leu Asp Asn Phe Asn
385                 390                 395                 400

TCG CAG CAA CGT TAT CAA CTG GTT GAT CTG CGG GGA GAA GGG TTG CCA        1248
Ser Gln Gln Arg Tyr Gln Leu Val Asp Leu Arg Gly Glu Gly Leu Pro
                    405                 410                 415

GGT ATG CTG TAT CAA GAT CGA GGC GCT TGG TGG TAT AAA GCT CCG CAA        1296
Gly Met Leu Tyr Gln Asp Arg Gly Ala Trp Trp Tyr Lys Ala Pro Gln
                420                 425                 430

CGT CAG GAA GAC GGA GAC AGC AAT GCC GTC ACT TAC GAC AAA ATC GCC        1344
Arg Gln Glu Asp Gly Asp Ser Asn Ala Val Thr Tyr Asp Lys Ile Ala
            435                 440                 445

CCA CTG CCT ACC CTA CCC AAT TTG CAG GAT AAT GCC TCA TTG ATG GAT        1392
```

```
                    Pro Leu Pro Thr Leu Pro Asn Leu Gln Asp Asn Ala Ser Leu Met Asp
                        450                 455                 460

ATC AAC GGA GAC GGC CAA CTG GAT TGG GTT GTT ACC GCC TCC GGT ATT      1440
Ile Asn Gly Asp Gly Gln Leu Asp Trp Val Val Thr Ala Ser Gly Ile
465                 470                 475                 480

CGC GGA TAC CAT AGT CAG CAA CCC GAT GGA AAG TGG ACG CAC TTT ACG      1488
Arg Gly Tyr His Ser Gln Gln Pro Asp Gly Lys Trp Thr His Phe Thr
                        485                 490                 495

CCA ATC AAT GCC TTG CCC GTG GAA TAT TTT CAT CCA AGC ATC CAG TTC      1536
Pro Ile Asn Ala Leu Pro Val Glu Tyr Phe His Pro Ser Ile Gln Phe
                500                 505                 510

GCT GAC CTT ACC GGG GCA GGC TTA TCT GAT TTA GTG TTG ATC GGG CCG      1584
Ala Asp Leu Thr Gly Ala Gly Leu Ser Asp Leu Val Leu Ile Gly Pro
            515                 520                 525

AAA AGC GTG CGT CTA TAT GCC AAC CAG CGA AAC GGC TGG CGT AAA GGA      1632
Lys Ser Val Arg Leu Tyr Ala Asn Gln Arg Asn Gly Trp Arg Lys Gly
        530                 535                 540

GAA GAT GTC CCC CAA TCC ACA GGT ATC ACC CTG CCT GTC ACA GGG ACC      1680
Glu Asp Val Pro Gln Ser Thr Gly Ile Thr Leu Pro Val Thr Gly Thr
545                 550                 555                 560

GAT GCC CGC AAA CTG GTG GCT TTC AGT GAT ATG CTC GGT TCC GGT CAA      1728
Asp Ala Arg Lys Leu Val Ala Phe Ser Asp Met Leu Gly Ser Gly Gln
                565                 570                 575

CAA CAT CTG GTG GAA ATC AAG GGT AAT CGC GTC ACC TGT TGG CCG AAT      1776
Gln His Leu Val Glu Ile Lys Gly Asn Arg Val Thr Cys Trp Pro Asn
                580                 585                 590

CTA GGG CAT GGC CGT TTC GGT CAA CCA CTA ACT CTG TCA GGA TTT AGC      1824
Leu Gly His Gly Arg Phe Gly Gln Pro Leu Thr Leu Ser Gly Phe Ser
            595                 600                 605

CAG CCC GAA AAT AGC TTC AAT CCC GAA CGG CTG TTT CTG GCG GAT ATC      1872
Gln Pro Glu Asn Ser Phe Asn Pro Glu Arg Leu Phe Leu Ala Asp Ile
        610                 615                 620

GAC GGC TCC GGC ACC ACC GAC CTT ATC TAT GCG CAA TCC GGC TCT TTG      1920
Asp Gly Ser Gly Thr Thr Asp Leu Ile Tyr Ala Gln Ser Gly Ser Leu
625                 630                 635                 640

CTC ATT TAT CTC AAC CAA AGT GGT AAT CAG TTT GAT GCC CCG TTG ACA      1968
Leu Ile Tyr Leu Asn Gln Ser Gly Asn Gln Phe Asp Ala Pro Leu Thr
                645                 650                 655

TTA GCG TTG CCA GAA GGC GTA CAA TTT GAC AAC ACT TGC CAA CTT CAA      2016
Leu Ala Leu Pro Glu Gly Val Gln Phe Asp Asn Thr Cys Gln Leu Gln
                660                 665                 670

GTC GCC GAT ATT CAG GGA TTA GGG ATA GCC AGC TTG ATT CTG ACT GTG      2064
Val Ala Asp Ile Gln Gly Leu Gly Ile Ala Ser Leu Ile Leu Thr Val
            675                 680                 685

CCA CAT ATC GCG CCA CAT CAC TGG CGT TGT GAC CTG TCA CTG ACC AAA      2112
Pro His Ile Ala Pro His His Trp Arg Cys Asp Leu Ser Leu Thr Lys
        690                 695                 700

CCC TGG TTG TTG AAT GTA ATG AAC AAT AAC CGG GGC GCA CAT CAC ACG      2160
Pro Trp Leu Leu Asn Val Met Asn Asn Asn Arg Gly Ala His His Thr
705                 710                 715                 720

CTA CAT TAT CGT AGT TCC GCG CAA TTC TGG TTG GAT GAA AAA TTA CAG      2208
Leu His Tyr Arg Ser Ser Ala Gln Phe Trp Leu Asp Glu Lys Leu Gln
                725                 730                 735

CTC ACC AAA GCA GGC AAA TCT CCG GCT TGT TAT CTG CCG TTT CCA ATG      2256
Leu Thr Lys Ala Gly Lys Ser Pro Ala Cys Tyr Leu Pro Phe Pro Met
                740                 745                 750

CAT TTG CTA TGG TAT ACC GAA ATT CAG GAT GAA ATC AGC GGC AAC CGG      2304
His Leu Leu Trp Tyr Thr Glu Ile Gln Asp Glu Ile Ser Gly Asn Arg
            755                 760                 765
```

```
CTC ACC AGT GAA GTC AAC TAC AGC CAC GGC GTC TGG GAT GGT AAA GAG       2352
Leu Thr Ser Glu Val Asn Tyr Ser His Gly Val Trp Asp Gly Lys Glu
    770             775                 780

CGG GAA TTC AGA GGA TTT GGC TGC ATC AAA CAG ACA GAT ACC ACA ACG       2400
Arg Glu Phe Arg Gly Phe Gly Cys Ile Lys Gln Thr Asp Thr Thr Thr
785             790                 795                 800

TTT TCT CAC GGC ACC GCC CCC GAA CAG GCG GCA CCG TCG CTG AGT ATT       2448
Phe Ser His Gly Thr Ala Pro Glu Gln Ala Ala Pro Ser Leu Ser Ile
                805                 810                 815

AGC TGG TTT GCC ACC GGC ATG GAT GAA GTA GAC AGC CAA TTA GCT ACG       2496
Ser Trp Phe Ala Thr Gly Met Asp Glu Val Asp Ser Gln Leu Ala Thr
            820                 825                 830

GAA TAT TGG CAG GCA GAC ACG CAA GCT TAT AGC GGA TTT GAA ACC CGT       2544
Glu Tyr Trp Gln Ala Asp Thr Gln Ala Tyr Ser Gly Phe Glu Thr Arg
        835                 840                 845

TAT ACC GTC TGG GAT CAC ACC AAC CAG ACA GAC CAA GCA TTT ACC CCC       2592
Tyr Thr Val Trp Asp His Thr Asn Gln Thr Asp Gln Ala Phe Thr Pro
    850                 855                 860

AAT GAG ACA CAA CGT AAC TGG CTG ACG CGA GCG CTT AAA GGC CAA CTG       2640
Asn Glu Thr Gln Arg Asn Trp Leu Thr Arg Ala Leu Lys Gly Gln Leu
865             870                 875                 880

CTA CGC ACT GAG CTC TAC GGT CTG GAC GGA ACA GAT AAG CAA ACA GTG       2688
Leu Arg Thr Glu Leu Tyr Gly Leu Asp Gly Thr Asp Lys Gln Thr Val
                885                 890                 895

CCT TAT ACC GTC AGT GAA TCG CGC TAT CAG GTA CGC TCT ATT CCC GTA       2736
Pro Tyr Thr Val Ser Glu Ser Arg Tyr Gln Val Arg Ser Ile Pro Val
            900                 905                 910

AAT AAA GAA ACT GAA TTA TCT GCC TGG GTG ACT GCT ATT GAA AAT CGC       2784
Asn Lys Glu Thr Glu Leu Ser Ala Trp Val Thr Ala Ile Glu Asn Arg
        915                 920                 925

AGC TAC CAC TAT GAA CGT ATC ATC ACT GAC CCA CAG TTC AGC CAG AGT       2832
Ser Tyr His Tyr Glu Arg Ile Ile Thr Asp Pro Gln Phe Ser Gln Ser
    930                 935                 940

ATC AAG TTG CAA CAC GAT ATC TTT GGT CAA TCA CTG CAA AGT GTC GAT       2880
Ile Lys Leu Gln His Asp Ile Phe Gly Gln Ser Leu Gln Ser Val Asp
945             950                 955                 960

ATT GCC TGG CCG CGC CGC GAA AAA CCA GCA GTG AAT CCC TAC CCG CCT       2928
Ile Ala Trp Pro Arg Arg Glu Lys Pro Ala Val Asn Pro Tyr Pro Pro
                965                 970                 975

ACC CTG CCG GAA ACG CTA TTT GAC AGC AGC TAT GAT GAT CAA CAA CAA       2976
Thr Leu Pro Glu Thr Leu Phe Asp Ser Ser Tyr Asp Asp Gln Gln Gln
            980                 985                 990

CTA TTA CGT CTG GTG AGA CAA AAA AAT AGC TGG CAT CAC CTG ACT GAT       3024
Leu Leu Arg Leu Val Arg Gln Lys Asn Ser Trp His His Leu Thr Asp
        995                 1000                1005

GGG GAA AAC TGG CGA TTA GGT TTA CCG AAT GCA CAA CGC CGT GAT GTT       3072
Gly Glu Asn Trp Arg Leu Gly Leu Pro Asn Ala Gln Arg Arg Asp Val
    1010                1015                1020

TAT ACT TAT GAC CGG AGC AAA ATT CCA ACC GAA GGG ATT TCC CTT GAA       3120
Tyr Thr Tyr Asp Arg Ser Lys Ile Pro Thr Glu Gly Ile Ser Leu Glu
1025                1030                1035                1040

ATC TTG CTG AAA GAT GAT GGC CTG CTA GCA GAT GAA AAA GCG GCC GTT       3168
Ile Leu Leu Lys Asp Asp Gly Leu Leu Ala Asp Glu Lys Ala Ala Val
                1045                1050                1055

TAT CTG GGA CAA CAA CAG ACG TTT TAC ACC GCC GGT CAA GCG GAA GTC       3216
Tyr Leu Gly Gln Gln Gln Thr Phe Tyr Thr Ala Gly Gln Ala Glu Val
            1060                1065                1070

ACT CTA GAA AAA CCC ACG TTA CAA GCA CTG GTC GCG TTC CAA GAA ACC       3264
Thr Leu Glu Lys Pro Thr Leu Gln Ala Leu Val Ala Phe Gln Glu Thr
        1075                1080                1085
```

-continued

```
GCC ATG ATG GAC GAT ACC TCA TTA CAG GCG TAT GAA GGC GTG ATT GAA         3312
Ala Met Met Asp Asp Thr Ser Leu Gln Ala Tyr Glu Gly Val Ile Glu
    1090                1095                1100

GAG CAA GAG TTG AAT ACC GCG CTG ACA CAG GCC GGT TAT CAG CAA GTC         3360
Glu Gln Glu Leu Asn Thr Ala Leu Thr Gln Ala Gly Tyr Gln Gln Val
1105                1110                1115                1120

GCG CGG TTG TTT AAT ACC AGA TCA GAA AGC CCG GTA TGG GCG GCA CGG         3408
Ala Arg Leu Phe Asn Thr Arg Ser Glu Ser Pro Val Trp Ala Ala Arg
                1125                1130                1135

CAA GGT TAT ACC GAT TAC GGT GAC GCC GCA CAG TTC TGG CGG CCT CAG         3456
Gln Gly Tyr Thr Asp Tyr Gly Asp Ala Ala Gln Phe Trp Arg Pro Gln
            1140                1145                1150

GCT CAG CGT AAC TCG TTG CTG ACA GGG AAA ACC ACA CTG ACC TGG GAT         3504
Ala Gln Arg Asn Ser Leu Leu Thr Gly Lys Thr Thr Leu Thr Trp Asp
        1155                1160                1165

ACC CAT CAT TGT GTA ATA ATA CAG ACT CAA GAT GCC GCT GGA TTA ACG         3552
Thr His His Cys Val Ile Ile Gln Thr Gln Asp Ala Ala Gly Leu Thr
    1170                1175                1180

ACG CAA GCC CAT TAC GAT TAT CGT TTC CTT ACA CCG GTA CAA CTG ACA         3600
Thr Gln Ala His Tyr Asp Tyr Arg Phe Leu Thr Pro Val Gln Leu Thr
1185                1190                1195                1200

GAT ATT AAT GAT AAT CAA CAT ATT GTG ACT CTG GAC GCG CTA GGT CGC         3648
Asp Ile Asn Asp Asn Gln His Ile Val Thr Leu Asp Ala Leu Gly Arg
                1205                1210                1215

GTA ACC ACC AGC CGG TTC TGG GGC ACA GAG GCA GGA CAA GCC GCA GGC         3696
Val Thr Thr Ser Arg Phe Trp Gly Thr Glu Ala Gly Gln Ala Ala Gly
            1220                1225                1230

TAT TCC AAC CAG CCC TTC ACA CCA CCG GAC TCC GTA GAT AAA GCG CTG         3744
Tyr Ser Asn Gln Pro Phe Thr Pro Pro Asp Ser Val Asp Lys Ala Leu
        1235                1240                1245

GCA TTA ACC GGC GCA CTC CCT GTT GCC CAA TGT TTA GTC TAT GCC GTT         3792
Ala Leu Thr Gly Ala Leu Pro Val Ala Gln Cys Leu Val Tyr Ala Val
    1250                1255                1260

GAT AGC TGG ATG CCG TCG TTA TCT TTG TCT CAG CTT TCT CAG TCA CAA         3840
Asp Ser Trp Met Pro Ser Leu Ser Leu Ser Gln Leu Ser Gln Ser Gln
1265                1270                1275                1280

GAA GAG GCA GAA GCG CTA TGG GCG CAA CTG CGT GCC GCT CAT ATG ATT         3888
Glu Glu Ala Glu Ala Leu Trp Ala Gln Leu Arg Ala Ala His Met Ile
                1285                1290                1295

ACC GAA GAT GGG AAA GTG TGT GCG TTA AGC GGG AAA CGA GGA ACA AGC         3936
Thr Glu Asp Gly Lys Val Cys Ala Leu Ser Gly Lys Arg Gly Thr Ser
            1300                1305                1310

CAT CAG AAC CTG ACG ATT CAA CTT ATT TCG CTA TTG GCA AGT ATT CCC         3984
His Gln Asn Leu Thr Ile Gln Leu Ile Ser Leu Leu Ala Ser Ile Pro
        1315                1320                1325

CGT TTA CCG CCA CAT GTA CTG GGG ATC ACC ACT GAT CGC TAT GAT AGC         4032
Arg Leu Pro Pro His Val Leu Gly Ile Thr Thr Asp Arg Tyr Asp Ser
    1330                1335                1340

GAT CCG CAA CAG CAG CAC CAA CAG ACG GTG AGC TTT AGT GAC GGT TTT         4080
Asp Pro Gln Gln Gln His Gln Gln Thr Val Ser Phe Ser Asp Gly Phe
1345                1350                1355                1360

GGC CGG TTA CTC CAG AGT TCA GCT CGT CAT GAG TCA GGT GAT GCC TGG         4128
Gly Arg Leu Leu Gln Ser Ser Ala Arg His Glu Ser Gly Asp Ala Trp
                1365                1370                1375

CAA CGT AAA GAG GAT GGC GGG CTG GTC GTG GAT GCA AAT GGC GTT CTG         4176
Gln Arg Lys Glu Asp Gly Gly Leu Val Val Asp Ala Asn Gly Val Leu
            1380                1385                1390

GTC AGT GCC CCT ACA GAC ACC CGA TGG GCC GTT TCC GGT CGC ACA GAA         4224
Val Ser Ala Pro Thr Asp Thr Arg Trp Ala Val Ser Gly Arg Thr Glu
```

-continued

```
         1395                1400                1405
TAT GAC GAC AAA GGC CAA CCT GTG CGT ACT TAT CAA CCC TAT TTT CTA     4272
Tyr Asp Asp Lys Gly Gln Pro Val Arg Thr Tyr Gln Pro Tyr Phe Leu
         1410                1415                1420

AAT GAC TGG CGT TAC GTT AGT GAT GAC AGC GCA CGA GAT GAC CTG TTT     4320
Asn Asp Trp Arg Tyr Val Ser Asp Asp Ser Ala Arg Asp Asp Leu Phe
1425                1430                1435                1440

GCC GAT ACC CAC CTT TAT GAT CCA TTG GGA CGG GAA TAC AAA GTC ATC     4368
Ala Asp Thr His Leu Tyr Asp Pro Leu Gly Arg Glu Tyr Lys Val Ile
             1445                1450                1455

ACT GCT AAG AAA TAT TTG CGA GAA AAG CTG TAC ACC CCG TGG TTT ATT     4416
Thr Ala Lys Lys Tyr Leu Arg Glu Lys Leu Tyr Thr Pro Trp Phe Ile
         1460                1465                1470

GTC AGT GAG GAT GAA AAC GAT ACA GCA TCA AGA ACC CCA TAG             4458
Val Ser Glu Asp Glu Asn Asp Thr Ala Ser Arg Thr Pro
         1475                1480                1485
```

(2) INFORMATION FOR SEQ ID NO:32:

(i) SEQUENCE CHARACTERISTICS:
    (A) LENGTH: 1484 amino acids
    (B) TYPE: amino acid
    (D) TOPOLOGY: linear (ii) MOLECULE TYPE: protein (xi) SEQUENCE DESCRIPTION: SEQ ID NO:32 (TCAC PROTEIN):

```
Met Gln Asp Ser Pro Glu Val Ser Ile Thr Thr Leu Ser Leu Pro Lys
 1               5                  10                  15

Gly Gly Gly Ala Ile Asn Gly Met Gly Glu Ala Leu Asn Ala Ala Gly
            20                  25                  30

Pro Asp Gly Met Ala Ser Leu Ser Leu Pro Leu Pro Leu Ser Thr Gly
        35                  40                  45

Arg Gly Thr Ala Pro Gly Leu Ser Leu Ile Tyr Ser Asn Ser Ala Gly
    50                  55                  60

Asn Gly Pro Phe Gly Ile Gly Trp Gln Cys Gly Val Met Ser Ile Ser
65                  70                  75                  80

Arg Arg Thr Gln His Gly Ile Pro Gln Tyr Gly Asn Asp Thr Phe
            85                  90                  95

Leu Ser Pro Gln Gly Glu Val Met Asn Ile Ala Leu Asn Asp Gln Gly
            100                 105                 110

Gln Pro Asp Ile Arg Gln Asp Val Lys Thr Leu Gln Gly Val Thr Leu
        115                 120                 125

Pro Ile Ser Tyr Thr Val Thr Arg Tyr Gln Ala Arg Gln Ile Leu Asp
    130                 135                 140

Phe Ser Lys Ile Glu Tyr Trp Gln Pro Ala Ser Gly Gln Glu Gly Arg
145                 150                 155                 160

Ala Phe Trp Leu Ile Ser Thr Pro Asp Gly His Leu His Ile Leu Gly
            165                 170                 175

Lys Thr Ala Gln Ala Cys Leu Ala Asn Pro Gln Asn Asp Gln Gln Ile
            180                 185                 190

Ala Gln Trp Leu Leu Glu Glu Thr Val Thr Pro Ala Gly Glu His Val
        195                 200                 205

Ser Tyr Gln Tyr Arg Ala Glu Asp Glu Ala His Cys Asp Asp Asn Glu
    210                 215                 220

Lys Thr Ala His Pro Asn Val Thr Ala Gln Arg Tyr Leu Val Gln Val
225                 230                 235                 240
```

```
Asn Tyr Gly Asn Ile Lys Pro Gln Ala Ser Leu Phe Val Leu Asp Asn
                245                 250                 255

Ala Pro Pro Ala Pro Glu Glu Trp Leu Phe His Leu Val Phe Asp His
            260                 265                 270

Gly Glu Arg Asp Thr Ser Leu His Thr Val Pro Thr Trp Asp Ala Gly
        275                 280                 285

Thr Ala Gln Trp Ser Val Arg Pro Asp Ile Phe Ser Arg Tyr Glu Tyr
    290                 295                 300

Gly Phe Glu Val Arg Thr Arg Leu Cys Gln Gln Val Leu Met Phe
305                 310                 315                 320

His Arg Thr Ala Leu Met Ala Gly Glu Ala Ser Thr Asn Asp Ala Pro
                325                 330                 335

Glu Leu Val Gly Arg Leu Ile Leu Glu Tyr Asp Lys Asn Ala Ser Val
            340                 345                 350

Thr Thr Leu Ile Thr Ile Arg Gln Leu Ser His Glu Ser Asp Gly Arg
        355                 360                 365

Pro Val Thr Gln Pro Pro Leu Glu Leu Ala Trp Gln Arg Phe Asp Leu
    370                 375                 380

Glu Lys Ile Pro Thr Trp Gln Arg Phe Asp Ala Leu Asp Asn Phe Asn
385                 390                 395                 400

Ser Gln Gln Arg Tyr Gln Leu Val Asp Leu Arg Gly Glu Gly Leu Pro
                405                 410                 415

Gly Met Leu Tyr Gln Asp Arg Gly Ala Trp Trp Tyr Lys Ala Pro Gln
            420                 425                 430

Arg Gln Glu Asp Gly Asp Ser Asn Ala Val Thr Tyr Asp Lys Ile Ala
        435                 440                 445

Pro Leu Pro Thr Leu Pro Asn Leu Gln Asp Asn Ala Ser Leu Met Asp
    450                 455                 460

Ile Asn Gly Asp Gly Gln Leu Asp Trp Val Val Thr Ala Ser Gly Ile
465                 470                 475                 480

Arg Gly Tyr His Ser Gln Gln Pro Asp Gly Lys Trp Thr His Phe Thr
                485                 490                 495

Pro Ile Asn Ala Leu Pro Val Glu Tyr Phe His Pro Ser Ile Gln Phe
            500                 505                 510

Ala Asp Leu Thr Gly Ala Gly Leu Ser Asp Leu Val Leu Ile Gly Pro
        515                 520                 525

Lys Ser Val Arg Leu Tyr Ala Asn Gln Arg Asn Gly Trp Arg Lys Gly
    530                 535                 540

Glu Asp Val Pro Gln Ser Thr Gly Ile Thr Leu Pro Val Thr Gly Thr
545                 550                 555                 560

Asp Ala Arg Lys Leu Val Ala Phe Ser Asp Met Leu Gly Ser Gly Gln
                565                 570                 575

Gln His Leu Val Glu Ile Lys Gly Asn Arg Val Thr Cys Trp Pro Asn
            580                 585                 590

Leu Gly His Gly Arg Phe Gly Gln Pro Leu Thr Leu Ser Gly Phe Ser
        595                 600                 605

Gln Pro Glu Asn Ser Phe Asn Pro Glu Arg Leu Phe Leu Ala Asp Ile
    610                 615                 620

Asp Gly Ser Gly Thr Thr Asp Leu Ile Tyr Ala Gln Ser Gly Ser Leu
625                 630                 635                 640

Leu Ile Tyr Leu Asn Gln Ser Gly Asn Gln Phe Asp Ala Pro Leu Thr
                645                 650                 655

Leu Ala Leu Pro Glu Gly Val Gln Phe Asp Asn Thr Cys Gln Leu Gln
```

-continued

```
            660                 665                 670
Val Ala Asp Ile Gln Gly Leu Gly Ile Ala Ser Leu Ile Leu Thr Val
        675                 680                 685
Pro His Ile Ala Pro His His Trp Arg Cys Asp Leu Ser Leu Thr Lys
        690                 695                 700
Pro Trp Leu Leu Asn Val Met Asn Asn Asn Arg Gly Ala His His Thr
705                 710                 715                 720
Leu His Tyr Arg Ser Ser Ala Gln Phe Trp Leu Asp Glu Lys Leu Gln
                725                 730                 735
Leu Thr Lys Ala Gly Lys Ser Pro Ala Cys Tyr Leu Pro Phe Pro Met
            740                 745                 750
His Leu Leu Trp Tyr Thr Glu Ile Gln Asp Glu Ile Ser Gly Asn Arg
            755                 760                 765
Leu Thr Ser Glu Val Asn Tyr Ser His Gly Val Trp Asp Gly Lys Glu
        770                 775                 780
Arg Glu Phe Arg Gly Phe Gly Cys Ile Lys Gln Thr Asp Thr Thr Thr
785                 790                 795                 800
Phe Ser His Gly Thr Ala Pro Glu Gln Ala Ala Pro Ser Leu Ser Ile
                805                 810                 815
Ser Trp Phe Ala Thr Gly Met Asp Glu Val Asp Ser Gln Leu Ala Thr
            820                 825                 830
Glu Tyr Trp Gln Ala Asp Thr Gln Ala Tyr Ser Gly Phe Glu Thr Arg
        835                 840                 845
Tyr Thr Val Trp Asp His Thr Asn Gln Thr Asp Gln Ala Phe Thr Pro
        850                 855                 860
Asn Glu Thr Gln Arg Asn Trp Leu Thr Arg Ala Leu Lys Gly Gln Leu
865                 870                 875                 880
Leu Arg Thr Glu Leu Tyr Gly Leu Asp Gly Thr Asp Lys Gln Thr Val
                885                 890                 895
Pro Tyr Thr Val Ser Glu Ser Arg Tyr Gln Val Arg Ser Ile Pro Val
            900                 905                 910
Asn Lys Glu Thr Glu Leu Ser Ala Trp Val Thr Ala Ile Glu Asn Arg
            915                 920                 925
Ser Tyr His Tyr Glu Arg Ile Ile Thr Asp Pro Gln Phe Ser Gln Ser
        930                 935                 940
Ile Lys Leu Gln His Asp Ile Phe Gly Gln Ser Leu Gln Ser Val Asp
945                 950                 955                 960
Ile Ala Trp Pro Arg Arg Glu Lys Pro Ala Val Asn Pro Tyr Pro Pro
                965                 970                 975
Thr Leu Pro Glu Thr Leu Phe Asp Ser Ser Tyr Asp Asp Gln Gln Gln
            980                 985                 990
Leu Leu Arg Leu Val Arg Gln Lys Asn Ser Trp His His Leu Thr Asp
            995                 1000                1005
Gly Glu Asn Trp Arg Leu Gly Leu Pro Asn Ala Gln Arg Arg Asp Val
        1010                1015                1020
Tyr Thr Tyr Asp Arg Ser Lys Ile Pro Thr Glu Gly Ile Ser Leu Glu
1025                1030                1035                1040
Ile Leu Leu Lys Asp Asp Gly Leu Leu Ala Asp Glu Lys Ala Ala Val
                1045                1050                1055
Tyr Leu Gly Gln Gln Gln Thr Phe Tyr Thr Ala Gly Gln Ala Glu Val
            1060                1065                1070
Thr Leu Glu Lys Pro Thr Leu Gln Ala Leu Val Ala Phe Gln Glu Thr
            1075                1080                1085
```

-continued

Ala Met Met Asp Asp Thr Ser Leu Gln Ala Tyr Glu Gly Val Ile Glu
    1090            1095                1100

Glu Gln Glu Leu Asn Thr Ala Leu Thr Gln Ala Gly Tyr Gln Gln Val
1105            1110            1115                1120

Ala Arg Leu Phe Asn Thr Arg Ser Glu Ser Pro Val Trp Ala Ala Arg
            1125            1130            1135

Gln Gly Tyr Thr Asp Tyr Gly Asp Ala Ala Gln Phe Trp Arg Pro Gln
        1140            1145            1150

Ala Gln Arg Asn Ser Leu Leu Thr Gly Lys Thr Thr Leu Thr Trp Asp
            1155            1160            1165

Thr His His Cys Val Ile Ile Gln Thr Gln Asp Ala Ala Gly Leu Thr
    1170            1175            1180

Thr Gln Ala His Tyr Asp Tyr Arg Phe Leu Thr Pro Val Gln Leu Thr
1185            1190            1195                1200

Asp Ile Asn Asp Asn Gln His Ile Val Thr Leu Asp Ala Leu Gly Arg
                1205            1210            1215

Val Thr Thr Ser Arg Phe Trp Gly Thr Glu Ala Gly Gln Ala Ala Gly
            1220            1225            1230

Tyr Ser Asn Gln Pro Phe Thr Pro Pro Asp Ser Val Asp Lys Ala Leu
        1235            1240            1245

Ala Leu Thr Gly Ala Leu Pro Val Ala Gln Cys Leu Val Tyr Ala Val
    1250            1255            1260

Asp Ser Trp Met Pro Ser Leu Ser Leu Ser Gln Leu Ser Gln Ser Gln
1265            1270            1275                1280

Glu Glu Ala Glu Ala Leu Trp Ala Gln Leu Arg Ala Ala His Met Ile
            1285            1290            1295

Thr Glu Asp Gly Lys Val Cys Ala Leu Ser Gly Lys Arg Gly Thr Ser
        1300            1305            1310

His Gln Asn Leu Thr Ile Gln Leu Ile Ser Leu Leu Ala Ser Ile Pro
        1315            1320            1325

Arg Leu Pro Pro His Val Leu Gly Ile Thr Thr Asp Arg Tyr Asp Ser
    1330            1335            1340

Asp Pro Gln Gln Gln His Gln Gln Thr Val Ser Phe Ser Asp Gly Phe
1345            1350            1355                1360

Gly Arg Leu Leu Gln Ser Ser Ala Arg His Glu Ser Gly Asp Ala Trp
            1365            1370            1375

Gln Arg Lys Glu Asp Gly Gly Leu Val Val Asp Ala Asn Gly Val Leu
        1380            1385            1390

Val Ser Ala Pro Thr Asp Thr Arg Trp Ala Val Ser Gly Arg Thr Glu
    1395            1400            1405

Tyr Asp Asp Lys Gly Gln Pro Val Arg Thr Tyr Gln Pro Tyr Phe Leu
    1410            1415            1420

Asn Asp Trp Arg Tyr Val Ser Asp Ser Ala Arg Asp Asp Leu Phe
1425            1430            1435            1440

Ala Asp Thr His Leu Tyr Asp Pro Leu Gly Arg Glu Tyr Lys Val Ile
            1445            1450            1455

Thr Ala Lys Lys Tyr Leu Arg Glu Lys Leu Tyr Thr Pro Trp Phe Ile
        1460            1465            1470

Val Ser Glu Asp Glu Asn Asp Thr Ala Ser Arg Thr Pro
    1475            1480            1485

(2) INFORMATION FOR SEQ ID NO:33:

(i) SEQUENCE CHARACTERISTICS:
    (A) LENGTH: 3287 amino acids
    (B) TYPE: nucleic acid
    (C) STRANDEDNESS: double
    (D) TOPOLOGY: linear (ii) MOLECULE TYPE: DNA (genomic)

(xi) SEQUENCE DESCRIPTION: SEQ ID NO:33 (TCAA GENE):

```
ATG GTG ACT GTT ATG CAA AAT AAA ATA TCA TTT TTA TCA GGT ACA TCC        48
Met Val Thr Val Met Gln Asn Lys Ile Ser Phe Leu Ser Gly Thr Ser
1               5                   10                  15

GAA CAG CCC CTG CTT GAC GCC GGT TAT CAA AAC GTA TTT GAT ATC GCA        96
Glu Gln Pro Leu Leu Asp Ala Gly Tyr Gln Asn Val Phe Asp Ile Ala
                20                  25                  30

TCA ATC AGC CGG GCT ACT TTC GTT CAA TCC GTT CCC ACC CTG CCC GTT        144
Ser Ile Ser Arg Ala Thr Phe Val Gln Ser Val Pro Thr Leu Pro Val
            35                  40                  45

AAA GAG GCT CAT ACC GTC TAT CGT CAG GCG CGG CAA CGT GCG GAA AAT        192
Lys Glu Ala His Thr Val Tyr Arg Gln Ala Arg Gln Arg Ala Glu Asn
        50                  55                  60

CTG AAA TCC CTC TAC CGA GCC TGG CAA TTG CGT CAG GAG CCG GTT ATT        240
Leu Lys Ser Leu Tyr Arg Ala Trp Gln Leu Arg Gln Glu Pro Val Ile
65              70                  75                  80

AAA GGG CTG GCT AAA CTT AAC CTA CAA TCC AAC GTT TCT GTG CTT CAA        288
Lys Gly Leu Ala Lys Leu Asn Leu Gln Ser Asn Val Ser Val Leu Gln
                85                  90                  95

GAT GCT TTG GTA GAG AAT ATT GGC GGT GAT GGG GAT TTC AGC GAT TTA        336
Asp Ala Leu Val Glu Asn Ile Gly Gly Asp Gly Asp Phe Ser Asp Leu
                100                 105                 110

ATG AAC CGT GCC AGT CAA TAT GCT GAC GCT GCC TCT ATT CAA TCC CTA        384
Met Asn Arg Ala Ser Gln Tyr Ala Asp Ala Ala Ser Ile Gln Ser Leu
            115                 120                 125

TTT TCA CCG GGC CGT TAT GCT TCC GCA CTC TAC AGA GTT GCT AAA GAT        432
Phe Ser Pro Gly Arg Tyr Ala Ser Ala Leu Tyr Arg Val Ala Lys Asp
        130                 135                 140

CTG CAT AAA TCA GAT TCC AGT TTG CAT ATT GAT AAT CGC CGC GCT GAT        480
Leu His Lys Ser Asp Ser Ser Leu His Ile Asp Asn Arg Arg Ala Asp
145                 150                 155                 160

CTG AAG GAT CTG ATA TTA AGC GAA ACG ACG ATG AAT AAA GAG GTC ACT        528
Leu Lys Asp Leu Ile Leu Ser Glu Thr Thr Met Asn Lys Glu Val Thr
                165                 170                 175

TCC CTT GAT ATC TTG TTG GAT GTG CTA CAA AAA GGC GGT AAA GAT ATT        576
Ser Leu Asp Ile Leu Leu Asp Val Leu Gln Lys Gly Gly Lys Asp Ile
                180                 185                 190

ACT GAG CTG TCC GGC GCA TTC TTC CCA ATG ACG TTA CCT TAT GAC GAT        624
Thr Glu Leu Ser Gly Ala Phe Phe Pro Met Thr Leu Pro Tyr Asp Asp
            195                 200                 205

CAT CTG TCG CAA ATC GAT TCC GCT TTA TCG GCA CAA GCC AGA ACG CTG        672
His Leu Ser Gln Ile Asp Ser Ala Leu Ser Ala Gln Ala Arg Thr Leu
        210                 215                 220

AAC GGT GTG TGG AAT ACT TTG ACA GAT ACC ACG GCA CAA GCG GTT TCA        720
Asn Gly Val Trp Asn Thr Leu Thr Asp Thr Thr Ala Gln Ala Val Ser
225                 230                 235                 240

GAA CAA ACC AGT AAT ACG AAT ACA CGC AAA CTG TTC GCT GCC CAA GAT        768
Glu Gln Thr Ser Asn Thr Asn Thr Arg Lys Leu Phe Ala Ala Gln Asp
                245                 250                 255

GGT AAT CAA GAT ACA TTT TTT TCC GGA AAC ACT TTT TAT TTC AAA GCG        816
Gly Asn Gln Asp Thr Phe Phe Ser Gly Asn Thr Phe Tyr Phe Lys Ala
                260                 265                 270

GTG GGA TTC AGC GGG CAA CCT ATG GTT TAC CTG TCA CAG TAC ACC AGC        864
Val Gly Phe Ser Gly Gln Pro Met Val Tyr Leu Ser Gln Tyr Thr Ser
```

-continued

| | | | | | | | | | | | | | | | |
|---|---|---|---|---|---|---|---|---|---|---|---|---|---|---|---|
| Val | Gly | Phe | Ser | Gly | Gln | Pro | Met | Val | Tyr | Leu | Ser | Gln | Tyr | Thr | Ser |
| | | 275 | | | | 280 | | | | 285 | | | | | |

```
GGG AAC GGC ATT GTC GGC GCA CAA TTG ATT GCA GGT AAT CCA GAC CAA        912
Gly Asn Gly Ile Val Gly Ala Gln Leu Ile Ala Gly Asn Pro Asp Gln
    290             295             300

GCC GCC GCC GCA ATA GTC GCA CCG TTG AAA CTC ACT TGG TCA ATG GCA        960
Ala Ala Ala Ala Ile Val Ala Pro Leu Lys Leu Thr Trp Ser Met Ala
305             310             315             320

AAA CAG TGT TAC TAC CTC GTC GCT CCC GAT GGT ACA ACG ATG GGA GAC       1008
Lys Gln Cys Tyr Tyr Leu Val Ala Pro Asp Gly Thr Thr Met Gly Asp
            325             330             335

GGT AAT GTT CTG ACC GGC TGT TTC TTA AGA GGC AAC AGC CCA ACT AAC       1056
Gly Asn Val Leu Thr Gly Cys Phe Leu Arg Gly Asn Ser Pro Thr Asn
        340             345             350

CCG GAT AAA GAC GGT ATT TTT GCT CAG GTA GCC AAC AAA TCA GGC AGT       1104
Pro Asp Lys Asp Gly Ile Phe Ala Gln Val Ala Asn Lys Ser Gly Ser
    355             360             365

ACT CAG CCT TTG CCA AGC TTC CAT CTG CCG GTC ACA CTG GAA CAC AGC       1152
Thr Gln Pro Leu Pro Ser Phe His Leu Pro Val Thr Leu Glu His Ser
370             375             380

GAG AAT AAA GAT CAG TAC TAT CTG AAA ACA GAG CAG GGT TAT ATC ACG       1200
Glu Asn Lys Asp Gln Tyr Tyr Leu Lys Thr Glu Gln Gly Tyr Ile Thr
385             390             395             400

GTA GAT AGT TCC GGA CAG TCA AAT TGG AAA AAC GCG CTG GTT ATC AAT       1248
Val Asp Ser Ser Gly Gln Ser Asn Trp Lys Asn Ala Leu Val Ile Asn
            405             410             415

GGG ACA AAA GAC AAG GGG CTG TTA TTA ACC TTT TGC AGC GAT AGC TCA       1296
Gly Thr Lys Asp Lys Gly Leu Leu Leu Thr Phe Cys Ser Asp Ser Ser
        420             425             430

GGC ACT CCG ACA AAC CCT GAT GAT GTG ATT CCT CCC GCT ATC AAT GAT       1344
Gly Thr Pro Thr Asn Pro Asp Asp Val Ile Pro Pro Ala Ile Asn Asp
    435             440             445

ATT CCA TCG CCG CCA GCC CGC GAA ACA CTG TCA CTG ACG CCG GTC AGT       1392
Ile Pro Ser Pro Pro Ala Arg Glu Thr Leu Ser Leu Thr Pro Val Ser
450             455             460

TAT CAA TTG ATG ACC AAT CCG GCA CCG ACA GAA GAT GAT ATT ACC AAC       1440
Tyr Gln Leu Met Thr Asn Pro Ala Pro Thr Glu Asp Asp Ile Thr Asn
465             470             475             480

CAT TAT GGT TTT AAC GGC GCT AGC TTA CGG GCT TCT CCA TTG TCA ACC       1488
His Tyr Gly Phe Asn Gly Ala Ser Leu Arg Ala Ser Pro Leu Ser Thr
            485             490             495

AGC GAG TTG ACC AGC AAA CTG AAT TCT ATC GAT ACT TTC TGT GAG AAG       1536
Ser Glu Leu Thr Ser Lys Leu Asn Ser Ile Asp Thr Phe Cys Glu Lys
        500             505             510

ACC CGG TTA AGC TTC AAT CAG TTA ATG GAT TTG ACC GCT CAG CAA TCT       1584
Thr Arg Leu Ser Phe Asn Gln Leu Met Asp Leu Thr Ala Gln Gln Ser
    515             520             525

TAC AGT CAA AGC AGC ATT GAT GCG AAA GCA GCC AGC CGC TAT GTT CGT       1632
Tyr Ser Gln Ser Ser Ile Asp Ala Lys Ala Ala Ser Arg Tyr Val Arg
530             535             540

TTT GGG GAA ACC ACC CCA ACC CGC GTC AAT GTC TAC GGT GCC GCT TAT       1680
Phe Gly Glu Thr Thr Pro Thr Arg Val Asn Val Tyr Gly Ala Ala Tyr
545             550             555             560

CTG AAC AGC ACA CTG GCA GAC GCG GCT GAT GGT CAA TAT CTG TGG ATT       1728
Leu Asn Ser Thr Leu Ala Asp Ala Ala Asp Gly Gln Tyr Leu Trp Ile
            565             570             575

CAG ACT GAT GGC AAG AGC CTA AAT TTC ACT GAC GAT ACG GTA GTC GCC       1776
Gln Thr Asp Gly Lys Ser Leu Asn Phe Thr Asp Asp Thr Val Val Ala
        580             585             590
```

```
TTA GCC GGT CGC GCT GAA AAG CTG GTA CGT TTA TCA TCC CAG ACC GGG      1824
Leu Ala Gly Arg Ala Glu Lys Leu Val Arg Leu Ser Ser Gln Thr Gly
        595                 600                 605

CTA TCA TTT GAA GAA TTG GAC TGG CTG ATT GCC AAT GCC AGT CGT AGT      1872
Leu Ser Phe Glu Glu Leu Asp Trp Leu Ile Ala Asn Ala Ser Arg Ser
610                 615                 620

GTG CCG GAC CAC CAC GAC AAA ATT GTG CTG GAT AAG CCG GTC CTT GAA      1920
Val Pro Asp His His Asp Lys Ile Val Leu Asp Lys Pro Val Leu Glu
625                 630                 635                 640

GCA CTG GCA GAG TAT GTC AGC CTA AAA CAG CGC TAT GGG CTT GAT GCC      1968
Ala Leu Ala Glu Tyr Val Ser Leu Lys Gln Arg Tyr Gly Leu Asp Ala
                645                 650                 655

AAT ACC TTT GCG ACC TTC ATT AGT GCA GTA AAT CCT TAT ACG CCA GAT      2016
Asn Thr Phe Ala Thr Phe Ile Ser Ala Val Asn Pro Tyr Thr Pro Asp
            660                 665                 670

CAG ACA CCC AGT TTC TAT GAA ACC GCT TTC CGC TCT GCC GAC GGT AAT      2064
Gln Thr Pro Ser Phe Tyr Glu Thr Ala Phe Arg Ser Ala Asp Gly Asn
        675                 680                 685

CAT GTC ATT GCG CTA GGT ACA GAG GTG AAA TAT GCA GAA AAT GAG CAG      2112
His Val Ile Ala Leu Gly Thr Glu Val Lys Tyr Ala Glu Asn Glu Gln
690                 695                 700

GAT GAG TTA GCC GCC ATA TGC TGC AAA GCA TTG GGT GTC ACC AGT GAT      2160
Asp Glu Leu Ala Ala Ile Cys Cys Lys Ala Leu Gly Val Thr Ser Asp
705                 710                 715                 720

GAA CTG CTC CGT ATT GGT CGC TAT TGC TTC GGT AAT GCA GGC AGT TTT      2208
Glu Leu Leu Arg Ile Gly Arg Tyr Cys Phe Gly Asn Ala Gly Ser Phe
                725                 730                 735

ACC TTG GAT GAA TAT ACC GCC AGT CAG TTG TAT CGC TTC GGC GCC ATT      2256
Thr Leu Asp Glu Tyr Thr Ala Ser Gln Leu Tyr Arg Phe Gly Ala Ile
            740                 745                 750

CCC CGT TTG TTT GGG CTG ACA TTT GCC CAA GCC GAA ATT TTA TGG CGT      2304
Pro Arg Leu Phe Gly Leu Thr Phe Ala Gln Ala Glu Ile Leu Trp Arg
        755                 760                 765

CTG ATG GAA GGC GGA AAA GAT ATC TTA TTG CAA CAG TTA GGT CAG GCA      2352
Leu Met Glu Gly Gly Lys Asp Ile Leu Leu Gln Gln Leu Gly Gln Ala
770                 775                 780

AAA TCC CTG CAA CCA CTG GCT ATT TTA CGC CGT ACC GAG CAG GTG CTG      2400
Lys Ser Leu Gln Pro Leu Ala Ile Leu Arg Arg Thr Glu Gln Val Leu
785                 790                 795                 800

GAT TGG ATG TCG TCC GTA AAT CTA AGT CTG ACT TAT CTG CAA GGG ATG      2448
Asp Trp Met Ser Ser Val Asn Leu Ser Leu Thr Tyr Leu Gln Gly Met
                805                 810                 815

GTA AGT ACG CAA TGG AGC GGT ACC GCC ACC GCT GAG ATG TTC AAT TTC      2496
Val Ser Thr Gln Trp Ser Gly Thr Ala Thr Ala Glu Met Phe Asn Phe
            820                 825                 830

TTG GAA AAC GTT TGT GAC AGC GTG AAT AGT CAA GCT GCC ACT AAA GAA      2544
Leu Glu Asn Val Cys Asp Ser Val Asn Ser Gln Ala Ala Thr Lys Glu
        835                 840                 845

ACA ATG GAT TCG GCG TTA CAG CAG AAA GTG CTG CGG GCG CTA AGC GCC      2592
Thr Met Asp Ser Ala Leu Gln Gln Lys Val Leu Arg Ala Leu Ser Ala
850                 855                 860

GGT TTC GGC ATT AAG AGC AAT GTG ATG GGT ATC GTC ACC TTC TGG CTG      2640
Gly Phe Gly Ile Lys Ser Asn Val Met Gly Ile Val Thr Phe Trp Leu
865                 870                 875                 880

GAG AAA ATC ACA ATC GGT AGT GAT AAT CCT TTT ACA TTG GCA AAC TAC      2688
Glu Lys Ile Thr Ile Gly Ser Asp Asn Pro Phe Thr Leu Ala Asn Tyr
                885                 890                 895

TGG CAT GAT ATT CAA ACC CTG TTT AGC CAT GAC AAT GCC ACG TTA GAG      2736
Trp His Asp Ile Gln Thr Leu Phe Ser His Asp Asn Ala Thr Leu Glu
            900                 905                 910
```

```
TCC TTA CAA ACC GAC ACT TCT CTG GTA ATT GCT ACT CAG CAA CTT AGC    2784
Ser Leu Gln Thr Asp Thr Ser Leu Val Ile Ala Thr Gln Gln Leu Ser
        915                 920                 925

CAG CTA GTG TTA ATT GTG AAA TGG CTG AGC CTG ACC GAG CAG GAT CTG    2832
Gln Leu Val Leu Ile Val Lys Trp Leu Ser Leu Thr Glu Gln Asp Leu
    930                 935                 940

CAA TTA CTG ACA ACC TAT CCC GAA CGT TTA ATC AAC GGC ATC ACG AAT    2880
Gln Leu Leu Thr Thr Tyr Pro Glu Arg Leu Ile Asn Gly Ile Thr Asn
945                 950                 955                 960

GTT CCT GTA CCC AAT CCG GAG CTA TTA CTC ACG CTA TCA CGT TTT AAG    2928
Val Pro Val Pro Asn Pro Glu Leu Leu Leu Thr Leu Ser Arg Phe Lys
                965                 970                 975

CAG TGG GAA ACT CAA GTC ACC GTT TCC CGT GAT GAA GCG ATG CGC TGT    2976
Gln Trp Glu Thr Gln Val Thr Val Ser Arg Asp Glu Ala Met Arg Cys
            980                 985                 990

TTC GAT CAA TTA AAT GCC AAT GAT ATG ACG ACT GAA AAT GCA GGT TCA    3024
Phe Asp Gln Leu Asn Ala Asn Asp Met Thr Thr Glu Asn Ala Gly Ser
        995                 1000                1005

CTG ATC GCC ACA TTG TAT GAG ATG GAT AAA GGT ACG GGA GCG CAA GTT    3072
Leu Ile Ala Thr Leu Tyr Glu Met Asp Lys Gly Thr Gly Ala Gln Val
    1010                1015                1020

AAT ACC TTG CTA TTA GGT GAA AAT AAC TGG CCG AAA AGT TTT ACC TCT    3120
Asn Thr Leu Leu Leu Gly Glu Asn Asn Trp Pro Lys Ser Phe Thr Ser
1025                1030                1035                1040

CTC TGG CAA CTT CTG ACC TGG TTA CGC GTC GGG CAA AGA CTG AAT GTC    3168
Leu Trp Gln Leu Leu Thr Trp Leu Arg Val Gly Gln Arg Leu Asn Val
                1045                1050                1055

GGT AGT ACC ACT CTG GGC AAT CTG TTG TCC ATG ATG CAA GCA GAC CCT    3216
Gly Ser Thr Thr Leu Gly Asn Leu Leu Ser Met Met Gln Ala Asp Pro
            1060                1065                1070

GCT GCC GAG AGT AGC GCT TTA TTG GCA TCA GTA GCC CAA AAC TTA AGT    3264
Ala Ala Glu Ser Ser Ala Leu Leu Ala Ser Val Ala Gln Asn Leu Ser
        1075                1080                1085

GCC GCA ATC AGC AAT CGT CAG TAA                                    3288
Ala Ala Ile Ser Asn Arg Gln
    1090                1095
```

(2) INFORMATION FOR SEQ ID NO:34:

(i) SEQUENCE CHARACTERISTICS:
        (A) LENGTH: 1095 amino acids
        (B) TYPE: amino acids
        (C) TOPOLOGY: linear (ii) MOLECULE TYPE: protein (xi) SEQUENCE DESCRIPTION: SEQ ID NO:34 (TCAA PROTEIN):

FeaturesFrom ToDescription

254267SEQ ID NO:15

254492TcaAii peptide

```
Met Val Thr Val Met Gln Asn Lys Ile Ser Phe Leu Ser Gly Thr Ser
1               5                   10                  15

Glu Gln Pro Leu Leu Asp Ala Gly Tyr Gln Asn Val Phe Asp Ile Ala
            20                  25                  30

Ser Ile Ser Arg Ala Thr Phe Val Gln Ser Val Pro Thr Leu Pro Val
        35                  40                  45

Lys Glu Ala His Thr Val Tyr Arg Gln Ala Arg Gln Arg Ala Glu Asn
    50                  55                  60
```

-continued

```
Leu Lys Ser Leu Tyr Arg Ala Trp Gln Leu Arg Gln Glu Pro Val Ile
 65                  70                  75                  80

Lys Gly Leu Ala Lys Leu Asn Leu Gln Ser Asn Val Ser Val Leu Gln
                 85                  90                  95

Asp Ala Leu Val Glu Asn Ile Gly Gly Asp Gly Asp Phe Ser Asp Leu
            100                 105                 110

Met Asn Arg Ala Ser Gln Tyr Ala Asp Ala Ser Ile Gln Ser Leu
        115                 120                 125

Phe Ser Pro Gly Arg Tyr Ala Ser Ala Leu Tyr Arg Val Ala Lys Asp
    130                 135                 140

Leu His Lys Ser Asp Ser Ser Leu His Ile Asp Asn Arg Arg Ala Asp
145                 150                 155                 160

Leu Lys Asp Leu Ile Leu Ser Glu Thr Thr Met Asn Lys Glu Val Thr
                165                 170                 175

Ser Leu Asp Ile Leu Leu Asp Val Leu Gln Lys Gly Gly Lys Asp Ile
            180                 185                 190

Thr Glu Leu Ser Gly Ala Phe Phe Pro Met Thr Leu Pro Tyr Asp Asp
        195                 200                 205

His Leu Ser Gln Ile Asp Ser Ala Leu Ser Ala Gln Ala Arg Thr Leu
    210                 215                 220

Asn Gly Val Trp Asn Thr Leu Thr Asp Thr Thr Ala Gln Ala Val Ser
225                 230                 235                 240

Glu Gln Thr Ser Asn Thr Asn Thr Arg Lys Leu Phe Ala Ala Gln Asp
                245                 250                 255

Gly Asn Gln Asp Thr Phe Phe Ser Gly Asn Thr Phe Tyr Phe Lys Ala
            260                 265                 270

Val Gly Phe Ser Gly Gln Pro Met Val Tyr Leu Ser Gln Tyr Thr Ser
        275                 280                 285

Gly Asn Gly Ile Val Gly Ala Gln Leu Ile Ala Gly Asn Pro Asp Gln
    290                 295                 300

Ala Ala Ala Ile Val Ala Pro Leu Lys Leu Thr Trp Ser Met Ala
305                 310                 315                 320

Lys Gln Cys Tyr Tyr Leu Val Ala Pro Asp Gly Thr Thr Met Gly Asp
                325                 330                 335

Gly Asn Val Leu Thr Gly Cys Phe Leu Arg Gly Asn Ser Pro Thr Asn
            340                 345                 350

Pro Asp Lys Asp Gly Ile Phe Ala Gln Val Ala Asn Lys Ser Gly Ser
        355                 360                 365

Thr Gln Pro Leu Pro Ser Phe His Leu Pro Val Thr Leu Glu His Ser
    370                 375                 380

Glu Asn Lys Asp Gln Tyr Tyr Leu Lys Thr Glu Gln Gly Tyr Ile Thr
385                 390                 395                 400

Val Asp Ser Ser Gly Gln Ser Asn Trp Lys Asn Ala Leu Val Ile Asn
                405                 410                 415

Gly Thr Lys Asp Lys Gly Leu Leu Thr Phe Cys Ser Asp Ser Ser
            420                 425                 430

Gly Thr Pro Thr Asn Pro Asp Asp Val Ile Pro Ala Ile Asn Asp
        435                 440                 445

Ile Pro Ser Pro Pro Ala Arg Glu Thr Leu Ser Leu Thr Pro Val Ser
    450                 455                 460

Tyr Gln Leu Met Thr Asn Pro Ala Pro Thr Glu Asp Asp Ile Thr Asn
465                 470                 475                 480

His Tyr Gly Phe Asn Gly Ala Ser Leu Arg Ala Ser Pro Leu Ser Thr
```

-continued

```
                            485                 490      W4 /  495
Ser Glu Leu Thr Ser Lys Leu Asn Ser Ile Asp Thr Phe Cys Glu Lys
                500                 505                 510

Thr Arg Leu Ser Phe Asn Gln Leu Met Asp Leu Thr Ala Gln Gln Ser
            515                 520                 525

Tyr Ser Gln Ser Ser Ile Asp Ala Lys Ala Ala Ser Arg Tyr Val Arg
        530                 535                 540

Phe Gly Glu Thr Thr Pro Thr Arg Val Asn Val Tyr Gly Ala Ala Tyr
545                 550                 555                 560

Leu Asn Ser Thr Leu Ala Asp Ala Ala Asp Gly Gln Tyr Leu Trp Ile
                565                 570                 575

Gln Thr Asp Gly Lys Ser Leu Asn Phe Thr Asp Asp Thr Val Val Ala
            580                 585                 590

Leu Ala Gly Arg Ala Glu Lys Leu Val Arg Leu Ser Ser Gln Thr Gly
        595                 600                 605

Leu Ser Phe Glu Glu Leu Asp Trp Leu Ile Ala Asn Ala Ser Arg Ser
    610                 615                 620

Val Pro Asp His His Asp Lys Ile Val Leu Asp Lys Pro Val Leu Glu
625                 630                 635                 640

Ala Leu Ala Glu Tyr Val Ser Leu Lys Gln Arg Tyr Gly Leu Asp Ala
                645                 650                 655

Asn Thr Phe Ala Thr Phe Ile Ser Ala Val Asn Pro Tyr Thr Pro Asp
            660                 665                 670

Gln Thr Pro Ser Phe Tyr Glu Thr Ala Phe Arg Ser Ala Asp Gly Asn
        675                 680                 685

His Val Ile Ala Leu Gly Thr Glu Val Lys Tyr Ala Glu Asn Glu Gln
    690                 695                 700

Asp Glu Leu Ala Ala Ile Cys Cys Lys Ala Leu Gly Val Thr Ser Asp
705                 710                 715                 720

Glu Leu Leu Arg Ile Gly Arg Tyr Cys Phe Gly Asn Ala Gly Ser Phe
                725                 730                 735

Thr Leu Asp Glu Tyr Thr Ala Ser Gln Leu Tyr Arg Phe Gly Ala Ile
            740                 745                 750

Pro Arg Leu Phe Gly Leu Thr Phe Ala Gln Ala Glu Ile Leu Trp Arg
        755                 760                 765

Leu Met Glu Gly Gly Lys Asp Ile Leu Leu Gln Gln Leu Gly Gln Ala
    770                 775                 780

Lys Ser Leu Gln Pro Leu Ala Ile Leu Arg Arg Thr Glu Gln Val Leu
785                 790                 795                 800

Asp Trp Met Ser Ser Val Asn Leu Ser Leu Thr Tyr Leu Gln Gly Met
                805                 810                 815

Val Ser Thr Gln Trp Ser Gly Thr Ala Thr Ala Glu Met Phe Asn Phe
            820                 825                 830

Leu Glu Asn Val Cys Asp Ser Val Asn Ser Gln Ala Ala Thr Lys Glu
        835                 840                 845

Thr Met Asp Ser Ala Leu Gln Gln Lys Val Leu Arg Ala Leu Ser Ala
    850                 855                 860

Gly Phe Gly Ile Lys Ser Asn Val Met Gly Ile Val Thr Phe Trp Leu
865                 870                 875                 880

Glu Lys Ile Thr Ile Gly Ser Asp Asn Pro Phe Thr Leu Ala Asn Tyr
                885                 890                 895

Trp His Asp Ile Gln Thr Leu Phe Ser His Asp Asn Ala Thr Leu Glu
            900                 905                 910
```

-continued

```
Ser Leu Gln Thr Asp Thr Ser Leu Val Ile Ala Thr Gln Gln Leu Ser
            915                 920                 925

Gln Leu Val Leu Ile Val Lys Trp Leu Ser Leu Thr Glu Gln Asp Leu
            930                 935                 940

Gln Leu Leu Thr Thr Tyr Pro Glu Arg Leu Ile Asn Gly Ile Thr Asn
945                 950                 955                 960

Val Pro Val Pro Asn Pro Glu Leu Leu Leu Thr Leu Ser Arg Phe Lys
            965                 970                 975

Gln Trp Glu Thr Gln Val Thr Val Ser Arg Asp Glu Ala Met Arg Cys
            980                 985                 990

Phe Asp Gln Leu Asn Ala Asn Asp Met Thr Thr Glu Asn Ala Gly Ser
            995                1000                1005

Leu Ile Ala Thr Leu Tyr Glu Met Asp Lys Gly Thr Gly Ala Gln Val
            1010                1015                1020

Asn Thr Leu Leu Leu Gly Glu Asn Asn Trp Pro Lys Ser Phe Thr Ser
1025                1030                1035                1040

Leu Trp Gln Leu Leu Thr Trp Leu Arg Val Gly Gln Arg Leu Asn Val
            1045                1050                1055

Gly Ser Thr Thr Leu Gly Asn Leu Leu Ser Met Met Gln Ala Asp Pro
            1060                1065                1070

Ala Ala Glu Ser Ser Ala Leu Leu Ala Ser Val Ala Gln Asn Leu Ser
            1075                1080                1085

Ala Ala Ile Ser Asn Arg Gln
            1090        1095
```

(2) INFORMATION FOR SEQ ID NO:35:

(i) SEQUENCE CHARACTERISTICS:
        (A) LENGTH: 602 amino acids
        (B) TYPE: amino acid
        (C) TOPOLOGY: linear (ii) MOLECULE TYPE: protein (xi) SEQUENCE DESCRIPTION: SEQ ID NO:35 (TCAAIII PROTEIN):

```
Pro Leu Ser Thr Ser Glu Leu Thr Ser Lys Leu Asn Ser Ile Asp Thr
1                   5                  10                  15

Phe Cys Glu Lys Thr Arg Leu Ser Phe Asn Gln Leu Met Asp Leu Thr
            20                  25                  30

Ala Gln Gln Ser Tyr Ser Gln Ser Ser Ile Asp Ala Lys Ala Ala Ser
            35                  40                  45

Arg Tyr Val Arg Phe Gly Glu Thr Thr Pro Thr Arg Val Asn Val Tyr
    50                  55                  60

Gly Ala Ala Tyr Leu Asn Ser Thr Leu Ala Asp Ala Asp Gly Gln
65                  70                  75                  80

Tyr Leu Trp Ile Gln Thr Asp Gly Lys Ser Leu Asn Phe Thr Asp Asp
            85                  90                  95

Thr Val Val Ala Leu Ala Gly Arg Ala Glu Lys Leu Val Arg Leu Ser
            100                 105                 110

Ser Gln Thr Gly Leu Ser Phe Glu Glu Leu Asp Trp Leu Ile Ala Asn
            115                 120                 125

Ala Ser Arg Ser Val Pro Asp His His Asp Lys Ile Val Leu Asp Lys
            130                 135                 140

Pro Val Leu Glu Ala Leu Ala Glu Tyr Val Ser Leu Lys Gln Arg Tyr
145                 150                 155                 160

Gly Leu Asp Ala Asn Thr Phe Ala Thr Phe Ile Ser Ala Val Asn Pro
```

-continued

```
                165                 170                 175
Tyr Thr Pro Asp Gln Thr Pro Ser Phe Tyr Glu Thr Ala Phe Arg Ser
            180                 185                 190
Ala Asp Gly Asn His Val Ile Ala Leu Gly Thr Glu Val Lys Tyr Ala
            195                 200                 205
Glu Asn Glu Gln Asp Glu Leu Ala Ala Ile Cys Cys Lys Ala Leu Gly
            210                 215                 220
Val Thr Ser Asp Glu Leu Leu Arg Ile Gly Arg Tyr Cys Phe Gly Asn
225                 230                 235                 240
Ala Gly Arg Phe Thr Leu Asp Glu Tyr Thr Ala Ser Gln Leu Tyr Arg
            245                 250                 255
Phe Gly Ala Ile Pro Arg Leu Phe Gly Leu Thr Phe Ala Gln Ala Glu
            260                 265                 270
Ile Leu Trp Arg Leu Met Glu Gly Gly Lys Asp Ile Leu Leu Gln Gln
            275                 280                 285
Xxx Gly Gln Ala Lys Ser Leu Gln Pro Leu Ala Ile Leu Arg Arg Thr
            290                 295                 300
Glu Gln Val Leu Asp Trp Met Ser Pro Val Asn Leu Ser Leu Thr Tyr
305                 310                 315                 320
Leu Gln Gly Met Val Ser Thr Gln Trp Ser Gly Thr Ala Thr Ala Glu
            325                 330                 335
Met Phe Asn Phe Leu Glu Asn Val Cys Asp Ser Val Asn Ser Gln Ala
            340                 345                 350
Xxx Thr Lys Glu Thr Met Asp Ser Ala Leu Gln Lys Val Leu Arg
            355                 360                 365
Ala Leu Ser Ala Gly Phe Gly Ile Lys Ser Asn Val Met Gly Ile Val
            370                 375                 380
Thr Phe Trp Leu Glu Lys Ile Thr Ile Gly Arg Asp Asn Pro Phe Thr
385                 390                 395                 400
Leu Ala Asn Tyr Trp His Asp Ile Gln Thr Leu Phe Ser His Asp Asn
            405                 410                 415
Ala Thr Leu Glu Ser Leu Gln Thr Asp Thr Ser Leu Val Ile Ala Thr
            420                 425                 430
Gln Gln Leu Ser Gln Leu Val Leu Ile Val Lys Trp Val Ser Leu Thr
            435                 440                 445
Glu Gln Asp Leu Gln Leu Leu Thr Thr Tyr Pro Glu Arg Leu Ile Asn
            450                 455                 460
Gly Ile Thr Asn Val Pro Val Pro Asn Pro Glu Leu Leu Leu Thr Leu
465                 470                 475                 480
Ser Arg Phe Lys Gln Trp Glu Thr Gln Val Thr Val Ser Arg Asp Glu
            485                 490                 495
Ala Met Arg Cys Phe Asp Gln Leu Asn Ala Asn Asp Met Thr Thr Glu
            500                 505                 510
Asn Ala Gly Ser Leu Ile Ala Thr Leu Tyr Glu Met Asp Lys Gly Thr
            515                 520                 525
Gly Ala Gln Val Asn Thr Leu Leu Gly Glu Asn Asn Trp Pro Lys
            530                 535                 540
Ser Phe Thr Ser Leu Trp Gln Leu Leu Thr Trp Leu Arg Val Gly Gln
545                 550                 555                 560
Arg Leu Asn Val Gly Ser Thr Thr Leu Gly Asn Leu Leu Ser Met Met
            565                 570                 575
Gln Ala Asp Pro Ala Ala Glu Ser Ser Ala Leu Leu Ala Ser Val Ala
            580                 585                 590
```

Gln Asn Leu Ser Ala Ala Ile Ser Asn Arg Gln
    595                    600

(2) INFORMATION FOR SEQ ID NO:36:

(i) SEQUENCE CHARACTERISTICS:
        (A) LENGTH: 2556 amino acids
        (B) TYPE: nucleic acid
        (C) TOPOLOGY: linear (ii) MOLECULE TYPE: DNA (genomic)

(xi) SEQUENCE DESCRIPTION: SEQ ID NO:36 (TCDA INTERNAL:
        fragment):

| | | | | | |
|---|---|---|---|---|---|
| GAATTCGGCT | TGCGTTTAAT | ATTGATGATG | TCTCGCTCTT | CCGCCTGCTT | AAAATTACCG | 60 |
| ACCATGATAA | TAAAGATGGA | AAAATTAAAA | ATAACCTAAA | GAATCTTTCC | AATTTATATA | 120 |
| TTGGAAAATT | ACTGGCAGAT | ATTCATCAAT | TAACCATTGA | TGAACTGGAT | TTATTACTGA | 180 |
| TTGCCGTAGG | TGAAGGAAAA | ACTAATTTAT | CCGCTATCAG | TGATAAGCAA | TTGGCTACCC | 240 |
| TGATCAGAAA | ACTCAATACT | ATTACCAGCT | GGCTACATAC | ACAGAAGTGG | AGTGTATTCC | 300 |
| AGCTATTTAT | CATGACCTCC | ACCAGCTATA | ACAAAACGCT | AACGCCTGAA | ATTAAGAATT | 360 |
| TGCTGGATAC | CGTCTACCAC | GGTTTACAAG | GTTTTGATAA | AGACAAAGCA | GATTTGCTAC | 420 |
| ATGTCATGGC | GCCCTATATT | GCGGCCACCT | TGCAATTATC | ATCGGAAAAT | GTCGCCCACT | 480 |
| CGGTACTCCT | TTGGGCAGAT | AAGTTACAGC | CCGGCGACGG | CGCAATGACA | GCAGAGGGAN | 540 |
| TCTGGGACTG | GTTGAATACT | AAGTATACGC | CGGGTTCATC | GGAAGCCGTA | GAAACGCAGG | 600 |
| AACATATCGT | TCAGTATTGT | CAGGCTCTGG | CACAATTGGA | AATGGTTTAC | CATTCCACCG | 660 |
| GCATCAACGA | AAACGCCTTC | CGTCTATTTG | TGACAAAACC | AGAGATGTTT | GGCGCTGCAA | 720 |
| CTGGAGCAGC | GCCCGCGCAT | GATGCCCTTT | CACTGATTAT | GCTGACACGT | TTTGCGGATT | 780 |
| GGGTGAACGC | ACTAGGCGAA | AAAGCGTCCT | CGGTGCTAGC | GGCATTTGAA | GCTAACTCGT | 840 |
| TAACGGCAGA | ACAACTGGCT | GATGCCATGA | ATCTTGATGC | TAATTTGCTG | TTGCAAGCCA | 900 |
| GTATTCAAGC | ACAAAATCAT | CAACATCTTC | CCCCAGTAAC | TCCAGAAAAT | GCGTTCTCCT | 960 |
| GTTGGACATC | TATCAATACT | ATCCTGCAAT | GGGTTAATGT | CGCACAACAA | TTGAAATGTC | 1020 |
| GCCCCACAGG | GCGTTTCCGC | TTTGGTCGGG | CTGGATTATA | TTCAATCAAT | GAAAGAGACA | 1080 |
| CCGACCTATG | CCCAGTGGGA | AAACGCGGCA | GGCGTATTAA | CCGCCGGGTT | GAATTCAACA | 1140 |
| ACAGGCTAAT | ACATTACAAC | GCTTTTCTGG | ATGAATCTCG | CAGTGCCGCA | TTAAGCACCT | 1200 |
| ACTATATCCG | TCAAGTCGCC | AAGGCAGCGG | CGGCTATTAA | AAGCCGTGAT | GACTTGTATC | 1260 |
| AATACTTACT | GATTGATAAT | CAGGTTTCTG | CGGCAATAAA | AACCACCCGG | ATCGCCGAAG | 1320 |
| CCATTGCCAG | TATTCAACTG | TACGTCAACC | GGGCATTGGA | AAATGTGGAA | GAAAATGCCA | 1380 |
| ATTCGGGGGT | TATCAGCCGC | CAATTCTTTA | TCGACTGGGA | CAAATACAAT | AAACGCTACA | 1440 |
| GCACTTGGGC | GGGTGTTTCT | CAATTAGTTT | ACTACCCGGA | AAACTATATT | GATCCGACCA | 1500 |
| TGCGTATCGG | ACAAACCAAA | ATGATGGACG | CATTACTGCA | ATCCGTCAGC | AAAGCCAATA | 1560 |
| TAAACGCCGA | TACCGTCGAA | GATGCCTTTA | TGTCTTATCT | GACATCGTTT | GAACAAGTGG | 1620 |
| CTAATCTTAA | AGTTATTAGC | GCATATACAG | ATAATATTAA | TAACGATCAA | GGGCTGACCT | 1680 |
| ATTTTATCGG | ACTCAGTGAA | ACTGATGCCG | GTGAATATTA | TTGGCGCAGT | GTCGATCACA | 1740 |
| GTAAATTCAA | CGACGGTAAA | TTCGCGGCTA | ATGCCTGGAG | TGAATGGCAT | AAAATTGATT | 1800 |
| GTCCAATTAA | CCCTTATAAA | AGCACTATCC | GTCCAGTGAT | ATATAAATCC | CGCCTGTATC | 1860 |

-continued

```
TGCTCTGGTT GGAACAAAAG GAGATCACCA AACAGACAGG AAATAGTAAA GATGGCTATC    1920

AAACTGAAAC GGATTATCGT TATGAACTAA AATTGGCGCA TATCCGCTAT GATGGCACTT    1980

GGAATACGCC AATCACCTTT GATGTCAATA AAAAAATATC CGAGCTAAAA CTGGAAAAAA    2040

ATAGAGCGCC CGGACTCTAT TGTGCCGGTT ATCAAGGTGA AGATACGTTG CTGGTGATGT    2100

TTTATAACCA ACAAGACACA CTAGATAGTT ATAAAAACGC TTCAATGCAA GGACTATATA    2160

TCTTTGCTGA TATGGCATCC AAAGATATGA CCCCAGAACA GAGCAATGTT TATCGGGATA    2220

ATAGCTATCA ACAATTTGAT ACCAATAATG TCAGAAGAGT GAATAACCGC TATGCAGAGG    2280

ATTATGAGAT TCCTTCTTCG GTAAGTAGCC GTAAAGACTA TGGTTGGGGA GATTATTACC    2340

TCAGCATGGT ATATAACGGA GATATTCCAA CTATCAATTA CAAAGCCGCA TCAAGTGATT    2400

TAAAAATTTA TATTTCACCA AAATTAAGAA TTATTCATAA TGGATATGAA GGACAGAAGC    2460

GCAATCAATG CAATTTGATG AATAAATATG GCAAACTAGG TGATAAATTT ATTGTGTATA    2520

CCAGCCTGGG CGTTAATCCG AATAATAAGC CGAATTC                             2557
```

(2) INFORMATION FOR SEQ ID NO:37:

(i) SEQUENCE CHARACTERISTICS:
        (A) LENGTH: 845 amino acids
        (B) TYPE: amino acids
        (C) TOPOLOGY: linear (ii) MOLECULE TYPE: protein (partial)

(xi) SEQUENCE DESCRIPTION: SEQ ID NO:37 (TCDA INTERNAL: peptide):

```
Ala Phe Asn Ile Asp Asp Val Ser Leu Phe Arg Leu Leu Lys Ile Thr
 1               5                  10                  15

Asp His Asp Asn Lys Asp Gly Lys Ile Lys Asn Asn Leu Lys Asn Leu
            20                  25                  30

Ser Asn Leu Tyr Ile Gly Lys Leu Leu Ala Asp Ile His Gln Leu Thr
        35                  40                  45

Ile Asp Glu Leu Asp Leu Leu Leu Ile Ala Val Gly Glu Gly Lys Thr
50                  55                  60

Asn Leu Ser Ala Ile Ser Asp Lys Gln Leu Ala Thr Leu Ile Arg Lys
65                  70                  75                  80

Leu Asn Thr Ile Thr Ser Trp Leu His Thr Gln Lys Trp Ser Val Phe
                85                  90                  95

Gln Leu Phe Ile Met Thr Ser Thr Ser Tyr Asn Lys Thr Leu Thr Pro
            100                 105                 110

Glu Ile Lys Asn Leu Leu Asp Thr Val Tyr His Gly Leu Gln Gly Phe
        115                 120                 125

Asp Lys Asp Lys Ala Asp Leu Leu His Val Met Ala Pro Tyr Ile Ala
    130                 135                 140

Ala Thr Leu Gln Leu Ser Ser Glu Asn Val Ala His Ser Val Leu Leu
145                 150                 155                 160

Trp Ala Asp Lys Leu Gln Pro Gly Asp Gly Ala Met Thr Ala Glu Gly
                165                 170                 175

Phe Trp Asp Trp Leu Asn Thr Lys Tyr Thr Pro Gly Ser Ser Glu Ala
            180                 185                 190

Val Glu Thr Gln Glu His Ile Val Gln Tyr Cys Gln Ala Leu Ala Gln
        195                 200                 205

Leu Glu Met Val Tyr His Ser Thr Gly Ile Asn Glu Asn Ala Phe Arg
    210                 215                 220
```

```
Leu Phe Val Thr Lys Pro Glu Met Phe Gly Ala Ala Thr Gly Ala Ala
225                 230                 235                 240

Pro Ala His Asp Ala Leu Ser Leu Ile Met Leu Thr Arg Phe Ala Asp
            245                 250                 255

Trp Val Asn Ala Leu Gly Glu Lys Ala Ser Ser Val Leu Ala Ala Phe
                260                 265                 270

Glu Ala Asn Ser Leu Thr Ala Glu Gln Leu Ala Asp Ala Met Asn Leu
            275                 280                 285

Asp Ala Asn Leu Leu Gln Ala Ser Ile Gln Ala Gln Asn His Gln
290                 295                 300

His Leu Pro Pro Val Thr Pro Glu Asn Ala Phe Ser Cys Trp Thr Ser
305                 310                 315                 320

Ile Asn Thr Ile Leu Gln Trp Val Asn Val Ala Gln Gln Leu Lys Cys
                325                 330                 335

Arg Pro Thr Gly Arg Phe Arg Phe Gly Arg Ala Gly Leu Tyr Ser Ile
                340                 345                 350

Asn Glu Arg Asp Thr Asp Leu Cys Pro Val Gly Lys Arg Gly Arg Arg
            355                 360                 365

Ile Asn Arg Arg Val Glu Phe Asn Asn Arg Leu Ile His Tyr Asn Ala
370                 375                 380

Phe Leu Asp Glu Ser Arg Ser Ala Ala Leu Ser Thr Tyr Tyr Ile Arg
385                 390                 395                 400

Gln Val Ala Lys Ala Ala Ala Ile Lys Ser Arg Asp Asp Leu Tyr
                405                 410                 415

Gln Tyr Leu Leu Ile Asp Asn Gln Val Ser Ala Ala Ile Lys Thr Thr
            420                 425                 430

Arg Ile Ala Glu Ala Ile Ala Ser Ile Gln Leu Tyr Val Asn Arg Ala
            435                 440                 445

Leu Glu Asn Val Glu Glu Asn Ala Asn Ser Gly Val Ile Ser Arg Gln
450                 455                 460

Phe Phe Ile Asp Trp Asp Lys Tyr Asn Lys Arg Tyr Ser Thr Trp Ala
465                 470                 475                 480

Gly Val Ser Gln Leu Val Tyr Tyr Pro Glu Asn Tyr Ile Asp Pro Thr
                485                 490                 495

Met Arg Ile Gly Gln Thr Lys Met Met Asp Ala Leu Leu Gln Ser Val
            500                 505                 510

Ser Gln Ser Gln Leu Asn Ala Asp Thr Val Glu Asp Ala Phe Met Ser
            515                 520                 525

Tyr Leu Thr Ser Phe Glu Gln Val Ala Asn Leu Lys Val Ile Ser Ala
530                 535                 540

Tyr His Asp Asn Ile Asn Asn Asp Gln Gly Leu Thr Tyr Phe Ile Gly
545                 550                 555                 560

Leu Ser Glu Thr Asp Ala Gly Glu Tyr Tyr Trp Arg Ser Val Asp His
            565                 570                 575

Ser Lys Phe Asn Asp Gly Lys Phe Ala Ala Asn Ala Trp Ser Glu Trp
            580                 585                 590

His Lys Ile Asp Cys Pro Ile Asn Pro Tyr Lys Ser Thr Ile Arg Pro
            595                 600                 605

Val Ile Tyr Lys Ser Arg Leu Tyr Leu Leu Trp Leu Glu Gln Lys Glu
            610                 615                 620

Ile Thr Lys Gln Thr Gly Asn Ser Lys Asp Gly Tyr Gln Thr Glu Thr
625                 630                 635                 640

Asp Tyr Arg Tyr Glu Leu Lys Leu Ala His Ile Arg Tyr Asp Gly Thr
```

```
                      645                 650                 655
Trp Asn Thr Pro Ile Thr Phe Asp Val Asn Lys Lys Ile Ser Glu Leu
                660                 665                 670
Lys Leu Glu Lys Asn Arg Ala Pro Gly Leu Tyr Cys Ala Gly Tyr Gln
                675                 680                 685
Gly Glu Asp Thr Leu Leu Val Met Phe Tyr Asn Gln Gln Asp Thr Leu
            690                 695                 700
Asp Ser Tyr Lys Asn Ala Ser Met Gln Gly Leu Tyr Ile Phe Ala Asp
705                 710                 715                 720
Met Ala Ser Lys Asp Met Thr Pro Glu Gln Ser Asn Val Tyr Arg Asp
                725                 730                 735
Asn Ser Tyr Gln Gln Phe Asp Thr Asn Asn Val Arg Arg Val Asn Asn
                740                 745                 750
Arg Tyr Ala Glu Asp Tyr Glu Ile Pro Ser Ser Val Ser Ser Arg Lys
                755                 760                 765
Asp Tyr Gly Trp Gly Asp Tyr Tyr Leu Ser Met Val Tyr Asn Gly Asp
                770                 775                 780
Ile Pro Thr Ile Asn Tyr Lys Ala Ala Ser Ser Asp Leu Lys Ile Tyr
785                 790                 795                 800
Ile Ser Pro Lys Leu Arg Ile Ile His Asn Gly Tyr Glu Gly Gln Lys
                805                 810                 815
Arg Asn Gln Cys Asn Leu Met Asn Lys Tyr Gly Lys Leu Gly Asp Lys
                820                 825                 830
Phe Ile Val Tyr Thr Ser Leu Gly Val Asn Pro Asn Asn
                835                 840                 845

(2) INFORMATION FOR SEQ ID NO:38:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: protein (v) FRAGMENT TYPE: N-terminal (xi) SEQUENCE DESCRIPTION: SEQ ID NO:38 (TCDAII- PK71:
         internal peptide):

Arg Tyr Tyr Asn Leu Ser Asp Glu Glu Leu Ser Gln Phe Ile Gly
1               5                   10                  15
Lys (2) INFORMATION FOR SEQ ID NO:39:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: protein (v) FRAGMENT TYPE: N-terminal (xi) SEQUENCE DESCRIPTION: SEQ ID NO:39 (TCDAII- PK44:
         internal peptide):

Gly Thr Ala Thr Asp Val Ser Gly Pro Val Glu Ile Asn Thr Ala
1               5                   10                  15
Ile Ser Pro Ala Lys
```

20

(2) INFORMATION FOR SEQ ID NO:40:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: protein (v) FRAGMENT TYPE: N-terminal (xi) SEQUENCE DESCRIPTION: SEQ ID NO:40 (TCBAIII N-TERMINUS):

```
Ala Asn Ser Leu Thr Ala Leu Phe Leu Pro Gln
1               5                   10
```

(2) INFORMATION FOR SEQ ID NO:41:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: protein (v) FRAGMENT TYPE: N-terminal (xi) SEQUENCE DESCRIPTION: SEQ ID NO:41 (TCDAIII N-TERMINUS):

```
Leu Arg Ser Ala Asn Thr Leu Thr Asp Leu Phe Leu Pro Gln
1               5                   10
```

(2) INFORMATION FOR SEQ ID NO:42:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: protein (v) FRAGMENT TYPE: N-terminal (xi) SEQUENCE DESCRIPTION: SEQ ID NO:42 (TCDA-PK57 INTERNAL:
        peptide):

```
Arg Ala Leu Glu Val Glu Arg Thr Val Ser Leu Ala Glu Val Tyr
1               5                   10                  15
Ala Gly Leu Glu
```

(2) INFORMATION FOR SEQ ID NO:43:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: protein (v) FRAGMENT TYPE: N-terminal (xi) SEQUENCE DESCRIPTION: SEQ ID NO:43 (TCDAIII-PK20:
        internal peptide):

```
Ile Arg Glu Asp Tyr Pro Ala Ser Leu Gly Lys
1               5                   10
```

(2) INFORMATION FOR SEQ ID NO:44:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: protein (v) FRAGMENT TYPE: N-terminal (xi) SEQUENCE DESCRIPTION: SEQ ID NO:44:

```
Asp Asp Ser Gly Asp Asp Asp Lys Val Thr Asn Thr Asp Ile His Arg
1               5                   10                  15
```

(2) INFORMATION FOR SEQ ID NO:45:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: protein (v) FRAGMENT TYPE: N-terminal (xi) SEQUENCE DESCRIPTION: SEQ ID NO:45:

```
Asp Val Xaa Gly Ser Glu Lys Ala Asn Glu Lys Leu Lys
1               5                   10
```

(2) INFORMATION FOR SEQ ID NO:46:

(i) SEQUENCE CHARACTERISTICS:
        (A) LENGTH: 7551 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:46 (TCDA):

```
ATG AAC GAG TCT GTA AAA GAG ATA CCT GAT GTA TTA AAA AGC CAG TGT       48
Met Asn Glu Ser Val Lys Glu Ile Pro Asp Val Leu Lys Ser Gln Cys
1               5                   10                  15

GGT TTT AAT TGT CTG ACA GAT ATT AGC CAC AGC TCT TTT AAT GAA TTT       96
Gly Phe Asn Cys Leu Thr Asp Ile Ser His Ser Ser Phe Asn Glu Phe
                20                  25                  30

CGC CAG CAA GTA TCT GAG CAC CTC TCC TGG TCC GAA ACA CAC GAC TTA      144
Arg Gln Gln Val Ser Glu His Leu Ser Trp Ser Glu Thr His Asp Leu
            35                  40                  45

TAT CAT GAT GCA CAA CAG GCA CAA AAG GAT AAT CGC CTG TAT GAA GCG      192
Tyr His Asp Ala Gln Gln Ala Gln Lys Asp Asn Arg Leu Tyr Glu Ala
        50                  55                  60

CGT ATT CTC AAA CGC GCC AAT CCC CAA TTA CAA AAT GCG GTG CAT CTT      240
Arg Ile Leu Lys Arg Ala Asn Pro Gln Leu Gln Asn Ala Val His Leu
65                  70                  75                  80

GCC ATT CTC GCT CCC AAT GCT GAA CTG ATA GGC TAT AAC AAT CAA TTT      288
Ala Ile Leu Ala Pro Asn Ala Glu Leu Ile Gly Tyr Asn Asn Gln Phe
                85                  90                  95

AGC GGT AGA GCC AGT CAA TAT GTT GCG CCG GGT ACC GTT TCT TCC ATG      336
Ser Gly Arg Ala Ser Gln Tyr Val Ala Pro Gly Thr Val Ser Ser Met
            100                 105                 110

TTC TCC CCC GCC GCT TAT TTG ACT GAA CTT TAT CGT GAA GCA CGC AAT      384
Phe Ser Pro Ala Ala Tyr Leu Thr Glu Leu Tyr Arg Glu Ala Arg Asn
        115                 120                 125
```

-continued

| | |
|---|---|
| TTA CAC GCA AGT GAC TCC GTT TAT TAT CTG GAT ACC CGC CGC CCA GAT<br>Leu His Ala Ser Asp Ser Val Tyr Tyr Leu Asp Thr Arg Arg Pro Asp<br>130                         135                    140 | 432 |
| CTC AAA TCA ATG GCG CTC AGT CAG CAA AAT ATG GAT ATA GAA TTA TCC<br>Leu Lys Ser Met Ala Leu Ser Gln Gln Asn Met Asp Ile Glu Leu Ser<br>145                      150                    155                  160 | 480 |
| ACA CTC TCT TTG TCC AAT GAG CTG TTA TTG GAA AGC ATT AAA ACT GAA<br>Thr Leu Ser Leu Ser Asn Glu Leu Leu Leu Glu Ser Ile Lys Thr Glu<br>                165                    170                  175 | 528 |
| TCT AAA CTG GAA AAC TAT ACT AAA GTG ATG GAA ATG CTC TCC ACT TTC<br>Ser Lys Leu Glu Asn Tyr Thr Lys Val Met Glu Met Leu Ser Thr Phe<br>     180                    185                  190 | 576 |
| CGT CCT TCC GGC GCA ACG CCT TAT CAT GAT GCT TAT GAA AAT GTG CGT<br>Arg Pro Ser Gly Ala Thr Pro Tyr His Asp Ala Tyr Glu Asn Val Arg<br>                195                    200                  205 | 624 |
| GAA GTT ATC CAG CTA CAA GAT CCT GGA CTT GAG CAA CTC AAT GCA TCA<br>Glu Val Ile Gln Leu Gln Asp Pro Gly Leu Glu Gln Leu Asn Ala Ser<br>210                         215                    220 | 672 |
| CCG GCA ATT GCC GGG TTG ATG CAT CAA GCC TCC CTA TTG GGT ATT AAC<br>Pro Ala Ile Ala Gly Leu Met His Gln Ala Ser Leu Leu Gly Ile Asn<br>225                         230                    235                  240 | 720 |
| GCT TCA ATC TCG CCT GAG CTA TTT AAT ATT CTG ACG GAG GAG ATT ACC<br>Ala Ser Ile Ser Pro Glu Leu Phe Asn Ile Leu Thr Glu Glu Ile Thr<br>                    245                    250                  255 | 768 |
| GAA GGT AAT GCT GAG GAA CTT TAT AAG AAA AAT TTT GGT AAT ATC GAA<br>Glu Gly Asn Ala Glu Glu Leu Tyr Lys Lys Asn Phe Gly Asn Ile Glu<br>             260                    265                  270 | 816 |
| CCG GCC TCA TTG GCT ATG CCG GAA TAC CTT AAA CGT TAT TAT AAT TTA<br>Pro Ala Ser Leu Ala Met Pro Glu Tyr Leu Lys Arg Tyr Tyr Asn Leu<br>                275                    280                  285 | 864 |
| AGC GAT GAA GAA CTT AGT CAG TTT ATT GGT AAA GCC AGC AAT TTT GGT<br>Ser Asp Glu Glu Leu Ser Gln Phe Ile Gly Lys Ala Ser Asn Phe Gly<br>290                         295                    300 | 912 |
| CAA CAG GAA TAT AGT AAT AAC CAA CTT ATT ACT CCG GTA GTC AAC AGC<br>Gln Gln Glu Tyr Ser Asn Asn Gln Leu Ile Thr Pro Val Val Asn Ser<br>305                       310                    315                  320 | 960 |
| AGT GAT GGC ACG GTT AAG GTA TAT CGG ATC ACC CGC GAA TAT ACA ACC<br>Ser Asp Gly Thr Val Lys Val Tyr Arg Ile Thr Arg Glu Tyr Thr Thr<br>                       325                    330                  335 | 1008 |
| AAT GCT TAT CAA ATG GAT GTG GAG CTA TTT CCC TTC GGT GGT GAG AAT<br>Asn Ala Tyr Gln Met Asp Val Glu Leu Phe Pro Phe Gly Gly Glu Asn<br>                      340                    345                  350 | 1056 |
| TAT CGG TTA GAT TAT AAA TTC AAA AAT TTT TAT AAT GCC TCT TAT TTA<br>Tyr Arg Leu Asp Tyr Lys Phe Lys Asn Phe Tyr Asn Ala Ser Tyr Leu<br>                  355                    360                  365 | 1104 |
| TCC ATC AAG TTA AAT GAT AAA AGA GAA CTT GTT CGA ACT GAA GGC GCT<br>Ser Ile Lys Leu Asn Asp Lys Arg Glu Leu Val Arg Thr Glu Gly Ala<br>370                         375                    380 | 1152 |
| CCT CAA GTC AAT ATA GAA TAC TCC GCA AAT ATC ACA TTA AAT ACC GCT<br>Pro Gln Val Asn Ile Glu Tyr Ser Ala Asn Ile Thr Leu Asn Thr Ala<br>385                       390                    395                  400 | 1200 |
| GAT ATC AGT CAA CCT TTT GAA ATT GGC CTG ACA CGA GTA CTT CCT TCC<br>Asp Ile Ser Gln Pro Phe Glu Ile Gly Leu Thr Arg Val Leu Pro Ser<br>                    405                    410                  415 | 1248 |
| GGT TCT TGG GCA TAT GCC GCC GCA AAA TTT ACC GTT GAA GAG TAT AAC<br>Gly Ser Trp Ala Tyr Ala Ala Ala Lys Phe Thr Val Glu Glu Tyr Asn<br>             420                    425                  430 | 1296 |
| CAA TAC TCT TTT CTG CTA AAA CTT AAC AAG GCT ATT CGT CTA TCA CGT<br>Gln Tyr Ser Phe Leu Leu Lys Leu Asn Lys Ala Ile Arg Leu Ser Arg | 1344 |

```
                435                 440                 445
GCG ACA GAA TTG TCA CCC ACG ATT CTG GAA GGC ATT GTG CGC AGT GTT       1392
Ala Thr Glu Leu Ser Pro Thr Ile Leu Glu Gly Ile Val Arg Ser Val
        450                 455                 460

AAT CTA CAA CTG GAT ATC AAC ACA GAC GTA TTA GGT AAA GTT TTT CTG       1440
Asn Leu Gln Leu Asp Ile Asn Thr Asp Val Leu Gly Lys Val Phe Leu
465                 470                 475                 480

ACT AAA TAT TAT ATG CAG CGT TAT GCT ATT CAT GCT GAA ACT GCC CTG       1488
Thr Lys Tyr Tyr Met Gln Arg Tyr Ala Ile His Ala Glu Thr Ala Leu
                485                 490                 495

ATA CTA TGC AAC GCG CCT ATT TCA CAA CGT TCA TAT GAT AAT CAA CCT       1536
Ile Leu Cys Asn Ala Pro Ile Ser Gln Arg Ser Tyr Asp Asn Gln Pro
        500                 505                 510

AGC CAA TTT GAT CGC CTG TTT AAT ACG CCA TTA CTG AAC GGA CAA TAT       1584
Ser Gln Phe Asp Arg Leu Phe Asn Thr Pro Leu Leu Asn Gly Gln Tyr
        515                 520                 525

TTT TCT ACC GGC GAT GAG GAG ATT GAT TTA AAT TCA GGT AGC ACC GGC       1632
Phe Ser Thr Gly Asp Glu Glu Ile Asp Leu Asn Ser Gly Ser Thr Gly
        530                 535                 540

GAT TGG CGA AAA ACC ATA CTT AAG CGT GCA TTT AAT ATT GAT GAT GTC       1680
Asp Trp Arg Lys Thr Ile Leu Lys Arg Ala Phe Asn Ile Asp Asp Val
545                 550                 555                 560

TCG CTC TTC CGC CTG CTT AAA ATT ACC GAC CAT GAT AAT AAA GAT GGA       1728
Ser Leu Phe Arg Leu Leu Lys Ile Thr Asp His Asp Asn Lys Asp Gly
                565                 570                 575

AAA ATT AAA AAT AAC CTA AAG AAT CTT TCC AAT TTA TAT ATT GGA AAA       1776
Lys Ile Lys Asn Asn Leu Lys Asn Leu Ser Asn Leu Tyr Ile Gly Lys
        580                 585                 590

TTA CTG GCA GAT ATT CAT CAA TTA ACC ATT GAT GAA CTG GAT TTA TTA       1824
Leu Leu Ala Asp Ile His Gln Leu Thr Ile Asp Glu Leu Asp Leu Leu
        595                 600                 605

CTG ATT GCC GTA GGT GAA GGA AAA ACT AAT TTA TCC GCT ATC AGT GAT       1872
Leu Ile Ala Val Gly Glu Gly Lys Thr Asn Leu Ser Ala Ile Ser Asp
        610                 615                 620

AAG CAA TTG GCT ACC CTG ATC AGA AAA CTC AAT ACT ATT ACC AGC TGG       1920
Lys Gln Leu Ala Thr Leu Ile Arg Lys Leu Asn Thr Ile Thr Ser Trp
625                 630                 635                 640

CTA CAT ACA CAG AAG TGG AGT GTA TTC CAG CTA TTT ATC ATG ACC TCC       1968
Leu His Thr Gln Lys Trp Ser Val Phe Gln Leu Phe Ile Met Thr Ser
                645                 650                 655

ACC AGC TAT AAC AAA ACG CTA ACG CCT GAA ATT AAG AAT TTG CTG GAT       2016
Thr Ser Tyr Asn Lys Thr Leu Thr Pro Glu Ile Lys Asn Leu Leu Asp
        660                 665                 670

ACC GTC TAC CAC GGT TTA CAA GGT TTT GAT AAA GAC AAA GCA GAT TTG       2064
Thr Val Tyr His Gly Leu Gln Gly Phe Asp Lys Asp Lys Ala Asp Leu
        675                 680                 685

CTA CAT GTC ATG GCG CCC TAT ATT GCG GCC ACC TTG CAA TTA TCA TCG       2112
Leu His Val Met Ala Pro Tyr Ile Ala Ala Thr Leu Gln Leu Ser Ser
        690                 695                 700

GAA AAT GTC GCC CAC TCG GTA CTC CTT TGG GCA GAT AAG TTA CAG CCC       2160
Glu Asn Val Ala His Ser Val Leu Leu Trp Ala Asp Lys Leu Gln Pro
705                 710                 715                 720

GGC GAC GGC GCA ATG ACA GCA GAA AAA TTC TGG GAC TGG TTG AAT ACT       2208
Gly Asp Gly Ala Met Thr Ala Glu Lys Phe Trp Asp Trp Leu Asn Thr
                725                 730                 735

AAG TAT ACG CCG GGT TCA TCG GAA GCC GTA GAA ACG CAG GAA CAT ATC       2256
Lys Tyr Thr Pro Gly Ser Ser Glu Ala Val Glu Thr Gln Glu His Ile
        740                 745                 750

GTT CAG TAT TGT CAG GCT CTG GCA CAA TTG GAA ATG GTT TAC CAT TCC       2304
```

```
                 Val Gln Tyr Cys Gln Ala Leu Ala Gln Leu Glu Met Val Tyr His Ser
                             755                 760                 765

ACC GGC ATC AAC GAA AAC GCC TTC CGT CTA TTT GTG ACA AAA CCA GAG                2352
Thr Gly Ile Asn Glu Asn Ala Phe Arg Leu Phe Val Thr Lys Pro Glu
            770                 775                 780

ATG TTT GGC GCT GCA ACT GGA GCA GCG CCC GCG CAT GAT GCC CTT TCA                2400
Met Phe Gly Ala Ala Thr Gly Ala Ala Pro Ala His Asp Ala Leu Ser
785                 790                 795                 800

CTG ATT ATG CTG ACA CGT TTT GCG GAT TGG GTG AAC GCA CTA GGC GAA                2448
Leu Ile Met Leu Thr Arg Phe Ala Asp Trp Val Asn Ala Leu Gly Glu
                805                 810                 815

AAA GCG TCC TCG GTG CTA GCG GCA TTT GAA GCT AAC TCG TTA ACG GCA                2496
Lys Ala Ser Ser Val Leu Ala Ala Phe Glu Ala Asn Ser Leu Thr Ala
            820                 825                 830

GAA CAA CTG GCT GAT GCC ATG AAT CTT GAT GCT AAT TTG CTG TTG CAA                2544
Glu Gln Leu Ala Asp Ala Met Asn Leu Asp Ala Asn Leu Leu Leu Gln
                835                 840                 845

GCC AGT ATT CAA GCA CAA AAT CAT CAA CAT CTT CCC CCA GTA ACT CCA                2592
Ala Ser Ile Gln Ala Gln Asn His Gln His Leu Pro Pro Val Thr Pro
850                 855                 860

GAA AAT GCG TTC TCC TGT TGG ACA TCT ATC AAT ACT ATC CTG CAA TGG                2640
Glu Asn Ala Phe Ser Cys Trp Thr Ser Ile Asn Thr Ile Leu Gln Trp
865                 870                 875                 880

GTT AAT GTC GCA CAA CAA TTG AAT GTC GCC CCA CAG GGC GTT TCC GCT                2688
Val Asn Val Ala Gln Gln Leu Asn Val Ala Pro Gln Gly Val Ser Ala
                885                 890                 895

TTG GTC GGG CTG GAT TAT ATT CAA TCA ATG AAA GAG ACA CCG ACC TAT                2736
Leu Val Gly Leu Asp Tyr Ile Gln Ser Met Lys Glu Thr Pro Thr Tyr
            900                 905                 910

GCC CAG TGG GAA AAC GCG GCA GGC GTA TTA ACC GCC GGG TTG AAT TCA                2784
Ala Gln Trp Glu Asn Ala Ala Gly Val Leu Thr Ala Gly Leu Asn Ser
                915                 920                 925

CAA CAG GCT AAT ACA TTA CAC GCT TTT CTG GAT GAA TCT CGC AGT GCC                2832
Gln Gln Ala Asn Thr Leu His Ala Phe Leu Asp Glu Ser Arg Ser Ala
            930                 935                 940

GCA TTA AGC ACC TAC TAT ATC CGT CAA GTC GCC AAG GCA GCG GCG GCT                2880
Ala Leu Ser Thr Tyr Tyr Ile Arg Gln Val Ala Lys Ala Ala Ala Ala
945                 950                 955                 960

ATT AAA AGC CGT GAT GAC TTG TAT CAA TAC TTA CTG ATT GAT AAT CAG                2928
Ile Lys Ser Arg Asp Asp Leu Tyr Gln Tyr Leu Leu Ile Asp Asn Gln
                965                 970                 975

GTT TCT GCG GCA ATA AAA ACC ACC CGG ATC GCC GAA GCC ATT GCC AGT                2976
Val Ser Ala Ala Ile Lys Thr Thr Arg Ile Ala Glu Ala Ile Ala Ser
            980                 985                 990

ATT CAA CTG TAC GTC AAC CGG GCA TTG GAA AAT GTG GAA GAA AAT GCC                3024
Ile Gln Leu Tyr Val Asn Arg Ala Leu Glu Asn Val Glu Glu Asn Ala
                995                 1000                1005

AAT TCG GGG GTT ATC AGC CGC CAA TTC TTT ATC GAC TGG GAC AAA TAC                3072
Asn Ser Gly Val Ile Ser Arg Gln Phe Phe Ile Asp Trp Asp Lys Tyr
            1010                1015                1020

AAT AAA CGC TAC AGC ACT TGG GCG GGT GTT TCT CAA TTA GTT TAC TAC                3120
Asn Lys Arg Tyr Ser Thr Trp Ala Gly Val Ser Gln Leu Val Tyr Tyr
1025                1030                1035                1040

CCG GAA AAC TAT ATT GAT CCG ACC ATG CGT ATC GGA CAA ACC AAA ATG                3168
Pro Glu Asn Tyr Ile Asp Pro Thr Met Arg Ile Gly Gln Thr Lys Met
                1045                1050                1055

ATG GAC GCA TTA CTG CAA TCC GTC AGC CAA AGC CAA TTA AAC GCC GAT                3216
Met Asp Ala Leu Leu Gln Ser Val Ser Gln Ser Gln Leu Asn Ala Asp
            1060                1065                1070
```

```
                                                                -continued
ACC GTC GAA GAT GCC TTT ATG TCT TAT CTG ACA TCG TTT GAA CAA GTG        3264
Thr Val Glu Asp Ala Phe Met Ser Tyr Leu Thr Ser Phe Glu Gln Val
        1075                1080                1085

GCT AAT CTT AAA GTT ATT AGC GCA TAT CAC GAT AAT ATT AAT AAC GAT        3312
Ala Asn Leu Lys Val Ile Ser Ala Tyr His Asp Asn Ile Asn Asn Asp
        1090                1095                1100

CAA GGG CTG ACC TAT TTT ATC GGA CTC AGT GAA ACT GAT GCC GGT GAA        3360
Gln Gly Leu Thr Tyr Phe Ile Gly Leu Ser Glu Thr Asp Ala Gly Glu
1105                1110                1115                1120

TAT TAT TGG CGC AGT GTC GAT CAC AGT AAA TTC AAC GAC GGT AAA TTC        3408
Tyr Tyr Trp Arg Ser Val Asp His Ser Lys Phe Asn Asp Gly Lys Phe
                1125                1130                1135

GCG GCT AAT GCC TGG AGT GAA TGG CAT AAA ATT GAT TGT CCA ATT AAC        3456
Ala Ala Asn Ala Trp Ser Glu Trp His Lys Ile Asp Cys Pro Ile Asn
        1140                1145                1150

CCT TAT AAA AGC ACT ATC CGT CCA GTG ATA TAT AAA TCC CGC CTG TAT        3504
Pro Tyr Lys Ser Thr Ile Arg Pro Val Ile Tyr Lys Ser Arg Leu Tyr
        1155                1160                1165

CTG CTC TGG TTG GAA CAA AAG GAG ATC ACC AAA CAG ACA GGA AAT AGT        3552
Leu Leu Trp Leu Glu Gln Lys Glu Ile Thr Lys Gln Thr Gly Asn Ser
        1170                1175                1180

AAA GAT GGC TAT CAA ACT GAA ACG GAT TAT CGT TAT GAA CTA AAA TTG        3600
Lys Asp Gly Tyr Gln Thr Glu Thr Asp Tyr Arg Tyr Glu Leu Lys Leu
1185                1190                1195                1200

GCG CAT ATC CGC TAT GAT GGC ACT TGG AAT ACG CCA ATC ACC TTT GAT        3648
Ala His Ile Arg Tyr Asp Gly Thr Trp Asn Thr Pro Ile Thr Phe Asp
                1205                1210                1215

GTC AAT AAA AAA ATA TCC GAG CTA AAA CTG GAA AAA AAT AGA GCG CCC        3696
Val Asn Lys Lys Ile Ser Glu Leu Lys Leu Glu Lys Asn Arg Ala Pro
        1220                1225                1230

GGA CTC TAT TGT GCC GGT TAT CAA GGT GAA GAT ACG TTG CTG GTG ATG        3744
Gly Leu Tyr Cys Ala Gly Tyr Gln Gly Glu Asp Thr Leu Leu Val Met
        1235                1240                1245

TTT TAT AAC CAA CAA GAC ACA CTA GAT AGT TAT AAA AAC GCT TCA ATG        3792
Phe Tyr Asn Gln Gln Asp Thr Leu Asp Ser Tyr Lys Asn Ala Ser Met
        1250                1255                1260

CAA GGA CTA TAT ATC TTT GCT GAT ATG GCA TCC AAA GAT ATG ACC CCA        3840
Gln Gly Leu Tyr Ile Phe Ala Asp Met Ala Ser Lys Asp Met Thr Pro
1265                1270                1275                1280

GAA CAG AGC AAT GTT TAT CGG GAT AAT AGC TAT CAA CAA TTT GAT ACC        3888
Glu Gln Ser Asn Val Tyr Arg Asp Asn Ser Tyr Gln Gln Phe Asp Thr
                1285                1290                1295

AAT AAT GTC AGA AGA GTG AAT AAC CGC TAT GCA GAG GAT TAT GAG ATT        3936
Asn Asn Val Arg Arg Val Asn Asn Arg Tyr Ala Glu Asp Tyr Glu Ile
        1300                1305                1310

CCT TCC TCG GTA AGT AGC CGT AAA GAC TAT GGT TGG GGA GAT TAT TAC        3984
Pro Ser Ser Val Ser Ser Arg Lys Asp Tyr Gly Trp Gly Asp Tyr Tyr
        1315                1320                1325

CTC AGC ATG GTA TAT AAC GGA GAT ATT CCA ACT ATC AAT TAC AAA GCC        4032
Leu Ser Met Val Tyr Asn Gly Asp Ile Pro Thr Ile Asn Tyr Lys Ala
        1330                1335                1340

GCA TCA AGT GAT TTA AAA ATC TAT ATC TCA CCA AAA TTA AGA ATT ATT        4080
Ala Ser Ser Asp Leu Lys Ile Tyr Ile Ser Pro Lys Leu Arg Ile Ile
1345                1350                1355                1360

CAT AAT GGA TAT GAA GGA CAG AAG CGC AAT CAA TGC AAT CTG ATG AAT        4128
His Asn Gly Tyr Glu Gly Gln Lys Arg Asn Gln Cys Asn Leu Met Asn
                1365                1370                1375

AAA TAT GGC AAA CTA GGT GAT AAA TTT ATT GTT TAT ACT AGC TTG GGG        4176
Lys Tyr Gly Lys Leu Gly Asp Lys Phe Ile Val Tyr Thr Ser Leu Gly
        1380                1385                1390
```

```
                                              -continued

GTC AAT CCA AAT AAC TCG TCA AAT AAG CTC ATG TTT TAC CCC GTC TAT      4224
Val Asn Pro Asn Asn Ser Ser Asn Lys Leu Met Phe Tyr Pro Val Tyr
        1395                1400                1405

CAA TAT AGC GGA AAC ACC AGT GGA CTC AAT CAA GGG AGA CTA CTA TTC      4272
Gln Tyr Ser Gly Asn Thr Ser Gly Leu Asn Gln Gly Arg Leu Leu Phe
    1410                1415                1420

CAC CGT GAC ACC ACT TAT CCA TCT AAA GTA GAA GCT TGG ATT CCT GGA      4320
His Arg Asp Thr Thr Tyr Pro Ser Lys Val Glu Ala Trp Ile Pro Gly
1425                1430                1435                1440

GCA AAA CGT TCT CTA ACC AAC CAA AAT GCC GCC ATT GGT GAT GAT TAT      4368
Ala Lys Arg Ser Leu Thr Asn Gln Asn Ala Ala Ile Gly Asp Asp Tyr
                1445                1450                1455

GCT ACA GAC TCT CTG AAT AAA CCG GAT GAT CTT AAG CAA TAT ATC TTT      4416
Ala Thr Asp Ser Leu Asn Lys Pro Asp Asp Leu Lys Gln Tyr Ile Phe
            1460                1465                1470

ATG ACT GAC AGT AAA GGG ACT GCT ACT GAT GTC TCA GGC CCA GTA GAG      4464
Met Thr Asp Ser Lys Gly Thr Ala Thr Asp Val Ser Gly Pro Val Glu
        1475                1480                1485

ATT AAT ACT GCA ATT TCT CCA GCA AAA GTT CAG ATA ATA GTC AAA GCG      4512
Ile Asn Thr Ala Ile Ser Pro Ala Lys Val Gln Ile Ile Val Lys Ala
    1490                1495                1500

GGT GGC AAG GAG CAA ACT TTT ACC GCA GAT AAA GAT GTC TCC ATT CAG      4560
Gly Gly Lys Glu Gln Thr Phe Thr Ala Asp Lys Asp Val Ser Ile Gln
1505                1510                1515                1520

CCA TCA CCT AGC TTT GAT GAA ATG AAT TAT CAA TTT AAT GCC CTT GAA      4608
Pro Ser Pro Ser Phe Asp Glu Met Asn Tyr Gln Phe Asn Ala Leu Glu
                1525                1530                1535

ATA GAC GGT TCT GGT CTG AAT TTT ATT AAC AAC TCA GCC AGT ATT GAT      4656
Ile Asp Gly Ser Gly Leu Asn Phe Ile Asn Asn Ser Ala Ser Ile Asp
            1540                1545                1550

GTT ACT TTT ACC GCA TTT GCG GAG GAT GGC CGC AAA CTG GGT TAT GAA      4704
Val Thr Phe Thr Ala Phe Ala Glu Asp Gly Arg Lys Leu Gly Tyr Glu
        1555                1560                1565

AGT TTC AGT ATT CCT GTT ACC CTC AAG GTA AGT ACC GAT AAT GCC CTG      4752
Ser Phe Ser Ile Pro Val Thr Leu Lys Val Ser Thr Asp Asn Ala Leu
    1570                1575                1580

ACC CTG CAC CAT AAT GAA AAT GGT GCG CAA TAT ATG CAA TGG CAA TCC      4800
Thr Leu His His Asn Glu Asn Gly Ala Gln Tyr Met Gln Trp Gln Ser
1585                1590                1595                1600

TAT CGT ACC CGC CTG AAT ACT CTA TTT GCC CGC CAG TTG GTT GCA CGC      4848
Tyr Arg Thr Arg Leu Asn Thr Leu Phe Ala Arg Gln Leu Val Ala Arg
                1605                1610                1615

GCC ACC ACC GGA ATC GAT ACA ATT CTG AGT ATG GAA ACT CAG AAT ATT      4896
Ala Thr Thr Gly Ile Asp Thr Ile Leu Ser Met Glu Thr Gln Asn Ile
            1620                1625                1630

CAG GAA CCG CAG TTA GGC AAA GGT TTC TAT GCT ACG TTC GTG ATA CCT      4944
Gln Glu Pro Gln Leu Gly Lys Gly Phe Tyr Ala Thr Phe Val Ile Pro
        1635                1640                1645

CCC TAT AAC CTA TCA ACT CAT GGT GAT GAA CGT TGG TTT AAG CTT TAT      4992
Pro Tyr Asn Leu Ser Thr His Gly Asp Glu Arg Trp Phe Lys Leu Tyr
    1650                1655                1660

ATC AAA CAT GTT GTT GAT AAT AAT TCA CAT ATT ATC TAT TCA GGC CAG      5040
Ile Lys His Val Val Asp Asn Asn Ser His Ile Ile Tyr Ser Gly Gln
1665                1670                1675                1680

CTA ACA GAT ACA AAT ATA AAC ATC ACA TTA TTT ATT CCT CTT GAT GAT      5088
Leu Thr Asp Thr Asn Ile Asn Ile Thr Leu Phe Ile Pro Leu Asp Asp
                1685                1690                1695

GTC CCA TTG AAT CAA GAT TAT CAC GCC AAG GTT TAT ATG ACC TTC AAG      5136
Val Pro Leu Asn Gln Asp Tyr His Ala Lys Val Tyr Met Thr Phe Lys
```

-continued

```
           1700                1705                1710
AAA TCA CCA TCA GAT GGT ACC TGG TGG GGC CCT CAC TTT GTT AGA GAT      5184
Lys Ser Pro Ser Asp Gly Thr Trp Trp Gly Pro His Phe Val Arg Asp
        1715                1720                1725

GAT AAA GGA ATA GTA ACA ATA AAC CCT AAA TCC ATT TTG ACC CAT TTT      5232
Asp Lys Gly Ile Val Thr Ile Asn Pro Lys Ser Ile Leu Thr His Phe
    1730                1735                1740

GAG AGC GTC AAT GTC CTG AAT AAT ATT AGT AGC GAA CCA ATG GAT TTC      5280
Glu Ser Val Asn Val Leu Asn Asn Ile Ser Ser Glu Pro Met Asp Phe
1745                1750                1755                1760

AGC GGC GCT AAC AGC CTC TAT TTC TGG GAA CTG TTC TAC TAT ACC CCG      5328
Ser Gly Ala Asn Ser Leu Tyr Phe Trp Glu Leu Phe Tyr Tyr Thr Pro
                1765                1770                1775

ATG CTG GTT GCT CAA CGT TTG CTG CAT GAA CAG AAC TTC GAT GAA GCC      5376
Met Leu Val Ala Gln Arg Leu Leu His Glu Gln Asn Phe Asp Glu Ala
            1780                1785                1790

AAC CGT TGG CTG AAA TAT GTC TGG AGT CCA TCC GGT TAT ATT GTC CAC      5424
Asn Arg Trp Leu Lys Tyr Val Trp Ser Pro Ser Gly Tyr Ile Val His
        1795                1800                1805

GGC CAG ATT CAG AAC TAC CAG TGG AAC GTC CGC CCG TTA CTG GAA GAC      5472
Gly Gln Ile Gln Asn Tyr Gln Trp Asn Val Arg Pro Leu Leu Glu Asp
    1810                1815                1820

ACC AGT TGG AAC AGT GAT CCT TTG GAT TCC GTC GAT CCT GAC GCG GTA      5520
Thr Ser Trp Asn Ser Asp Pro Leu Asp Ser Val Asp Pro Asp Ala Val
1825                1830                1835                1840

GCA CAG CAC GAT CCA ATG CAC TAC AAA GTT TCA ACT TTT ATG CGT ACC      5568
Ala Gln His Asp Pro Met His Tyr Lys Val Ser Thr Phe Met Arg Thr
                1845                1850                1855

TTG GAT CTA TTG ATA GCA CGC GGC GAC CAT GCT TAT CGC CAA CTG GAA      5616
Leu Asp Leu Leu Ile Ala Arg Gly Asp His Ala Tyr Arg Gln Leu Glu
            1860                1865                1870

CGA GAT ACA CTC AAC GAA GCG AAG ATG TGG TAT ATG CAA GCG CTG CAT      5664
Arg Asp Thr Leu Asn Glu Ala Lys Met Trp Tyr Met Gln Ala Leu His
        1875                1880                1885

CTA TTA GGT GAC AAA CCT TAT CTA CCG CTG AGT ACG ACA TGG AGT GAT      5712
Leu Leu Gly Asp Lys Pro Tyr Leu Pro Leu Ser Thr Thr Trp Ser Asp
    1890                1895                1900

CCA CGA CTA GAC AGA GCC GCG GAT ATC ACT ACC CAA AAT GCT CAC GAC      5760
Pro Arg Leu Asp Arg Ala Ala Asp Ile Thr Thr Gln Asn Ala His Asp
1905                1910                1915                1920

AGC GCA ATA GTC GCT CTG CGG CAG AAT ATA CCT ACA CCG GCA CCT TTA      5808
Ser Ala Ile Val Ala Leu Arg Gln Asn Ile Pro Thr Pro Ala Pro Leu
                1925                1930                1935

TCA TTG CGC AGC GCT AAT ACC CTG ACT GAT CTC TTC CTG CCG CAA ATC      5856
Ser Leu Arg Ser Ala Asn Thr Leu Thr Asp Leu Phe Leu Pro Gln Ile
            1940                1945                1950

AAT GAA GTG ATG ATG AAT TAC TGG CAG ACA TTA GCT CAG AGA GTA TAC      5904
Asn Glu Val Met Met Asn Tyr Trp Gln Thr Leu Ala Gln Arg Val Tyr
        1955                1960                1965

AAT CTG CGT CAT AAC CTC TCT ATC GAC GGC CAG CCG TTA TAT CTG CCA      5952
Asn Leu Arg His Asn Leu Ser Ile Asp Gly Gln Pro Leu Tyr Leu Pro
    1970                1975                1980

ATC TAT GCC ACA CCG GCC GAT CCG AAA GCG TTA CTC AGC GCC GCC GTT      6000
Ile Tyr Ala Thr Pro Ala Asp Pro Lys Ala Leu Leu Ser Ala Ala Val
1985                1990                1995                2000

GCC ACT TCT CAA GGT GGA GGC AAG CTA CCG GAA TCA TTT ATG TCC CTG      6048
Ala Thr Ser Gln Gly Gly Gly Lys Leu Pro Glu Ser Phe Met Ser Leu
                2005                2010                2015

TGG CGT TTC CCG CAC ATG CTG GAA AAT GCG CGC GGC ATG GTT AGC CAG      6096
```

```
                    -continued

Trp Arg Phe Pro His Met Leu Glu Asn Ala Arg Gly Met Val Ser Gln
            2020                2025                2030

CTC ACC CAG TTC GGC TCC ACG TTA CAA AAT ATT ATC GAA CGT CAG GAC       6144
Leu Thr Gln Phe Gly Ser Thr Leu Gln Asn Ile Ile Glu Arg Gln Asp
            2035                2040                2045

GCG GAA GCG CTC AAT GCG TTA TTA CAA AAT CAG GCC GCC GAG CTG ATA       6192
Ala Glu Ala Leu Asn Ala Leu Leu Gln Asn Gln Ala Ala Glu Leu Ile
            2050                2055                2060

TTG ACT AAC CTG AGC ATT CAG GAC AAA ACC ATT GAA GAA TTG GAT GCC       6240
Leu Thr Asn Leu Ser Ile Gln Asp Lys Thr Ile Glu Glu Leu Asp Ala
2065                2070                2075                2080

GAG AAA ACG GTG TTG GAA AAA TCC AAA GCG GGA GCA CAA TCG CGC TTT       6288
Glu Lys Thr Val Leu Glu Lys Ser Lys Ala Gly Ala Gln Ser Arg Phe
            2085                2090                2095

GAT AGC TAC GGC AAA CTG TAC GAT GAG AAT ATC AAC GCC GGT GAA AAC       6336
Asp Ser Tyr Gly Lys Leu Tyr Asp Glu Asn Ile Asn Ala Gly Glu Asn
            2100                2105                2110

CAA GCC ATG ACG CTA CGA GCG TCC GCC GCC GGG CTT ACC ACG GCA GTT       6384
Gln Ala Met Thr Leu Arg Ala Ser Ala Ala Gly Leu Thr Thr Ala Val
            2115                2120                2125

CAG GCA TCC CGT CTG GCC GGT GCG GCG GCT GAT CTG GTG CCT AAC ATC       6432
Gln Ala Ser Arg Leu Ala Gly Ala Ala Ala Asp Leu Val Pro Asn Ile
            2130                2135                2140

TTC GGC TTT GCC GGT GGC GGC AGC CGT TGG GGG GCT ATC GCT GAG GCG       6480
Phe Gly Phe Ala Gly Gly Gly Ser Arg Trp Gly Ala Ile Ala Glu Ala
2145                2150                2155                2160

ACA GGT TAT GTG ATG GAA TTC TCC GCG AAT GTT ATG AAC ACC GAA GCG       6528
Thr Gly Tyr Val Met Glu Phe Ser Ala Asn Val Met Asn Thr Glu Ala
            2165                2170                2175

GAT AAA ATT AGC CAA TCT GAA ACC TAC CGT CGT CGC CGT CAG GAG TGG       6576
Asp Lys Ile Ser Gln Ser Glu Thr Tyr Arg Arg Arg Arg Gln Glu Trp
            2180                2185                2190

GAG ATC CAG CGG AAT AAT GCC GAA GCG GAA TTG AAG CAA ATC GAT GCT       6624
Glu Ile Gln Arg Asn Asn Ala Glu Ala Glu Leu Lys Gln Ile Asp Ala
            2195                2200                2205

CAG CTC AAA TCA CTC GCT GTA CGC CGC GAA GCC GCC GTA TTG CAG AAA       6672
Gln Leu Lys Ser Leu Ala Val Arg Arg Glu Ala Ala Val Leu Gln Lys
            2210                2215                2220

ACC AGT CTG AAA ACC CAA CAA GAA CAG ACC CAA TCT CAA TTG GCC TTC       6720
Thr Ser Leu Lys Thr Gln Gln Glu Gln Thr Gln Ser Gln Leu Ala Phe
2225                2230                2235                2240

CTG CAA CGT AAG TTC AGC AAT CAG GCG TTA TAC AAC TGG CTG CGT GGT       6768
Leu Gln Arg Lys Phe Ser Asn Gln Ala Leu Tyr Asn Trp Leu Arg Gly
            2245                2250                2255

CGA CTG GCG GCG ATT TAC TTC CAG TTC TAC GAT TTG GCC GTC GCG CGT       6816
Arg Leu Ala Ala Ile Tyr Phe Gln Phe Tyr Asp Leu Ala Val Ala Arg
            2260                2265                2270

TGC CTG ATG GCA GAA CAA GCT TAC CGT TGG GAA CTC AAT GAT GAC TCT       6864
Cys Leu Met Ala Glu Gln Ala Tyr Arg Trp Glu Leu Asn Asp Asp Ser
            2275                2280                2285

GCC CGC TTC ATT AAA CCG GGC GCC TGG CAG GGA ACC TAT GCC GGT CTG       6912
Ala Arg Phe Ile Lys Pro Gly Ala Trp Gln Gly Thr Tyr Ala Gly Leu
            2290                2295                2300

CTT GCA GGT GAA ACC TTG ATG CTG AGT CTG GCA CAA ATG GAA GAC GCT       6960
Leu Ala Gly Glu Thr Leu Met Leu Ser Leu Ala Gln Met Glu Asp Ala
2305                2310                2315                2320

CAT CTG AAA CGC GAT AAA CGC GCA TTA GAG GTT GAA CGC ACA GTA TCG       7008
His Leu Lys Arg Asp Lys Arg Ala Leu Glu Val Glu Arg Thr Val Ser
            2325                2330                2335
```

| | | |
|---|---|---|
| CTG GCC GAA GTT TAT GCA GGA TTA CCA AAA GAT AAC GGT CCA TTT TCC<br>Leu Ala Glu Val Tyr Ala Gly Leu Pro Lys Asp Asn Gly Pro Phe Ser<br>           2340                  2345                 2350 | 7056 |
| CTG GCT CAG GAA ATT GAC AAG CTG GTG AGT CAA GGT TCA GGC AGT GCC<br>Leu Ala Gln Glu Ile Asp Lys Leu Val Ser Gln Gly Ser Gly Ser Ala<br>    2355                  2360                 2365 | 7104 |
| GGC AGT GGT AAT AAT AAT TTG GCG TTC GGC GCC GGC ACG GAC ACT AAA<br>Gly Ser Gly Asn Asn Asn Leu Ala Phe Gly Ala Gly Thr Asp Thr Lys<br>2370                 2375                 2380 | 7152 |
| ACC TCT TTG CAG GCA TCA GTT TCA TTC GCT GAT TTG AAA ATT CGT GAA<br>Thr Ser Leu Gln Ala Ser Val Ser Phe Ala Asp Leu Lys Ile Arg Glu<br>2385                 2390                 2395                 2400 | 7200 |
| GAT TAC CCG GCA TCG CTT GGC AAA ATT CGA CGT ATC AAA CAG ATC AGC<br>Asp Tyr Pro Ala Ser Leu Gly Lys Ile Arg Arg Ile Lys Gln Ile Ser<br>           2405                 2410                 2415 | 7248 |
| GTC ACT TTG CCC GCG CTA CTG GGA CCG TAT CAG GAT GTA CAG GCA ATA<br>Val Thr Leu Pro Ala Leu Leu Gly Pro Tyr Gln Asp Val Gln Ala Ile<br>           2420                 2425                 2430 | 7296 |
| TTG TCT TAC GGC GAT AAA GCC GGA TTA GCT AAC GGC TGT GAA GCG CTG<br>Leu Ser Tyr Gly Asp Lys Ala Gly Leu Ala Asn Gly Cys Glu Ala Leu<br>           2435                 2440                 2445 | 7344 |
| GCA GTT TCT CAC GGT ATG AAT GAC AGC GGC CAA TTC CAG CTC GAT TTC<br>Ala Val Ser His Gly Met Asn Asp Ser Gly Gln Phe Gln Leu Asp Phe<br>2450                 2455                 2460 | 7392 |
| AAC GAT GGC AAA TTC CTG CCA TTC GAA GGC ATC GCC ATT GAT CAA GGC<br>Asn Asp Gly Lys Phe Leu Pro Phe Glu Gly Ile Ala Ile Asp Gln Gly<br>2465                 2470                 2475                 2480 | 7440 |
| ACG CTG ACA CTG AGC TTC CCA AAT GCA TCT ATG CCG GAG AAA GGT AAA<br>Thr Leu Thr Leu Ser Phe Pro Asn Ala Ser Met Pro Glu Lys Gly Lys<br>           2485                 2490                 2495 | 7488 |
| CAA GCC ACT ATG TTA AAA ACC CTG AAC GAT ATC ATT TTG CAT ATT CGC<br>Gln Ala Thr Met Leu Lys Thr Leu Asn Asp Ile Ile Leu His Ile Arg<br>           2500                 2505                 2510 | 7536 |
| TAC ACC ATT AAA TAA<br>Tyr Thr Ile Lys<br>           2516 | 7551 |

(2) INFORMATION FOR SEQ ID NO:47:

(i) SEQUENCE CHARACTERISTICS:
        (A) LENGTH: 2516 amino acids
        (B) TYPE: amino acids
        (C) STRANDEDNESS: single
        (D) TOPOLOGY: linear (ii) MOLECULE TYPE: protein (xi) SEQUENCE DESCRIPTION: SEQ ID NO:47 (TCDA):

FeaturesFromToDescription

Peptide12516TcdA proteins

Peptide891937TcdAii peptide

Fragment89100TcdAii N-terminus (SEQID NO:13)

Fragment284299(SEQ ID NO:38)

Fragment554563(SEQ ID NO:17)

Fragment10801092(SEQ ID NO:23;12/13)

Fragment13851400(SEQ ID NO:18)

Fragment14781497(SEQ ID NO:39)

Fragment16201642(SEQ ID NO:21;19/23)

Fragment19381948(SEQ ID NO:41)

Peptide19382516TcdAiii peptide

Fragment23272345(SEQ ID NO:42)

Fragment23982408(SEQ ID NO:43)

```
Met Asn Glu Ser Val Lys Glu Ile Pro Asp Val Leu Lys Ser Gln Cys
 1               5                  10                  15

Gly Phe Asn Cys Leu Thr Asp Ile Ser His Ser Ser Phe Asn Glu Phe
            20                  25                  30

Arg Gln Gln Val Ser Glu His Leu Ser Trp Ser Glu Thr His Asp Leu
        35                  40                  45

Tyr His Asp Ala Gln Gln Ala Gln Lys Asp Asn Arg Leu Tyr Glu Ala
    50                  55                  60

Arg Ile Leu Lys Arg Ala Asn Pro Gln Leu Gln Asn Ala Val His Leu
65                  70                  75                  80

Ala Ile Leu Ala Pro Asn Ala Glu Leu Ile Gly Tyr Asn Asn Gln Phe
                85                  90                  95

Ser Gly Arg Ala Ser Gln Tyr Val Ala Pro Gly Thr Val Ser Ser Met
            100                 105                 110

Phe Ser Pro Ala Ala Tyr Leu Thr Glu Leu Tyr Arg Glu Ala Arg Asn
        115                 120                 125

Leu His Ala Ser Asp Ser Val Tyr Tyr Leu Asp Thr Arg Arg Pro Asp
    130                 135                 140

Leu Lys Ser Met Ala Leu Ser Gln Gln Asn Met Asp Ile Glu Leu Ser
145                 150                 155                 160

Thr Leu Ser Leu Ser Asn Glu Leu Leu Leu Glu Ser Ile Lys Thr Glu
                165                 170                 175

Ser Lys Leu Glu Asn Tyr Thr Lys Val Met Glu Met Leu Ser Thr Phe
            180                 185                 190

Arg Pro Ser Gly Ala Thr Pro Tyr His Asp Ala Tyr Glu Asn Val Arg
        195                 200                 205

Glu Val Ile Gln Leu Gln Asp Pro Gly Leu Glu Gln Leu Asn Ala Ser
    210                 215                 220

Pro Ala Ile Ala Gly Leu Met His Gln Ala Ser Leu Leu Gly Ile Asn
225                 230                 235                 240

Ala Ser Ile Ser Pro Glu Leu Phe Asn Ile Leu Thr Glu Glu Ile Thr
                245                 250                 255

Glu Gly Asn Ala Glu Glu Leu Tyr Lys Lys Asn Phe Gly Asn Ile Glu
            260                 265                 270

Pro Ala Ser Leu Ala Met Pro Glu Tyr Leu Lys Arg Tyr Tyr Asn Leu
        275                 280                 285

Ser Asp Glu Glu Leu Ser Gln Phe Ile Gly Lys Ala Ser Asn Phe Gly
    290                 295                 300

Gln Gln Glu Tyr Ser Asn Asn Gln Leu Ile Thr Pro Val Val Asn Ser
305                 310                 315                 320

Ser Asp Gly Thr Val Lys Val Tyr Arg Ile Thr Arg Glu Tyr Thr Thr
                325                 330                 335

Asn Ala Tyr Gln Met Asp Val Glu Leu Phe Pro Phe Gly Gly Glu Asn
            340                 345                 350

Tyr Arg Leu Asp Tyr Lys Phe Lys Asn Phe Tyr Asn Ala Ser Tyr Leu
        355                 360                 365
```

-continued

```
Ser Ile Lys Leu Asn Asp Lys Arg Glu Leu Val Arg Thr Glu Gly Ala
370                 375                 380

Pro Gln Val Asn Ile Glu Tyr Ser Ala Asn Ile Thr Leu Asn Thr Ala
385                 390                 395                 400

Asp Ile Ser Gln Pro Phe Glu Ile Gly Leu Thr Arg Val Leu Pro Ser
                405                 410                 415

Gly Ser Trp Ala Tyr Ala Ala Lys Phe Thr Val Glu Glu Tyr Asn
                420                 425                 430

Gln Tyr Ser Phe Leu Leu Lys Leu Asn Lys Ala Ile Arg Leu Ser Arg
                435                 440                 445

Ala Thr Glu Leu Ser Pro Thr Ile Leu Glu Gly Ile Val Arg Ser Val
    450                 455                 460

Asn Leu Gln Leu Asp Ile Asn Thr Asp Val Leu Gly Lys Val Phe Leu
465                 470                 475                 480

Thr Lys Tyr Tyr Met Gln Arg Tyr Ala Ile His Ala Glu Thr Ala Leu
                485                 490                 495

Ile Leu Cys Asn Ala Pro Ile Ser Gln Arg Ser Tyr Asp Asn Gln Pro
                500                 505                 510

Ser Gln Phe Asp Arg Leu Phe Asn Thr Pro Leu Leu Asn Gly Gln Tyr
                515                 520                 525

Phe Ser Thr Gly Asp Glu Glu Ile Asp Leu Asn Ser Gly Ser Thr Gly
                530                 535                 540

Asp Trp Arg Lys Thr Ile Leu Lys Arg Ala Phe Asn Ile Asp Asp Val
545                 550                 555                 560

Ser Leu Phe Arg Leu Leu Lys Ile Thr Asp His Asp Asn Lys Asp Gly
                565                 570                 575

Lys Ile Lys Asn Asn Leu Lys Asn Leu Ser Asn Leu Tyr Ile Gly Lys
                580                 585                 590

Leu Leu Ala Asp Ile His Gln Leu Thr Ile Asp Glu Leu Asp Leu Leu
                595                 600                 605

Leu Ile Ala Val Gly Glu Gly Lys Thr Asn Leu Ser Ala Ile Ser Asp
    610                 615                 620

Lys Gln Leu Ala Thr Leu Ile Arg Lys Leu Asn Thr Ile Thr Ser Trp
625                 630                 635                 640

Leu His Thr Gln Lys Trp Ser Val Phe Gln Leu Phe Ile Met Thr Ser
                645                 650                 655

Thr Ser Tyr Asn Lys Thr Leu Thr Pro Glu Ile Lys Asn Leu Leu Asp
                660                 665                 670

Thr Val Tyr His Gly Leu Gln Gly Phe Asp Lys Asp Lys Ala Asp Leu
                675                 680                 685

Leu His Val Met Ala Pro Tyr Ile Ala Ala Thr Leu Gln Leu Ser Ser
    690                 695                 700

Glu Asn Val Ala His Ser Val Leu Leu Trp Ala Asp Lys Leu Gln Pro
705                 710                 715                 720

Gly Asp Gly Ala Met Thr Ala Glu Lys Phe Trp Asp Trp Leu Asn Thr
                725                 730                 735

Lys Tyr Thr Pro Gly Ser Ser Glu Ala Val Glu Thr Gln Glu His Ile
                740                 745                 750

Val Gln Tyr Cys Gln Ala Leu Ala Gln Leu Glu Met Val Tyr His Ser
                755                 760                 765

Thr Gly Ile Asn Glu Asn Ala Phe Arg Leu Phe Val Thr Lys Pro Glu
    770                 775                 780

Met Phe Gly Ala Ala Thr Gly Ala Ala Pro Ala His Asp Ala Leu Ser
```

-continued

```
            785                 790                 795                 800
Leu Ile Met Leu Thr Arg Phe Ala Asp Trp Val Asn Ala Leu Gly Glu
                805                 810                 815
Lys Ala Ser Ser Val Leu Ala Ala Phe Glu Ala Asn Ser Leu Thr Ala
                820                 825                 830
Glu Gln Leu Ala Asp Ala Met Asn Leu Asp Ala Asn Leu Leu Leu Gln
                835                 840                 845
Ala Ser Ile Gln Ala Gln Asn His Gln His Leu Pro Pro Val Thr Pro
            850                 855                 860
Glu Asn Ala Phe Ser Cys Trp Thr Ser Ile Asn Thr Ile Leu Gln Trp
865                 870                 875                 880
Val Asn Val Ala Gln Gln Leu Asn Val Ala Pro Gln Gly Val Ser Ala
                885                 890                 895
Leu Val Gly Leu Asp Tyr Ile Gln Ser Met Lys Glu Thr Pro Thr Tyr
                900                 905                 910
Ala Gln Trp Glu Asn Ala Ala Gly Val Leu Thr Ala Gly Leu Asn Ser
                915                 920                 925
Gln Gln Ala Asn Thr Leu His Ala Phe Leu Asp Glu Ser Arg Ser Ala
            930                 935                 940
Ala Leu Ser Thr Tyr Tyr Ile Arg Gln Val Ala Lys Ala Ala Ala Ala
945                 950                 955                 960
Ile Lys Ser Arg Asp Asp Leu Tyr Gln Tyr Leu Leu Ile Asp Asn Gln
                965                 970                 975
Val Ser Ala Ala Ile Lys Thr Arg Ile Ala Glu Ala Ile Ala Ser
                980                 985                 990
Ile Gln Leu Tyr Val Asn Arg Ala Leu Glu Asn Val Glu Glu Asn Ala
                995                 1000                1005
Asn Ser Gly Val Ile Ser Arg Gln Phe Phe Ile Asp Trp Asp Lys Tyr
            1010                1015                1020
Asn Lys Arg Tyr Ser Thr Trp Ala Gly Val Ser Gln Leu Val Tyr Tyr
1025                1030                1035                1040
Pro Glu Asn Tyr Ile Asp Pro Thr Met Arg Ile Gly Gln Thr Lys Met
                1045                1050                1055
Met Asp Ala Leu Leu Gln Ser Val Ser Gln Ser Gln Leu Asn Ala Asp
                1060                1065                1070
Thr Val Glu Asp Ala Phe Met Ser Tyr Leu Thr Ser Phe Glu Gln Val
            1075                1080                1085
Ala Asn Leu Lys Val Ile Ser Ala Tyr His Asp Asn Ile Asn Asn Asp
            1090                1095                1100
Gln Gly Leu Thr Tyr Phe Ile Gly Leu Ser Glu Thr Asp Ala Gly Glu
1105                1110                1115                1120
Tyr Tyr Trp Arg Ser Val Asp His Ser Lys Phe Asn Asp Gly Lys Phe
                1125                1130                1135
Ala Ala Asn Ala Trp Ser Glu Trp His Lys Ile Asp Cys Pro Ile Asn
                1140                1145                1150
Pro Tyr Lys Ser Thr Ile Arg Pro Val Ile Tyr Lys Ser Arg Leu Tyr
            1155                1160                1165
Leu Leu Trp Leu Glu Gln Lys Glu Ile Thr Lys Gln Thr Gly Asn Ser
            1170                1175                1180
Lys Asp Gly Tyr Gln Thr Glu Thr Asp Tyr Arg Tyr Glu Leu Lys Leu
1185                1190                1195                1200
Ala His Ile Arg Tyr Asp Gly Thr Trp Asn Thr Pro Ile Thr Phe Asp
                1205                1210                1215
```

-continued

Val Asn Lys Lys Ile Ser Glu Leu Lys Leu Glu Lys Asn Arg Ala Pro
        1220                1225                1230

Gly Leu Tyr Cys Ala Gly Tyr Gln Gly Glu Asp Thr Leu Leu Val Met
            1235                1240                1245

Phe Tyr Asn Gln Gln Asp Thr Leu Asp Ser Tyr Lys Asn Ala Ser Met
    1250                1255                1260

Gln Gly Leu Tyr Ile Phe Ala Asp Met Ala Ser Lys Asp Met Thr Pro
1265                1270                1275                1280

Glu Gln Ser Asn Val Tyr Arg Asp Asn Ser Tyr Gln Gln Phe Asp Thr
                1285                1290                1295

Asn Asn Val Arg Arg Val Asn Arg Tyr Ala Glu Asp Tyr Glu Ile
            1300                1305                1310

Pro Ser Ser Val Ser Ser Arg Lys Asp Tyr Gly Trp Gly Asp Tyr Tyr
                1315                1320                1325

Leu Ser Met Val Tyr Asn Gly Asp Ile Pro Thr Ile Asn Tyr Lys Ala
    1330                1335                1340

Ala Ser Ser Asp Leu Lys Ile Tyr Ile Ser Pro Lys Leu Arg Ile Ile
1345                1350                1355                1360

His Asn Gly Tyr Glu Gly Gln Lys Arg Asn Gln Cys Asn Leu Met Asn
                1365                1370                1375

Lys Tyr Gly Lys Leu Gly Asp Lys Phe Ile Val Tyr Thr Ser Leu Gly
            1380                1385                1390

Val Asn Pro Asn Asn Ser Ser Asn Lys Leu Met Phe Tyr Pro Val Tyr
        1395                1400                1405

Gln Tyr Ser Gly Asn Thr Ser Gly Leu Asn Gln Gly Arg Leu Leu Phe
    1410                1415                1420

His Arg Asp Thr Thr Tyr Pro Ser Lys Val Glu Ala Trp Ile Pro Gly
1425                1430                1435                1440

Ala Lys Arg Ser Leu Thr Asn Gln Asn Ala Ala Ile Gly Asp Asp Tyr
            1445                1450                1455

Ala Thr Asp Ser Leu Asn Lys Pro Asp Asp Leu Lys Gln Tyr Ile Phe
        1460                1465                1470

Met Thr Asp Ser Lys Gly Thr Ala Thr Asp Val Ser Gly Pro Val Glu
    1475                1480                1485

Ile Asn Thr Ala Ile Ser Pro Ala Lys Val Gln Ile Ile Val Lys Ala
    1490                1495                1500

Gly Gly Lys Glu Gln Thr Phe Thr Ala Asp Lys Asp Val Ser Ile Gln
1505                1510                1515                1520

Pro Ser Pro Ser Phe Asp Glu Met Asn Tyr Gln Phe Asn Ala Leu Glu
                1525                1530                1535

Ile Asp Gly Ser Gly Leu Asn Phe Ile Asn Asn Ser Ala Ser Ile Asp
            1540                1545                1550

Val Thr Phe Thr Ala Phe Ala Glu Asp Gly Arg Lys Leu Gly Tyr Glu
        1555                1560                1565

Ser Phe Ser Ile Pro Val Thr Leu Lys Val Ser Thr Asp Asn Ala Leu
    1570                1575                1580

Thr Leu His His Asn Glu Asn Gly Ala Gln Tyr Met Gln Trp Gln Ser
1585                1590                1595                1600

Tyr Arg Thr Arg Leu Asn Thr Leu Phe Ala Arg Gln Leu Val Ala Arg
                1605                1610                1615

Ala Thr Thr Gly Ile Asp Thr Ile Leu Ser Met Glu Thr Gln Asn Ile
            1620                1625                1630

-continued

```
Gln Glu Pro Gln Leu Gly Lys Gly Phe Tyr Ala Thr Phe Val Ile Pro
        1635                1640                1645
Pro Tyr Asn Leu Ser Thr His Gly Asp Glu Arg Trp Phe Lys Leu Tyr
        1650                1655                1660
Ile Lys His Val Val Asp Asn Ser His Ile Ile Tyr Ser Gly Gln
1665                1670                1675                1680
Leu Thr Asp Thr Asn Ile Asn Ile Thr Leu Phe Ile Pro Leu Asp Asp
                    1685                1690                1695
Val Pro Leu Asn Gln Asp Tyr His Ala Lys Val Tyr Met Thr Phe Lys
            1700                1705                1710
Lys Ser Pro Ser Asp Gly Thr Trp Trp Gly Pro His Phe Val Arg Asp
        1715                1720                1725
Asp Lys Gly Ile Val Thr Ile Asn Pro Lys Ser Ile Leu Thr His Phe
    1730                1735                1740
Glu Ser Val Asn Val Leu Asn Asn Ile Ser Ser Glu Pro Met Asp Phe
1745                1750                1755                1760
Ser Gly Ala Asn Ser Leu Tyr Phe Trp Glu Leu Phe Tyr Tyr Thr Pro
                1765                1770                1775
Met Leu Val Ala Gln Arg Leu Leu His Glu Gln Asn Phe Asp Glu Ala
            1780                1785                1790
Asn Arg Trp Leu Lys Tyr Val Trp Ser Pro Ser Gly Tyr Ile Val His
        1795                1800                1805
Gly Gln Ile Gln Asn Tyr Gln Trp Asn Val Arg Pro Leu Leu Glu Asp
    1810                1815                1820
Thr Ser Trp Asn Ser Asp Pro Leu Asp Ser Val Asp Pro Asp Ala Val
1825                1830                1835                1840
Ala Gln His Asp Pro Met His Tyr Lys Val Ser Thr Phe Met Arg Thr
                1845                1850                1855
Leu Asp Leu Leu Ile Ala Arg Gly Asp His Ala Tyr Arg Gln Leu Glu
            1860                1865                1870
Arg Asp Thr Leu Asn Glu Ala Lys Met Trp Tyr Met Gln Ala Leu His
        1875                1880                1885
Leu Leu Gly Asp Lys Pro Tyr Leu Pro Leu Ser Thr Thr Trp Ser Asp
    1890                1895                1900
Pro Arg Leu Asp Arg Ala Ala Asp Ile Thr Thr Gln Asn Ala His Asp
1905                1910                1915                1920
Ser Ala Ile Val Ala Leu Arg Gln Asn Ile Pro Thr Pro Ala Pro Leu
                1925                1930                1935
Ser Leu Arg Ser Ala Asn Thr Leu Thr Asp Leu Phe Leu Pro Gln Ile
            1940                1945                1950
Asn Glu Val Met Met Asn Tyr Trp Gln Thr Leu Ala Gln Arg Val Tyr
        1955                1960                1965
Asn Leu Arg His Asn Leu Ser Ile Asp Gly Gln Pro Leu Tyr Leu Pro
    1970                1975                1980
Ile Tyr Ala Thr Pro Ala Asp Pro Lys Ala Leu Leu Ser Ala Ala Val
1985                1990                1995                2000
Ala Thr Ser Gln Gly Gly Lys Leu Pro Glu Ser Phe Met Ser Leu
                2005                2010                2015
Trp Arg Phe Pro His Met Leu Glu Asn Ala Arg Gly Met Val Ser Gln
            2020                2025                2030
Leu Thr Gln Phe Gly Ser Thr Leu Gln Asn Ile Ile Glu Arg Gln Asp
        2035                2040                2045
Ala Glu Ala Leu Asn Ala Leu Leu Gln Asn Gln Ala Ala Glu Leu Ile
```

```
                2050                2055                2060
Leu Thr Asn Leu Ser Ile Gln Asp Lys Thr Ile Glu Glu Leu Asp Ala
2065                2070                2075                2080

Glu Lys Thr Val Leu Glu Lys Ser Lys Ala Gly Ala Gln Ser Arg Phe
            2085                2090                2095

Asp Ser Tyr Gly Lys Leu Tyr Asp Glu Asn Ile Asn Ala Gly Glu Asn
            2100                2105                2110

Gln Ala Met Thr Leu Arg Ala Ser Ala Ala Gly Leu Thr Thr Ala Val
            2115                2120                2125

Gln Ala Ser Arg Leu Ala Gly Ala Ala Asp Leu Val Pro Asn Ile
            2130                2135                2140

Phe Gly Phe Ala Gly Gly Gly Ser Arg Trp Gly Ala Ile Ala Glu Ala
2145                2150                2155                2160

Thr Gly Tyr Val Met Glu Phe Ser Ala Asn Val Met Asn Thr Glu Ala
            2165                2170                2175

Asp Lys Ile Ser Gln Ser Glu Thr Tyr Arg Arg Arg Gln Glu Trp
            2180                2185                2190

Glu Ile Gln Arg Asn Asn Ala Glu Ala Glu Leu Lys Gln Ile Asp Ala
            2195                2200                2205

Gln Leu Lys Ser Leu Ala Val Arg Arg Glu Ala Ala Val Leu Gln Lys
            2210                2215                2220

Thr Ser Leu Lys Thr Gln Gln Glu Gln Thr Gln Ser Gln Leu Ala Phe
2225                2230                2235                2240

Leu Gln Arg Lys Phe Ser Asn Gln Ala Leu Tyr Asn Trp Leu Arg Gly
            2245                2250                2255

Arg Leu Ala Ala Ile Tyr Phe Gln Phe Tyr Asp Leu Ala Val Ala Arg
            2260                2265                2270

Cys Leu Met Ala Glu Gln Ala Tyr Arg Trp Glu Leu Asn Asp Asp Ser
            2275                2280                2285

Ala Arg Phe Ile Lys Pro Gly Ala Trp Gln Gly Thr Tyr Ala Gly Leu
            2290                2295                2300

Leu Ala Gly Glu Thr Leu Met Leu Ser Leu Ala Gln Met Glu Asp Ala
2305                2310                2315                2320

His Leu Lys Arg Asp Lys Arg Ala Leu Glu Val Glu Arg Thr Val Ser
            2325                2330                2335

Leu Ala Glu Val Tyr Ala Gly Leu Pro Lys Asp Asn Gly Pro Phe Ser
            2340                2345                2350

Leu Ala Gln Glu Ile Asp Lys Leu Val Ser Gln Gly Ser Gly Ser Ala
            2355                2360                2365

Gly Ser Gly Asn Asn Asn Leu Ala Phe Gly Ala Gly Thr Asp Thr Lys
            2370                2375                2380

Thr Ser Leu Gln Ala Ser Val Ser Phe Ala Asp Leu Lys Ile Arg Glu
2385                2390                2395                2400

Asp Tyr Pro Ala Ser Leu Gly Lys Ile Arg Arg Ile Lys Gln Ile Ser
            2405                2410                2415

Val Thr Leu Pro Ala Leu Leu Gly Pro Tyr Gln Asp Val Gln Ala Ile
            2420                2425                2430

Leu Ser Tyr Gly Asp Lys Ala Gly Leu Ala Asn Gly Cys Glu Ala Leu
            2435                2440                2445

Ala Val Ser His Gly Met Asn Asp Ser Gly Gln Phe Gln Leu Asp Phe
            2450                2455                2460

Asn Asp Gly Lys Phe Leu Pro Phe Glu Gly Ile Ala Ile Asp Gln Gly
2465                2470                2475                2480
```

-continued

```
Thr Leu Thr Leu Ser Phe Pro Asn Ala Ser Met Pro Glu Lys Gly Lys
            2485                2490                2495

Gln Ala Thr Met Leu Lys Thr Leu Asn Asp Ile Ile Leu His Ile Arg
            2500                2505                2510

Tyr Thr Ile Lys
            2516

(2) INFORMATION FOR SEQ ID NO:48:

(i) SEQUENCE CHARACTERISTICS:
        (A) LENGTH: 5547 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:48 (TCDAII CODING:region):

CTG ATA GGC TAT AAC AAT CAA TTT AGC GGT AGA GCC AGT CAA TAT GTT       48
Leu Ile Gly Tyr Asn Asn Gln Phe Ser Gly Arg Ala Ser Gln Tyr Val
 1               5                  10                  15

GCG CCG GGT ACC GTT TCT TCC ATG TTC TCC CCC GCC GCT TAT TTG ACT       96
Ala Pro Gly Thr Val Ser Ser Met Phe Ser Pro Ala Ala Tyr Leu Thr
             20                  25                  30

GAA CTT TAT CGT GAA GCA CGC AAT TTA CAC GCA AGT GAC TCC GTT TAT      144
Glu Leu Tyr Arg Glu Ala Arg Asn Leu His Ala Ser Asp Ser Val Tyr
         35                  40                  45

TAT CTG GAT ACC CGC CGC CCA GAT CTC AAA TCA ATG GCG CTC AGT CAG      192
Tyr Leu Asp Thr Arg Arg Pro Asp Leu Lys Ser Met Ala Leu Ser Gln
     50                  55                  60

CAA AAT ATG GAT ATA GAA TTA TCC ACA CTC TCT TTG TCC AAT GAG CTG      240
Gln Asn Met Asp Ile Glu Leu Ser Thr Leu Ser Leu Ser Asn Glu Leu
 65                  70                  75                  80

TTA TTG GAA AGC ATT AAA ACT GAA TCT AAA CTG GAA AAC TAT ACT AAA      288
Leu Leu Glu Ser Ile Lys Thr Glu Ser Lys Leu Glu Asn Tyr Thr Lys
                 85                  90                  95

GTG ATG GAA ATG CTC TCC ACT TTC CGT CCT TCC GGC GCA ACG CCT TAT      336
Val Met Glu Met Leu Ser Thr Phe Arg Pro Ser Gly Ala Thr Pro Tyr
            100                 105                 110

CAT GAT GCT TAT GAA AAT GTG CGT GAA GTT ATC CAG CTA CAA GAT CCT      384
His Asp Ala Tyr Glu Asn Val Arg Glu Val Ile Gln Leu Gln Asp Pro
        115                 120                 125

GGA CTT GAG CAA CTC AAT GCA TCA CCG GCA ATT GCC GGG TTG ATG CAT      432
Gly Leu Glu Gln Leu Asn Ala Ser Pro Ala Ile Ala Gly Leu Met His
    130                 135                 140

CAA GCC TCC CTA TTG GGT ATT AAC GCT TCA ATC TCG CCT GAG CTA TTT      480
Gln Ala Ser Leu Leu Gly Ile Asn Ala Ser Ile Ser Pro Glu Leu Phe
145                 150                 155                 160

AAT ATT CTG ACG GAG GAG ATT ACC GAA GGT AAT GCT GAG GAA CTT TAT      528
Asn Ile Leu Thr Glu Glu Ile Thr Glu Gly Asn Ala Glu Glu Leu Tyr
                165                 170                 175

AAG AAA AAT TTT GGT AAT ATC GAA CCG GCC TCA TTG GCT ATG CCG GAA      576
Lys Lys Asn Phe Gly Asn Ile Glu Pro Ala Ser Leu Ala Met Pro Glu
            180                 185                 190

TAC CTT AAA CGT TAT TAT AAT TTA AGC GAT GAA GAA CTT AGT CAG TTT      624
Tyr Leu Lys Arg Tyr Tyr Asn Leu Ser Asp Glu Glu Leu Ser Gln Phe
        195                 200                 205

ATT GGT AAA GCC AGC AAT TTT GGT CAA CAG GAA TAT AGT AAT AAC CAA      672
Ile Gly Lys Ala Ser Asn Phe Gly Gln Gln Glu Tyr Ser Asn Asn Gln
    210                 215                 220
```

-continued

| | |
|---|---|
| CTT ATT ACT CCG GTA GTC AAC AGC AGT GAT GGC ACG GTT AAG GTA TAT<br>Leu Ile Thr Pro Val Val Asn Ser Ser Asp Gly Thr Val Lys Val Tyr<br>225                     230                           235                     240 | 720 |
| CGG ATC ACC CGC GAA TAT ACA ACC AAT GCT TAT CAA ATG GAT GTG GAG<br>Arg Ile Thr Arg Glu Tyr Thr Thr Asn Ala Tyr Gln Met Asp Val Glu<br>245                     250                     255 | 768 |
| CTA TTT CCC TTC GGT GGT GAG AAT TAT CGG TTA GAT TAT AAA TTC AAA<br>Leu Phe Pro Phe Gly Gly Glu Asn Tyr Arg Leu Asp Tyr Lys Phe Lys<br>260                     265                     270 | 816 |
| AAT TTT TAT AAT GCC TCT TAT TTA TCC ATC AAG TTA AAT GAT AAA AGA<br>Asn Phe Tyr Asn Ala Ser Tyr Leu Ser Ile Lys Leu Asn Asp Lys Arg<br>275                     280                     285 | 864 |
| GAA CTT GTT CGA ACT GAA GGC GCT CCT CAA GTC AAT ATA GAA TAC TCC<br>Glu Leu Val Arg Thr Glu Gly Ala Pro Gln Val Asn Ile Glu Tyr Ser<br>290                     295                     300 | 912 |
| GCA AAT ATC ACA TTA AAT ACC GCT GAT ATC AGT CAA CCT TTT GAA ATT<br>Ala Asn Ile Thr Leu Asn Thr Ala Asp Ile Ser Gln Pro Phe Glu Ile<br>305                     310                     315                     320 | 960 |
| GGC CTG ACA CGA GTA CTT CCT TCC GGT TCT TGG GCA TAT GCC GCC GCA<br>Gly Leu Thr Arg Val Leu Pro Ser Gly Ser Trp Ala Tyr Ala Ala Ala<br>                  325                     330                     335 | 1008 |
| AAA TTT ACC GTT GAA GAG TAT AAC CAA TAC TCT TTT CTG CTA AAA CTT<br>Lys Phe Thr Val Glu Glu Tyr Asn Gln Tyr Ser Phe Leu Leu Lys Leu<br>                  340                     345                     350 | 1056 |
| AAC AAG GCT ATT CGT CTA TCA CGT GCG ACA GAA TTG TCA CCC ACG ATT<br>Asn Lys Ala Ile Arg Leu Ser Arg Ala Thr Glu Leu Ser Pro Thr Ile<br>                  355                     360                     365 | 1104 |
| CTG GAA GGC ATT GTG CGC AGT GTT AAT CTA CAA CTG GAT ATC AAC ACA<br>Leu Glu Gly Ile Val Arg Ser Val Asn Leu Gln Leu Asp Ile Asn Thr<br>370                     375                     380 | 1152 |
| GAC GTA TTA GGT AAA GTT TTT CTG ACT AAA TAT TAT ATG CAG CGT TAT<br>Asp Val Leu Gly Lys Val Phe Leu Thr Lys Tyr Tyr Met Gln Arg Tyr<br>385                     390                     395                     400 | 1200 |
| GCT ATT CAT GCT GAA ACT GCC CTG ATA CTA TGC AAC GCG CCT ATT TCA<br>Ala Ile His Ala Glu Thr Ala Leu Ile Leu Cys Asn Ala Pro Ile Ser<br>                  405                     410                     415 | 1248 |
| CAA CGT TCA TAT GAT AAT CAA CCT AGC CAA TTT GAT CGC CTG TTT AAT<br>Gln Arg Ser Tyr Asp Asn Gln Pro Ser Gln Phe Asp Arg Leu Phe Asn<br>                  420                     425                     430 | 1296 |
| ACG CCA TTA CTG AAC GGA CAA TAT TTT TCT ACC GGC GAT GAG GAG ATT<br>Thr Pro Leu Leu Asn Gly Gln Tyr Phe Ser Thr Gly Asp Glu Glu Ile<br>                  435                     440                     445 | 1344 |
| GAT TTA AAT TCA GGT AGC ACC GGC GAT TGG CGA AAA ACC ATA CTT AAG<br>Asp Leu Asn Ser Gly Ser Thr Gly Asp Trp Arg Lys Thr Ile Leu Lys<br>450                     455                     460 | 1392 |
| CGT GCA TTT AAT ATT GAT GAT GTC TCG CTC TTC CGC CTG CTT AAA ATT<br>Arg Ala Phe Asn Ile Asp Asp Val Ser Leu Phe Arg Leu Leu Lys Ile<br>465                     470                     475                     480 | 1440 |
| ACC GAC CAT GAT AAT AAA GAT GGA AAA ATT AAA AAT AAC CTA AAG AAT<br>Thr Asp His Asp Asn Lys Asp Gly Lys Ile Lys Asn Asn Leu Lys Asn<br>                  485                     490                     495 | 1488 |
| CTT TCC AAT TTA TAT ATT GGA AAA TTA CTG GCA GAT ATT CAT CAA TTA<br>Leu Ser Asn Leu Tyr Ile Gly Lys Leu Leu Ala Asp Ile His Gln Leu<br>                  500                     505                     510 | 1536 |
| ACC ATT GAT GAA CTG GAT TTA TTA CTG ATT GCC GTA GGT GAA GGA AAA<br>Thr Ile Asp Glu Leu Asp Leu Leu Leu Ile Ala Val Gly Glu Gly Lys<br>                  515                     520                     525 | 1584 |
| ACT AAT TTA TCC GCT ATC AGT GAT AAG CAA TTG GCT ACC CTG ATC AGA<br>Thr Asn Leu Ser Ala Ile Ser Asp Lys Gln Leu Ala Thr Leu Ile Arg<br>530                     535                     540 | 1632 |

```
                                                    -continued

AAA CTC AAT ACT ATT ACC AGC TGG CTA CAT ACA CAG AAG TGG AGT GTA         1680
Lys Leu Asn Thr Ile Thr Ser Trp Leu His Thr Gln Lys Trp Ser Val
545                 550                 555                 560

TTC CAG CTA TTT ATC ATG ACC TCC ACC AGC TAT AAC AAA ACG CTA ACG         1728
Phe Gln Leu Phe Ile Met Thr Ser Thr Ser Tyr Asn Lys Thr Leu Thr
                565                 570                 575

CCT GAA ATT AAG AAT TTG CTG GAT ACC GTC TAC CAC GGT TTA CAA GGT         1776
Pro Glu Ile Lys Asn Leu Leu Asp Thr Val Tyr His Gly Leu Gln Gly
            580                 585                 590

TTT GAT AAA GAC AAA GCA GAT TTG CTA CAT GTC ATG GCG CCC TAT ATT         1824
Phe Asp Lys Asp Lys Ala Asp Leu Leu His Val Met Ala Pro Tyr Ile
        595                 600                 605

GCG GCC ACC TTG CAA TTA TCA TCG GAA AAT GTC GCC CAC TCG GTA CTC         1872
Ala Ala Thr Leu Gln Leu Ser Ser Glu Asn Val Ala His Ser Val Leu
    610                 615                 620

CTT TGG GCA GAT AAG TTA CAG CCC GGC GAC GGC GCA ATG ACA GCA GAA         1920
Leu Trp Ala Asp Lys Leu Gln Pro Gly Asp Gly Ala Met Thr Ala Glu
625                 630                 635                 640

AAA TTC TGG GAC TGG TTG AAT ACT AAG TAT ACG CCG GGT TCA TCG GAA         1968
Lys Phe Trp Asp Trp Leu Asn Thr Lys Tyr Thr Pro Gly Ser Ser Glu
                645                 650                 655

GCC GTA GAA ACG CAG GAA CAT ATC GTT CAG TAT TGT CAG GCT CTG GCA         2016
Ala Val Glu Thr Gln Glu His Ile Val Gln Tyr Cys Gln Ala Leu Ala
            660                 665                 670

CAA TTG GAA ATG GTT TAC CAT TCC ACC GGC ATC AAC GAA AAC GCC TTC         2064
Gln Leu Glu Met Val Tyr His Ser Thr Gly Ile Asn Glu Asn Ala Phe
        675                 680                 685

CGT CTA TTT GTG ACA AAA CCA GAG ATG TTT GGC GCT GCA ACT GGA GCA         2112
Arg Leu Phe Val Thr Lys Pro Glu Met Phe Gly Ala Ala Thr Gly Ala
    690                 695                 700

GCG CCC GCG CAT GAT GCC CTT TCA CTG ATT ATG CTG ACA CGT TTT GCG         2160
Ala Pro Ala His Asp Ala Leu Ser Leu Ile Met Leu Thr Arg Phe Ala
705                 710                 715                 720

GAT TGG GTG AAC GCA CTA GGC GAA AAA GCG TCC TCG GTG CTA GCG GCA         2208
Asp Trp Val Asn Ala Leu Gly Glu Lys Ala Ser Ser Val Leu Ala Ala
                725                 730                 735

TTT GAA GCT AAC TCG TTA ACG GCA GAA CAA CTG GCT GAT GCC ATG AAT         2256
Phe Glu Ala Asn Ser Leu Thr Ala Glu Gln Leu Ala Asp Ala Met Asn
            740                 745                 750

CTT GAT GCT AAT TTG CTG TTG CAA GCC AGT ATT CAA GCA CAA AAT CAT         2304
Leu Asp Ala Asn Leu Leu Leu Gln Ala Ser Ile Gln Ala Gln Asn His
        755                 760                 765

CAA CAT CTT CCC CCA GTA ACT CCA GAA AAT GCG TTC TCC TGT TGG ACA         2352
Gln His Leu Pro Pro Val Thr Pro Glu Asn Ala Phe Ser Cys Trp Thr
    770                 775                 780

TCT ATC AAT ACT ATC CTG CAA TGG GTT AAT GTC GCA CAA CAA TTG AAT         2400
Ser Ile Asn Thr Ile Leu Gln Trp Val Asn Val Ala Gln Gln Leu Asn
785                 790                 795                 800

GTC GCC CCA CAG GGC GTT TCC GCT TTG GTC GGG CTG GAT TAT ATT CAA         2448
Val Ala Pro Gln Gly Val Ser Ala Leu Val Gly Leu Asp Tyr Ile Gln
                805                 810                 815

TCA ATG AAA GAG ACA CCG ACC TAT GCC CAG TGG GAA AAC GCG GCA GGC         2496
Ser Met Lys Glu Thr Pro Thr Tyr Ala Gln Trp Glu Asn Ala Ala Gly
            820                 825                 830

GTA TTA ACC GCC GGG TTG AAT TCA CAA CAG GCT AAT ACA TTA CAC GCT         2544
Val Leu Thr Ala Gly Leu Asn Ser Gln Gln Ala Asn Thr Leu His Ala
        835                 840                 845

TTT CTG GAT GAA TCT CGC AGT GCC GCA TTA AGC ACC TAC TAT ATC CGT         2592
Phe Leu Asp Glu Ser Arg Ser Ala Ala Leu Ser Thr Tyr Tyr Ile Arg
```

-continued

```
              850                 855                 860
CAA GTC GCC AAG GCA GCG GCG GCT ATT AAA AGC CGT GAT GAC TTG TAT        2640
Gln Val Ala Lys Ala Ala Ala Ala Ile Lys Ser Arg Asp Asp Leu Tyr
865                 870                 875                 880

CAA TAC TTA CTG ATT GAT AAT CAG GTT TCT GCG GCA ATA AAA ACC ACC        2688
Gln Tyr Leu Leu Ile Asp Asn Gln Val Ser Ala Ala Ile Lys Thr Thr
                    885                 890                 895

CGG ATC GCC GAA GCC ATT GCC AGT ATT CAA CTG TAC GTC AAC CGG GCA        2736
Arg Ile Ala Glu Ala Ile Ala Ser Ile Gln Leu Tyr Val Asn Arg Ala
            900                 905                 910

TTG GAA AAT GTG GAA GAA AAT GCC AAT TCG GGG GTT ATC AGC CGC CAA        2784
Leu Glu Asn Val Glu Glu Asn Ala Asn Ser Gly Val Ile Ser Arg Gln
        915                 920                 925

TTC TTT ATC GAC TGG GAC AAA TAC AAT AAA CGC TAC AGC ACT TGG GCG        2832
Phe Phe Ile Asp Trp Asp Lys Tyr Asn Lys Arg Tyr Ser Thr Trp Ala
930                 935                 940

GGT GTT TCT CAA TTA GTT TAC TAC CCG GAA AAC TAT ATT GAT CCG ACC        2880
Gly Val Ser Gln Leu Val Tyr Tyr Pro Glu Asn Tyr Ile Asp Pro Thr
945                 950                 955                 960

ATG CGT ATC GGA CAA ACC AAA ATG ATG GAC GCA TTA CTG CAA TCC GTC        2928
Met Arg Ile Gly Gln Thr Lys Met Met Asp Ala Leu Leu Gln Ser Val
                    965                 970                 975

AGC CAA AGC CAA TTA AAC GCC GAT ACC GTC GAA GAT GCC TTT ATG TCT        2976
Ser Gln Ser Gln Leu Asn Ala Asp Thr Val Glu Asp Ala Phe Met Ser
            980                 985                 990

TAT CTG ACA TCG TTT GAA CAA GTG GCT AAT CTT AAA GTT ATT AGC GCA        3024
Tyr Leu Thr Ser Phe Glu Gln Val Ala Asn Leu Lys Val Ile Ser Ala
        995                 1000                1005

TAT CAC GAT AAT ATT AAT AAC GAT CAA GGG CTG ACC TAT TTT ATC GGA        3072
Tyr His Asp Asn Ile Asn Asn Asp Gln Gly Leu Thr Tyr Phe Ile Gly
    1010                1015                1020

CTC AGT GAA ACT GAT GCC GGT GAA TAT TAT TGG CGC AGT GTC GAT CAC        3120
Leu Ser Glu Thr Asp Ala Gly Glu Tyr Tyr Trp Arg Ser Val Asp His
1025                1030                1035                1040

AGT AAA TTC AAC GAC GGT AAA TTC GCG GCT AAT GCC TGG AGT GAA TGG        3168
Ser Lys Phe Asn Asp Gly Lys Phe Ala Ala Asn Ala Trp Ser Glu Trp
                    1045                1050                1055

CAT AAA ATT GAT TGT CCA ATT AAC CCT TAT AAA AGC ACT ATC CGT CCA        3216
His Lys Ile Asp Cys Pro Ile Asn Pro Tyr Lys Ser Thr Ile Arg Pro
            1060                1065                1070

GTG ATA TAT AAA TCC CGC CTG TAT CTG CTC TGG TTG GAA CAA AAG GAG        3264
Val Ile Tyr Lys Ser Arg Leu Tyr Leu Leu Trp Leu Glu Gln Lys Glu
        1075                1080                1085

ATC ACC AAA CAG ACA GGA AAT AGT AAA GAT GGC TAT CAA ACT GAA ACG        3312
Ile Thr Lys Gln Thr Gly Asn Ser Lys Asp Gly Tyr Gln Thr Glu Thr
    1090                1095                1100

GAT TAT CGT TAT GAA CTA AAA TTG GCG CAT ATC CGC TAT GAT GGC ACT        3360
Asp Tyr Arg Tyr Glu Leu Lys Leu Ala His Ile Arg Tyr Asp Gly Thr
1105                1110                1115                1120

TGG AAT ACG CCA ATC ACC TTT GAT GTC AAT AAA AAA ATA TCC GAG CTA        3408
Trp Asn Thr Pro Ile Thr Phe Asp Val Asn Lys Lys Ile Ser Glu Leu
                    1125                1130                1135

AAA CTG GAA AAA AAT AGA GCG CCC GGA CTC TAT TGT GCC GGT TAT CAA        3456
Lys Leu Glu Lys Asn Arg Ala Pro Gly Leu Tyr Cys Ala Gly Tyr Gln
            1140                1145                1150

GGT GAA GAT ACG TTG CTG GTG ATG TTT TAT AAC CAA CAA GAC ACA CTA        3504
Gly Glu Asp Thr Leu Leu Val Met Phe Tyr Asn Gln Gln Asp Thr Leu
        1155                1160                1165

GAT AGT TAT AAA AAC GCT TCA ATG CAA GGA CTA TAT ATC TTT GCT GAT        3552
```

```
                                    -continued

Asp Ser Tyr Lys Asn Ala Ser Met Gln Gly Leu Tyr Ile Phe Ala Asp
    1170                1175                1180

ATG GCA TCC AAA GAT ATG ACC CCA GAA CAG AGC AAT GTT TAT CGG GAT      3600
Met Ala Ser Lys Asp Met Thr Pro Glu Gln Ser Asn Val Tyr Arg Asp
1185                1190                1195                1200

AAT AGC TAT CAA CAA TTT GAT ACC AAT AAT GTC AGA AGA GTG AAT AAC      3648
Asn Ser Tyr Gln Gln Phe Asp Thr Asn Asn Val Arg Arg Val Asn Asn
                1205                1210                1215

CGC TAT GCA GAG GAT TAT GAG ATT CCT TCC TCG GTA AGT AGC CGT AAA      3696
Arg Tyr Ala Glu Asp Tyr Glu Ile Pro Ser Ser Val Ser Ser Arg Lys
            1220                1225                1230

GAC TAT GGT TGG GGA GAT TAT TAC CTC AGC ATG GTA TAT AAC GGA GAT      3744
Asp Tyr Gly Trp Gly Asp Tyr Tyr Leu Ser Met Val Tyr Asn Gly Asp
        1235                1240                1245

ATT CCA ACT ATC AAT TAC AAA GCC GCA TCA AGT GAT TTA AAA ATC TAT      3792
Ile Pro Thr Ile Asn Tyr Lys Ala Ala Ser Ser Asp Leu Lys Ile Tyr
    1250                1255                1260

ATC TCA CCA AAA TTA AGA ATT ATT CAT AAT GGA TAT GAA GGA CAG AAG      3840
Ile Ser Pro Lys Leu Arg Ile Ile His Asn Gly Tyr Glu Gly Gln Lys
1265                1270                1275                1280

CGC AAT CAA TGC AAT CTG ATG AAT AAA TAT GGC AAA CTA GGT GAT AAA      3888
Arg Asn Gln Cys Asn Leu Met Asn Lys Tyr Gly Lys Leu Gly Asp Lys
                1285                1290                1295

TTT ATT GTT TAT ACT AGC TTG GGG GTC AAT CCA AAT AAC TCG TCA AAT      3936
Phe Ile Val Tyr Thr Ser Leu Gly Val Asn Pro Asn Asn Ser Ser Asn
            1300                1305                1310

AAG CTC ATG TTT TAC CCC GTC TAT CAA TAT AGC GGA AAC ACC AGT GGA      3984
Lys Leu Met Phe Tyr Pro Val Tyr Gln Tyr Ser Gly Asn Thr Ser Gly
        1315                1320                1325

CTC AAT CAA GGG AGA CTA CTA TTC CAC CGT GAC ACC ACT TAT CCA TCT      4032
Leu Asn Gln Gly Arg Leu Leu Phe His Arg Asp Thr Thr Tyr Pro Ser
    1330                1335                1340

AAA GTA GAA GCT TGG ATT CCT GGA GCA AAA CGT TCT CTA ACC AAC CAA      4080
Lys Val Glu Ala Trp Ile Pro Gly Ala Lys Arg Ser Leu Thr Asn Gln
1345                1350                1355                1360

AAT GCC GCC ATT GGT GAT GAT TAT GCT ACA GAC TCT CTG AAT AAA CCG      4128
Asn Ala Ala Ile Gly Asp Asp Tyr Ala Thr Asp Ser Leu Asn Lys Pro
                1365                1370                1375

GAT GAT CTT AAG CAA TAT ATC TTT ATG ACT GAC AGT AAA GGG ACT GCT      4176
Asp Asp Leu Lys Gln Tyr Ile Phe Met Thr Asp Ser Lys Gly Thr Ala
            1380                1385                1390

ACT GAT GTC TCA GGC CCA GTA GAG ATT AAT ACT GCA ATT TCT CCA GCA      4224
Thr Asp Val Ser Gly Pro Val Glu Ile Asn Thr Ala Ile Ser Pro Ala
        1395                1400                1405

AAA GTT CAG ATA ATA GTC AAA GCG GGT GGC AAG GAG CAA ACT TTT ACC      4272
Lys Val Gln Ile Ile Val Lys Ala Gly Gly Lys Glu Gln Thr Phe Thr
    1410                1415                1420

GCA GAT AAA GAT GTC TCC ATT CAG CCA TCA CCT AGC TTT GAT GAA ATG      4320
Ala Asp Lys Asp Val Ser Ile Gln Pro Ser Pro Ser Phe Asp Glu Met
1425                1430                1435                1440

AAT TAT CAA TTT AAT GCC CTT GAA ATA GAC GGT TCT GGT CTG AAT TTT      4368
Asn Tyr Gln Phe Asn Ala Leu Glu Ile Asp Gly Ser Gly Leu Asn Phe
                1445                1450                1455

ATT AAC AAC TCA GCC AGT ATT GAT GTT ACT TTT ACC GCA TTT GCG GAG      4416
Ile Asn Asn Ser Ala Ser Ile Asp Val Thr Phe Thr Ala Phe Ala Glu
            1460                1465                1470

GAT GGC CGC AAA CTG GGT TAT GAA AGT TTC AGT ATT CCT GTT ACC CTC      4464
Asp Gly Arg Lys Leu Gly Tyr Glu Ser Phe Ser Ile Pro Val Thr Leu
        1475                1480                1485
```

-continued

```
AAG GTA AGT ACC GAT AAT GCC CTG ACC CTG CAC CAT AAT GAA AAT GGT      4512
Lys Val Ser Thr Asp Asn Ala Leu Thr Leu His His Asn Glu Asn Gly
    1490                1495                1500

GCG CAA TAT ATG CAA TGG CAA TCC TAT CGT ACC CGC CTG AAT ACT CTA      4560
Ala Gln Tyr Met Gln Trp Gln Ser Tyr Arg Thr Arg Leu Asn Thr Leu
1505                1510                1515                1520

TTT GCC CGC CAG TTG GTT GCA CGC GCC ACC ACC GGA ATC GAT ACA ATT      4608
Phe Ala Arg Gln Leu Val Ala Arg Ala Thr Thr Gly Ile Asp Thr Ile
                1525                1530                1535

CTG AGT ATG GAA ACT CAG AAT ATT CAG GAA CCG CAG TTA GGC AAA GGT      4656
Leu Ser Met Glu Thr Gln Asn Ile Gln Glu Pro Gln Leu Gly Lys Gly
    1540                1545                1550

TTC TAT GCT ACG TTC GTG ATA CCT CCC TAT AAC CTA TCA ACT CAT GGT      4704
Phe Tyr Ala Thr Phe Val Ile Pro Pro Tyr Asn Leu Ser Thr His Gly
1555                1560                1565

GAT GAA CGT TGG TTT AAG CTT TAT ATC AAA CAT GTT GTT GAT AAT AAT      4752
Asp Glu Arg Trp Phe Lys Leu Tyr Ile Lys His Val Val Asp Asn Asn
    1570                1575                1580

TCA CAT ATT ATC TAT TCA GGC CAG CTA ACA GAT ACA AAT ATA AAC ATC      4800
Ser His Ile Ile Tyr Ser Gly Gln Leu Thr Asp Thr Asn Ile Asn Ile
1585                1590                1595                1600

ACA TTA TTT ATT CCT CTT GAT GAT GTC CCA TTG AAT CAA GAT TAT CAC      4848
Thr Leu Phe Ile Pro Leu Asp Asp Val Pro Leu Asn Gln Asp Tyr His
                1605                1610                1615

GCC AAG GTT TAT ATG ACC TTC AAG AAA TCA CCA TCA GAT GGT ACC TGG      4896
Ala Lys Val Tyr Met Thr Phe Lys Lys Ser Pro Ser Asp Gly Thr Trp
    1620                1625                1630

TGG GGC CCT CAC TTT GTT AGA GAT GAT AAA GGA ATA GTA ACA ATA AAC      4944
Trp Gly Pro His Phe Val Arg Asp Asp Lys Gly Ile Val Thr Ile Asn
                1635                1640                1645

CCT AAA TCC ATT TTG ACC CAT TTT GAG AGC GTC AAT GTC CTG AAT AAT      4992
Pro Lys Ser Ile Leu Thr His Phe Glu Ser Val Asn Val Leu Asn Asn
    1650                1655                1660

ATT AGT AGC GAA CCA ATG GAT TTC AGC GGC GCT AAC AGC CTC TAT TTC      5040
Ile Ser Ser Glu Pro Met Asp Phe Ser Gly Ala Asn Ser Leu Tyr Phe
1665                1670                1675                1680

TGG GAA CTG TTC TAC TAT ACC CCG ATG CTG GTT GCT CAA CGT TTG CTG      5088
Trp Glu Leu Phe Tyr Tyr Thr Pro Met Leu Val Ala Gln Arg Leu Leu
                1685                1690                1695

CAT GAA CAG AAC TTC GAT GAA GCC AAC CGT TGG CTG AAA TAT GTC TGG      5136
His Glu Gln Asn Phe Asp Glu Ala Asn Arg Trp Leu Lys Tyr Val Trp
    1700                1705                1710

AGT CCA TCC GGT TAT ATT GTC CAC GGC CAG ATT CAG AAC TAC CAG TGG      5184
Ser Pro Ser Gly Tyr Ile Val His Gly Gln Ile Gln Asn Tyr Gln Trp
                1715                1720                1725

AAC GTC CGC CCG TTA CTG GAA GAC ACC AGT TGG AAC AGT GAT CCT TTG      5232
Asn Val Arg Pro Leu Leu Glu Asp Thr Ser Trp Asn Ser Asp Pro Leu
    1730                1735                1740

GAT TCC GTC GAT CCT GAC GCG GTA GCA CAG CAC GAT CCA ATG CAC TAC      5280
Asp Ser Val Asp Pro Asp Ala Val Ala Gln His Asp Pro Met His Tyr
1745                1750                1755                1760

AAA GTT TCA ACT TTT ATG CGT ACC TTG GAT CTA TTG ATA GCA CGC GGC      5328
Lys Val Ser Thr Phe Met Arg Thr Leu Asp Leu Leu Ile Ala Arg Gly
                1765                1770                1775

GAC CAT GCT TAT CGC CAA CTG GAA CGA GAT ACA CTC AAC GAA GCG AAG      5376
Asp His Ala Tyr Arg Gln Leu Glu Arg Asp Thr Leu Asn Glu Ala Lys
    1780                1785                1790

ATG TGG TAT ATG CAA GCG CTG CAT CTA TTA GGT GAC AAA CCT TAT CTA      5424
Met Trp Tyr Met Gln Ala Leu His Leu Leu Gly Asp Lys Pro Tyr Leu
                1795                1800                1805
```

-continued

```
CCG CTG AGT ACG ACA TGG AGT GAT CCA CGA CTA GAC AGA GCC GCG GAT    5472
Pro Leu Ser Thr Thr Trp Ser Asp Pro Arg Leu Asp Arg Ala Ala Asp
    1810                1815                1820

ATC ACT ACC CAA AAT GCT CAC GAC AGC GCA ATA GTC GCT CTG CGG CAG    5520
Ile Thr Thr Gln Asn Ala His Asp Ser Ala Ile Val Ala Leu Arg Gln
1825                1830                1835                1840

AAT ATA CCT ACA CCG GCA CCT TTA TCA                                5547
Asn Ile Pro Thr Pro Ala Pro Leu Ser
            1845            1849
```

(2) INFORMATION FOR SEQ ID NO:49:

(i) SEQUENCE CHARACTERISTICS:
        (A) LENGTH: 1849 amino acids
        (B) TYPE: amino acids
        (C) STRANDEDNESS: single
        (D) TOPOLOGY: linear (ii) MOLECULE TYPE: protein (xi) SEQUENCE DESCRIPTION: SEQ ID NO:49 (TCDAII):

FeaturesFrom ToDescription

Peptide11849TcdAii peptide

Fragment112TcdAii N-terminus (SEQ ID NO:13)

Fragment196211(SEQ ID NO:38)

Fragment466475(SEQ ID NO:17)

Fragment9931004(SEQ ID NO:23; 12/13)

Fragment12971312(SEQ ID NO:18)

Fragment13901409(SEQ ID NO:39)

Fragment15321554(SEQ ID NO:21; 19/23)

```
Leu Ile Gly Tyr Asn Asn Gln Phe Ser Gly Arg Ala Ser Gln Tyr Val
1               5                   10                  15

Ala Pro Gly Thr Val Ser Ser Met Phe Ser Pro Ala Ala Tyr Leu Thr
            20                  25                  30

Glu Leu Tyr Arg Glu Ala Arg Asn Leu His Ala Ser Asp Ser Val Tyr
        35                  40                  45

Tyr Leu Asp Thr Arg Arg Pro Asp Leu Lys Ser Met Ala Leu Ser Gln
50                  55                  60

Gln Asn Met Asp Ile Glu Leu Ser Thr Leu Ser Leu Ser Asn Glu Leu
65                  70                  75                  80

Leu Leu Glu Ser Ile Lys Thr Glu Ser Lys Leu Glu Asn Tyr Thr Lys
                85                  90                  95

Val Met Glu Met Leu Ser Thr Phe Arg Pro Ser Gly Ala Thr Pro Tyr
            100                 105                 110

His Asp Ala Tyr Glu Asn Val Arg Glu Val Ile Gln Leu Gln Asp Pro
        115                 120                 125

Gly Leu Glu Gln Leu Asn Ala Ser Pro Ala Ile Ala Gly Leu Met His
130                 135                 140

Gln Ala Ser Leu Leu Gly Ile Asn Ala Ser Ile Ser Pro Glu Leu Phe
145                 150                 155                 160

Asn Ile Leu Thr Glu Glu Ile Thr Glu Gly Asn Ala Glu Glu Leu Tyr
                165                 170                 175

Lys Lys Asn Phe Gly Asn Ile Glu Pro Ala Ser Leu Ala Met Pro Glu
            180                 185                 190
```

```
Tyr Leu Lys Arg Tyr Tyr Asn Leu Ser Asp Glu Glu Leu Ser Gln Phe
        195                 200                 205

Ile Gly Lys Ala Ser Asn Phe Gly Gln Gln Glu Tyr Ser Asn Asn Gln
        210                 215                 220

Leu Ile Thr Pro Val Val Asn Ser Ser Asp Gly Thr Val Lys Val Tyr
225                 230                 235                 240

Arg Ile Thr Arg Glu Tyr Thr Thr Asn Ala Tyr Gln Met Asp Val Glu
                245                 250                 255

Leu Phe Pro Phe Gly Glu Asn Tyr Arg Leu Asp Tyr Lys Phe Lys
            260                 265                 270

Asn Phe Tyr Asn Ala Ser Tyr Leu Ser Ile Lys Leu Asn Asp Lys Arg
        275                 280                 285

Glu Leu Val Arg Thr Glu Gly Ala Pro Gln Val Asn Ile Glu Tyr Ser
        290                 295                 300

Ala Asn Ile Thr Leu Asn Thr Ala Asp Ile Ser Gln Pro Phe Glu Ile
305                 310                 315                 320

Gly Leu Thr Arg Val Leu Pro Ser Gly Ser Trp Ala Tyr Ala Ala Ala
                325                 330                 335

Lys Phe Thr Val Glu Glu Tyr Asn Gln Tyr Ser Phe Leu Leu Lys Leu
                340                 345                 350

Asn Lys Ala Ile Arg Leu Ser Arg Ala Thr Glu Leu Ser Pro Thr Ile
        355                 360                 365

Leu Glu Gly Ile Val Arg Ser Val Asn Leu Gln Leu Asp Ile Asn Thr
        370                 375                 380

Asp Val Leu Gly Lys Val Phe Leu Thr Lys Tyr Tyr Met Gln Arg Tyr
385                 390                 395                 400

Ala Ile His Ala Glu Thr Ala Leu Ile Leu Cys Asn Ala Pro Ile Ser
                405                 410                 415

Gln Arg Ser Tyr Asp Asn Gln Pro Ser Gln Phe Asp Arg Leu Phe Asn
            420                 425                 430

Thr Pro Leu Leu Asn Gly Gln Tyr Phe Ser Thr Gly Asp Glu Glu Ile
        435                 440                 445

Asp Leu Asn Ser Gly Ser Thr Gly Asp Trp Arg Lys Thr Ile Leu Lys
450                 455                 460

Arg Ala Phe Asn Ile Asp Asp Val Ser Leu Phe Arg Leu Leu Lys Ile
465                 470                 475                 480

Thr Asp His Asp Asn Lys Asp Gly Lys Ile Lys Asn Asn Leu Lys Asn
            485                 490                 495

Leu Ser Asn Leu Tyr Ile Gly Lys Leu Leu Ala Asp Ile His Gln Leu
            500                 505                 510

Thr Ile Asp Glu Leu Asp Leu Leu Ile Ala Val Gly Glu Gly Lys
        515                 520                 525

Thr Asn Leu Ser Ala Ile Ser Asp Lys Gln Leu Ala Thr Leu Ile Arg
        530                 535                 540

Lys Leu Asn Thr Ile Thr Ser Trp Leu His Thr Gln Lys Trp Ser Val
545                 550                 555                 560

Phe Gln Leu Phe Ile Met Thr Ser Thr Ser Tyr Asn Lys Thr Leu Thr
            565                 570                 575

Pro Glu Ile Lys Asn Leu Leu Asp Thr Val Tyr His Gly Leu Gln Gly
            580                 585                 590

Phe Asp Lys Asp Lys Ala Asp Leu Leu His Val Met Ala Pro Tyr Ile
595                 600                 605
```

```
Ala Ala Thr Leu Gln Leu Ser Ser Glu Asn Val Ala His Ser Val Leu
        610                 615                 620

Leu Trp Ala Asp Lys Leu Gln Pro Gly Asp Gly Ala Met Thr Ala Glu
625                 630                 635                 640

Lys Phe Trp Asp Trp Leu Asn Thr Lys Tyr Thr Pro Gly Ser Ser Glu
                645                 650                 655

Ala Val Glu Thr Gln Glu His Ile Val Gln Tyr Cys Gln Ala Leu Ala
                660                 665                 670

Gln Leu Glu Met Val Tyr His Ser Thr Gly Ile Asn Glu Asn Ala Phe
                675                 680                 685

Arg Leu Phe Val Thr Lys Pro Glu Met Phe Gly Ala Ala Thr Gly Ala
        690                 695                 700

Ala Pro Ala His Asp Ala Leu Ser Leu Ile Met Leu Thr Arg Phe Ala
705                 710                 715                 720

Asp Trp Val Asn Ala Leu Gly Glu Lys Ala Ser Ser Val Leu Ala Ala
                725                 730                 735

Phe Glu Ala Asn Ser Leu Thr Ala Glu Gln Leu Ala Asp Ala Met Asn
                740                 745                 750

Leu Asp Ala Asn Leu Leu Gln Ala Ser Ile Gln Ala Gln Asn His
        755                 760                 765

Gln His Leu Pro Pro Val Thr Pro Glu Asn Ala Phe Ser Cys Trp Thr
        770                 775                 780

Ser Ile Asn Thr Ile Leu Gln Trp Val Asn Val Ala Gln Gln Leu Asn
785                 790                 795                 800

Val Ala Pro Gln Gly Val Ser Ala Leu Val Gly Leu Asp Tyr Ile Gln
                805                 810                 815

Ser Met Lys Glu Thr Pro Thr Tyr Ala Gln Trp Glu Asn Ala Ala Gly
                820                 825                 830

Val Leu Thr Ala Gly Leu Asn Ser Gln Gln Ala Asn Thr Leu His Ala
                835                 840                 845

Phe Leu Asp Glu Ser Arg Ser Ala Ala Leu Ser Thr Tyr Tyr Ile Arg
        850                 855                 860

Gln Val Ala Lys Ala Ala Ala Ile Lys Ser Arg Asp Asp Leu Tyr
865                 870                 875                 880

Gln Tyr Leu Leu Ile Asp Asn Gln Val Ser Ala Ile Lys Thr Thr
                885                 890                 895

Arg Ile Ala Glu Ala Ile Ala Ser Ile Gln Leu Tyr Val Asn Arg Ala
                900                 905                 910

Leu Glu Asn Val Glu Glu Asn Ala Asn Ser Gly Val Ile Ser Arg Gln
        915                 920                 925

Phe Phe Ile Asp Trp Asp Lys Tyr Asn Lys Arg Tyr Ser Thr Trp Ala
        930                 935                 940

Gly Val Ser Gln Leu Val Tyr Tyr Pro Glu Asn Tyr Ile Asp Pro Thr
945                 950                 955                 960

Met Arg Ile Gly Gln Thr Lys Met Met Asp Ala Leu Leu Gln Ser Val
                965                 970                 975

Ser Gln Ser Gln Leu Asn Ala Asp Thr Val Glu Asp Ala Phe Met Ser
                980                 985                 990

Tyr Leu Thr Ser Phe Glu Gln Val Ala Asn Leu Lys Val Ile Ser Ala
                995                 1000                1005

Tyr His Asp Asn Ile Asn Asn Asp Gln Gly Leu Thr Tyr Phe Ile Gly
        1010                1015                1020

Leu Ser Glu Thr Asp Ala Gly Glu Tyr Tyr Trp Arg Ser Val Asp His
```

-continued

```
              1025                1030                1035                1040
Ser Lys Phe Asn Asp Gly Lys Phe Ala Ala Asn Ala Trp Ser Glu Trp
                    1045                1050                1055
His Lys Ile Asp Cys Pro Ile Asn Pro Tyr Lys Ser Thr Ile Arg Pro
                    1060                1065                1070
Val Ile Tyr Lys Ser Arg Leu Tyr Leu Leu Trp Leu Glu Gln Lys Glu
                    1075                1080                1085
Ile Thr Lys Gln Thr Gly Asn Ser Lys Asp Gly Tyr Gln Thr Glu Thr
                    1090                1095                1100
Asp Tyr Arg Tyr Glu Leu Lys Leu Ala His Ile Arg Tyr Asp Gly Thr
1105                1110                1115                1120
Trp Asn Thr Pro Ile Thr Phe Asp Val Asn Lys Lys Ile Ser Glu Leu
                    1125                1130                1135
Lys Leu Glu Lys Asn Arg Ala Pro Gly Leu Tyr Cys Ala Gly Tyr Gln
                    1140                1145                1150
Gly Glu Asp Thr Leu Leu Val Met Phe Tyr Asn Gln Gln Asp Thr Leu
                    1155                1160                1165
Asp Ser Tyr Lys Asn Ala Ser Met Gln Gly Leu Tyr Ile Phe Ala Asp
                    1170                1175                1180
Met Ala Ser Lys Asp Met Thr Pro Glu Gln Ser Asn Val Tyr Arg Asp
1185                1190                1195                1200
Asn Ser Tyr Gln Gln Phe Asp Thr Asn Asn Val Arg Arg Val Asn Asn
                    1205                1210                1215
Arg Tyr Ala Glu Asp Tyr Glu Ile Pro Ser Ser Val Ser Ser Arg Lys
                    1220                1225                1230
Asp Tyr Gly Trp Gly Asp Tyr Tyr Leu Ser Met Val Tyr Asn Gly Asp
                    1235                1240                1245
Ile Pro Thr Ile Asn Tyr Lys Ala Ala Ser Ser Asp Leu Lys Ile Tyr
                    1250                1255                1260
Ile Ser Pro Lys Leu Arg Ile Ile His Asn Gly Tyr Glu Gly Gln Lys
1265                1270                1275                1280
Arg Asn Gln Cys Asn Leu Met Asn Lys Tyr Gly Lys Leu Gly Asp Lys
                    1285                1290                1295
Phe Ile Val Tyr Thr Ser Leu Gly Val Asn Pro Asn Ser Ser Asn
                    1300                1305                1310
Lys Leu Met Phe Tyr Pro Val Tyr Gln Tyr Ser Gly Asn Thr Ser Gly
                    1315                1320                1325
Leu Asn Gln Gly Arg Leu Leu Phe His Arg Asp Thr Thr Tyr Pro Ser
                    1330                1335                1340
Lys Val Glu Ala Trp Ile Pro Gly Ala Lys Arg Ser Leu Thr Asn Gln
1345                1350                1355                1360
Asn Ala Ala Ile Gly Asp Asp Tyr Ala Thr Asp Ser Leu Asn Lys Pro
                    1365                1370                1375
Asp Asp Leu Lys Gln Tyr Ile Phe Met Thr Asp Ser Lys Gly Thr Ala
                    1380                1385                1390
Thr Asp Val Ser Gly Pro Val Glu Ile Asn Thr Ala Ile Ser Pro Ala
                    1395                1400                1405
Lys Val Gln Ile Ile Val Lys Ala Gly Gly Lys Glu Gln Thr Phe Thr
                    1410                1415                1420
Ala Asp Lys Asp Val Ser Ile Gln Pro Ser Pro Ser Phe Asp Glu Met
1425                1430                1435                1440
Asn Tyr Gln Phe Asn Ala Leu Glu Ile Asp Gly Ser Gly Leu Asn Phe
                    1445                1450                1455
```

```
Ile Asn Asn Ser Ala Ser Ile Asp Val Thr Phe Thr Ala Phe Ala Glu
            1460                1465                1470

Asp Gly Arg Lys Leu Gly Tyr Glu Ser Phe Ser Ile Pro Val Thr Leu
        1475                1480                1485

Lys Val Ser Thr Asp Asn Ala Leu Thr Leu His His Asn Glu Asn Gly
    1490                1495                1500

Ala Gln Tyr Met Gln Trp Gln Ser Tyr Arg Thr Arg Leu Asn Thr Leu
1505                1510                1515                1520

Phe Ala Arg Gln Leu Val Ala Arg Ala Thr Thr Gly Ile Asp Thr Ile
                1525                1530                1535

Leu Ser Met Glu Thr Gln Asn Ile Gln Glu Pro Gln Leu Gly Lys Gly
            1540                1545                1550

Phe Tyr Ala Thr Phe Val Ile Pro Pro Tyr Asn Leu Ser Thr His Gly
            1555                1560                1565

Asp Glu Arg Trp Phe Lys Leu Tyr Ile Lys His Val Val Asp Asn Asn
        1570                1575                1580

Ser His Ile Ile Tyr Ser Gly Gln Leu Thr Asp Thr Asn Ile Asn Ile
1585                1590                1595                1600

Thr Leu Phe Ile Pro Leu Asp Asp Val Pro Leu Asn Gln Asp Tyr His
                1605                1610                1615

Ala Lys Val Tyr Met Thr Phe Lys Lys Ser Pro Ser Asp Gly Thr Trp
            1620                1625                1630

Trp Gly Pro His Phe Val Arg Asp Asp Lys Gly Ile Val Thr Ile Asn
            1635                1640                1645

Pro Lys Ser Ile Leu Thr His Phe Glu Ser Val Asn Val Leu Asn Asn
        1650                1655                1660

Ile Ser Ser Glu Pro Met Asp Phe Ser Gly Ala Asn Ser Leu Tyr Phe
1665                1670                1675                1680

Trp Glu Leu Phe Tyr Tyr Thr Pro Met Leu Val Ala Gln Arg Leu Leu
                1685                1690                1695

His Glu Gln Asn Phe Asp Glu Ala Asn Arg Trp Leu Lys Tyr Val Trp
            1700                1705                1710

Ser Pro Ser Gly Tyr Ile Val His Gly Gln Ile Gln Asn Tyr Gln Trp
        1715                1720                1725

Asn Val Arg Pro Leu Leu Glu Asp Thr Ser Trp Asn Ser Asp Pro Leu
    1730                1735                1740

Asp Ser Val Asp Pro Asp Ala Val Ala Gln His Asp Pro Met His Tyr
1745                1750                1755                1760

Lys Val Ser Thr Phe Met Arg Thr Leu Asp Leu Leu Ile Ala Arg Gly
                1765                1770                1775

Asp His Ala Tyr Arg Gln Leu Glu Arg Asp Thr Leu Asn Glu Ala Lys
            1780                1785                1790

Met Trp Tyr Met Gln Ala Leu His Leu Leu Gly Asp Lys Pro Tyr Leu
        1795                1800                1805

Pro Leu Ser Thr Thr Trp Ser Asp Pro Arg Leu Asp Arg Ala Ala Asp
    1810                1815                1820

Ile Thr Thr Gln Asn Ala His Asp Ser Ala Ile Val Ala Leu Arg Gln
1825                1830                1835                1840

Asn Ile Pro Thr Pro Ala Pro Leu Ser
                1845                1849

(2) INFORMATION FOR SEQ ID NO:50:
```

-continued (i) SEQUENCE CHARACTERISTICS:
    (A) LENGTH: 1740 base pairs
    (B) TYPE: nucleic acid
    (C) STRANDEDNESS: double
    (D) TOPOLOGY: linear (ii) MOLECULE TYPE: DNA (genomic)

(xi) SEQUENCE DESCRIPTION: SEQ ID NO:50 (TCDAIII CODING:region):

```
TTG CGC AGC GCT AAT ACC CTG ACT GAT CTC TTC CTG CCG CAA ATC AAT        48
Leu Arg Ser Ala Asn Thr Leu Thr Asp Leu Phe Leu Pro Gln Ile Asn
 1               5                  10                  15

GAA GTG ATG ATG AAT TAC TGG CAG ACA TTA GCT CAG AGA GTA TAC AAT        96
Glu Val Met Met Asn Tyr Trp Gln Thr Leu Ala Gln Arg Val Tyr Asn
                 20                  25                  30

CTG CGT CAT AAC CTC TCT ATC GAC GGC CAG CCG TTA TAT CTG CCA ATC       144
Leu Arg His Asn Leu Ser Ile Asp Gly Gln Pro Leu Tyr Leu Pro Ile
             35                  40                  45

TAT GCC ACA CCG GCC GAT CCG AAA GCG TTA CTC AGC GCC GCC GTT GCC       192
Tyr Ala Thr Pro Ala Asp Pro Lys Ala Leu Leu Ser Ala Ala Val Ala
         50                  55                  60

ACT TCT CAA GGT GGA GGC AAG CTA CCG GAA TCA TTT ATG TCC CTG TGG       240
Thr Ser Gln Gly Gly Gly Lys Leu Pro Glu Ser Phe Met Ser Leu Trp
 65                  70                  75                  80

CGT TTC CCG CAC ATG CTG GAA AAT GCG CGC GGC ATG GTT AGC CAG CTC       288
Arg Phe Pro His Met Leu Glu Asn Ala Arg Gly Met Val Ser Gln Leu
                 85                  90                  95

ACC CAG TTC GGC TCC ACG TTA CAA AAT ATT ATC GAA CGT CAG GAC GCG       336
Thr Gln Phe Gly Ser Thr Leu Gln Asn Ile Ile Glu Arg Gln Asp Ala
                100                 105                 110

GAA GCG CTC AAT GCG TTA TTA CAA AAT CAG GCC GCC GAG CTG ATA TTG       384
Glu Ala Leu Asn Ala Leu Leu Gln Asn Gln Ala Ala Glu Leu Ile Leu
            115                 120                 125

ACT AAC CTG AGC ATT CAG GAC AAA ACC ATT GAA GAA TTG GAT GCC GAG       432
Thr Asn Leu Ser Ile Gln Asp Lys Thr Ile Glu Glu Leu Asp Ala Glu
        130                 135                 140

AAA ACG GTG TTG GAA AAA TCC AAA GCG GGA GCA CAA TCG CGC TTT GAT       480
Lys Thr Val Leu Glu Lys Ser Lys Ala Gly Ala Gln Ser Arg Phe Asp
145                 150                 155                 160

AGC TAC GGC AAA CTG TAC GAT GAG AAT ATC AAC GCC GGT GAA AAC CAA       528
Ser Tyr Gly Lys Leu Tyr Asp Glu Asn Ile Asn Ala Gly Glu Asn Gln
                165                 170                 175

GCC ATG ACG CTA CGA GCG TCC GCC GCC GGG CTT ACC ACG GCA GTT CAG       576
Ala Met Thr Leu Arg Ala Ser Ala Ala Gly Leu Thr Thr Ala Val Gln
            180                 185                 190

GCA TCC CGT CTG GCC GGT GCG GCG GCT GAT CTG GTG CCT AAC ATC TTC       624
Ala Ser Arg Leu Ala Gly Ala Ala Ala Asp Leu Val Pro Asn Ile Phe
        195                 200                 205

GGC TTT GCC GGT GGC GGC AGC CGT TGG GGG GCT ATC GCT GAG GCG ACA       672
Gly Phe Ala Gly Gly Gly Ser Arg Trp Gly Ala Ile Ala Glu Ala Thr
    210                 215                 220

GGT TAT GTG ATG GAA TTC TCC GCG AAT GTT ATG AAC ACC GAA GCG GAT       720
Gly Tyr Val Met Glu Phe Ser Ala Asn Val Met Asn Thr Glu Ala Asp
225                 230                 235                 240

AAA ATT AGC CAA TCT GAA ACC TAC CGT CGT CGC CGT CAG GAG TGG GAG       768
Lys Ile Ser Gln Ser Glu Thr Tyr Arg Arg Arg Gln Glu Trp Glu
                245                 250                 255

ATC CAG CGG AAT AAT GCC GAA GCG GAA TTG AAG CAA ATC GAT GCT CAG       816
Ile Gln Arg Asn Asn Ala Glu Ala Glu Leu Lys Gln Ile Asp Ala Gln
            260                 265                 270

CTC AAA TCA CTC GCT GTA CGC CGC GAA GCC GCC GTA TTG CAG AAA ACC       864
```

```
                Leu Lys Ser Leu Ala Val Arg Arg Glu Ala Ala Val Leu Gln Lys Thr
                    275                 280                 285

AGT CTG AAA ACC CAA CAA GAA CAG ACC CAA TCT CAA TTG GCC TTC CTG         912
Ser Leu Lys Thr Gln Gln Glu Gln Thr Gln Ser Gln Leu Ala Phe Leu
    290                 295                 300

CAA CGT AAG TTC AGC AAT CAG GCG TTA TAC AAC TGG CTG CGT GGT CGA         960
Gln Arg Lys Phe Ser Asn Gln Ala Leu Tyr Asn Trp Leu Arg Gly Arg
305                 310                 315                 320

CTG GCG GCG ATT TAC TTC CAG TTC TAC GAT TTG GCC GTC GCG CGT TGC        1008
Leu Ala Ala Ile Tyr Phe Gln Phe Tyr Asp Leu Ala Val Ala Arg Cys
                325                 330                 335

CTG ATG GCA GAA CAA GCT TAC CGT TGG GAA CTC AAT GAT GAC TCT GCC        1056
Leu Met Ala Glu Gln Ala Tyr Arg Trp Glu Leu Asn Asp Asp Ser Ala
            340                 345                 350

CGC TTC ATT AAA CCG GGC GCC TGG CAG GGA ACC TAT GCC GGT CTG CTT        1104
Arg Phe Ile Lys Pro Gly Ala Trp Gln Gly Thr Tyr Ala Gly Leu Leu
        355                 360                 365

GCA GGT GAA ACC TTG ATG CTG AGT CTG GCA CAA ATG GAA GAC GCT CAT        1152
Ala Gly Glu Thr Leu Met Leu Ser Leu Ala Gln Met Glu Asp Ala His
    370                 375                 380

CTG AAA CGC GAT AAA CGC GCA TTA GAG GTT GAA CGC ACA GTA TCG CTG        1200
Leu Lys Arg Asp Lys Arg Ala Leu Glu Val Glu Arg Thr Val Ser Leu
385                 390                 395                 400

GCC GAA GTT TAT GCA GGA TTA CCA AAA GAT AAC GGT CCA TTT TCC CTG        1248
Ala Glu Val Tyr Ala Gly Leu Pro Lys Asp Asn Gly Pro Phe Ser Leu
                405                 410                 415

GCT CAG GAA ATT GAC AAG CTG GTG AGT CAA GGT TCA GGC AGT GCC GGC        1296
Ala Gln Glu Ile Asp Lys Leu Val Ser Gln Gly Ser Gly Ser Ala Gly
            420                 425                 430

AGT GGT AAT AAT AAT TTG GCG TTC GGC GCC GGC ACG GAC ACT AAA ACC        1344
Ser Gly Asn Asn Asn Leu Ala Phe Gly Ala Gly Thr Asp Thr Lys Thr
        435                 440                 445

TCT TTG CAG GCA TCA GTT TCA TTC GCT GAT TTG AAA ATT CGT GAA GAT        1392
Ser Leu Gln Ala Ser Val Ser Phe Ala Asp Leu Lys Ile Arg Glu Asp
    450                 455                 460

TAC CCG GCA TCG CTT GGC AAA ATT CGA CGT ATC AAA CAG ATC AGC GTC        1440
Tyr Pro Ala Ser Leu Gly Lys Ile Arg Arg Ile Lys Gln Ile Ser Val
465                 470                 475                 480

ACT TTG CCC GCG CTA CTG GGA CCG TAT CAG GAT GTA CAG GCA ATA TTG        1488
Thr Leu Pro Ala Leu Leu Gly Pro Tyr Gln Asp Val Gln Ala Ile Leu
                485                 490                 495

TCT TAC GGC GAT AAA GCC GGA TTA GCT AAC GGC TGT GAA GCG CTG GCA        1536
Ser Tyr Gly Asp Lys Ala Gly Leu Ala Asn Gly Cys Glu Ala Leu Ala
            500                 505                 510

GTT TCT CAC GGT ATG AAT GAC AGC GGC CAA TTC CAG CTC GAT TTC AAC        1584
Val Ser His Gly Met Asn Asp Ser Gly Gln Phe Gln Leu Asp Phe Asn
        515                 520                 525

GAT GGC AAA TTC CTG CCA TTC GAA GGC ATC GCC ATT GAT CAA GGC ACG        1632
Asp Gly Lys Phe Leu Pro Phe Glu Gly Ile Ala Ile Asp Gln Gly Thr
    530                 535                 540

CTG ACA CTG AGC TTC CCA AAT GCA TCT ATG CCG GAG AAA GGT AAA CAA        1680
Leu Thr Leu Ser Phe Pro Asn Ala Ser Met Pro Glu Lys Gly Lys Gln
545                 550                 555                 560

GCC ACT ATG TTA AAA ACC CTG AAC GAT ATC ATT TTG CAT ATT CGC TAC        1728
Ala Thr Met Leu Lys Thr Leu Asn Asp Ile Ile Leu His Ile Arg Tyr
                565                 570                 575

ACC ATT AAA TAA                                                        1740
Thr Ile Lys
        579
```

(2) INFORMATION FOR SEQ ID NO:51:

(i) SEQUENCE CHARACTERISTICS:
        (A) LENGTH: 579 amino acids
        (B) TYPE: amino acids
        (C) STRANDEDNESS: single
        (D) TOPOLOGY: linear (ii) MOLECULE TYPE: protein (xi) SEQUENCE DESCRIPTION: SEQ ID NO:51 (TCDAIII):

```
Leu Arg Ser Ala Asn Thr Leu Thr Asp Leu Phe Leu Pro Gln Ile Asn
 1               5                  10                  15

Glu Val Met Met Asn Tyr Trp Gln Thr Leu Ala Gln Arg Val Tyr Asn
             20                  25                  30

Leu Arg His Asn Leu Ser Ile Asp Gly Gln Pro Leu Tyr Leu Pro Ile
         35                  40                  45

Tyr Ala Thr Pro Ala Asp Pro Lys Ala Leu Leu Ser Ala Ala Val Ala
 50                  55                  60

Thr Ser Gln Gly Gly Gly Lys Leu Pro Glu Ser Phe Met Ser Leu Trp
 65                  70                  75                  80

Arg Phe Pro His Met Leu Glu Asn Ala Arg Gly Met Val Ser Gln Leu
             85                  90                  95

Thr Gln Phe Gly Ser Thr Leu Gln Asn Ile Ile Glu Arg Gln Asp Ala
            100                 105                 110

Glu Ala Leu Asn Ala Leu Leu Gln Asn Gln Ala Ala Glu Leu Ile Leu
            115                 120                 125

Thr Asn Leu Ser Ile Gln Asp Lys Thr Ile Glu Glu Leu Asp Ala Glu
130                 135                 140

Lys Thr Val Leu Glu Lys Ser Lys Ala Gly Ala Gln Ser Arg Phe Asp
145                 150                 155                 160

Ser Tyr Gly Lys Leu Tyr Asp Glu Asn Ile Asn Ala Gly Glu Asn Gln
                165                 170                 175

Ala Met Thr Leu Arg Ala Ser Ala Ala Gly Leu Thr Thr Ala Val Gln
            180                 185                 190

Ala Ser Arg Leu Ala Gly Ala Ala Ala Asp Leu Val Pro Asn Ile Phe
            195                 200                 205

Gly Phe Ala Gly Gly Gly Ser Arg Trp Gly Ala Ile Ala Glu Ala Thr
210                 215                 220

Gly Tyr Val Met Glu Phe Ser Ala Asn Val Met Asn Thr Glu Ala Asp
225                 230                 235                 240

Lys Ile Ser Gln Ser Glu Thr Tyr Arg Arg Arg Gln Glu Trp Glu
                245                 250                 255

Ile Gln Arg Asn Asn Ala Glu Ala Glu Leu Lys Gln Ile Asp Ala Gln
            260                 265                 270

Leu Lys Ser Leu Ala Val Arg Arg Glu Ala Ala Val Leu Gln Lys Thr
            275                 280                 285

Ser Leu Lys Thr Gln Gln Glu Gln Thr Gln Ser Gln Leu Ala Phe Leu
290                 295                 300

Gln Arg Lys Phe Ser Asn Gln Ala Leu Tyr Asn Trp Leu Arg Gly Arg
305                 310                 315                 320

Leu Ala Ala Ile Tyr Phe Gln Phe Tyr Asp Leu Ala Val Ala Arg Cys
                325                 330                 335

Leu Met Ala Glu Gln Ala Tyr Arg Trp Glu Leu Asn Asp Asp Ser Ala
            340                 345                 350
```

-continued

```
Arg Phe Ile Lys Pro Gly Ala Trp Gln Gly Thr Tyr Ala Gly Leu Leu
        355                 360                 365

Ala Gly Glu Thr Leu Met Leu Ser Leu Ala Gln Met Glu Asp Ala His
    370                 375                 380

Leu Lys Arg Asp Lys Arg Ala Leu Glu Val Glu Arg Thr Val Ser Leu
385                 390                 395                 400

Ala Glu Val Tyr Ala Gly Leu Pro Lys Asp Asn Gly Pro Phe Ser Leu
                405                 410                 415

Ala Gln Glu Ile Asp Lys Leu Val Ser Gln Gly Ser Gly Ser Ala Gly
                420                 425                 430

Ser Gly Asn Asn Asn Leu Ala Phe Gly Ala Gly Thr Asp Thr Lys Thr
        435                 440                 445

Ser Leu Gln Ala Ser Val Ser Phe Ala Asp Leu Lys Ile Arg Glu Asp
    450                 455                 460

Tyr Pro Ala Ser Leu Gly Lys Ile Arg Arg Ile Lys Gln Ile Ser Val
465                 470                 475                 480

Thr Leu Pro Ala Leu Leu Gly Pro Tyr Gln Asp Val Gln Ala Ile Leu
                485                 490                 495

Ser Tyr Gly Asp Lys Ala Gly Leu Ala Asn Gly Cys Glu Ala Leu Ala
                500                 505                 510

Val Ser His Gly Met Asn Asp Ser Gly Gln Phe Gln Leu Asp Phe Asn
        515                 520                 525

Asp Gly Lys Phe Leu Pro Phe Glu Gly Ile Ala Ile Asp Gln Gly Thr
    530                 535                 540

Leu Thr Leu Ser Phe Pro Asn Ala Ser Met Pro Glu Lys Gly Lys Gln
545                 550                 555                 560

Ala Thr Met Leu Lys Thr Leu Asn Asp Ile Ile Leu His Ile Arg Tyr
                565                 570                 575

Thr Ile Lys
        579

(2) INFORMATION FOR SEQ ID NO:52:

(i) SEQUENCE CHARACTERISTICS:
        (A) LENGTH: 5532 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:52 (TCBAII CODING:region):

TTT ATA CAA GGT TAT AGT GAT CTG TTT GGT AAT CGT GCT GAT AAC TAT      48
Phe Ile Gln Gly Tyr Ser Asp Leu Phe Gly Asn Arg Ala Asp Asn Tyr
1               5                   10                  15

GCC GCG CCG GGC TCG GTT GCA TCG ATG TTC TCA CCG GCG GCT TAT TTG     96
Ala Ala Pro Gly Ser Val Ala Ser Met Phe Ser Pro Ala Ala Tyr Leu
                20                  25                  30

ACG GAA TTG TAC CGT GAA GCC AAA AAC TTG CAT GAC AGC AGC TCA ATT    144
Thr Glu Leu Tyr Arg Glu Ala Lys Asn Leu His Asp Ser Ser Ser Ile
            35                  40                  45

TAT TAC CTA GAT AAA CGT CGC CCG GAT TTA GCA AGC TTA ATG CTC AGC    192
Tyr Tyr Leu Asp Lys Arg Arg Pro Asp Leu Ala Ser Leu Met Leu Ser
    50                  55                  60

CAG AAA AAT ATG GAT GAG GAA ATT TCA ACG CTG GCT CTC TCT AAT GAA    240
Gln Lys Asn Met Asp Glu Glu Ile Ser Thr Leu Ala Leu Ser Asn Glu
65                  70                  75                  80

TTG TGC CTT GCC GGG ATC GAA ACA AAA ACA GGA AAA TCA CAA GAT GAA    288
```

```
                 Leu Cys Leu Ala Gly Ile Glu Thr Lys Thr Gly Lys Ser Gln Asp Glu
                                 85                  90                  95

GTG ATG GAT ATG TTG TCA ACT TAT CGT TTA AGT GGA GAG ACA CCT TAT              336
Val Met Asp Met Leu Ser Thr Tyr Arg Leu Ser Gly Glu Thr Pro Tyr
            100                 105                 110

CAT CAC GCT TAT GAA ACT GTT CGT GAA ATC GTT CAT GAA CGT GAT CCA              384
His His Ala Tyr Glu Thr Val Arg Glu Ile Val His Glu Arg Asp Pro
            115                 120                 125

GGA TTT CGT CAT TTG TCA CAG GCA CCC ATT GTT GCT GCT AAG CTC GAT              432
Gly Phe Arg His Leu Ser Gln Ala Pro Ile Val Ala Ala Lys Leu Asp
130             135                 140

CCT GTG ACT TTG TTG GGT ATT AGC TCC CAT ATT TCG CCA GAA CTG TAT              480
Pro Val Thr Leu Leu Gly Ile Ser Ser His Ile Ser Pro Glu Leu Tyr
145             150                 155                 160

AAC TTG CTG ATT GAG GAG ATC CCG GAA AAA GAT GAA GCC GCG CTT GAT              528
Asn Leu Leu Ile Glu Glu Ile Pro Glu Lys Asp Glu Ala Ala Leu Asp
                165                 170                 175

ACG CTT TAT AAA ACA AAC TTT GGC GAT ATT ACT ACT GCT CAG TTA ATG              576
Thr Leu Tyr Lys Thr Asn Phe Gly Asp Ile Thr Thr Ala Gln Leu Met
            180                 185                 190

TCC CCA AGT TAT CTG GCC CGG TAT TAT GGC GTC TCA CCG GAA GAT ATT              624
Ser Pro Ser Tyr Leu Ala Arg Tyr Tyr Gly Val Ser Pro Glu Asp Ile
            195                 200                 205

GCC TAC GTG ACG ACT TCA TTA TCA CAT GTT GGA TAT AGC AGT GAT ATT              672
Ala Tyr Val Thr Thr Ser Leu Ser His Val Gly Tyr Ser Ser Asp Ile
210             215                 220

CTG GTT ATT CCG TTG GTC GAT GGT GTG GGT AAG ATG GAA GTA GTT CGT              720
Leu Val Ile Pro Leu Val Asp Gly Val Gly Lys Met Glu Val Val Arg
225             230                 235                 240

GTT ACC CGA ACA CCA TCG GAT AAT TAT ACC AGT CAG ACG AAT TAT ATT              768
Val Thr Arg Thr Pro Ser Asp Asn Tyr Thr Ser Gln Thr Asn Tyr Ile
                245                 250                 255

GAG CTG TAT CCA CAG GGT GGC GAC AAT TAT TTG ATC AAA TAC AAT CTA              816
Glu Leu Tyr Pro Gln Gly Gly Asp Asn Tyr Leu Ile Lys Tyr Asn Leu
            260                 265                 270

AGC AAT AGT TTT GGT TTG GAT GAT TTT TAT CTG CAA TAT AAA GAT GGT              864
Ser Asn Ser Phe Gly Leu Asp Asp Phe Tyr Leu Gln Tyr Lys Asp Gly
            275                 280                 285

TCC GCT GAT TGG ACT GAG ATT GCC CAT AAT CCC TAT CCT GAT ATG GTC              912
Ser Ala Asp Trp Thr Glu Ile Ala His Asn Pro Tyr Pro Asp Met Val
290             295                 300

ATA AAT CAA AAG TAT GAA TCA CAG GCG ACA ATC AAA CGT AGT GAC TCT              960
Ile Asn Gln Lys Tyr Glu Ser Gln Ala Thr Ile Lys Arg Ser Asp Ser
305             310                 315                 320

GAC AAT ATA CTC AGT ATA GGG TTA CAA AGA TGG CAT AGC GGT AGT TAT              1008
Asp Asn Ile Leu Ser Ile Gly Leu Gln Arg Trp His Ser Gly Ser Tyr
                325                 330                 335

AAT TTT GCC GCC GCC AAT TTT AAA ATT GAC CAA TAC TCC CCG AAA GCT              1056
Asn Phe Ala Ala Ala Asn Phe Lys Ile Asp Gln Tyr Ser Pro Lys Ala
            340                 345                 350

TTC CTG CTT AAA ATG AAT AAG GCT ATT CGG TTG CTC AAA GCT ACC GGC              1104
Phe Leu Leu Lys Met Asn Lys Ala Ile Arg Leu Leu Lys Ala Thr Gly
            355                 360                 365

CTC TCT TTT GCT ACG TTG GAG CGT ATT GTT GAT AGT GTT AAT AGC ACC              1152
Leu Ser Phe Ala Thr Leu Glu Arg Ile Val Asp Ser Val Asn Ser Thr
            370                 375                 380

AAA TCC ATC ACG GTT GAG GTA TTA AAC AAG GTT TAT CGG GTA AAA TTC              1200
Lys Ser Ile Thr Val Glu Val Leu Asn Lys Val Tyr Arg Val Lys Phe
385             390                 395                 400
```

```
TAT ATT GAT CGT TAT GGC ATC AGT GAA GAG ACA GCC GCT ATT TTG GCT      1248
Tyr Ile Asp Arg Tyr Gly Ile Ser Glu Glu Thr Ala Ala Ile Leu Ala
                405                 410                 415

AAT ATT AAT ATC TCT CAG CAA GCT GTT GGC AAT CAG CTT AGC CAG TTT      1296
Asn Ile Asn Ile Ser Gln Gln Ala Val Gly Asn Gln Leu Ser Gln Phe
            420                 425                 430

GAG CAA CTA TTT AAT CAC CCG CCG CTC AAT GGT ATT CGC TAT GAA ATC      1344
Glu Gln Leu Phe Asn His Pro Pro Leu Asn Gly Ile Arg Tyr Glu Ile
        435                 440                 445

AGT GAG GAC AAC TCC AAA CAT CTT CCT AAT CCT GAT CTG AAC CTT AAA      1392
Ser Glu Asp Asn Ser Lys His Leu Pro Asn Pro Asp Leu Asn Leu Lys
    450                 455                 460

CCA GAC AGT ACC GGT GAT GAT CAA CGC AAG GCG GTT TTA AAA CGC GCG      1440
Pro Asp Ser Thr Gly Asp Asp Gln Arg Lys Ala Val Leu Lys Arg Ala
465                 470                 475                 480

TTT CAG GTT AAC GCC AGT GAG TTG TAT CAG ATG TTA TTG ATC ACT GAT      1488
Phe Gln Val Asn Ala Ser Glu Leu Tyr Gln Met Leu Leu Ile Thr Asp
                485                 490                 495

CGT AAA GAA GAC GGT GTT ATC AAA AAT AAC TTA GAG AAT TTG TCT GAT      1536
Arg Lys Glu Asp Gly Val Ile Lys Asn Asn Leu Glu Asn Leu Ser Asp
            500                 505                 510

CTG TAT TTG GTT AGT TTG CTG GCC CAG ATT CAT AAC CTG ACT ATT GCT      1584
Leu Tyr Leu Val Ser Leu Leu Ala Gln Ile His Asn Leu Thr Ile Ala
        515                 520                 525

GAA TTG AAC ATT TTG TTG GTG ATT TGT GGC TAT GGC GAC ACC AAC ATT      1632
Glu Leu Asn Ile Leu Leu Val Ile Cys Gly Tyr Gly Asp Thr Asn Ile
    530                 535                 540

TAT CAG ATT ACC GAC GAT AAT TTA GCC AAA ATA GTG GAA ACA TTG TTG      1680
Tyr Gln Ile Thr Asp Asp Asn Leu Ala Lys Ile Val Glu Thr Leu Leu
545                 550                 555                 560

TGG ATC ACT CAA TGG TTG AAG ACC CAA AAA TGG ACA GTT ACC GAC CTG      1728
Trp Ile Thr Gln Trp Leu Lys Thr Gln Lys Trp Thr Val Thr Asp Leu
                565                 570                 575

TTT CTG ATG ACC ACG GCC ACT TAC AGC ACC ACT TTA ACG CCA GAA ATT      1776
Phe Leu Met Thr Thr Ala Thr Tyr Ser Thr Thr Leu Thr Pro Glu Ile
            580                 585                 590

AGC AAT CTG ACG GCT ACG TTG TCT TCA ACT TTG CAT GGC AAA GAG AGT      1824
Ser Asn Leu Thr Ala Thr Leu Ser Ser Thr Leu His Gly Lys Glu Ser
        595                 600                 605

CTG ATT GGG GAA GAT CTG AAA AGA GCA ATG GCG CCT TGC TTC ACT TCG      1872
Leu Ile Gly Glu Asp Leu Lys Arg Ala Met Ala Pro Cys Phe Thr Ser
    610                 615                 620

GCT TTG CAT TTG ACT TCT CAA GAA GTT GCG TAT GAC CTG CTG TTG TGG      1920
Ala Leu His Leu Thr Ser Gln Glu Val Ala Tyr Asp Leu Leu Leu Trp
625                 630                 635                 640

ATA GAC CAG ATT CAA CCG GCA CAA ATA ACT GTT GAT GGG TTT TGG GAA      1968
Ile Asp Gln Ile Gln Pro Ala Gln Ile Thr Val Asp Gly Phe Trp Glu
                645                 650                 655

GAA GTG CAA ACA ACA CCA ACC AGC TTG AAG GTG ATT ACC TTT GCT CAG      2016
Glu Val Gln Thr Thr Pro Thr Ser Leu Lys Val Ile Thr Phe Ala Gln
            660                 665                 670

GTG CTG GCA CAA TTG AGC CTG ATC TAT CGT CGT ATT GGG TTA AGT GAA      2064
Val Leu Ala Gln Leu Ser Leu Ile Tyr Arg Arg Ile Gly Leu Ser Glu
        675                 680                 685

ACG GAA CTG TCA CTG ATC GTG ACT CAA TCT TCT CTG CTA GTG GCA GGC      2112
Thr Glu Leu Ser Leu Ile Val Thr Gln Ser Ser Leu Leu Val Ala Gly
    690                 695                 700

AAA AGC ATA CTG GAT CAC GGT CTG TTA ACC CTG ATG GCC TTG GAA GGT      2160
Lys Ser Ile Leu Asp His Gly Leu Leu Thr Leu Met Ala Leu Glu Gly
705                 710                 715                 720
```

```
TTT CAT ACC TGG GTT AAT GGC TTG GGG CAA CAT GCC TCC TTG ATA TTG        2208
Phe His Thr Trp Val Asn Gly Leu Gly Gln His Ala Ser Leu Ile Leu
                725                 730                 735

GCG GCG TTG AAA GAC GGA GCC TTG ACA GTT ACC GAT GTA GCA CAA GCT        2256
Ala Ala Leu Lys Asp Gly Ala Leu Thr Val Thr Asp Val Ala Gln Ala
                740                 745                 750

ATG AAT AAG GAG GAA TCT CTC CTA CAA ATG GCA GCT AAT CAG GTG GAG        2304
Met Asn Lys Glu Glu Ser Leu Leu Gln Met Ala Ala Asn Gln Val Glu
                755                 760                 765

AAG GAT CTA ACA AAA CTG ACC AGT TGG ACA CAG ATT GAC GCT ATT CTG        2352
Lys Asp Leu Thr Lys Leu Thr Ser Trp Thr Gln Ile Asp Ala Ile Leu
770                 775                 780

CAA TGG TTA CAG ATG TCT TCG GCC TTG GCG GTT TCT CCA CTG GAT CTG        2400
Gln Trp Leu Gln Met Ser Ser Ala Leu Ala Val Ser Pro Leu Asp Leu
785                 790                 795                 800

GCA GGG ATG ATG GCC CTG AAA TAT GGG ATA GAT CAT AAC TAT GCT GCC        2448
Ala Gly Met Met Ala Leu Lys Tyr Gly Ile Asp His Asn Tyr Ala Ala
                805                 810                 815

TGG CAA GCT GCG GCG GCT GCG CTG ATG GCT GAT CAT GCT AAT CAG GCA        2496
Trp Gln Ala Ala Ala Ala Ala Leu Met Ala Asp His Ala Asn Gln Ala
                820                 825                 830

CAG AAA AAA CTG GAT GAG ACG TTC AGT AAG GCA TTA TGT AAC TAT TAT        2544
Gln Lys Lys Leu Asp Glu Thr Phe Ser Lys Ala Leu Cys Asn Tyr Tyr
                835                 840                 845

ATT AAT GCT GTT GTC GAT AGT GCT GCT GGA GTA CGT GAT CGT AAC GGT        2592
Ile Asn Ala Val Val Asp Ser Ala Ala Gly Val Arg Asp Arg Asn Gly
850                 855                 860

TTA TAT ACC TAT TTG CTG ATT GAT AAT CAG GTT TCT GCC GAT GTG ATC        2640
Leu Tyr Thr Tyr Leu Leu Ile Asp Asn Gln Val Ser Ala Asp Val Ile
865                 870                 875                 880

ACT TCA CGT ATT GCA GAA GCT ATC GCC GGT ATT CAA CTG TAC GTT AAC        2688
Thr Ser Arg Ile Ala Glu Ala Ile Ala Gly Ile Gln Leu Tyr Val Asn
                885                 890                 895

CGG GCT TTA AAC CGA GAT GAA GGT CAG CTT GCA TCG GAC GTT AGT ACC        2736
Arg Ala Leu Asn Arg Asp Glu Gly Gln Leu Ala Ser Asp Val Ser Thr
                900                 905                 910

CGT CAG TTC TTC ACT GAC TGG GAA CGT TAC AAT AAA CGT TAC AGT ACT        2784
Arg Gln Phe Phe Thr Asp Trp Glu Arg Tyr Asn Lys Arg Tyr Ser Thr
                915                 920                 925

TGG GCT GGT GTC TCT GAA CTG GTC TAT TAT CCA GAA AAC TAT GTT GAT        2832
Trp Ala Gly Val Ser Glu Leu Val Tyr Tyr Pro Glu Asn Tyr Val Asp
930                 935                 940

CCC ACT CAG CGC ATT GGG CAA ACC AAA ATG ATG GAT GCG CTG TTG CAA        2880
Pro Thr Gln Arg Ile Gly Gln Thr Lys Met Met Asp Ala Leu Leu Gln
945                 950                 955                 960

TCC ATC AAC CAG AGC CAG CTA AAT GCG GAT ACG GTG GAA GAT GCT TTC        2928
Ser Ile Asn Gln Ser Gln Leu Asn Ala Asp Thr Val Glu Asp Ala Phe
                965                 970                 975

AAA ACT TAT TTG ACC AGC TTT GAG CAG GTA GCA AAT CTG AAA GTA ATT        2976
Lys Thr Tyr Leu Thr Ser Phe Glu Gln Val Ala Asn Leu Lys Val Ile
                980                 985                 990

AGT GCT TAC CAC GAT AAT GTG AAT GTG GAT CAA GGA TTA ACT TAT TTT        3024
Ser Ala Tyr His Asp Asn Val Asn Val Asp Gln Gly Leu Thr Tyr Phe
                995                 1000                1005

ATC GGT ATC GAC CAA GCA GCT CCG GGT ACG TAT TAC TGG CGT AGT GTT        3072
Ile Gly Ile Asp Gln Ala Ala Pro Gly Thr Tyr Tyr Trp Arg Ser Val
        1010                1015                1020

GAT CAC AGC AAA TGT GAA AAT GGC AAG TTT GCC GCT AAT GCT TGG GGT        3120
Asp His Ser Lys Cys Glu Asn Gly Lys Phe Ala Ala Asn Ala Trp Gly
```

```
                                                    -continued
1025            1030            1035            1040

GAG TGG AAT AAA ATT ACC TGT GCT GTC AAT CCT TGG AAA AAT ATC ATC    3168
Glu Trp Asn Lys Ile Thr Cys Ala Val Asn Pro Trp Lys Asn Ile Ile
                1045            1050            1055

CGT CCG GTT GTT TAT ATG TCC CGC TTA TAT CTG CTA TGG CTG GAG CAG    3216
Arg Pro Val Val Tyr Met Ser Arg Leu Tyr Leu Leu Trp Leu Glu Gln
                1060            1065            1070

CAA TCA AAG AAA AGT GAT GAT GGT AAA ACC ACG ATT TAT CAA TAT AAC    3264
Gln Ser Lys Lys Ser Asp Asp Gly Lys Thr Thr Ile Tyr Gln Tyr Asn
                1075            1080            1085

TTA AAA CTG GCT CAT ATT CGT TAC GAC GGT AGT TGG AAT ACA CCA TTT    3312
Leu Lys Leu Ala His Ile Arg Tyr Asp Gly Ser Trp Asn Thr Pro Phe
        1090            1095            1100

ACT TTT GAT GTG ACA GAA AAG GTA AAA AAT TAC ACG TCG AGT ACT GAT    3360
Thr Phe Asp Val Thr Glu Lys Val Lys Asn Tyr Thr Ser Ser Thr Asp
1105            1110            1115            1120

GCT GCT GAA TCT TTA GGG TTG TAT TGT ACT GGT TAT CAA GGG GAA GAC    3408
Ala Ala Glu Ser Leu Gly Leu Tyr Cys Thr Gly Tyr Gln Gly Glu Asp
                1125            1130            1135

ACT CTA TTA GTT ATG TTC TAT TCG ATG CAG AGT AGT TAT AGC TCC TAT    3456
Thr Leu Leu Val Met Phe Tyr Ser Met Gln Ser Ser Tyr Ser Ser Tyr
                1140            1145            1150

ACC GAT AAT AAT GCG CCG GTC ACT GGG CTA TAT ATT TTC GCT GAT ATG    3504
Thr Asp Asn Asn Ala Pro Val Thr Gly Leu Tyr Ile Phe Ala Asp Met
                1155            1160            1165

TCA TCA GAC AAT ATG ACG AAT GCA CAA GCA ACT AAC TAT TGG AAT AAC    3552
Ser Ser Asp Asn Met Thr Asn Ala Gln Ala Thr Asn Tyr Trp Asn Asn
        1170            1175            1180

AGT TAT CCG CAA TTT GAT ACT GTG ATG GCA GAT CCG GAT AGC GAC AAT    3600
Ser Tyr Pro Gln Phe Asp Thr Val Met Ala Asp Pro Asp Ser Asp Asn
1185            1190            1195            1200

AAA AAA GTC ATA ACC AGA AGA GTT AAT AAC CGT TAT GCG GAG GAT TAT    3648
Lys Lys Val Ile Thr Arg Arg Val Asn Asn Arg Tyr Ala Glu Asp Tyr
                1205            1210            1215

GAA ATT CCT TCC TCT GTG ACA AGT AAC AGT AAT TAT TCT TGG GGT GAT    3696
Glu Ile Pro Ser Ser Val Thr Ser Asn Ser Asn Tyr Ser Trp Gly Asp
                1220            1225            1230

CAC AGT TTA ACC ATG CTT TAT GGT GGT AGT GTT CCT AAT ATT ACT TTT    3744
His Ser Leu Thr Met Leu Tyr Gly Gly Ser Val Pro Asn Ile Thr Phe
                1235            1240            1245

GAA TCG GCG GCA GAA GAT TTA AGG CTA TCT ACC AAT ATG GCA TTG AGT    3792
Glu Ser Ala Ala Glu Asp Leu Arg Leu Ser Thr Asn Met Ala Leu Ser
        1250            1255            1260

ATT ATT CAT AAT GGA TAT GCG GGA ACC CGC CGT ATA CAA TGT AAT CTT    3840
Ile Ile His Asn Gly Tyr Ala Gly Thr Arg Arg Ile Gln Cys Asn Leu
1265            1270            1275            1280

ATG AAA CAA TAC GCT TCA TTA GGT GAT AAA TTT ATA ATT TAT GAT TCA    3888
Met Lys Gln Tyr Ala Ser Leu Gly Asp Lys Phe Ile Ile Tyr Asp Ser
                1285            1290            1295

TCA TTT GAT GAT GCA AAC CGT TTT AAT CTG GTG CCA TTG TTT AAA TTC    3936
Ser Phe Asp Asp Ala Asn Arg Phe Asn Leu Val Pro Leu Phe Lys Phe
        1300            1305            1310

GGA AAA GAC GAG AAC TCA GAT GAT AGT ATT TGT ATA TAT AAT GAA AAC    3984
Gly Lys Asp Glu Asn Ser Asp Asp Ser Ile Cys Ile Tyr Asn Glu Asn
                1315            1320            1325

CCT TCC TCT GAA GAT AAG AAG TGG TAT TTT TCT TCG AAA GAT GAC AAT    4032
Pro Ser Ser Glu Asp Lys Lys Trp Tyr Phe Ser Ser Lys Asp Asp Asn
                1330            1335            1340

AAA ACA GCG GAT TAT AAT GGT GGA ACT CAA TGT ATA GAT GCT GGA ACC    4080
```

```
                                              -continued

Lys Thr Ala Asp Tyr Asn Gly Thr Gln Cys Ile Asp Ala Gly Thr
1345                1350                1355                1360

AGT AAC AAA GAT TTT TAT TAT AAT CTC CAG GAG ATT GAA GTA ATT AGT      4128
Ser Asn Lys Asp Phe Tyr Tyr Asn Leu Gln Glu Ile Glu Val Ile Ser
                1365                1370                1375

GTT ACT GGT GGG TAT TGG TCG AGT TAT AAA ATA TCC AAC CCG ATT AAT      4176
Val Thr Gly Gly Tyr Trp Ser Ser Tyr Lys Ile Ser Asn Pro Ile Asn
            1380                1385                1390

ATC AAT ACG GGC ATT GAT AGT GCT AAA GTA AAA GTC ACC GTA AAA GCG      4224
Ile Asn Thr Gly Ile Asp Ser Ala Lys Val Lys Val Thr Val Lys Ala
        1395                1400                1405

GGT GGT GAC GAT CAA ATC TTT ACT GCT GAT AAT AGT ACC TAT GTT CCT      4272
Gly Gly Asp Asp Gln Ile Phe Thr Ala Asp Asn Ser Thr Tyr Val Pro
    1410                1415                1420

CAG CAA CCG GCA CCC AGT TTT GAG GAG ATG ATT TAT CAG TTC AAT AAC      4320
Gln Gln Pro Ala Pro Ser Phe Glu Glu Met Ile Tyr Gln Phe Asn Asn
1425                1430                1435                1440

CTG ACA ATA GAT TGT AAG AAT TTA AAT TTC ATC GAC AAT CAG GCA CAT      4368
Leu Thr Ile Asp Cys Lys Asn Leu Asn Phe Ile Asp Asn Gln Ala His
                1445                1450                1455

ATT GAG ATT GAT TTC ACC GCT ACG GCA CAA GAT GGC CGA TTC TTG GGT      4416
Ile Glu Ile Asp Phe Thr Ala Thr Ala Gln Asp Gly Arg Phe Leu Gly
            1460                1465                1470

GCA GAA ACT TTT ATT ATC CCG GTA ACT AAA AAA GTT CTC GGT ACT GAG      4464
Ala Glu Thr Phe Ile Ile Pro Val Thr Lys Lys Val Leu Gly Thr Glu
        1475                1480                1485

AAC GTG ATT GCG TTA TAT AGC GAA AAT AAC GGT GTT CAA TAT ATG CAA      4512
Asn Val Ile Ala Leu Tyr Ser Glu Asn Asn Gly Val Gln Tyr Met Gln
    1490                1495                1500

ATT GGC GCA TAT CGT ACC CGT TTG AAT ACG TTA TTC GCT CAA CAG TTG      4560
Ile Gly Ala Tyr Arg Thr Arg Leu Asn Thr Leu Phe Ala Gln Gln Leu
1505                1510                1515                1520

GTT AGC CGT GCT AAT CGT GGC ATT GAT GCA GTG CTC AGT ATG GAA ACT      4608
Val Ser Arg Ala Asn Arg Gly Ile Asp Ala Val Leu Ser Met Glu Thr
                1525                1530                1535

CAG AAT ATT CAG GAA CCG CAA TTA GGA GCG GGC ACA TAT GTG CAG CTT      4656
Gln Asn Ile Gln Glu Pro Gln Leu Gly Ala Gly Thr Tyr Val Gln Leu
            1540                1545                1550

GTG TTG GAT AAA TAT GAT GAG TCT ATT CAT GGC ACT AAT AAA AGC TTT      4704
Val Leu Asp Lys Tyr Asp Glu Ser Ile His Gly Thr Asn Lys Ser Phe
        1555                1560                1565

GCT ATT GAA TAT GTT GAT ATA TTT AAA GAG AAC GAT AGT TTT GTG ATT      4752
Ala Ile Glu Tyr Val Asp Ile Phe Lys Glu Asn Asp Ser Phe Val Ile
    1570                1575                1580

TAT CAA GGA GAA CTT AGC GAA ACA AGT CAA ACT GTT GTG AAA GTT TTC      4800
Tyr Gln Gly Glu Leu Ser Glu Thr Ser Gln Thr Val Val Lys Val Phe
1585                1590                1595                1600

TTA TCC TAT TTT ATA GAG GCG ACT GGA AAT AAG AAC CAC TTA TGG GTA      4848
Leu Ser Tyr Phe Ile Glu Ala Thr Gly Asn Lys Asn His Leu Trp Val
                1605                1610                1615

CGT GCT AAA TAC CAA AAG GAA ACG ACT GAT AAG ATC TTG TTC GAC CGT      4896
Arg Ala Lys Tyr Gln Lys Glu Thr Thr Asp Lys Ile Leu Phe Asp Arg
            1620                1625                1630

ACT GAT GAG AAA GAT CCG CAC GGT TGG TTT CTC AGC GAC GAT CAC AAG      4944
Thr Asp Glu Lys Asp Pro His Gly Trp Phe Leu Ser Asp Asp His Lys
        1635                1640                1645

ACC TTT AGT GGT CTC TCT TCC GCA CAG GCA TTA AAG AAC GAC AGT GAA      4992
Thr Phe Ser Gly Leu Ser Ser Ala Gln Ala Leu Lys Asn Asp Ser Glu
    1650                1655                1660
```

```
CCG ATG GAT TTC TCT GGC GCC AAT GCT CTC TAT TTC TGG GAA CTG TTC      5040
Pro Met Asp Phe Ser Gly Ala Asn Ala Leu Tyr Phe Trp Glu Leu Phe
1665                1670                1675                1680

TAT TAC ACG CCG ATG ATG ATG GCT CAT CGT TTG TTG CAG GAA CAG AAT      5088
Tyr Tyr Thr Pro Met Met Met Ala His Arg Leu Leu Gln Glu Gln Asn
            1685                1690                1695

TTT GAT GCG GCG AAC CAT TGG TTC CGT TAT GTC TGG AGT CCA TCC GGT      5136
Phe Asp Ala Ala Asn His Trp Phe Arg Tyr Val Trp Ser Pro Ser Gly
1700                1705                1710

TAT ATC GTT GAT GGT AAA ATT GCT ATC TAC CAC TGG AAC GTG CGA CCG      5184
Tyr Ile Val Asp Gly Lys Ile Ala Ile Tyr His Trp Asn Val Arg Pro
        1715                1720                1725

CTG GAA GAA GAC ACC AGT TGG AAT GCA CAA CAA CTG GAC TCC ACC GAT      5232
Leu Glu Glu Asp Thr Ser Trp Asn Ala Gln Gln Leu Asp Ser Thr Asp
    1730                1735                1740

CCA GAT GCT GTA GCC CAA GAT GAT CCG ATG CAC TAC AAG GTG GCT ACC      5280
Pro Asp Ala Val Ala Gln Asp Asp Pro Met His Tyr Lys Val Ala Thr
1745                1750                1755                1760

TTT ATG GCG ACG TTG GAT CTG CTA ATG GCC CGT GGT GAT GCT GCT TAC      5328
Phe Met Ala Thr Leu Asp Leu Leu Met Ala Arg Gly Asp Ala Ala Tyr
            1765                1770                1775

CGC CAG TTA GAG CGT GAT ACG TTG GCT GAA GCT AAA ATG TGG TAT ACA      5376
Arg Gln Leu Glu Arg Asp Thr Leu Ala Glu Ala Lys Met Trp Tyr Thr
        1780                1785                1790

CAG GCG CTT AAT CTG TTG GGT GAT GAG CCA CAA GTG ATG CTG AGT ACG      5424
Gln Ala Leu Asn Leu Leu Gly Asp Glu Pro Gln Val Met Leu Ser Thr
    1795                1800                1805

ACT TGG GCT AAT CCA ACA TTG GGT AAT GCT GCT TCA AAA ACC ACA CAG      5472
Thr Trp Ala Asn Pro Thr Leu Gly Asn Ala Ala Ser Lys Thr Thr Gln
1810                1815                1820

CAG GTT CGT CAG CAA GTG CTT ACC CAG TTG CGT CTC AAT AGC AGG GTA      5520
Gln Val Arg Gln Gln Val Leu Thr Gln Leu Arg Leu Asn Ser Arg Val
1825                1830                1835                1840

AAA ACC CCG TTG                                                      5532
Lys Thr Pro Leu
        1844

(2) INFORMATION FOR SEQ ID NO:53:

(i) SEQUENCE CHARACTERISTICS:
        (A) LENGTH: 1844 amino acids
        (B) TYPE: amino acids
        (C) STRANDEDNESS: single
        (D) TOPOLOGY: linear (ii) MOLECULE TYPE: protein (xi) SEQUENCE DESCRIPTION: SEQ ID NO:53 (TCBAII):

Features From To Description

Peptide  1    1844  TcbAii peptide

Fragment 1    11    (SEQ ID NO:1)

Fragment 978  990   (SEQ ID NO:23)

Fragment 1387 1401  (SEQ ID NO:22)

Fragment 1484 1505  (SEQ ID NO:24)

Fragment 1527 1552  (SEQ ID NO:21)

Phe Ile Gln Gly Tyr Ser Asp Leu Phe Gly Asn Arg Ala Asp Asn Tyr
1               5                   10                  15

Ala Ala Pro Gly Ser Val Ala Ser Met Phe Ser Pro Ala Ala Tyr Leu
```

-continued

```
                20                  25                  30
Thr Glu Leu Tyr Arg Glu Ala Lys Asn Leu His Asp Ser Ser Ile
            35                  40                  45
Tyr Tyr Leu Asp Lys Arg Arg Pro Asp Leu Ala Ser Leu Met Leu Ser
        50                  55                  60
Gln Lys Asn Met Asp Glu Glu Ile Ser Thr Leu Ala Leu Ser Asn Glu
 65                  70                  75                  80
Leu Cys Leu Ala Gly Ile Glu Thr Lys Thr Gly Lys Ser Gln Asp Glu
                85                  90                  95
Val Met Asp Met Leu Ser Thr Tyr Arg Leu Ser Gly Glu Thr Pro Tyr
            100                 105                 110
His His Ala Tyr Glu Thr Val Arg Glu Ile Val His Glu Arg Asp Pro
        115                 120                 125
Gly Phe Arg His Leu Ser Gln Ala Pro Ile Val Ala Ala Lys Leu Asp
    130                 135                 140
Pro Val Thr Leu Leu Gly Ile Ser Ser His Ile Ser Pro Glu Leu Tyr
145                 150                 155                 160
Asn Leu Leu Ile Glu Glu Ile Pro Glu Lys Asp Glu Ala Ala Leu Asp
                165                 170                 175
Thr Leu Tyr Lys Thr Asn Phe Gly Asp Ile Thr Thr Ala Gln Leu Met
            180                 185                 190
Ser Pro Ser Tyr Leu Ala Arg Tyr Tyr Gly Val Ser Pro Glu Asp Ile
        195                 200                 205
Ala Tyr Val Thr Thr Ser Leu Ser His Val Gly Tyr Ser Ser Asp Ile
    210                 215                 220
Leu Val Ile Pro Leu Val Asp Gly Val Gly Lys Met Glu Val Val Arg
225                 230                 235                 240
Val Thr Arg Thr Pro Ser Asp Asn Tyr Thr Ser Gln Thr Asn Tyr Ile
                245                 250                 255
Glu Leu Tyr Pro Gln Gly Gly Asp Asn Tyr Leu Ile Lys Tyr Asn Leu
            260                 265                 270
Ser Asn Ser Phe Gly Leu Asp Asp Phe Tyr Leu Gln Tyr Lys Asp Gly
        275                 280                 285
Ser Ala Asp Trp Thr Glu Ile Ala His Asn Pro Tyr Pro Asp Met Val
    290                 295                 300
Ile Asn Gln Lys Tyr Glu Ser Gln Ala Thr Ile Lys Arg Ser Asp Ser
305                 310                 315                 320
Asp Asn Ile Leu Ser Ile Gly Leu Gln Arg Trp His Ser Gly Ser Tyr
                325                 330                 335
Asn Phe Ala Ala Ala Asn Phe Lys Ile Asp Gln Tyr Ser Pro Lys Ala
            340                 345                 350
Phe Leu Leu Lys Met Asn Lys Ala Ile Arg Leu Leu Lys Ala Thr Gly
        355                 360                 365
Leu Ser Phe Ala Thr Leu Glu Arg Ile Val Asp Ser Val Asn Ser Thr
    370                 375                 380
Lys Ser Ile Thr Val Glu Val Leu Asn Lys Val Tyr Arg Val Lys Phe
385                 390                 395                 400
Tyr Ile Asp Arg Tyr Gly Ile Ser Glu Glu Thr Ala Ala Ile Leu Ala
                405                 410                 415
Asn Ile Asn Ile Ser Gln Gln Ala Val Gly Asn Gln Leu Ser Gln Phe
            420                 425                 430
Glu Gln Leu Phe Asn His Pro Pro Leu Asn Gly Ile Arg Tyr Glu Ile
        435                 440                 445
```

```
Ser Glu Asp Asn Ser Lys His Leu Pro Asn Pro Asp Leu Asn Leu Lys
    450                 455                 460

Pro Asp Ser Thr Gly Asp Asp Gln Arg Lys Ala Val Leu Lys Arg Ala
465                 470                 475                 480

Phe Gln Val Asn Ala Ser Glu Leu Tyr Gln Met Leu Leu Ile Thr Asp
                485                 490                 495

Arg Lys Glu Asp Gly Val Ile Lys Asn Leu Glu Asn Leu Ser Asp
                500                 505                 510

Leu Tyr Leu Val Ser Leu Leu Ala Gln Ile His Asn Leu Thr Ile Ala
        515                 520                 525

Glu Leu Asn Ile Leu Leu Val Ile Cys Gly Tyr Gly Asp Thr Asn Ile
    530                 535                 540

Tyr Gln Ile Thr Asp Asp Asn Leu Ala Lys Ile Val Glu Thr Leu Leu
545                 550                 555                 560

Trp Ile Thr Gln Trp Leu Lys Thr Gln Lys Trp Thr Val Thr Asp Leu
                565                 570                 575

Phe Leu Met Thr Thr Ala Thr Tyr Ser Thr Thr Leu Thr Pro Glu Ile
            580                 585                 590

Ser Asn Leu Thr Ala Thr Leu Ser Ser Thr Leu His Gly Lys Glu Ser
        595                 600                 605

Leu Ile Gly Glu Asp Leu Lys Arg Ala Met Ala Pro Cys Phe Thr Ser
    610                 615                 620

Ala Leu His Leu Thr Ser Gln Glu Val Ala Tyr Asp Leu Leu Leu Trp
625                 630                 635                 640

Ile Asp Gln Ile Gln Pro Ala Gln Ile Thr Val Asp Gly Phe Trp Glu
                645                 650                 655

Glu Val Gln Thr Thr Pro Thr Ser Leu Lys Val Ile Thr Phe Ala Gln
            660                 665                 670

Val Leu Ala Gln Leu Ser Leu Ile Tyr Arg Arg Ile Gly Leu Ser Glu
        675                 680                 685

Thr Glu Leu Ser Leu Ile Val Thr Gln Ser Ser Leu Leu Val Ala Gly
    690                 695                 700

Lys Ser Ile Leu Asp His Gly Leu Leu Thr Leu Met Ala Leu Glu Gly
705                 710                 715                 720

Phe His Thr Trp Val Asn Gly Leu Gly Gln His Ala Ser Leu Ile Leu
                725                 730                 735

Ala Ala Leu Lys Asp Gly Ala Leu Thr Val Thr Asp Val Ala Gln Ala
            740                 745                 750

Met Asn Lys Glu Glu Ser Leu Leu Gln Met Ala Ala Asn Gln Val Glu
        755                 760                 765

Lys Asp Leu Thr Lys Leu Thr Ser Trp Thr Gln Ile Asp Ala Ile Leu
    770                 775                 780

Gln Trp Leu Gln Met Ser Ser Ala Leu Ala Val Ser Pro Leu Asp Leu
785                 790                 795                 800

Ala Gly Met Met Ala Leu Lys Tyr Gly Ile Asp His Asn Tyr Ala Ala
                805                 810                 815

Trp Gln Ala Ala Ala Ala Leu Met Ala Asp His Ala Asn Gln Ala
            820                 825                 830

Gln Lys Lys Leu Asp Glu Thr Phe Ser Lys Ala Leu Cys Asn Tyr Tyr
        835                 840                 845

Ile Asn Ala Val Val Asp Ser Ala Ala Gly Val Arg Asp Arg Asn Gly
    850                 855                 860
```

```
Leu Tyr Thr Tyr Leu Leu Ile Asp Asn Gln Val Ser Ala Asp Val Ile
865                 870                 875                 880

Thr Ser Arg Ile Ala Glu Ala Ile Ala Gly Ile Gln Leu Tyr Val Asn
            885                 890                 895

Arg Ala Leu Asn Arg Asp Glu Gly Gln Leu Ala Ser Asp Val Ser Thr
            900                 905                 910

Arg Gln Phe Phe Thr Asp Trp Glu Arg Tyr Asn Lys Arg Tyr Ser Thr
            915                 920                 925

Trp Ala Gly Val Ser Glu Leu Val Tyr Tyr Pro Glu Asn Tyr Val Asp
930                 935                 940

Pro Thr Gln Arg Ile Gly Gln Thr Lys Met Met Asp Ala Leu Leu Gln
945                 950                 955                 960

Ser Ile Asn Gln Ser Gln Leu Asn Ala Asp Thr Val Glu Asp Ala Phe
            965                 970                 975

Lys Thr Tyr Leu Thr Ser Phe Glu Gln Val Ala Asn Leu Lys Val Ile
            980                 985                 990

Ser Ala Tyr His Asp Asn Val Asn Val Asp Gln Gly Leu Thr Tyr Phe
            995                 1000                1005

Ile Gly Ile Asp Gln Ala Ala Pro Gly Thr Tyr Tyr Trp Arg Ser Val
    1010                1015                1020

Asp His Ser Lys Cys Glu Asn Gly Lys Phe Ala Ala Asn Ala Trp Gly
1025                1030                1035                1040

Glu Trp Asn Lys Ile Thr Cys Ala Val Asn Pro Trp Lys Asn Ile Ile
            1045                1050                1055

Arg Pro Val Val Tyr Met Ser Arg Leu Tyr Leu Trp Leu Glu Gln
            1060                1065                1070

Gln Ser Lys Lys Ser Asp Asp Gly Lys Thr Thr Ile Tyr Gln Tyr Asn
    1075                1080                1085

Leu Lys Leu Ala His Ile Arg Tyr Asp Gly Ser Trp Asn Thr Pro Phe
    1090                1095                1100

Thr Phe Asp Val Thr Glu Lys Val Lys Asn Tyr Thr Ser Ser Thr Asp
1105                1110                1115                1120

Ala Ala Glu Ser Leu Gly Leu Tyr Cys Thr Gly Tyr Gln Gly Glu Asp
            1125                1130                1135

Thr Leu Leu Val Met Phe Tyr Ser Met Gln Ser Ser Tyr Ser Ser Tyr
            1140                1145                1150

Thr Asp Asn Asn Ala Pro Val Thr Gly Leu Tyr Ile Phe Ala Asp Met
        1155                1160                1165

Ser Ser Asp Asn Met Thr Asn Ala Gln Ala Thr Asn Tyr Trp Asn Asn
    1170                1175                1180

Ser Tyr Pro Gln Phe Asp Thr Val Met Ala Asp Pro Asp Ser Asp Asn
1185                1190                1195                1200

Lys Lys Val Ile Thr Arg Arg Val Asn Asn Arg Tyr Ala Glu Asp Tyr
            1205                1210                1215

Glu Ile Pro Ser Ser Val Thr Ser Asn Ser Asn Tyr Ser Trp Gly Asp
        1220                1225                1230

His Ser Leu Thr Met Leu Tyr Gly Gly Ser Val Pro Asn Ile Thr Phe
    1235                1240                1245

Glu Ser Ala Ala Glu Asp Leu Arg Leu Ser Thr Asn Met Ala Leu Ser
    1250                1255                1260

Ile Ile His Asn Gly Tyr Ala Gly Thr Arg Arg Ile Gln Cys Asn Leu
1265                1270                1275                1280

Met Lys Gln Tyr Ala Ser Leu Gly Asp Lys Phe Ile Ile Tyr Asp Ser
```

-continued

```
                1285                1290                1295
Ser Phe Asp Asp Ala Asn Arg Phe Asn Leu Val Pro Leu Phe Lys Phe
            1300                1305                1310
Gly Lys Asp Glu Asn Ser Asp Asp Ser Ile Cys Ile Tyr Asn Glu Asn
            1315                1320                1325
Pro Ser Ser Glu Asp Lys Lys Trp Tyr Phe Ser Lys Asp Asp Asn
            1330                1335                1340
Lys Thr Ala Asp Tyr Asn Gly Gly Thr Gln Cys Ile Asp Ala Gly Thr
1345                1350                1355                1360
Ser Asn Lys Asp Phe Tyr Tyr Asn Leu Gln Glu Ile Glu Val Ile Ser
            1365                1370                1375
Val Thr Gly Gly Tyr Trp Ser Ser Tyr Lys Ile Ser Asn Pro Ile Asn
            1380                1385                1390
Ile Asn Thr Gly Ile Asp Ser Ala Lys Val Lys Val Thr Val Lys Ala
            1395                1400                1405
Gly Gly Asp Asp Gln Ile Phe Thr Ala Asp Asn Ser Thr Tyr Val Pro
            1410                1415                1420
Gln Gln Pro Ala Pro Ser Phe Glu Glu Met Ile Tyr Gln Phe Asn Asn
1425                1430                1435                1440
Leu Thr Ile Asp Cys Lys Asn Leu Asn Phe Ile Asp Asn Gln Ala His
            1445                1450                1455
Ile Glu Ile Asp Phe Thr Ala Thr Ala Gln Asp Gly Arg Phe Leu Gly
            1460                1465                1470
Ala Glu Thr Phe Ile Ile Pro Val Thr Lys Lys Val Leu Gly Thr Glu
            1475                1480                1485
Asn Val Ile Ala Leu Tyr Ser Glu Asn Asn Gly Val Gln Tyr Met Gln
            1490                1495                1500
Ile Gly Ala Tyr Arg Thr Arg Leu Asn Thr Leu Phe Ala Gln Gln Leu
1505                1510                1515                1520
Val Ser Arg Ala Asn Arg Gly Ile Asp Ala Val Leu Ser Met Glu Thr
            1525                1530                1535
Gln Asn Ile Gln Glu Pro Gln Leu Gly Ala Gly Thr Tyr Val Gln Leu
            1540                1545                1550
Val Leu Asp Lys Tyr Asp Glu Ser Ile His Gly Thr Asn Lys Ser Phe
            1555                1560                1565
Ala Ile Glu Tyr Val Asp Ile Phe Lys Glu Asn Asp Ser Phe Val Ile
1570                1575                1580
Tyr Gln Gly Glu Leu Ser Glu Thr Ser Gln Thr Val Val Lys Val Phe
1585                1590                1595                1600
Leu Ser Tyr Phe Ile Glu Ala Thr Gly Asn Lys Asn His Leu Trp Val
            1605                1610                1615
Arg Ala Lys Tyr Gln Lys Glu Thr Thr Asp Lys Ile Leu Phe Asp Arg
            1620                1625                1630
Thr Asp Glu Lys Asp Pro His Gly Trp Phe Leu Ser Asp His Lys
            1635                1640                1645
Thr Phe Ser Gly Leu Ser Ser Ala Gln Ala Leu Lys Asn Asp Ser Glu
            1650                1655                1660
Pro Met Asp Phe Ser Gly Ala Asn Ala Leu Tyr Phe Trp Glu Leu Phe
1665                1670                1675                1680
Tyr Tyr Thr Pro Met Met Met Ala His Arg Leu Leu Gln Glu Gln Asn
            1685                1690                1695
Phe Asp Ala Ala Asn His Trp Phe Arg Tyr Val Trp Ser Pro Ser Gly
            1700                1705                1710
```

-continued

```
Tyr Ile Val Asp Gly Lys Ile Ala Ile Tyr His Trp Asn Val Arg Pro
        1715                1720                1725

Leu Glu Glu Asp Thr Ser Trp Asn Ala Gln Gln Leu Asp Ser Thr Asp
            1730                1735                1740

Pro Asp Ala Val Ala Gln Asp Pro Met His Tyr Lys Val Ala Thr
1745                1750                1755                1760

Phe Met Ala Thr Leu Asp Leu Leu Met Ala Arg Gly Asp Ala Ala Tyr
                1765                1770                1775

Arg Gln Leu Glu Arg Asp Thr Leu Ala Glu Ala Lys Met Trp Tyr Thr
            1780                1785                1790

Gln Ala Leu Asn Leu Leu Gly Asp Glu Pro Gln Val Met Leu Ser Thr
            1795                1800                1805

Thr Trp Ala Asn Pro Thr Leu Gly Asn Ala Ala Ser Lys Thr Thr Gln
            1810                1815                1820

Gln Val Arg Gln Val Leu Thr Gln Leu Arg Leu Asn Ser Arg Val
1825                1830                1835                1840

Lys Thr Pro Leu
            1844
```

(2) INFORMATION FOR SEQ ID NO:54:

(i) SEQUENCE CHARACTERISTICS:
        (A) LENGTH: 1722 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:54 (TCBAIII CODING:region):

```
CTA GGA ACA GCC AAT TCC CTG ACC GCT TTA TTC CTG CCG CAG GAA AAT      48
Leu Gly Thr Ala Asn Ser Leu Thr Ala Leu Phe Leu Pro Gln Glu Asn
 1               5                  10                  15

AGC AAG CTC AAA GGC TAC TGG CGG ACA CTG GCG CAG CGT ATG TTT AAT      96
Ser Lys Leu Lys Gly Tyr Trp Arg Thr Leu Ala Gln Arg Met Phe Asn
            20                  25                  30

TTA CGT CAT AAT CTG TCG ATT GAC GGC CAG CCG CTC TCC TTG CCG CTG     144
Leu Arg His Asn Leu Ser Ile Asp Gly Gln Pro Leu Ser Leu Pro Leu
        35                  40                  45

TAT GCT AAA CCG GCT GAT CCA AAA GCT TTA CTG AGT GCG GCG GTT TCA     192
Tyr Ala Lys Pro Ala Asp Pro Lys Ala Leu Leu Ser Ala Ala Val Ser
    50                  55                  60

GCT TCT CAA GGG GGA GCC GAC TTG CCG AAG GCG CCG CTG ACT ATT CAC     240
Ala Ser Gln Gly Gly Ala Asp Leu Pro Lys Ala Pro Leu Thr Ile His
65                  70                  75                  80

CGC TTC CCT CAA ATG CTA GAA GGG GCA CGG GGC TTG GTT AAC CAG CTT     288
Arg Phe Pro Gln Met Leu Glu Gly Ala Arg Gly Leu Val Asn Gln Leu
                85                  90                  95

ATA CAG TTC GGT AGT TCA CTA TTG GGG TAC AGT GAG CGT CAG GAT GCG     336
Ile Gln Phe Gly Ser Ser Leu Leu Gly Tyr Ser Glu Arg Gln Asp Ala
            100                 105                 110

GAA GCT ATG AGT CAA CTA CTG CAA ACC CAA GCC AGC GAG TTA ATA CTG     384
Glu Ala Met Ser Gln Leu Leu Gln Thr Gln Ala Ser Glu Leu Ile Leu
        115                 120                 125

ACC AGT ATT CGT ATG CAG GAT AAC CAA TTG GCA GAG CTG GAT TCG GAA     432
Thr Ser Ile Arg Met Gln Asp Asn Gln Leu Ala Glu Leu Asp Ser Glu
    130                 135                 140

AAA ACC GCC TTG CAA GTC TCT TTA GCT GGA GTG CAA CAA CGG TTT GAC     480
Lys Thr Ala Leu Gln Val Ser Leu Ala Gly Val Gln Gln Arg Phe Asp
```

```
                      145                 150                 155                 160
AGC TAT AGC CAA CTG TAT GAG GAG AAC ATC AAC GCA GGT GAG CAG CGA                    528
Ser Tyr Ser Gln Leu Tyr Glu Glu Asn Ile Asn Ala Gly Glu Gln Arg
                165                 170                 175

GCG CTG GCG TTA CGC TCA GAA TCT GCT ATT GAG TCT CAG GGA GCG CAG                    576
Ala Leu Ala Leu Arg Ser Glu Ser Ala Ile Glu Ser Gln Gly Ala Gln
            180                 185                 190

ATT TCC CGT ATG GCA GGC GCG GGT GTT GAT ATG GCA CCA AAT ATC TTC                    624
Ile Ser Arg Met Ala Gly Ala Gly Val Asp Met Ala Pro Asn Ile Phe
        195                 200                 205

GGC CTG GCT GAT GGC GGC ATG CAT TAT GGT GCT ATT GCC TAT GCC ATC                    672
Gly Leu Ala Asp Gly Gly Met His Tyr Gly Ala Ile Ala Tyr Ala Ile
    210                 215                 220

GCT GAC GGT ATT GAG TTG AGT GCT TCT GCC AAG ATG GTT GAT GCG GAG                    720
Ala Asp Gly Ile Glu Leu Ser Ala Ser Ala Lys Met Val Asp Ala Glu
225                 230                 235                 240

AAA GTT GCT CAG TCG GAA ATA TAT CGC CGT CGC CGT CAA GAA TGG AAA                    768
Lys Val Ala Gln Ser Glu Ile Tyr Arg Arg Arg Arg Gln Glu Trp Lys
                245                 250                 255

ATT CAG CGT GAC AAC GCA CAA GCG GAG ATT AAC CAG TTA AAC GCG CAA                    816
Ile Gln Arg Asp Asn Ala Gln Ala Glu Ile Asn Gln Leu Asn Ala Gln
            260                 265                 270

CTG GAA TCA CTG TCT ATT CGC CGT GAA GCC GCT GAA ATG CAA AAA GAG                    864
Leu Glu Ser Leu Ser Ile Arg Arg Glu Ala Ala Glu Met Gln Lys Glu
        275                 280                 285

TAC CTG AAA ACC CAG CAA GCT CAG GCG CAG GCA CAA CTT ACT TTC TTA                    912
Tyr Leu Lys Thr Gln Gln Ala Gln Ala Gln Ala Gln Leu Thr Phe Leu
    290                 295                 300

AGA AGC AAA TTC AGT AAT CAA GCG TTA TAT AGT TGG TTA CGA GGG CGT                    960
Arg Ser Lys Phe Ser Asn Gln Ala Leu Tyr Ser Trp Leu Arg Gly Arg
305                 310                 315                 320

TTG TCA GGT ATT TAT TTC CAG TTC TAT GAC TTG GCC GTA TCA CGT TGC                   1008
Leu Ser Gly Ile Tyr Phe Gln Phe Tyr Asp Leu Ala Val Ser Arg Cys
                325                 330                 335

CTG ATG GCA GAG CAA TCC TAT CAA TGG GAA GCT AAT GAT AAT TCC ATT                   1056
Leu Met Ala Glu Gln Ser Tyr Gln Trp Glu Ala Asn Asp Asn Ser Ile
            340                 345                 350

AGC TTT GTC AAA CCG GGT GCA TGG CAA GGA ACT TAC GCC GGC TTA TTG                   1104
Ser Phe Val Lys Pro Gly Ala Trp Gln Gly Thr Tyr Ala Gly Leu Leu
        355                 360                 365

TGT GGA GAA GCT TTG ATA CAA AAT CTG GCA CAA ATG GAA GAG GCA TAT                   1152
Cys Gly Glu Ala Leu Ile Gln Asn Leu Ala Gln Met Glu Glu Ala Tyr
    370                 375                 380

CTG AAA TGG GAA TCT CGC GCT TTG GAA GTA GAA CGC ACG GTT TCA TTG                   1200
Leu Lys Trp Glu Ser Arg Ala Leu Glu Val Glu Arg Thr Val Ser Leu
385                 390                 395                 400

GCA GTG GTT TAT GAT TCA CTG GAA GGT AAT GAT CGT TTT AAT TTA GCG                   1248
Ala Val Val Tyr Asp Ser Leu Glu Gly Asn Asp Arg Phe Asn Leu Ala
                405                 410                 415

GAA CAA ATA CCT GCA TTA TTG GAT AAG GGG GAG GGA ACA GCA GGA ACT                   1296
Glu Gln Ile Pro Ala Leu Leu Asp Lys Gly Glu Gly Thr Ala Gly Thr
            420                 425                 430

AAA GAA AAT GGG TTA TCA TTG GCT AAT GCT ATC CTG TCA GCT TCG GTC                   1344
Lys Glu Asn Gly Leu Ser Leu Ala Asn Ala Ile Leu Ser Ala Ser Val
        435                 440                 445

AAA TTG TCC GAC TTG AAA CTG GGA ACG GAT TAT CCA GAC AGT ATC GTT                   1392
Lys Leu Ser Asp Leu Lys Leu Gly Thr Asp Tyr Pro Asp Ser Ile Val
    450                 455                 460

GGT AGC AAC AAG GTT CGT CGT ATT AAG CAA ATC AGT GTT TCG CTA CCT                   1440
```

```
Gly Ser Asn Lys Val Arg Arg Ile Lys Gln Ile Ser Val Ser Leu Pro
465                 470                 475                 480

GCA TTG GTT GGG CCT TAT CAG GAT GTT CAG GCT ATG CTC AGC TAT GGT      1488
Ala Leu Val Gly Pro Tyr Gln Asp Val Gln Ala Met Leu Ser Tyr Gly
                485                 490                 495

GGC AGT ACT CAA TTG CCG AAA GGT TGT TCA GCG TTG GCT GTG TCT CAT      1536
Gly Ser Thr Gln Leu Pro Lys Gly Cys Ser Ala Leu Ala Val Ser His
            500                 505                 510

GGT ACC AAT GAT AGT GGT CAG TTC CAG TTG GAT TTC AAT GAC GGC AAA      1584
Gly Thr Asn Asp Ser Gly Gln Phe Gln Leu Asp Phe Asn Asp Gly Lys
            515                 520                 525

TAC CTG CCA TTT GAA GGT ATT GCT CTT GAT GAT CAG GGT ACA CTG AAT      1632
Tyr Leu Pro Phe Glu Gly Ile Ala Leu Asp Asp Gln Gly Thr Leu Asn
            530                 535                 540

CTT CAA TTT CCG AAT GCT ACC GAC AAG CAG AAA GCA ATA TTG CAA ACT      1680
Leu Gln Phe Pro Asn Ala Thr Asp Lys Gln Lys Ala Ile Leu Gln Thr
545                 550                 555                 560

ATG AGC GAT ATT ATT TTG CAT ATT CGT TAT ACC ATC CGT TAA              1722
Met Ser Asp Ile Ile Leu His Ile Arg Tyr Thr Ile Arg
                565                 570         573

(2) INFORMATION FOR SEQ ID NO:55:

(i) SEQUENCE CHARACTERISTICS:
        (A) LENGTH: 573 amino acids
        (B) TYPE: amino acids
        (C) STRANDEDNESS: single
        (D) TOPOLOGY: linear (ii) MOLECULE TYPE: protein (xi) SEQUENCE DESCRIPTION: SEQ ID NO:55 (TCBAIII):

Leu Gly Thr Ala Asn Ser Leu Thr Ala Leu Phe Leu Pro Gln Glu Asn
1               5                   10                  15

Ser Lys Leu Lys Gly Tyr Trp Arg Thr Leu Ala Gln Arg Met Phe Asn
                20                  25                  30

Leu Arg His Asn Leu Ser Ile Asp Gly Gln Pro Leu Ser Leu Pro Leu
            35                  40                  45

Tyr Ala Lys Pro Ala Asp Pro Lys Ala Leu Leu Ser Ala Ala Val Ser
    50                  55                  60

Ala Ser Gln Gly Gly Ala Asp Leu Pro Lys Ala Pro Leu Thr Ile His
65                  70                  75                  80

Arg Phe Pro Gln Met Leu Glu Gly Ala Arg Gly Leu Val Asn Gln Leu
                85                  90                  95

Ile Gln Phe Gly Ser Ser Leu Leu Gly Tyr Ser Glu Arg Gln Asp Ala
            100                 105                 110

Glu Ala Met Ser Gln Leu Leu Gln Thr Gln Ala Ser Glu Leu Ile Leu
        115                 120                 125

Thr Ser Ile Arg Met Gln Asp Asn Gln Leu Ala Glu Leu Asp Ser Glu
    130                 135                 140

Lys Thr Ala Leu Gln Val Ser Leu Ala Gly Val Gln Gln Arg Phe Asp
145                 150                 155                 160

Ser Tyr Ser Gln Leu Tyr Glu Glu Asn Ile Asn Ala Gly Glu Gln Arg
                165                 170                 175

Ala Leu Ala Leu Arg Ser Glu Ser Ala Ile Glu Ser Gln Gly Ala Gln
            180                 185                 190

Ile Ser Arg Met Ala Gly Ala Gly Val Asp Met Ala Pro Asn Ile Phe
        195                 200                 205
```

-continued

```
Gly Leu Ala Asp Gly Gly Met His Tyr Gly Ala Ile Ala Tyr Ala Ile
    210                 215                 220

Ala Asp Gly Ile Glu Leu Ser Ala Ser Ala Lys Met Val Asp Ala Glu
225                 230                 235                 240

Lys Val Ala Gln Ser Glu Ile Tyr Arg Arg Arg Gln Glu Trp Lys
                245                 250                 255

Ile Gln Arg Asp Asn Ala Gln Ala Glu Ile Asn Gln Leu Asn Ala Gln
            260                 265                 270

Leu Glu Ser Leu Ser Ile Arg Arg Glu Ala Ala Glu Met Gln Lys Glu
                275                 280                 285

Tyr Leu Lys Thr Gln Gln Ala Gln Ala Gln Leu Thr Phe Leu
            290                 295                 300

Arg Ser Lys Phe Ser Asn Gln Ala Leu Tyr Ser Trp Leu Arg Gly Arg
305                 310                 315                 320

Leu Ser Gly Ile Tyr Phe Gln Phe Tyr Asp Leu Ala Val Ser Arg Cys
                325                 330                 335

Leu Met Ala Glu Gln Ser Tyr Gln Trp Glu Ala Asn Asp Asn Ser Ile
                340                 345                 350

Ser Phe Val Lys Pro Gly Ala Trp Gln Gly Thr Tyr Ala Gly Leu Leu
            355                 360                 365

Cys Gly Glu Ala Leu Ile Gln Asn Leu Ala Gln Met Glu Glu Ala Tyr
370                 375                 380

Leu Lys Trp Glu Ser Arg Ala Leu Glu Val Glu Arg Thr Val Ser Leu
385                 390                 395                 400

Ala Val Val Tyr Asp Ser Leu Glu Gly Asn Asp Arg Phe Asn Leu Ala
                405                 410                 415

Glu Gln Ile Pro Ala Leu Leu Asp Lys Gly Glu Gly Thr Ala Gly Thr
            420                 425                 430

Lys Glu Asn Gly Leu Ser Leu Ala Asn Ala Ile Leu Ser Ala Ser Val
                435                 440                 445

Lys Leu Ser Asp Leu Lys Leu Gly Thr Asp Tyr Pro Asp Ser Ile Val
    450                 455                 460

Gly Ser Asn Lys Val Arg Arg Ile Lys Gln Ile Ser Val Ser Leu Pro
465                 470                 475                 480

Ala Leu Val Gly Pro Tyr Gln Asp Val Gln Ala Met Leu Ser Tyr Gly
                485                 490                 495

Gly Ser Thr Gln Leu Pro Lys Gly Cys Ser Ala Leu Ala Val Ser His
            500                 505                 510

Gly Thr Asn Asp Ser Gly Gln Phe Gln Leu Asp Phe Asn Asp Gly Lys
                515                 520                 525

Tyr Leu Pro Phe Glu Gly Ile Ala Leu Asp Asp Gln Gly Thr Leu Asn
    530                 535                 540

Leu Gln Phe Pro Asn Ala Thr Asp Lys Gln Lys Ala Ile Leu Gln Thr
545                 550                 555                 560

Met Ser Asp Ile Ile Leu His Ile Arg Tyr Thr Ile Arg
                565                 570             573
```

(2) INFORMATION FOR SEQ ID NO:56:

(i) SEQUENCE CHARACTERISTICS:
       (A) LENGTH: 2994 base pairs
       (B) TYPE: nucleic acid
       (C) STRANDEDNESS: double
       (D) TOPOLOGY: linear (ii) MOLECULE TYPE: DNA (genomic)

-continued (xi) SEQUENCE DESCRIPTION: SEQ ID NO:56 (TCCA):

```
  1  ATG AAT CAA CTC GCC AGT CCC CTG ATT TCC CGC ACC GAA GAG ATC CAC        48
  1  Met Asn Gln Leu Ala Ser Pro Leu Ile Ser Arg Thr Glu Glu Ile His        16

49  AAC TTA CCC GGT AAA TTG ACC GAT CTT GGT TAT ACC TCA GTG TTT GAT        96
 17  Asn Leu Pro Gly Lys Leu Thr Asp Leu Gly Tyr Thr Ser Val Phe Asp        32

97  GTG GTA CGT ATG CCG CGT GAG CGT TTT ATT CGT GAG CAT CGT GCT GAT       144
 33  Val Val Arg Met Pro Arg Glu Arg Phe Ile Arg Glu His Arg Ala Asp        48

145  CTC GGG CGC AGT GCT GAA AAA ATG TAT GAC CTG GCA GTG GGC TAT GC        192
 49  Leu Gly Arg Ser Ala Glu Lys Met Tyr Asp Leu Ala Val Gly Tyr Ala        64

193  CAT CAG GTG TTA CAC CAT TTT CGC CGT AAT TCT CTT AGT GAA GCT GT        240
 65  His Gln Val Leu His His Phe Arg Arg Asn Ser Leu Ser Glu Ala Val        80

241  CAG TTT GGC TTG AGA AGT CCG TTC TCC GTA TCA GGC CCG GAT TAC GC        288
 81  Gln Phe Gly Leu Arg Ser Pro Phe Ser Val Ser Gly Pro Asp Tyr Ala        96

289  AAT CAG TTT CTT GAT GCA AAC ACG GGT TGG AAA GAT AAA GCA CCA AG        336
 97  Asn Gln Phe Leu Asp Ala Asn Thr Gly Trp Lys Asp Lys Ala Pro Ser       112

337  GGA TCA CCG GAA GCC AAT GAT GCG CCG GTA GCC TAT CTG ACT CAT AT        384
113  Gly Ser Pro Glu Ala Asn Asp Ala Pro Val Ala Tyr Leu Thr His Ile       128

385  TAT CAA TTG GCC CTT GAA CAG GAA AAG AAT GGC GCC ACT ACC ATT AT        432
129  Tyr Gln Leu Ala Leu Glu Gln Glu Lys Asn Gly Ala Thr Thr Ile Met       144

433  AAT ACG CTG GCG GAG CGT CGC CCC GAT CTG GGT GCT TTG TTA ATT AA        480
145  Asn Thr Leu Ala Glu Arg Arg Pro Asp Leu Gly Ala Leu Leu Ile Asn       160

481  GAT AAA GCA ATC AAT GAG GTG ATA CCG CAA TTG CAG TTG GTC AAT GA        528
161  Asp Lys Ala Ile Asn Glu Val Ile Pro Gln Leu Gln Leu Val Asn Gly       176

529  ATT CTG TCC AAA GCT ATT CAG AAG AAA CTG AGT TTG ACT GAT CTG GA        576
177  Ile Leu Ser Lys Ala Ile Gln Lys Lys Leu Ser Leu Thr Asp Leu Gly       192

577  GCG GTA AAC GCC AGA CTT TCC ACT ACC CGT TAC CCG AAT AAT CTG CC        624
193  Ala Val Asn Ala Arg Leu Ser Thr Thr Arg Tyr Pro Asn Asn Leu Pro       208

625  TAT CAT TAT GGT CAT CAG CAG ATT CAG ACA GCT CAA TCG GTA TTG GG        672
209  Tyr His Tyr Gly His Gln Gln Ile Gln Thr Ala Gln Ser Val Leu Gly       224

673  ACT ACG TTG CAA GAT ATC ACT TTG CCA CAG ACG CTG GAT CTG CCG CA        720
225  Thr Thr Leu Gln Asp Ile Thr Leu Pro Gln Thr Leu Asp Leu Pro Gly       240

721  AAC TTC TGG GCA ACA GCA AAA GGA AAA CTG AGC GAT ACG ACT GCC AG        768
241  Asn Phe Trp Ala Thr Ala Lys Gly Lys Leu Ser Asp Thr Thr Ala Ser       256

769  GCT TTG ACC CGA CTG CAA ATC ATG GCG AGT CAG TTT TCG CCA GAG CA        816
257  Ala Leu Thr Arg Leu Gln Ile Met Ala Ser Gln Phe Ser Pro Glu Gln       272

817  CAG AAA ATC ATT ACG GAG ACT GTC GGT CAG GAT TTC TAT CAG CTT AA        864
273  Gln Lys Ile Ile Thr Glu Thr Val Gly Gln Asp Phe Tyr Gln Leu Asn       288

865  TAT GGT GAC AGT TCG CTT ACT GTG AAT AGT TTC AGC GAC ATG ACC AT        912
289  Tyr Gly Asp Ser Ser Leu Thr Val Asn Ser Phe Ser Asp Met Thr Ile       304
```

-continued

```
 913  ATG ACT GAT CGA ACA AGT TTG ACT GTA CCC CAG GTA GAA CTG ATG TT  960
 305  Met Thr Asp Arg Thr Ser Leu Thr Val Pro Gln Val Glu Leu Met Le   320

961  TGT TCA ACT GTC GGA GGT TCT ACG GTT GTT AAG TCT GAT AAT GTG AGT 1008
 321  Cys Ser Thr Val Gly Gly Ser Thr Val Val Lys Ser Asp Asn Val Se   336

1009  TCT GGT GAC ACG ACA GCG ACG CCA TTT GCG TAT GGC GCC CGC TTT ATT
1056
 337  Ser Gly Asp Thr Thr Ala Thr Pro Phe Ala Tyr Gly Ala Arg Phe      352

1057  CAT GCC GGT AAG CCG GAG GCG ATT ACC CTG AGT CGC AGT GGT GCG GAG
1104
 353  His Ala Gly Lys Pro Glu Ala Ile Thr Leu Ser Arg Ser Gly Ala      368

1105  GCG CAT TTT GCT CTG ACG GTT AAC AAT CTG ACA GAT GAC AAG TTG GAC
1152
 369  Ala His Phe Ala Leu Thr Val Asn Asn Leu Thr Asp Asp Lys Leu      384

1153  CGT ATT AAC CGC ACA GTG CGC CTG CAA AAA TGG CTG AAT CTG CCT TAT
1200
 385  Arg Ile Asn Arg Thr Val Arg Leu Gln Lys Trp Leu Asn Leu Pro      400

1201  GAG GAT ATT GAC CTG TTA GTG ACT TCT GCT ATG GAT GCG GAA ACA GGA
1248
 401  Glu Asp Ile Asp Leu Leu Val Thr Ser Ala Met Asp Ala Glu Thr      416

1249  AAT ACC GCG CTG TCG ATG AAC GAC AAT ACG CTG CGT ATG TTG GGA GTG
1296
 417  Asn Thr Ala Leu Ser Met Asn Asp Asn Thr Leu Arg Met Leu Gly      432

1297  TTC AAA CAT TAT CAG GCG AAG TAT GGT GTT AGC GCT AAA CAA TTT GCT
1344
 433  Phe Lys His Tyr Gln Ala Lys Tyr Gly Val Ser Ala Lys Gln Phe      448

1345  GGC TGG CTG CGC GTA GTG GCC CCG TTT GCC ATT ACA CCG GCA ACG CCG
1392
 449  Gly Trp Leu Arg Val Val Ala Pro Phe Ala Ile Thr Pro Ala Thr      464

1393  TTT TTA GAC CAA GTG TTT AAC TCC GTC GGC ACC TTT GAT ACA CCG TTT
1440
 465  Phe Leu Asp Gln Val Phe Asn Ser Val Gly Thr Phe Asp Thr Pro      480

1441  GTG ATA GAT AAT CAG GAT TTT GTC TAT ACA TTG ACC ACC GGG GGC GAT
1488
 481  Val Ile Asp Asn Gln Asp Phe Val Tyr Thr Leu Thr Thr Gly Gly      496

1489  GGG GCG CGT GTT AAG CAT ATC AGC ACG GCA CTG GGC CTC AAT CAT CGT
1536
 497  Gly Ala Arg Val Lys His Ile Ser Thr Ala Leu Gly Leu Asn His      512

1537  CAG TTC CTG TTA TTG GCG GAT AAT ATT GCC CGT CAA CAG GGG AAT GTC
1584
 513  Gln Phe Leu Leu Leu Ala Asp Asn Ile Ala Arg Gln Gln Gly Asn      528

1585  ACG CAA AGC ACA CTC AAC TGT AAT CTG TTT GTG GTG TCA GCT TTC TAC
1632
 529  Thr Gln Ser Thr Leu Asn Cys Asn Leu Phe Val Val Ser Ala Phe      544

1633  CGT CTG GCT AAT TTG GCG CGC ACA TTG GGG ATA AAT CCA GAG TCT TTC
1680
 545  Arg Leu Ala Asn Leu Ala Arg Thr Leu Gly Ile Asn Pro Glu Ser      560

1681  TGT GCC TTG GTT GAT CGA TTA GAT GCA GGT ACA GGC ATC GTC TGG CAG
```

-continued

```
1728

561 Cys Ala Leu Val Asp Arg Leu Asp Ala Gly Thr Gly Ile Val Trp 561 576

1729 CAA TTG GCA GGG AAA CCC ACA ATC ACG GTA CCA CAA AAA GAT TCC CCG
1776

577 Gln Leu Ala Gly Lys Pro Thr Ile Thr Val Pro Gln Lys Asp Ser 577 592

1777 CTG GCG GCG GAT ATT CTG AGT TTG CTG CAA GCG CTA AGT GCG ATT GCT
1824

593 Leu Ala Ala Asp Ile Leu Ser Leu Leu Gln Ala Leu Ser Ala Ile 593 608

1825 CAA TGG CAA CAA CAG CAC GAT TTA GAA TTT TCA GCA CTG CTT TTG CTG
1872

609 Gln Trp Gln Gln Gln His Asp Leu Glu Phe Ser Ala Leu Leu Leu 609 624

1873 TTG AGT GAC AAC CCT ATT TCT ACC TCG CAG GGC ACT GAC GAT CAA TTG
1920

625 Leu Ser Asp Asn Pro Ile Ser Thr Ser Gln Gly Thr Asp Asp Gln 625 640

1921 AAC TTT ATC CGT CAA GTG TGG CAG AAC CTA GGC AGT ACG TTT GTG GGT
1968

641 Asn Phe Ile Arg Gln Val Trp Gln Asn Leu Gly Ser Thr Phe Val 641 656

1969 GCA ACA TTG TTG TCC CGC AGT GGG GCA CCA TTA GTC GAT ACC AAC GGC
2016

657 Ala Thr Leu Leu Ser Arg Ser Gly Ala Pro Leu Val Asp Thr Asn 657 672

2017 CAC GCT ATT GAC TGG TTT GCT CTG CTC TCA GCA GGT AAT AGT CCG CTT
2064

673 His Ala Ile Asp Trp Phe Ala Leu Leu Ser Ala Gly Asn Ser Pro 673 688

2065 ATC GAT AAG GTT GGT CTG GTG ACT GAT GCT GGC ATA CAA AGT GTT ATA
2112

689 Ile Asp Lys Val Gly Leu Val Thr Asp Ala Gly Ile Gln Ser Val 689 704

2113 GCA ACG GTG GTC AAT ACA CAA AGC TTA TCT GAT GAA GAT AAG AAG CTG
2160

705 Ala Thr Val Val Asn Thr Gln Ser Leu Ser Asp Glu Asp Lys Lys 705 720

2161 GCA ATC ACT ACT CTG ACT AAT ACG TTG AAT CAG GTA CAG AAA ACT CAA
2208

721 Ala Ile Thr Thr Leu Thr Asn Thr Leu Asn Gln Val Gln Lys Thr 721 736

2209 CAG GGC GTG GCC GTC AGT CTG TTG GCG CAG ACT CTG AAC GTG AGT CAG
2256

737 Gln Gly Val Ala Val Ser Leu Leu Ala Gln Thr Leu Asn Val Ser 737 752

2257 TCA CTG CCT GCG TTA TTG TTG CGC TGG AGT GGA CAA ACA ACC TAC CAG
2304

753 Ser Leu Pro Ala Leu Leu Leu Arg Trp Ser Gly Gln Thr Thr Tyr 753 768

2305 TGG TTG AGT GCG ACT TGG GCA TTG AAG GAT GCC GTT AAG ACT GCC GCC
2352

769 Trp Leu Ser Ala Thr Trp Ala Leu Lys Asp Ala Val Lys Thr Ala 769 784

2353 GAT ATT CCC GCT GAC TAT CTG CGT CAA TTA CGT GAA GTG GTA CGC CGC
2400

785 Asp Ile Pro Ala Asp Tyr Leu Arg Gln Leu Arg Glu Val Val Arg 785 800

2401 TCC TTG TTG ACC CAA CAA TTC ACG CTG AGT CCT GCA ATG GTG CAA ACC
2448

801 Ser Leu Leu Thr Gln Gln Phe Thr Leu Ser Pro Ala Met Val Gln 801 816
```

-continued

```
2449  TTG CTG GAC TAT CCA GCC TAT TTT GGC GCT TCC GCA GAA ACA GTG ACC
2496

817  Leu Leu Asp Tyr Pro Ala Tyr Phe Gly Ala Ser Ala Glu Thr Val  817832

2497  GAT ATC AGT TTG TGG ATG CTT TAT ACC CTG AGC TGT TAT AGC GAT TTA
2544

833  Asp Ile Ser Leu Trp Met Leu Tyr Thr Leu Ser Cys Tyr Ser Asp  833848

2545  TTG CTC CAA ATG GGT GAA GCT GGT GGT ACC GAA GAT GAT GTA CTG GCC
2592

849  Leu Leu Gln Met Gly Glu Ala Gly Gly Thr Glu Asp Asp Val Leu  849864

2593  TAC TTA CGC ACA GCT AAT GCT ACC ACA CCG TTG AGC CAA TCT GAT GCT
2640

865  Tyr Leu Arg Thr Ala Asn Ala Thr Thr Pro Leu Ser Gln Ser Asp  865880

2641  GCA CAG ACG TTG GCA ACG CTA TTG GGT TGG GAG GTT AAC GAG TTG CAA
2688

881  Ala Gln Thr Leu Ala Thr Leu Leu Gly Trp Glu Val Asn Glu Leu  881896

2689  GCC GCT TGG TCG GTA TTG GGC GGG ATT GCC AAA ACC ACA CCG CAA CTG
2736

897  Ala Ala Trp Ser Val Leu Gly Gly Ile Ala Lys Thr Thr Pro Gln  897912

2737  GAT GCG CTT CTG CGT TTG CAA CAG GCA CAG AAC CAA ACT GGT CTT GGC
2784

913  Asp Ala Leu Leu Arg Leu Gln Gln Ala Gln Asn Gln Thr Gly Leu  913928

2785  GTT ACA CAG CAA CAG CAA GGC TAT CTC CTG AGT CGT GAC AGT GAT TAT
2832

929  Val Thr Gln Gln Gln Gln Gly Tyr Leu Leu Ser Arg Asp Ser Asp  929944

2833  ACC CTT TGG CAA AGC ACC GGT CAG GCG CTG GTG GCT GGC GTA TCC CAT
2880

945  Thr Leu Trp Gln Ser Thr Gly Gln Ala Leu Val Ala Gly Val Ser  945960

2881  GTC AAG GGC AGT AAC TGA GCATGGCAGA GCTCACTACC TGAGTGGATT TGATTT
2934

961  Val Lys Gly Ser Asn End                                       961965

2935  TTCCGTATGG CCTAATGAGG CTATTTCTAA ACCGCCATTT AAGTAAGGCA GATAATTATG
2994
```

(2) INFORMATION FOR SEQ ID NO:57:

(i) SEQUENCE CHARACTERISTICS:
        (A) LENGTH: 965 amino acids
        (B) TYPE: amino acid
        (C) TOPOLOGY: linear (ii) MOLECULE TYPE: protein (xi) SEQUENCE DESCRIPTION: SEQ ID NO:57 (TCCA PEPTIDE):

FeaturesFromToDescription

110SEQ ID NO:8

```
 1  Met Asn Gln Leu Ala Ser Pro Leu Ile Ser Arg Thr Glu Glu Ile His    116

17  Asn Leu Pro Gly Lys Leu Thr Asp Leu Gly Tyr Thr Ser Val Phe Asp  1732

33  Val Val Arg Met Pro Arg Glu Arg Phe Ile Arg Glu His Arg Ala Asp  3348

49  Leu Gly Arg Ser Ala Glu Lys Met Tyr Asp Leu Ala Val Gly Tyr Ala  4964

65  His Gln Val Leu His His Phe Arg Arg Asn Ser Leu Ser Glu Ala Val  6580
```

```
 81  Gln Phe Gly Leu Arg Ser Pro Phe Ser Val Ser Gly Pro Asp Tyr Ala  8196
 97  Asn Gln Phe Leu Asp Ala Asn Thr Gly Trp Lys Asp Lys Ala Pro Se9  7112
113  Gly Ser Pro Glu Ala Asn Asp Ala Pro Val Ala Tyr Leu Thr His Il13128
129  Tyr Gln Leu Ala Leu Glu Gln Glu Lys Asn Gly Ala Thr Thr Ile Me29144
145  Asn Thr Leu Ala Glu Arg Arg Pro Asp Leu Gly Ala Leu Leu Ile As45160
161  Asp Lys Ala Ile Asn Glu Val Ile Pro Gln Leu Gln Leu Val Asn Gl61176
177  Ile Leu Ser Lys Ala Ile Gln Lys Lys Leu Ser Leu Thr Asp Leu Gl77192
193  Ala Val Asn Ala Arg Leu Ser Thr Thr Arg Tyr Pro Asn Asn Leu Pr93208
209  Tyr His Tyr Gly His Gln Gln Ile Gln Thr Ala Gln Ser Val Leu Gl09224
225  Thr Thr Leu Gln Asp Ile Thr Leu Pro Gln Thr Leu Asp Leu Pro Gl25240
241  Asn Phe Trp Ala Thr Ala Lys Gly Lys Leu Ser Asp Thr Thr Ala Se41256
257  Ala Leu Thr Arg Leu Gln Ile Met Ala Ser Gln Phe Ser Pro Glu Gl57272
273  Gln Lys Ile Ile Thr Glu Thr Val Gly Gln Asp Phe Tyr Gln Leu As73288
289  Tyr Gly Asp Ser Ser Leu Thr Val Asn Ser Phe Ser Asp Met Thr Il89304
305  Met Thr Asp Arg Thr Ser Leu Thr Val Pro Gln Val Glu Leu Met Le05320
321  Cys Ser Thr Val Gly Gly Ser Thr Val Val Lys Ser Asp Asn Val Se21336
337  Ser Gly Asp Thr Thr Ala Thr Pro Phe Ala Tyr Gly Ala Arg Phe Il37352
353  His Ala Gly Lys Pro Glu Ala Ile Thr Leu Ser Arg Ser Gly Ala Gl53368
369  Ala His Phe Ala Leu Thr Val Asn Asn Leu Thr Asp Asp Lys Leu As69384
385  Arg Ile Asn Arg Thr Val Arg Leu Gln Lys Trp Leu Asn Leu Pro Ty85400
401  Glu Asp Ile Asp Leu Leu Val Thr Ser Ala Met Asp Ala Glu Thr Gl01416
417  Asn Thr Ala Leu Ser Met Asn Asp Asn Thr Leu Arg Met Leu Gly Va17432
433  Phe Lys His Tyr Gln Ala Lys Tyr Gly Val Ser Ala Lys Gln Phe Al33448
449  Gly Trp Leu Arg Val Val Ala Pro Phe Ala Ile Thr Pro Ala Thr Pr49464
465  Phe Leu Asp Gln Val Phe Asn Ser Val Gly Thr Phe Asp Thr Pro Ph65480
481  Val Ile Asp Asn Gln Asp Phe Val Tyr Thr Leu Thr Thr Gly Gly As81496
497  Gly Ala Arg Val Lys His Ile Ser Thr Ala Leu Gly Leu Asn His Ar97512
513  Gln Phe Leu Leu Leu Ala Asp Asn Ile Ala Arg Gln Gln Gly Asn Va13528
529  Thr Gln Ser Thr Leu Asn Cys Asn Leu Phe Val Val Ser Ala Phe Ty29544
545  Arg Leu Ala Asn Leu Ala Arg Thr Leu Gly Ile Asn Pro Glu Ser Ph45560
561  Cys Ala Leu Val Asp Arg Leu Asp Ala Gly Thr Gly Ile Val Trp Gl61576
577  Gln Leu Ala Gly Lys Pro Thr Ile Thr Val Pro Gln Lys Asp Ser Pr77592
593  Leu Ala Ala Asp Ile Leu Ser Leu Leu Gln Ala Leu Ser Ala Ile Al93608
609  Gln Trp Gln Gln Gln His Asp Leu Glu Phe Ser Ala Leu Leu Leu Le09624
625  Leu Ser Asp Asn Pro Ile Ser Thr Ser Gln Gly Thr Asp Asp Gln Le25640
641  Asn Phe Ile Arg Gln Val Trp Gln Asn Leu Gly Ser Thr Phe Val Gl41656
657  Ala Thr Leu Leu Ser Arg Ser Gly Ala Pro Leu Val Asp Thr Asn Gl57672
673  His Ala Ile Asp Trp Phe Ala Leu Leu Ser Ala Gly Asn Ser Pro Le73688
689  Ile Asp Lys Val Gly Leu Val Thr Asp Ala Gly Ile Gln Ser Val Il89704
705  Ala Thr Val Val Asn Thr Gln Ser Leu Ser Asp Glu Asp Lys Lys Le05720
```

```
721  Ala Ile Thr Thr Leu Thr Asn Thr Leu Asn Gln Val Gln Lys Thr Gl  736
737  Gln Gly Val Ala Val Ser Leu Leu Ala Gln Thr Leu Asn Val Ser Gl  752
753  Ser Leu Pro Ala Leu Leu Leu Arg Trp Ser Gly Gln Thr Thr Tyr Gl  768
769  Trp Leu Ser Ala Thr Trp Ala Leu Lys Asp Ala Val Lys Thr Ala Al  784
785  Asp Ile Pro Ala Asp Tyr Leu Arg Gln Leu Arg Glu Val Val Arg Ar  800
801  Ser Leu Leu Thr Gln Gln Phe Thr Leu Ser Pro Ala Met Val Gln Th  816
817  Leu Leu Asp Tyr Pro Ala Tyr Phe Gly Ala Ser Ala Glu Thr Val Th  832
833  Asp Ile Ser Leu Trp Met Leu Tyr Thr Leu Ser Cys Tyr Ser Asp Le  848
849  Leu Leu Gln Met Gly Glu Ala Gly Gly Thr Glu Asp Asp Val Leu Al  864
865  Tyr Leu Arg Thr Ala Asn Ala Thr Thr Pro Leu Ser Gln Ser Asp Al  880
881  Ala Gln Thr Leu Ala Thr Leu Leu Gly Trp Glu Val Asn Glu Leu Gl  896
897  Ala Ala Trp Ser Val Leu Gly Gly Ile Ala Lys Thr Thr Pro Gln Le  912
913  Asp Ala Leu Leu Arg Leu Gln Gln Ala Gln Asn Gln Thr Gly Leu Gl  928
929  Val Thr Gln Gln Gln Gln Gly Tyr Leu Leu Ser Arg Asp Ser Asp Ty  944
945  Thr Leu Trp Gln Ser Thr Gly Gln Ala Leu Val Ala Gly Val Ser Hi  960
961  Val Lys Gly Ser Asn                                              965
```

(2) INFORMATION FOR SEQ ID NO:58:

(i) SEQUENCE CHARACTERISTICS:
        (A) LENGTH: 4932 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:58 (TCCB):

```
1    ATG TTA TCG ACA ATG GAA AAA CAA CTG AAT GAA TCC CAG CGT GAT GCG    48
1    Met Leu Ser Thr Met Glu Lys Gln Leu Asn Glu Ser Gln Arg Asp Ala    16
49   TTG GTG ACT GGC TAT ATG AAT TTT GTG GCG CCG ACG TTG AAA GGC GT     96
17   Leu Val Thr Gly Tyr Met Asn Phe Val Ala Pro Thr Leu Lys Gly Va     32
97   AGT GGT CAG CCG GTG ACG GTG GAA GAT TTA TAC GAA TAT TTG CTG A     144
33   Ser Gly Gln Pro Val Thr Val Glu Asp Leu Tyr Glu Tyr Leu Leu Il     48
145  GAC CCG GAA GTG GCT GAT GAG GTT GAG ACG AGT CGG GTA GCA CAA       192
49   Asp Pro Glu Val Ala Asp Glu Val Glu Thr Ser Arg Val Ala Gln A     64
193  ATT GCC AGC ATA CAG CAA TAT ATG ACT CGT CTG GTC AAC GGC TCT       240
65   Ile Ala Ser Ile Gln Gln Tyr Met Thr Arg Leu Val Asn Gly Ser G     80
241  CCG GGG CGT CAG GCG ATG GAG CCT TCT ACA GCT AAC GAA TGG CGT       288
81   Pro Gly Arg Gln Ala Met Glu Pro Ser Thr Ala Asn Glu Trp Arg As    96
289  AAT GAT AAC CAA TAT GCT ATC TGG GCT GCG GGG GCT GAG GTT CGA       336
97   Asn Asp Asn Gln Tyr Ala Ile Trp Ala Ala Gly Ala Glu Val Arg A    112
337  TAC GCT GAA AAC TAT ATT TCA CCC ATC ACC CGG CAG GAA AAA AGC       384
113  Tyr Ala Glu Asn Tyr Ile Ser Pro Ile Thr Arg Gln Glu Lys Ser      128
385  TAT TTC TCG GAG CTG GAG ACG ACT TTA AAT CAG AAT CGA CTC GAT       432
```

```
129  Tyr Phe Ser Glu Leu Glu Thr Thr Leu Asn Gln Asn Arg Leu Asp   129144

433  GAT CGT GTG CAG GAT GCT GTT TTG GCG TAT CTC AAT GAG TTT GAG   433480

145  Asp Arg Val Gln Asp Ala Val Leu Ala Tyr Leu Asn Glu Phe Glu   145160

481  GTG AGT AAT CTA TAT GTG CTC AGT GGT TAT ATT AAT CAG GAT AAA   481528

161  Val Ser Asn Leu Tyr Val Leu Ser Gly Tyr Ile Asn Gln Asp Lys   161176

529  GAC CAA GCT ATC TAC TAC TTT ATT GGT CGC ACT ACC ACT AAA CCG   529576

177  Asp Gln Ala Ile Tyr Tyr Phe Ile Gly Arg Thr Thr Thr Lys Pro   177192

577  CGC TAC TAC TGG CGT CAG ATG GAT TTG AGT AAG AAC CGT CAA GAT   577624

193  Arg Tyr Tyr Trp Arg Gln Met Asp Leu Ser Lys Asn Arg Gln Asp   193208

625  GCA GGG AAT CCG GTG ACG CCA AAT TGC TGG AAT GAT TGG CAG GAA   625672

209  Ala Gly Asn Pro Val Thr Pro Asn Cys Trp Asn Asp Trp Gln Glu   209224

673  ACT TTG CCG CTG TCT GGT GAT ACG GTG CTG GAG CAT ACA GTT CGC   673720

225  Thr Leu Pro Leu Ser Gly Asp Thr Val Leu Glu His Thr Val Arg   225240

721  GTA TTT TAT AAT GAT CGA CTA TAT GTG GCT TGG GTT GAG CGT GAC   721768

241  Val Phe Tyr Asn Asp Arg Leu Tyr Val Ala Trp Val Glu Arg Asp   241256

769  GCA GTA CAG AAG GAT GCT GAC GGT AAA AAC ATC GGT AAA ACC CAT   769816

257  Ala Val Gln Lys Asp Ala Asp Gly Lys Asn Ile Gly Lys Thr His   257272

817  TAC AAC ATA AAG TTT GGT TAT AAA CGT TAT GAT GAT ACT TGG ACA   817864

273  Tyr Asn Ile Lys Phe Gly Tyr Lys Arg Tyr Asp Asp Thr Trp Thr   273288

865  CCG AAT ACG ACC ACG TTA ATG ACA CAA CAA GCA GGG GAA AGT TCA   865912

289  Pro Asn Thr Thr Thr Leu Met Thr Gln Gln Ala Gly Glu Ser Ser   289304

913  ACA CAG CGA TCC AGC CTG CTG ATT GAT GAA TCT AGC ACC ACA TTG   913960

305  Thr Gln Arg Ser Ser Leu Leu Ile Asp Glu Ser Ser Thr Thr Leu   305320

961  CAA GTT AAT CTG TTG GCT ACC ACC GAT TTT AGT ATC GAT CCG ACG  GAG1008

321  Gln Val Asn Leu Leu Ala Thr Thr Asp Phe Ser Ile Asp Pro Thr   321336

1009  GAA ACG GAC AGT AAC CCG TAT GGC CGC CTA ATG TTG GGG GTG TTT GTC
1056

337  Glu Thr Asp Ser Asn Pro Tyr Gly Arg Leu Met Leu Gly Val Phe   337352
1057  CGT CAA TTT GAA GGT GAT GGG GCC AAT AGA AAA AAT AAA CCC GTT GTT
1104

353  Arg Gln Phe Glu Gly Asp Gly Ala Asn Arg Lys Asn Lys Pro Val   353368

1105  TAT GGT TAT CTC TAT TGT GAC TCA GCT TTC AAT CGT CAT GTT CTC AGG
1152

369  Tyr Gly Tyr Leu Tyr Cys Asp Ser Ala Phe Asn Arg His Val Leu   369384

1153  CCG TTA AGT AAG AAC TTT TTG TTC AGT ACT TAC CGT GAT GAA ACG GAT
1200

385  Pro Leu Ser Lys Asn Phe Leu Phe Ser Thr Tyr Arg Asp Glu Thr   385400

1201  GGT CAA AAC AGC TTG CAA TTT GCG GTA TAC GAT AAA AAG TAT GTA ATT
1248

401  Gly Gln Asn Ser Leu Gln Phe Ala Val Tyr Asp Lys Lys Tyr Val   401416

1249  ACT AAG GTT GTT ACA GGT GCA ACG GAA GAT CCC GAA AAT ACA GGA TGG
1296

417  Thr Lys Val Val Thr Gly Ala Thr Glu Asp Pro Glu Asn Thr Gly   417432
```

```
1297 GTA AGT AAA GTT GAT GAC TTG AAA CAA GGC ACT ACT GGG GCC TAT GTG
1344

433  Val Ser Lys Val Asp Asp Leu Lys Gln Gly Thr Thr Gly Ala Tyr   433448

1345 TAT ATC GAT CAA GAT GGC CTG ACG CTT CAT ATA CAA ACC ACA ACT AAT
1392

449  Tyr Ile Asp Gln Asp Gly Leu Thr Leu His Ile Gln Thr Thr Thr    449464

1393 GGG GAT TTT ATT AAC CGT CAT ACG TTT GGA TAT AAC GAT CTT GTA TAT
1440

465  Gly Asp Phe Ile Asn Arg His Thr Phe Gly Tyr Asn Asp Leu Val    465480

1441 GAT TCT AAG TCT GGT TAT GGT TTC ACG TGG TCA GGA AAT GAA GGT TTT
1488

481  Asp Ser Lys Ser Gly Tyr Gly Phe Thr Trp Ser Gly Asn Glu Gly    481496

1489 TAT CTG GAT TAC CAT GAT GGA AAT TAT TAC ACC TTT CAT AAT GCA ATA
1536

497  Tyr Leu Asp Tyr His Asp Gly Asn Tyr Tyr Thr Phe His Asn Ala    497512

1537 ATC AAC TAC TAT CCG TCT GGA TAT GGT GGT GGA TCT GTT CCT AAT GGA
1584

513  Ile Asn Tyr Tyr Pro Ser Gly Tyr Gly Gly Gly Ser Val Pro Asn    513528

1585 ACG TGG GCG TTA GAG CAA AGG ATT AAT GAG GGA TGG GCT ATT GCT CCC
1632

529  Thr Trp Ala Leu Glu Gln Arg Ile Asn Glu Gly Trp Ala Ile Ala    529544

1633 CTG CTT GAT ACT CTC CAT ACT GTT ACT GTG AAG GGC AGT TAT ATC GCT
1680

545  Leu Leu Asp Thr Leu His Thr Val Thr Val Lys Gly Ser Tyr Ile    545560

1681 TGG GAA GGG GAA ACA CCT ACC GGT TAT AAT CTG TAT ATT CCA GAT GGT
1728

561  Trp Glu Gly Glu Thr Pro Thr Gly Tyr Asn Leu Tyr Ile Pro Asp    561576

1729 ACC GTG TTG CTA GAT TGG TTT GAT AAA ATA AAT TTT GCT ATT GGT CTT
1776

577  Thr Val Leu Leu Asp Trp Phe Asp Lys Ile Asn Phe Ala Ile Gly    577592

1777 AAT AAG CTT GAG TCT GTA TTT ACG TCG CCA GAT TGG CCA ACA CTA ACC
1824

593  Asn Lys Leu Glu Ser Val Phe Thr Ser Pro Asp Trp Pro Thr Leu    593608

1825 ACT ATC AAA AAT TTC AGT AAA ATC GCC GAT AAC CGC AAA TTC TAT CAG
1872

609  Thr Ile Lys Asn Phe Ser Lys Ile Ala Asp Asn Arg Lys Phe Tyr    609624

1873 GAA ATC AAT GCT GAG ACG GCG GAT GGA CGC AAC CTG TTT AAA CGT TAC
1920

625  Glu Ile Asn Ala Glu Thr Ala Asp Gly Arg Asn Leu Phe Lys Arg    625640

1921 AGT ACT CAA ACT TTC GGA CTT ACC AGC GGT GCG ACT TAT TCT ACA ACT
1968

641  Ser Thr Gln Thr Phe Gly Leu Thr Ser Gly Ala Thr Tyr Ser Thr    641656

1969 TAT ACT TTG TCT GAG GCG GAT TTC TCC ACT GAT CCG GAC AAA AAC TAC
2016

657  Tyr Thr Leu Ser Glu Ala Asp Phe Ser Thr Asp Pro Asp Lys Asn    657672

2017 CTA CAG GTT TGT TTG AAT GTC GTG TGG GAT CAT TAT GAC CGC CCG TCA
2064
```

-continued

| | | | | | | | | | | | | | | | |
|---|---|---|---|---|---|---|---|---|---|---|---|---|---|---|---|
|673|Leu|Gln|Val|Cys|Leu|Asn|Val|Val|Trp|Asp|His|Tyr|Asp|Arg|Pro|688|

2065 GGG AAA AAA GGG GCT TAT TCT TGG GTC AGT AAG TGG TTT AAC GTC TAT 2112

| | | | | | | | | | | | | | | | |
|---|---|---|---|---|---|---|---|---|---|---|---|---|---|---|---|
|689|Gly|Lys|Lys|Gly|Ala|Tyr|Ser|Trp|Val|Ser|Lys|Trp|Phe|Asn|Val|704|

2113 GTT GCG TTG CAA GAT AGC AAA GCT CCG GAT GCC ATT CCT CGA TTA GTT 2160

| | | | | | | | | | | | | | | | |
|---|---|---|---|---|---|---|---|---|---|---|---|---|---|---|---|
|705|Val|Ala|Leu|Gln|Asp|Ser|Lys|Ala|Pro|Asp|Ala|Ile|Pro|Arg|Leu|720|

2161 TCC CGT TAC GAT AGT AAA CGT GGT CTG GTG CAA TAT CTG GAC TTC TGG 2208

| | | | | | | | | | | | | | | | |
|---|---|---|---|---|---|---|---|---|---|---|---|---|---|---|---|
|721|Ser|Arg|Tyr|Asp|Ser|Lys|Arg|Gly|Leu|Val|Gln|Tyr|Leu|Asp|Phe|736|

2209 ACC TCA TCA TTA CCC GCG AAA ACC CGT CTT AAC ACC ACC TTT GTG CGT 2256

| | | | | | | | | | | | | | | | |
|---|---|---|---|---|---|---|---|---|---|---|---|---|---|---|---|
|737|Thr|Ser|Ser|Leu|Pro|Ala|Lys|Thr|Arg|Leu|Asn|Thr|Thr|Phe|Val|752|

2257 ACT TTG ATT GAG AAG GCT AAT CTG GGG CTG GAT AGT TTG CTG GAT TAC 2304

| | | | | | | | | | | | | | | | |
|---|---|---|---|---|---|---|---|---|---|---|---|---|---|---|---|
|753|Thr|Leu|Ile|Glu|Lys|Ala|Asn|Leu|Gly|Leu|Asp|Ser|Leu|Leu|Asp|768|

2305 ACC TTG CAG GCA GAT CCT TCT CTG GAA GCA GAT TTA GTG ACT GAC GGC 2352

| | | | | | | | | | | | | | | | |
|---|---|---|---|---|---|---|---|---|---|---|---|---|---|---|---|
|769|Thr|Leu|Gln|Ala|Asp|Pro|Ser|Leu|Glu|Ala|Asp|Leu|Val|Thr|Asp|784|

2353 AAA AGC GAA CCA ATG GAC TTT AAT GGT TCA AAC GGT CTC TAT TTC TGG 2400

| | | | | | | | | | | | | | | | |
|---|---|---|---|---|---|---|---|---|---|---|---|---|---|---|---|
|785|Lys|Ser|Glu|Pro|Met|Asp|Phe|Asn|Gly|Ser|Asn|Gly|Leu|Tyr|Phe|800|

2401 GAA TTG TTC TTT CAC CTG CCG TTT TTG GTT GCT ACA CGC TTT GCC AAC 2448

| | | | | | | | | | | | | | | | |
|---|---|---|---|---|---|---|---|---|---|---|---|---|---|---|---|
|801|Glu|Leu|Phe|Phe|His|Leu|Pro|Phe|Leu|Val|Ala|Thr|Arg|Phe|Ala|816|

2449 GAA CAG CAA TTT TCG CCG GCA CAA AAG AGT TTG CAT TAC ATC TTT GAC 2496

| | | | | | | | | | | | | | | | |
|---|---|---|---|---|---|---|---|---|---|---|---|---|---|---|---|
|817|Glu|Gln|Gln|Phe|Ser|Pro|Ala|Gln|Lys|Ser|Leu|His|Tyr|Ile|Phe|832|

2497 CCG GCG ATG AAA AAC AAG CCA CAC AAT GCC CCG GCT TAT TGG AAT GTA 2544

| | | | | | | | | | | | | | | | |
|---|---|---|---|---|---|---|---|---|---|---|---|---|---|---|---|
|833|Pro|Ala|Met|Lys|Asn|Lys|Pro|His|Asn|Ala|Pro|Ala|Tyr|Trp|Asn|848|

2545 CGT CCG TTG GTT GAA GGA AAC AGC GAT TTG TCA CGT CAT TTG GAC GAT 2592

| | | | | | | | | | | | | | | | |
|---|---|---|---|---|---|---|---|---|---|---|---|---|---|---|---|
|849|Arg|Pro|Leu|Val|Glu|Gly|Asn|Ser|Asp|Leu|Ser|Arg|His|Leu|Asp|864|

2593 TCT ATA GAC CCA GAT ACT CAA GCT TAT GCT CAT CCG GTG ATA TAC CAG 2640

| | | | | | | | | | | | | | | | |
|---|---|---|---|---|---|---|---|---|---|---|---|---|---|---|---|
|865|Ser|Ile|Asp|Pro|Asp|Thr|Gln|Ala|Tyr|Ala|His|Pro|Val|Ile|Tyr|880|

2641 AAA GCG GTG TTT ATT GCC TAT GTC AGT AAC CTG ATT GCT CAG GGA GAT 2688

| | | | | | | | | | | | | | | | |
|---|---|---|---|---|---|---|---|---|---|---|---|---|---|---|---|
|881|Lys|Ala|Val|Phe|Ile|Ala|Tyr|Val|Ser|Asn|Leu|Ile|Ala|Gln|Gly|896|

2689 ATG TGG TAT CGC CAA TTG ACT CGT GAC GGT CTG ACT CAG GCC CGT GTC 2736

| | | | | | | | | | | | | | | | |
|---|---|---|---|---|---|---|---|---|---|---|---|---|---|---|---|
|897|Met|Trp|Tyr|Arg|Gln|Leu|Thr|Arg|Asp|Gly|Leu|Thr|Gln|Ala|Arg|912|

2737 TAT TAC AAT CTG GCC GCT GAA TTG CTA GGG CCT CGT CCG GAT GTA TCG 2784

| | | | | | | | | | | | | | | | |
|---|---|---|---|---|---|---|---|---|---|---|---|---|---|---|---|
|913|Tyr|Tyr|Asn|Leu|Ala|Ala|Glu|Leu|Leu|Gly|Pro|Arg|Pro|Asp|Val|928|

2785 CTG AGT AGC ATT TGG ACG CCG CAA ACC CTG GAT ACC TTA GCA GCC GGG 2832

```
929   Leu Ser Ser Ile Trp Thr Pro Gln Thr Leu Asp Thr Leu Ala Ala   929 944

2833  CAA AAA GCG GTT TTA CGT GAT TTT GAG CAC CAG TTG GCT AAT AGT GAT
2880

945   Gln Lys Ala Val Leu Arg Asp Phe Glu His Gln Leu Ala Asn Ser   945 960

2881  ACC GCT TTA CCC GCA TTG CCG GGC CGC AAT GTC AGC TAC TTG AAA CTG
2928

961   Thr Ala Leu Pro Ala Leu Pro Gly Arg Asn Val Ser Tyr Leu Lys   961 976

2929  GCA GAT AAT GGC TAC TTT AAT GAA CCG CTC AAT GTT CTG ATG TTG TCT
2976

977   Ala Asp Asn Gly Tyr Phe Asn Glu Pro Leu Asn Val Leu Met Leu   977 992

2977  CAC TGG GAT ACG TTG GAT GCA CGG TTA TAC AAT CTG CGT CAT AAC CTG
3024

993   His Trp Asp Thr Leu Asp Ala Arg Leu Tyr Asn Leu Arg His Asn Leu 1008

3025  ACC GTT GAT GGC AAG CCG CTT TCG CTG CCG CTG TAT GCT GCG CCT GTT
3072

1009  Thr Val Asp Gly Lys Pro Leu Ser Leu Pro Leu Tyr Ala Ala Pro Val
1024

3073  GAT CCG GTA GCG TTG TTG GCT CAG CGT GCT CAG TCC GGC ACG TTG ACG
3120

1025  Asp Pro Val Ala Leu Leu Ala Gln Arg Ala Gln Ser Gly Thr Leu Thr
1040

3121  AAT GGC GTC AGT GGC GCC ATG TTG ACG GTG CCG CCA TAC CGT TTC AGC
3168

1041  Asn Gly Val Ser Gly Ala Met Leu Thr Val Pro Pro Tyr Arg Phe Ser
1056

3169  GCT ATG TTG CCG CGA GCT TAC AGC GCC GTG GGT ACG TTG ACC AGT TTT
3216

1057  Ala Met Leu Pro Arg Ala Tyr Ser Ala Val Gly Thr Leu Thr Ser Phe
1072

3217  GGT CAG AAC CTG CTT AGT TTG TTG GAA CGT AGC GAA CGA GCC TGT CAA
3264

1073  Gly Gln Asn Leu Leu Ser Leu Leu Glu Arg Ser Glu Arg Ala Cys Gln
1088

3265  GAA GAG TTG GCG CAA CAG CAA CTG TTG GAT ATG TCC AGC TAT GCC ATC
3312

1089  Glu Glu Leu Ala Gln Gln Gln Leu Leu Asp Met Ser Ser Tyr Ala Ile
1104

3313  ACG TTG CAA CAA CAG GCG CTG GAT GGA TTG GCG GCA GAT CGT CTG GCG
3360

1105  Thr Leu Gln Gln Gln Ala Leu Asp Gly Leu Ala Ala Asp Arg Leu Ala
1120

3361  CTG CTA GCT AGT CAG GCT ACG GCA CAA CAG CGT CAT GAC CAT TAT TAC
3408

1121  Leu Leu Ala Ser Gln Ala Thr Ala Gln Gln Arg His Asp His Tyr Tyr
1136

3409  ACT CTG TAT CAG AAC AAC ATC TCC AGT GCG GAA CAA CTG GTG ATG GAC
3456

1137  Thr Leu Tyr Gln Asn Asn Ile Ser Ser Ala Glu Gln Leu Val Met Asp
1152

3457  ACC CAA ACG TCA GCA CAA TCC CTG ATT TCT TCT TCC ACT GGT GTA CAA
3504
```

```
1153  Thr Gln Thr Ser Ala Gln Ser Leu Ile Ser Ser Ser Thr Gly Val Gln
1168

3505  ACT GCC AGT GGG GCA CTG AAA GTG ATC CCG AAT ATC TTT GGT TTG GCT
3552

1169  Thr Ala Ser Gly Ala Leu Lys Val Ile Pro Asn Ile Phe Gly Leu Ala
1184

3553  GAT GGC GGC TCG CGC TAT GAA GGA GTA ACG GAA GCG ATT GCC ATC GGG
3600

1185  Asp Gly Gly Ser Arg Tyr Glu Gly Val Thr Glu Ala Ile Ala Ile Gly
1200

3601  TTA ATG GCT GCC GGA CAA GCC ACC AGC GTG GTG GCC GAG CGT CTG GCA
3648

1201  Leu Met Ala Ala Gly Gln Ala Thr Ser Val Val Ala Glu Arg Leu Ala
1216

3649  ACC ACG GAG AAT TAC CGC CGC CGC CGT GAA GAG TGG CAA ATC CAA TAC
3696

1217  Thr Thr Glu Asn Tyr Arg Arg Arg Arg Glu Glu Trp Gln Ile Gln Tyr
1232

3697  CAG CAG GCA CAG TCT GAG GTC GAC GCA TTA CAG AAA CAG TTG GAT GCG
3744

1233  Gln Gln Ala Gln Ser Glu Val Asp Ala Leu Gln Lys Gln Leu Asp Ala
1248

3745  CTG GCA GTG CGC GAG AAA GCA GCT CAA ACT TCC CTG CAA CAG GCG AAG
3792

1249  Leu Ala Val Arg Glu Lys Ala Ala Gln Thr Ser Leu Gln Gln Ala Lys
1264

3793  GCA CAG CAG GTA CAA ATT CGG ACC ATG CTG ACT TAC TTA ACT ACT CGT
3840

1265  Ala Gln Gln Val Gln Ile Arg Thr Met Leu Thr Tyr Leu Thr Thr Arg
1280

3841  TTC ACC CAG GCG ACT CTG TAC CAG TGG CTG AGT GGT CAA TTA TCC GCG
3888

1281  Phe Thr Gln Ala Thr Leu Tyr Gln Trp Leu Ser Gly Gln Leu Ser Ala
1296

3889  TTG TAT TAT CAA GCG TAT GAT GCC GTG GTT GCT CTC TGC CTC TCC GCC
3936

1297  Leu Tyr Tyr Gln Ala Tyr Asp Ala Val Val Ala Leu Cys Leu Ser Ala
1312

3937  CAA GCT TGC TGG CAG TAT GAA TTG GGT GAT TAC GCT ACC ACT TTT ATC
3984

1313  Gln Ala Cys Trp Gln Tyr Glu Leu Gly Asp Tyr Ala Thr Thr Phe Ile
1328

3985  CAG ACC GGT ACC TGG AAC GAC CAT TAC CGT GGT TTG CAA GTG GGG GAG
4032

1329  Gln Thr Gly Thr Trp Asn Asp His Tyr Arg Gly Leu Gln Val Gly Glu
1344

4033  ACA CTG CAA CTC AAT TTG CAT CAG ATG GAA GCG GCC TAT TTA GTT CGT
4080

1345  Thr Leu Gln Leu Asn Leu His Gln Met Glu Ala Ala Tyr Leu Val Arg
1360

4081  CAC GAA CGC CGT CTT AAT GTG ATC CGT ACT GTG TCG CTC AAA AGC CTA
4128
```

-continued

| | | | | | | | | | | | | | | |
|---|---|---|---|---|---|---|---|---|---|---|---|---|---|---|
|1361|His|Glu|Arg|Arg|Leu|Asn|Val|Ile|Arg|Thr|Val|Ser|Leu|Lys|Ser|Leu
1376

4129 TTG GGT GAT GAT GGT TTT GGT AAG TTA AAA ACC GAA GGC AAA GTC GAC 4176

1377 Leu Gly Asp Asp Gly Phe Gly Lys Leu Lys Thr Glu Gly Lys Val Asp 1392

4177 TTT CCA TTA AGC GAA AAG CTG TTT GAC AAC GAC TAT CCG GGG CAC TAT 4224

1393 Phe Pro Leu Ser Glu Lys Leu Phe Asp Asn Asp Tyr Pro Gly His Tyr 1408

4225 TTG CGC CAG ATT AAA ACT GTG TCA GTG ACG TTG CCG ACG TTA GTC GGG 4272

1409 Leu Arg Gln Ile Lys Thr Val Ser Val Thr Leu Pro Thr Leu Val Gly 1424

4273 CCG TAT CAA AAC GTG AAG GCA ACG CTC ACT CAG ACC AGC AGC AGT ATA 4320

1425 Pro Tyr Gln Asn Val Lys Ala Thr Leu Thr Gln Thr Ser Ser Ser Ile 1440

4321 TTG TTA GCA GCA GAT ATC AAT GGT GTT AAA CGT CTC AAT GAT CCG ACA 4368

1441 Leu Leu Ala Ala Asp Ile Asn Gly Val Lys Arg Leu Asn Asp Pro Thr 1456

4369 GGT AAA GAG GGT GAT GCG ACG CAT ATT GTC ACC AAT CTG CGT GCC AGC 4416

1457 Gly Lys Glu Gly Asp Ala Thr His Ile Val Thr Asn Leu Arg Ala Ser 1472

4417 CAG CAG GTG GCG CTC TCT TCT GGC ATT AAT GAT GCC GGT AGC TTT GAG 4464

1473 Gln Gln Val Ala Leu Ser Ser Gly Ile Asn Asp Ala Gly Ser Phe Glu 1488

4465 TTG CGT TTG GAA GAT GAG CGC TAT CTA TCA TTT GAG GGG ACT GGA GCT 4512

1489 Leu Arg Leu Glu Asp Glu Arg Tyr Leu Ser Phe Glu Gly Thr Gly Ala 1504

4513 GTT TCC AAA TGG ACT CTT AAC TTC CCG CGT TCT GTG GAT GAG CAT ATT 4560

1505 Val Ser Lys Trp Thr Leu Asn Phe Pro Arg Ser Val Asp Glu His Ile 1520

4561 GAC GAT AAG ACA TTG AAA GCG GAT GAG ATG CAG GCC GCA CTG TTG GCG 4608

1521 Asp Asp Lys Thr Leu Lys Ala Asp Glu Met Gln Ala Ala Leu Leu Ala 1536

4609 AAT ATG GAT GAT GTG CTG GTG CAG GTG CAT TAT ACC GCC TGC GAC GGC 4656

1537 Asn Met Asp Asp Val Leu Val Gln Val His Tyr Thr Ala Cys Asp Gly 1552

4657 GGC GCC AGT TTC GCA AAC CAG GTC AAG AAA ACA CTC TCT TAA CATT 4708

1553 Gly Ala Ser Phe Ala Asn Gln Val Lys Lys Thr Leu Ser End   5531565

4709 TAACTAATCC CTCCCACTCT GTTCGCCAGA GTGGGAGAAG GTTTGTCATA TCTA 4768

4770 ATCTTGCGAT CTTTCTCCAT TCATTGGAA GGGAAGCTGT AAAACAAATA AGGA 4828

4829 TATG  8294932

-continued (2) INFORMATION FOR SEQ ID NO:59:

(i) SEQUENCE CHARACTERISTICS:
        (A) LENGTH: 1565 amino acids
        (B) TYPE: amino acid
        (C) TOPOLOGY: linear (ii) MOLECULE TYPE: protein (xi) SEQUENCE DESCRIPTION: SEQ ID NO:59 (TCCB PEPTIDE):

FeaturesFromToDescription

```
  1  Met Leu Ser Thr Met Glu Lys Gln Leu Asn Glu Ser Gln Arg Asp Ala
 16

17  Leu Val Thr Gly Tyr Met Asn Phe Val Ala Pro Thr Leu Lys Gly Val
 32

33  Ser Gly Gln Pro Val Thr Val Glu Asp Leu Tyr Glu Tyr Leu Leu Ile
 48

49  Asp Pro Glu Val Ala Asp Glu Val Glu Thr Ser Arg Val Ala Gln Ala
 64

65  Ile Ala Ser Ile Gln Gln Tyr Met Thr Arg Leu Val Asn Gly Ser Glu
 80

81  Pro Gly Arg Gln Ala Met Glu Pro Ser Thr Ala Asn Glu Trp Arg Asp
 96

97  Asn Asp Asn Gln Tyr Ala Ile Trp Ala Ala Gly Ala Glu Val Arg Asn
112

113  Tyr Ala Glu Asn Tyr Ile Ser Pro Ile Thr Arg Gln Glu Lys Ser His
128

129  Tyr Phe Ser Glu Leu Glu Thr Thr Leu Asn Gln Asn Arg Leu Asp Pro
144

145  Asp Arg Val Gln Asp Ala Val Leu Ala Tyr Leu Asn Glu Phe Glu Ala
160

161  Val Ser Asn Leu Tyr Val Leu Ser Gly Tyr Ile Asn Gln Asp Lys Phe
176

177  Asp Gln Ala Ile Tyr Tyr Phe Ile Gly Arg Thr Thr Thr Lys Pro Tyr
192

193  Arg Tyr Tyr Trp Arg Gln Met Asp Leu Ser Lys Asn Arg Gln Asp Pro
208

209  Ala Gly Asn Pro Val Thr Pro Asn Cys Trp Asn Asp Trp Gln Glu Ile
224

225  Thr Leu Pro Leu Ser Gly Asp Thr Val Leu Glu His Thr Val Arg Pro
240

241  Val Phe Tyr Asn Asp Arg Leu Tyr Val Ala Trp Val Glu Arg Asp Pro
256

257  Ala Val Gln Lys Asp Ala Asp Gly Lys Asn Ile Gly Lys Thr His Ala
272

273  Tyr Asn Ile Lys Phe Gly Tyr Lys Arg Tyr Asp Asp Thr Trp Thr Ala
288

289  Pro Asn Thr Thr Thr Leu Met Thr Gln Gln Ala Gly Glu Ser Ser Glu
304

305  Thr Gln Arg Ser Ser Leu Leu Ile Asp Glu Ser Ser Thr Thr Leu Arg
320

321  Gln Val Asn Leu Leu Ala Thr Thr Asp Phe Ser Ile Asp Pro Thr Glu
336

337  Glu Thr Asp Ser Asn Pro Tyr Gly Arg Leu Met Leu Gly Val Phe Val
352
```

```
353  Arg Gln Phe Glu Gly Asp Gly Ala Asn Arg Lys Asn Lys Pro Val Val
368

369  Tyr Gly Tyr Leu Tyr Cys Asp Ser Ala Phe Asn Arg His Val Leu Arg
384

385  Pro Leu Ser Lys Asn Phe Leu Phe Ser Thr Tyr Arg Asp Glu Thr Asp
400

401  Gly Gln Asn Ser Leu Gln Phe Ala Val Tyr Asp Lys Lys Tyr Val Ile
416

417  Thr Lys Val Val Thr Gly Ala Thr Glu Asp Pro Glu Asn Thr Gly Trp
432

433  Val Ser Lys Val Asp Asp Leu Lys Gln Gly Thr Thr Gly Ala Tyr Val
448

449  Tyr Ile Asp Gln Asp Gly Leu Thr Leu His Ile Gln Thr Thr Thr Asn
464

465  Gly Asp Phe Ile Asn Arg His Thr Phe Gly Tyr Asn Asp Leu Val Tyr
480

481  Asp Ser Lys Ser Gly Tyr Gly Phe Thr Trp Ser Gly Asn Glu Gly Phe
496

497  Tyr Leu Asp Tyr His Asp Gly Asn Tyr Tyr Thr Phe His Asn Ala Ile
512

513  Ile Asn Tyr Tyr Pro Ser Gly Tyr Gly Gly Gly Ser Val Pro Asn Gly
528

529  Thr Trp Ala Leu Glu Gln Arg Ile Asn Glu Gly Trp Ala Ile Ala Pro
544

545  Leu Leu Asp Thr Leu His Thr Val Thr Val Lys Gly Ser Tyr Ile Ala
560

561  Trp Glu Gly Glu Thr Pro Thr Gly Tyr Asn Leu Tyr Ile Pro Asp Gly
576

577  Thr Val Leu Leu Asp Trp Phe Asp Lys Ile Asn Phe Ala Ile Gly Leu
592

593  Asn Lys Leu Glu Ser Val Phe Thr Ser Pro Asp Trp Pro Thr Leu Thr
608

609  Thr Ile Lys Asn Phe Ser Lys Ile Ala Asp Asn Arg Lys Phe Tyr Gln
624

625  Glu Ile Asn Ala Glu Thr Ala Asp Gly Arg Asn Leu Phe Lys Arg Tyr
640

641  Ser Thr Gln Thr Phe Gly Leu Thr Ser Gly Ala Thr Tyr Ser Thr Thr
656

657  Tyr Thr Leu Ser Glu Ala Asp Phe Ser Thr Asp Pro Asp Lys Asn Tyr
672

673  Leu Gln Val Cys Leu Asn Val Val Trp Asp His Tyr Asp Arg Pro Ser
688

689  Gly Lys Lys Gly Ala Tyr Ser Trp Val Ser Lys Trp Phe Asn Val Tyr
704

705  Val Ala Leu Gln Asp Ser Lys Ala Pro Asp Ala Ile Pro Arg Leu Val
720

721  Ser Arg Tyr Asp Ser Lys Arg Gly Leu Val Gln Tyr Leu Asp Phe Trp
736

737  Thr Ser Ser Leu Pro Ala Lys Thr Arg Leu Asn Thr Thr Phe Val Arg
752

753  Thr Leu Ile Glu Lys Ala Asn Leu Gly Leu Asp Ser Leu Leu Asp Tyr
768
```

```
769  Thr Leu Gln Ala Asp Pro Ser Leu Glu Ala Asp Leu Val Thr Asp Gly
784

785  Lys Ser Glu Pro Met Asp Phe Asn Gly Ser Asn Gly Leu Tyr Phe Trp
800

801  Glu Leu Phe Phe His Leu Pro Phe Leu Val Ala Thr Arg Phe Ala Asn
816

817  Glu Gln Gln Phe Ser Pro Ala Gln Lys Ser Leu His Tyr Ile Phe Asp
832

833  Pro Ala Met Lys Asn Lys Pro His Asn Ala Pro Ala Tyr Trp Asn Val
848

849  Arg Pro Leu Val Glu Gly Asn Ser Asp Leu Ser Arg His Leu Asp Asp
864

865  Ser Ile Asp Pro Asp Thr Gln Ala Tyr Ala His Pro Val Ile Tyr Gln
880

881  Lys Ala Val Phe Ile Ala Tyr Val Ser Asn Leu Ile Ala Gln Gly Asp
896

897  Met Trp Tyr Arg Gln Leu Thr Arg Asp Gly Leu Thr Gln Ala Arg Val
912

913  Tyr Tyr Asn Leu Ala Ala Glu Leu Leu Gly Pro Arg Pro Asp Val Ser
928

929  Leu Ser Ser Ile Trp Thr Pro Gln Thr Leu Asp Thr Leu Ala Ala Gly
944

945  Gln Lys Ala Val Leu Arg Asp Phe Glu His Gln Leu Ala Asn Ser Asp
960

961  Thr Ala Leu Pro Ala Leu Pro Gly Arg Asn Val Ser Tyr Leu Lys Leu
976

977  Ala Asp Asn Gly Tyr Phe Asn Glu Pro Leu Asn Val Leu Met Leu Ser
992

993  His Trp Asp Thr Leu Asp Ala Arg Leu Tyr Asn Leu Arg His Asn Leu
1008

1009 Thr Val Asp Gly Lys Pro Leu Ser Leu Pro Leu Tyr Ala Ala Pro Val
1024

1025 Asp Pro Val Ala Leu Leu Ala Gln Arg Ala Gln Ser Gly Thr Leu Thr
1040

1041 Asn Gly Val Ser Gly Ala Met Leu Thr Val Pro Pro Tyr Arg Phe Ser
1056

1057 Ala Met Leu Pro Arg Ala Tyr Ser Ala Val Gly Thr Leu Thr Ser Phe
1072

1073 Gly Gln Asn Leu Leu Ser Leu Leu Glu Arg Ser Glu Arg Ala Cys Gln
1088

1089 Glu Glu Leu Ala Gln Gln Gln Leu Leu Asp Met Ser Ser Tyr Ala Ile
1104

1105 Thr Leu Gln Gln Gln Ala Leu Asp Gly Leu Ala Ala Asp Arg Leu Ala
1120

1121 Leu Leu Ala Ser Gln Ala Thr Ala Gln Gln Arg His Asp His Tyr Tyr
1136

1137 Thr Leu Tyr Gln Asn Asn Ile Ser Ser Ala Glu Gln Leu Val Met Asp
1152

1153 Thr Gln Thr Ser Ala Gln Ser Leu Ile Ser Ser Ser Thr Gly Val Gln
1168

1169 Thr Ala Ser Gly Ala Leu Lys Val Ile Pro Asn Ile Phe Gly Leu Ala
1184

1185 Asp Gly Gly Ser Arg Tyr Glu Gly Val Thr Glu Ala Ile Ala Ile Gly
```

```
1200

1201  Leu Met Ala Ala Gly Gln Ala Thr Ser Val Val Ala Glu Arg Leu Ala
1216

1217  Thr Thr Glu Asn Tyr Arg Arg Arg Glu Glu Trp Gln Ile Gln Tyr
1232

1233  Gln Gln Ala Gln Ser Glu Val Asp Ala Leu Gln Lys Gln Leu Asp Ala
1248

1249  Leu Ala Val Arg Glu Lys Ala Ala Gln Thr Ser Leu Gln Gln Ala Lys
1264

1265  Ala Gln Gln Val Gln Ile Arg Thr Met Leu Thr Tyr Leu Thr Thr Arg
1280

1281  Phe Thr Gln Ala Thr Leu Tyr Gln Trp Leu Ser Gly Gln Leu Ser Ala
1296

1297  Leu Tyr Tyr Gln Ala Tyr Asp Ala Val Val Ala Leu Cys Leu Ser Ala
1312

1313  Gln Ala Cys Trp Gln Tyr Glu Leu Gly Asp Tyr Ala Thr Thr Phe Ile
1328

1329  Gln Thr Gly Thr Trp Asn Asp His Tyr Arg Gly Leu Gln Val Gly Glu
1344

1345  Thr Leu Gln Leu Asn Leu His Gln Met Glu Ala Ala Tyr Leu Val Arg
1360

1361  His Glu Arg Arg Leu Asn Val Ile Arg Thr Val Ser Leu Lys Ser Leu
1376

1377  Leu Gly Asp Asp Gly Phe Gly Lys Leu Lys Thr Glu Gly Lys Val Asp
1392

1393  Phe Pro Leu Ser Glu Lys Leu Phe Asp Asn Asp Tyr Pro Gly His Tyr
1408

1409  Leu Arg Gln Ile Lys Thr Val Ser Val Thr Leu Pro Thr Leu Val Gly
1424

1425  Pro Tyr Gln Asn Val Lys Ala Thr Leu Thr Gln Thr Ser Ser Ser Ile
1440

1441  Leu Leu Ala Ala Asp Ile Asn Gly Val Lys Arg Leu Asn Asp Pro Thr
1456

1457  Gly Lys Glu Gly Asp Ala Thr His Ile Val Thr Asn Leu Arg Ala Ser
1472

1473  Gln Gln Val Ala Leu Ser Ser Gly Ile Asn Asp Ala Gly Ser Phe Glu
1488

1489  Leu Arg Leu Glu Asp Glu Arg Tyr Leu Ser Phe Glu Gly Thr Gly Ala
1504

1505  Val Ser Lys Trp Thr Leu Asn Phe Pro Arg Ser Val Asp Glu His Ile
1520

1521  Asp Asp Lys Thr Leu Lys Ala Asp Glu Met Gln Ala Ala Leu Leu Ala
1536

1537  Asn Met Asp Asp Val Leu Val Gln Val His Tyr Thr Ala Cys Asp Gly
1552

1553  Gly Ala Ser Phe Ala Asn Gln Val Lys Lys Thr Leu Ser
1565

(2) INFORMATION FOR SEQ ID NO:60:

(i) SEQUENCE CHARACTERISTICS:
        (A) LENGTH: 3132 base pairs
        (B) TYPE: nucleic acid
        (C) STRANDEDNESS: double
        (D) TOPOLOGY: linear
```

-continued (ii) MOLECULE TYPE: DNA (genomic)

(xi) SEQUENCE DESCRIPTION: SEQ ID NO:60 (TCCC):

```
1    ATG AGT CCG TCT GAG ACT ACT CTT TAT ACT CAA ACC CCA ACA GTC AGC    148
1    Met Ser Pro Ser Glu Thr Thr Leu Tyr Thr Gln Thr Pro Thr Val Ser    116

49   GTG TTA GAT AAT CGC GGT CTG TCC ATT CGT GAT ATT GGT TTT CAC CG     4996
17   Val Leu Asp Asn Arg Gly Leu Ser Ile Arg Asp Ile Gly Phe His Ar     1732

97   ATT GTA ATC GGG GGG GAT ACT GAC ACC CGC GTC ACC CGT CAC CAG TAT    144
33   Ile Val Ile Gly Gly Asp Thr Asp Thr Arg Val Thr Arg His Gln Ty     3348

145  GAT GCC CGT GGA CAC CTG AAC TAC AGT ATT GAC CCA CGC TTG TAT GAT    192
49   Asp Ala Arg Gly His Leu Asn Tyr Ser Ile Asp Pro Arg Leu Tyr As     4964

193  GCA AAG CAG GCT GAT AAC TCA GTA AAG CCT AAT TTT GTC TGG CAG CAT    240
65   Ala Lys Gln Ala Asp Asn Ser Val Lys Pro Asn Phe Val Trp Gln Hi     6580

241  GAT CTG GCC GGT CAT GCC CTG CGG ACA GAG AGT GTC GAT GCT GGT CGT    288
81   Asp Leu Ala Gly His Ala Leu Arg Thr Glu Ser Val Asp Ala Gly Ar     8196

289  ACT GTT GCA TTG AAT GAT ATT GAA GGT CGT TCG GTA ATG ACA ATG AAT    336
97   Thr Val Ala Leu Asn Asp Ile Glu Gly Arg Ser Val Met Thr Met Asn    112

337  GCG ACC GGT GTT CGT CAG ACC CGT CGC TAT GAA GGC AAC ACC TTG CCC    384
113  Ala Thr Gly Val Arg Gln Thr Arg Arg Tyr Glu Gly Asn Thr Leu Pro    128

385  GGT CGC TTG TTA TCT GTG AGC GAG CAA GTT TTC AAC CAA GAG AGT GCT    432
129  Gly Arg Leu Leu Ser Val Ser Glu Gln Val Phe Asn Gln Glu Ser Ala    144

433  AAA GTG ACA GAG CGC TTT ATC TGG GCT GGG AAT ACA ACC TCG GAG AAA    480
145  Lys Val Thr Glu Arg Phe Ile Trp Ala Gly Asn Thr Thr Ser Glu Lys    160

481  GAG TAT AAC CTC TCC GGT CTG TGT ATA CGC CAC TAC GAC ACA GCG GGA    528
161  Glu Tyr Asn Leu Ser Gly Leu Cys Ile Arg His Tyr Asp Thr Ala Gly    176

529  GTG ACC CGG TTG ATG AGT CAG TCA CTG GCG GGC GCC ATG CTA TCC CAA    576
177  Val Thr Arg Leu Met Ser Gln Ser Leu Ala Gly Ala Met Leu Ser Gln    192

577  TCT CAC CAA TTG CTG GCG GAA GGG CAG GAG GCT AAC TGG AGC GGT GAC    624
193  Ser His Gln Leu Leu Ala Glu Gly Gln Glu Ala Asn Trp Ser Gly Asp    208

625  GAC GAA ACT GTC TGG CAG GGA ATG CTG GCA AGT GAG GTC TAT ACG ACA    672
209  Asp Glu Thr Val Trp Gln Gly Met Leu Ala Ser Glu Val Tyr Thr Thr    224

673  CAA AGT ACC ACT AAT GCC ATC GGG GCT TTA CTG ACC CAA ACC GAT GCG    720
225  Gln Ser Thr Thr Asn Ala Ile Gly Ala Leu Leu Thr Gln Thr Asp Ala    240

721  AAA GGC AAT ATT CAG CGT CTG GCT TAT GAC ATT GCC GGT CAG TTA AAA    768
241  Lys Gly Asn Ile Gln Arg Leu Ala Tyr Asp Ile Ala Gly Gln Leu Lys    256

769  GGG AGT TGG TTG ACG GTG AAA GGC CAG AGT GAA CAG GTG ATT GTT AAG    816
257  Gly Ser Trp Leu Thr Val Lys Gly Gln Ser Glu Gln Val Ile Val Lys    272

817  TCC CTG AGC TGG TCA GCC GCA GGT CAT AAA TTG CGT GAA GAG CAC GGT    864
273  Ser Leu Ser Trp Ser Ala Ala Gly His Lys Leu Arg Glu Glu His Gly    288

865  AAC GGC GTG GTT ACG GAG TAC AGT TAT GAG CCG GAA ACT CAA CGT CTG    912
```

-continued

```
289  Asn Gly Val Val Thr Glu Tyr Ser Tyr Glu Pro Glu Thr Gln Arg Leu  304
913  ATA GGT ATC ACC ACC CGG CGT GCC GAA GGG AGT CAA TCA GGA GCC AGA  960

305  Ile Gly Ile Thr Thr Arg Arg Ala Glu Gly Ser Gln Ser Gly Ala Arg  320
961  GTA TTG CAG GAT CTA CGC TAT AAG TAT GAT CCG GTG GGG AAT GTT ATC 1008

321  Val Leu Gln Asp Leu Arg Tyr Lys Tyr Asp Pro Val Gly Asn Val       321336
1009 AGT ATC CAT AAT GAT GCC GAA GCT ACC CGC TTT TGG CGT AAT CAG AAA
1056

337  Ser Ile His Asn Asp Ala Glu Ala Thr Arg Phe Trp Arg Asn Gln       337352
1057 GTG GAG CCG GAG AAT CGC TAT GTT TAT GAT TCT CTG TAT CAG CTT ATG
1104

353  Val Glu Pro Glu Asn Arg Tyr Val Tyr Asp Ser Leu Tyr Gln Leu       353368
1105 AGT GCG ACA GGG CGT GAA ATG GCT AAT ATC GGT CAG CAA AGC AAC CAA
1152

369  Ser Ala Thr Gly Arg Glu Met Ala Asn Ile Gly Gln Gln Ser Asn Gln  384
1153 CTT CCC TCA CCC GTT ATA CCT GTT CCT ACT GAC GAC AGC ACT TAT ACC
1200

385  Leu Pro Ser Pro Val Ile Pro Val Pro Thr Asp Asp Ser Thr Tyr       385400
1201 AAT TAC CTT CGT ACC TAT ACT TAT GAC CGT GGC GGT AAT TTG GTT CAA
1248

401  Asn Tyr Leu Arg Thr Tyr Thr Tyr Asp Arg Gly Gly Asn Leu Val       401416
1249 ATC CGA CAC AGT TCA CCC GCG ACT CAA AAT AGT TAC ACC ACA GAT ATC
1296

417  Ile Arg His Ser Ser Pro Ala Thr Gln Asn Ser Tyr Thr Thr Asp       417432
1297 ACC GTT TCA AGC CGC AGT AAC CGG GCG GTA TTG AGT ACA TTA ACG ACA
1344

433  Thr Val Ser Ser Arg Ser Asn Arg Ala Val Leu Ser Thr Leu Thr       433448
1345 GAT CCA ACC CGA GTG GAT GCG CTA TTT GAT TCC GGC GGT CAT CAG AAG
1392

449  Asp Pro Thr Arg Val Asp Ala Leu Phe Asp Ser Gly Gly His Gln       449464
1393 ATG TTA ATA CCG GGG CAA AAT CTG GAT TGG AAT ATT CGG GGT GAA TTG
1440

465  Met Leu Ile Pro Gly Gln Asn Leu Asp Trp Asn Ile Arg Gly Glu       465480
1441 CAA CGA GTC ACA CCG GTG AGC CGT GAA AAT AGC AGT GAC AGT GAA TGG
1488

481  Gln Arg Val Thr Pro Val Ser Arg Glu Asn Ser Ser Asp Ser Glu       481496
1489 TAT CGC TAT AGC AGT GAT GGC ATG CGG CTG CTA AAA GTG AGT GAA CAG
1536

497  Tyr Arg Tyr Ser Ser Asp Gly Met Arg Leu Leu Lys Val Ser Glu       497512
1537 CAG ACG GGC AAC AGT ACT CAA GTA CAA CGG GTG ACT TAT CTG CCG GGA
1584

513  Gln Thr Gly Asn Ser Thr Gln Val Gln Arg Val Thr Tyr Leu Pro       513528
1585 TTA GAG CTA CGG ACA ACT GGG GTT GCA GAT AAA ACA ACC GAA GAT TTG
1632

529  Leu Glu Leu Arg Thr Thr Gly Val Ala Asp Lys Thr Thr Glu Asp       529544
1633 CAG GTG ATT ACG GTA GGT GAA GCG GGT CGC GCA CAG GTA AGG GTA TTG
1680

545  Gln Val Ile Thr Val Gly Glu Ala Gly Arg Ala Gln Val Arg Val       545560
```

```
-continued

1681 CAC TGG GAA AGT GGT AAG CCG ACA GAT ATT GAC AAC AAT CAG GTG CGC
1728

561  His Trp Glu Ser Gly Lys Pro Thr Asp Ile Asp Asn Asn Gln Val  561576

1729 TAC AGC TAC GAT AAT CTG CTT GGC TCC AGC CAG CTT GAA CTG GAT AGC
1776

577  Tyr Ser Tyr Asp Asn Leu Leu Gly Ser Ser Gln Leu Glu Leu Asp  577592

1777 GAA GGG CAG ATT CTC AGT CAG GAA GAG TAT TAT CCG TAT GGC GGT ACG
1824

593  Glu Gly Gln Ile Leu Ser Gln Glu Glu Tyr Tyr Pro Tyr Gly Gly  593608

1825 GCG ATA TGG GCG GCG AGA AAT CAG ACA GAA GCC AGC TAC AAA TTT ATT
1872

609  Ala Ile Trp Ala Ala Arg Asn Gln Thr Glu Ala Ser Tyr Lys Phe  609624

1873 CGT TAC TCC GGT AAA GAG CGG GAT GCC ACT GGA TTG TAT TAT TAC GGC
1920

625  Arg Tyr Ser Gly Lys Glu Arg Asp Ala Thr Gly Leu Tyr Tyr Tyr  625640

1921 TAC CGT TAT TAT CAA CCT TGG GTG GGT CGA TGG TTG AGT GCT GAT CCG
1968

641  Tyr Arg Tyr Tyr Gln Pro Trp Val Gly Arg Trp Leu Ser Ala Asp  641656

1969 GCG GGA ACC GTG GAT GGG CTG AAT TTG TAC CGA ATG GTG AGG AAT AAC
2016

657  Ala Gly Thr Val Asp Gly Leu Asn Leu Tyr Arg Met Val Arg Asn  657672

2017 CCC ATC ACA TTG ACT GAC CAT GAC GGA TTA GCA CCG TCT CCA AAT AGA
2064

673  Pro Ile Thr Leu Thr Asp His Asp Gly Leu Ala Pro Ser Pro Asn  673688

2065 AAT CGA AAT ACA TTT TGG TTT GCT TCA TTT TTG TTT CGT AAA CCT GAT
2112

689  Asn Arg Asn Thr Phe Trp Phe Ala Ser Phe Leu Phe Arg Lys Pro  689704

2113 GAG GGA ATG TCC GCG TCA ATG AGA CGG GGA CAA AAA ATT GGC AGA GCC
2160

705  Glu Gly Met Ser Ala Ser Met Arg Arg Gly Gln Lys Ile Gly Arg  705720

2161 ATT GCC GGC GGG ATT GCG ATT GCC GGT CTT GCG GCT ACC ATT GCC GCT
2208

721  Ile Ala Gly Gly Ile Ala Ile Gly Gly Leu Ala Ala Thr Ile Ala  721736

2209 ACG GCT GGC GCG GCT ATC CCC GTC ATT CTG GGG GTT GCG GCC GTA GGC
2256

737  Thr Ala Gly Ala Ala Ile Pro Val Ile Leu Gly Val Ala Ala Val  737752

2257 GCG GGG ATT GGC GCG TTG ATG GGA TAT AAC GTC GGT AGC CTG CTG GAA
2304

753  Ala Gly Ile Gly Ala Leu Met Gly Tyr Asn Val Gly Ser Leu Leu  753768

2305 AAA GGC GGG GCA TTA CTT GCT CGA CTC GTA CAG GGG AAA TCG ACG TTA
2352

769  Lys Gly Gly Ala Leu Leu Ala Arg Leu Val Gln Gly Lys Ser Thr  769784

2353 GTA CAG TCG GCG GCT GGC GCG GCT GCC GGA GCG AGT TCA GCC GCG GCT
2400

785  Val Gln Ser Ala Ala Gly Ala Ala Ala Gly Ala Ser Ser Ala Ala  785800

2401 TAT GGC GCA CGG GCA CAA GGT GTC GGT GTT GCA TCA GCC GCC GGG GCG
2448
```

-continued

```
 801  Tyr Gly Ala Arg Ala Gln Gly Val Gly Val Ala Ser Ala Ala Gly  801816

2449  GTA ACA GGG GCT GTG GGA TCA TGG ATA AAT AAT GCT GAT CGG GGG ATT
2496

817  Val Thr Gly Ala Val Gly Ser Trp Ile Asn Asn Ala Asp Arg Gly  817832

2497  GGC GGC GCT ATT GGG GCC GGG AGT GCG GTA GGC ACC ATT GAT ACT ATG
2544

833  Gly Gly Ala Ile Gly Ala Gly Ser Ala Val Gly Thr Ile Asp Thr  833848

2545  TTA GGG ACT GCC TCT ACC CTT ACC CAT GAA GTC GGG GCA GCG GCG GGT
2592

849  Leu Gly Thr Ala Ser Thr Leu Thr His Glu Val Gly Ala Ala Ala  849864

2593  GGG GCG GCG GGT GGG ATG ATC ACC GGT ACG CAA GGG AGT ACT CGG GCA
2640

865  Gly Ala Ala Gly Gly Met Ile Thr Gly Thr Gln Gly Ser Thr Arg  865880

2641  GGT ATC CAT GCC GGT ATT GGC ACC TAT TAT GGC TCC TGG ATT GGT TTT
2688

881  Gly Ile His Ala Gly Ile Gly Thr Tyr Tyr Gly Ser Trp Ile Gly  881896

2689  GGT TTA GAT GTC GCT AGT AAC CCC GCC GGA CAT TTA GCG AAT TAC GCA
2736

897  Gly Leu Asp Val Ala Ser Asn Pro Ala Gly His Leu Ala Asn Tyr  897912

2737  GTG GGT TAT GCC GCT GGT TTG GGT GCT GAA ATG GCT GTC AAC AGA ATA
2784

913  Val Gly Tyr Ala Ala Gly Leu Gly Ala Glu Met Ala Val Asn Arg  913928

2785  ATG GGT GGT GGA TTT TTG AGT AGG CTC TTA GGC CGG GTT GTC AGC CCA
2832

929  Met Gly Gly Gly Phe Leu Ser Arg Leu Leu Gly Arg Val Val Ser  929944

2833  TAT GCC GCC GGT TTA GCC AGA CAA TTA GTA CAT TTC AGT GTC GCC AGA
2880

945  Tyr Ala Ala Gly Leu Ala Arg Gln Leu Val His Phe Ser Val Ala  945960

2881  CCT GTC TTT GAG CCG ATA TTT AGT GTT CTC GGC GGG CTT GTC GGT GGT
2928

961  Pro Val Phe Glu Pro Ile Phe Ser Val Leu Gly Gly Leu Val Gly  961976

2929  ATT GGA ACT GGC CTG CAC AGA GTG ATG GGA AGA GAG AGT TGG ATT TCC
2976

977  Ile Gly Thr Gly Leu His Arg Val Met Gly Arg Glu Ser Trp Ile  977992

2977  AGA GCG TTA AGT GCT GCC GGT AGT GGT ATA GAT CAT GTC GCT GGC ATG
3024

993  Arg Ala Leu Ser Ala Ala Gly Ser Gly Ile Asp His Val Ala Gly Met1008

3025  ATT GGT AAT CAG ATC AGA GGC AGG GTC TTG ACC ACA ACC GGG ATC GCT
3072

1009  Ile Gly Asn Gln Ile Arg Gly Arg Val Leu Thr Thr Thr Gly Ile Ala
1024

3073  AAT GCG ATA GAC TAT GGC ACC AGT GCT GTG GGA GCC GCA CGA CGA GTT
3120

1025  Asn Ala Ile Asp Tyr Gly Thr Ser Ala Val Gly Ala Ala Arg Arg Val
1040

3121  TTT TCT TTG TAA                                             3132

1041  Phe Ser Leu End                                             1043
```

-continued (2) INFORMATION FOR SEQ ID NO:61:

(i) SEQUENCE CHARACTERISTICS:
        (A) LENGTH: 1043 amino acids
        (B) TYPE: amino acid
        (C) TOPOLOGY: linear (ii) MOLECULE TYPE: protein (xi) SEQUENCE DESCRIPTION: SEQ ID NO:61 (TCCC PEPTIDE):

| | | | | | | | | | | | | | | | | |
|---|---|---|---|---|---|---|---|---|---|---|---|---|---|---|---|---|
| 1 | Met | Ser | Pro | Ser | Glu | Thr | Thr | Leu | Tyr | Thr | Gln | Thr | Pro | Thr | Val | Ser | 116 |
| 17 | Val | Leu | Asp | Asn | Arg | Gly | Leu | Ser | Ile | Arg | Asp | Ile | Gly | Phe | His | Ar | 1732 |
| 33 | Ile | Val | Ile | Gly | Gly | Asp | Thr | Asp | Thr | Arg | Val | Thr | Arg | His | Gln | Ty | 3348 |
| 49 | Asp | Ala | Arg | Gly | His | Leu | Asn | Tyr | Ser | Ile | Asp | Pro | Arg | Leu | Tyr | As | 4964 |
| 65 | Ala | Lys | Gln | Ala | Asp | Asn | Ser | Val | Lys | Pro | Asn | Phe | Val | Trp | Gln | Hi | 6580 |
| 81 | Asp | Leu | Ala | Gly | His | Ala | Leu | Arg | Thr | Glu | Ser | Val | Asp | Ala | Gly | Ar | 8196 |
| 97 | Thr | Val | Ala | Leu | Asn | Asp | Ile | Glu | Gly | Arg | Ser | Val | Met | Thr | Met | A | 97112 |
| 113 | Ala | Thr | Gly | Val | Arg | Gln | Thr | Arg | Arg | Tyr | Glu | Gly | Asn | Thr | Leu | | 113128 |
| 129 | Gly | Arg | Leu | Leu | Ser | Val | Ser | Glu | Gln | Val | Phe | Asn | Gln | Glu | Ser | | 129144 |
| 145 | Lys | Val | Thr | Glu | Arg | Phe | Ile | Trp | Ala | Gly | Asn | Thr | Thr | Ser | Glu | | 145160 |
| 161 | Glu | Tyr | Asn | Leu | Ser | Gly | Leu | Cys | Ile | Arg | His | Tyr | Asp | Thr | Ala | | 161176 |
| 177 | Val | Thr | Arg | Leu | Met | Ser | Gln | Ser | Leu | Ala | Gly | Ala | Met | Leu | Ser | | 177192 |
| 193 | Ser | His | Gln | Leu | Leu | Ala | Glu | Gly | Gln | Glu | Ala | Asn | Trp | Ser | Gly | | 193208 |
| 209 | Asp | Glu | Thr | Val | Trp | Gln | Gly | Met | Leu | Ala | Ser | Glu | Val | Tyr | Thr | | 209224 |
| 225 | Gln | Ser | Thr | Thr | Asn | Ala | Ile | Gly | Ala | Leu | Leu | Thr | Gln | Thr | Asp | | 225240 |
| 241 | Lys | Gly | Asn | Ile | Gln | Arg | Leu | Ala | Tyr | Asp | Ile | Ala | Gly | Gln | Leu | | 241256 |
| 257 | Gly | Ser | Trp | Leu | Thr | Val | Lys | Gly | Gln | Ser | Glu | Gln | Val | Ile | Val | | 257272 |
| 273 | Ser | Leu | Ser | Trp | Ser | Ala | Ala | Gly | His | Lys | Leu | Arg | Glu | Glu | His | | 273288 |
| 289 | Asn | Gly | Val | Val | Thr | Glu | Tyr | Ser | Tyr | Glu | Pro | Glu | Thr | Gln | Arg | | 289304 |
| 305 | Ile | Gly | Ile | Thr | Thr | Arg | Arg | Ala | Glu | Gly | Ser | Gln | Ser | Gly | Ala | | 305320 |
| 321 | Val | Leu | Gln | Asp | Leu | Arg | Tyr | Lys | Tyr | Asp | Pro | Val | Gly | Asn | Val | | 321336 |
| 337 | Ser | Ile | His | Asn | Asp | Ala | Glu | Ala | Thr | Arg | Phe | Trp | Arg | Asn | Gln | | 337352 |
| 353 | Val | Glu | Pro | Glu | Asn | Arg | Tyr | Val | Tyr | Asp | Ser | Leu | Tyr | Gln | Leu | | 353368 |
| 369 | Ser | Ala | Thr | Gly | Arg | Glu | Met | Ala | Asn | Ile | Gly | Gln | Gln | Ser | Asn | | 369384 |
| 385 | Leu | Pro | Ser | Pro | Val | Ile | Pro | Val | Pro | Thr | Asp | Asp | Ser | Thr | Tyr | | 385400 |
| 401 | Asn | Tyr | Leu | Arg | Thr | Tyr | Thr | Tyr | Asp | Arg | Gly | Gly | Asn | Leu | Val | | 401416 |
| 417 | Ile | Arg | His | Ser | Ser | Pro | Ala | Thr | Gln | Asn | Ser | Tyr | Thr | Thr | Asp | | 417432 |
| 433 | Thr | Val | Ser | Ser | Arg | Ser | Asn | Arg | Ala | Val | Leu | Ser | Thr | Leu | Thr | | 433448 |
| 449 | Asp | Pro | Thr | Arg | Val | Asp | Ala | Leu | Phe | Asp | Ser | Gly | Gly | His | Gln | | 449464 |
| 465 | Met | Leu | Ile | Pro | Gly | Gln | Asn | Leu | Asp | Trp | Asn | Ile | Arg | Gly | Glu | | 465480 |
| 481 | Gln | Arg | Val | Thr | Pro | Val | Ser | Arg | Glu | Asn | Ser | Ser | Asp | Ser | Glu | | 481496 |
| 497 | Tyr | Arg | Tyr | Ser | Ser | Asp | Gly | Met | Arg | Leu | Leu | Lys | Val | Ser | Glu | | 497512 |
| 513 | Gln | Thr | Gly | Asn | Ser | Thr | Gln | Val | Gln | Arg | Val | Thr | Tyr | Leu | Pro | | 513528 |
| 529 | Leu | Glu | Leu | Arg | Thr | Thr | Gly | Val | Ala | Asp | Lys | Thr | Thr | Glu | Asp | | 529544 |

```
545  Gln Val Ile Thr Val Gly Glu Ala Gly Arg Ala Gln Val Arg Val     545560
561  His Trp Glu Ser Gly Lys Pro Thr Asp Ile Asp Asn Asn Gln Val     561576
577  Tyr Ser Tyr Asp Asn Leu Leu Gly Ser Ser Gln Leu Glu Leu Asp     577592
593  Glu Gly Gln Ile Leu Ser Gln Glu Glu Tyr Tyr Pro Tyr Gly Gly     593608
609  Ala Ile Trp Ala Ala Arg Asn Gln Thr Glu Ala Ser Tyr Lys Phe     609624
625  Arg Tyr Ser Gly Lys Glu Arg Asp Ala Thr Gly Leu Tyr Tyr Tyr     625640
641  Tyr Arg Tyr Tyr Gln Pro Trp Val Gly Arg Trp Leu Ser Ala Asp     641656
657  Ala Gly Thr Val Asp Gly Leu Asn Leu Tyr Arg Met Val Arg Asn     657672
673  Pro Ile Thr Leu Thr Asp His Asp Gly Leu Ala Pro Ser Pro Asn     673688
689  Asn Arg Asn Thr Phe Trp Phe Ala Ser Phe Leu Phe Arg Lys Pro     689704
705  Glu Gly Met Ser Ala Ser Met Arg Arg Gly Gln Lys Ile Gly Arg     705720
721  Ile Ala Gly Gly Ile Ala Ile Gly Gly Leu Ala Ala Thr Ile Ala     721736
737  Thr Ala Gly Ala Ala Ile Pro Val Ile Leu Gly Val Ala Ala Val     737752
753  Ala Gly Ile Gly Ala Leu Met Gly Tyr Asn Val Gly Ser Leu Leu     753768
769  Lys Gly Gly Ala Leu Leu Ala Arg Leu Val Gln Gly Lys Ser Thr     769784
785  Val Gln Ser Ala Ala Gly Ala Ala Ala Gly Ala Ser Ser Ala Ala     785800
801  Tyr Gly Ala Arg Ala Gln Gly Val Gly Val Ala Ser Ala Ala Gly     801816
817  Val Thr Gly Ala Val Gly Ser Trp Ile Asn Asn Ala Asp Arg Gly     817832
833  Gly Gly Ala Ile Gly Ala Gly Ser Ala Val Gly Thr Ile Asp Thr     833848
849  Leu Gly Thr Ala Ser Thr Leu Thr His Glu Val Gly Ala Ala Ala     849864
865  Gly Ala Ala Gly Gly Met Ile Thr Gly Thr Gln Gly Ser Thr Arg     865880
881  Gly Ile His Ala Gly Ile Gly Thr Tyr Tyr Gly Ser Trp Ile Gly     881896
897  Gly Leu Asp Val Ala Ser Asn Pro Ala Gly His Leu Ala Asn Tyr     897912
913  Val Gly Tyr Ala Ala Gly Leu Gly Ala Glu Met Ala Val Asn Arg     913928
929  Met Gly Gly Gly Phe Leu Ser Arg Leu Leu Gly Arg Val Val Ser     929944
945  Tyr Ala Ala Gly Leu Ala Arg Gln Leu Val His Phe Ser Val Ala     945960
961  Pro Val Phe Glu Pro Ile Phe Ser Val Leu Gly Gly Leu Val Gly     961976
977  Ile Gly Thr Gly Leu His Arg Val Met Gly Arg Glu Ser Trp Ile     977992
993  Arg Ala Leu Ser Ala Ala Gly Ser Gly Ile Asp His Val Ala Gly     9931008
1009 Ile Gly Asn Gln Ile Arg Gly Arg Val Leu Thr Thr Thr Gly Ile     10091024
1025 Asn Ala Ile Asp Tyr Gly Thr Ser Ala Val Gly Ala Ala Arg Arg    10251040
1041 Phe Ser Leu                                                     1043
```

(2) INFORMATION FOR SEQ ID NO:62: TcaAiv:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:62: TCAAIV:

```
Asn Ile Gly Gly Asp
1               5
```

(2) INFORMATION FOR SEQ ID NO:63: TcaAii-syn:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:63: TCAAII-SYN:

```
Cys Leu Arg Gly Asn Ser Pro Thr Asn Pro Asp Lys Asp Gly Ile
1               5                   10                  15
Phe Ala Gln Val Ala
20
```

(2) INFORMATION FOR SEQ ID NO:64: TcaAiii-syn:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: protein (v) FRAGMENT TYPE: Internal (xi) SEQUENCE DESCRIPTION: SEQ ID NO:64: TCAAIII-SYN:

```
Cys Tyr Thr Pro Asp Gln Thr Pro Ser Phe Tyr Glu Thr Ala Phe
1               5                   10                  15
Arg Ser Ala Asp Gly
20
```

(2) INFORMATION FOR SEQ ID NO:65: TcaBi-syn:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: protein (v) FRAGMENT TYPE: Internal (xi) SEQUENCE DESCRIPTION: SEQ ID NO: 65: TCABI-SYN:

```
His Gly Gln Ser Tyr Asn Asp Asn Asn Tyr Cys Asn Phe Thr Leu
1               5                   10                  15
Ser Ile Asn Thr
19
```

(2) INFORMATION FOR SEQ ID NO:66: TcaBii-syn:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:66: TCABII-SYN:

Cys Val Asp Pro Lys Thr Leu Gln Arg Gln Gln Ala Gly Gly Asp
1               5                   10                  15

Gly Thr Gly Ser Ser
20

(2) INFORMATION FOR SEQ ID NO:67: TcaC-syn:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:67: TCAC-SYN:

Cys Tyr Lys Ala Pro Gln Arg Gln Glu Asp Gly Asp Ser Asn Ala
1               5                   10                  15

Val Thr Tyr Asp Lys
20

(2) INFORMATION FOR SEQ ID NO:68: TcbAii-syn:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:68: TCBAII-SYN:

Cys Tyr Asn Glu Asn Pro Ser Ser Glu Asp Lys Lys Trp Tyr Phe
1               5                   10                  15

Ser Ser Lys Asp Asp
20

(2) INFORMATION FOR SEQ ID NO:69: TcbAiii-syn:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:69: TCBAIII-SYN:

Cys Phe Asp Ser Tyr Ser Gln Leu Tyr Glu Glu Asn Ile Asn Ala
1               5                   10                  15

Gly Glu Gln Arg Ala
20

(2) INFORMATION FOR SEQ ID NO:70: TcdAii-syn:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:70: TCDAII-SYN:

```
Cys Asn Pro Asn Asn Ser Ser Asn Lys Leu Met Phe Tyr Pro Val
1               5                   10                  15
Tyr Gln Tyr Ser Gly Asn Thr
20
```

(2) INFORMATION FOR SEQ ID NO:71: TcdAiii-syn:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:71: TCDAIII-SYN:

```
Val Ser Gln Gly Ser Gly Ser Ala Gly Ser Gly Asn Asn Asn Leu
1               5                   10                  15
Ala Phe Gly Ala Gly
20
```

(2) INFORMATION FOR SEQ ID NO:72:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: protein (v) FRAGMENT TYPE: N-terminal (xi) SEQUENCE DESCRIPTION: SEQ ID NO:72: 160 KDA - HB:

```
Met Gln Asp Ser Pro Glu Val Ala Ile Thr Thr Leu
1               5                   10
```

(2) INFORMATION FOR SEQ ID NO:73:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: protein (v) FRAGMENT TYPE: N-terminal (xi) SEQUENCE DESCRIPTION: SEQ ID NO:73: 170 KDA - WIR:

```
Met Gln Arg Ser Ser Glu Val Ser
1               5
```

(2) INFORMATION FOR SEQ ID NO:74:

(i) SEQUENCE CHARACTERISTICS:
        (A) LENGTH: 12 amino acids
        (B) TYPE: amino acid
        (C) STRANDEDNESS: single
        (D) TOPOLOGY: linear

```
        (ii) MOLECULE TYPE: protein (v) FRAGMENT TYPE: N-terminal (xi) SEQUENCE DESCRIPTION:   SEQ ID NO:74: 180 KDA - H9:

Met Gln Asp Ile Pro Glu Val Gln Leu Asn
1               5                   10

(xi) SEQUENCE DESCRIPTION:   SEQ ID NO:75: 170 KDA - HM(2):
             INFORMATION FOR SEQ ID NO:75:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: protein (v) FRAGMENT TYPE: N-terminal Met Gln Asp Ser Pro Glu Val Ser Val Thr Gln Asn
1               5                   10

(2) INFORMATION FOR SEQ ID NO:76:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: protein (v) FRAGMENT TYPE: N-terminal (xi) SEQUENCE DESCRIPTION:   SEQ ID NO:76: 74 KDA - H9:

Ser Glu Ser Leu Phe Thr Gln Ser Leu Lys Glu Ala Arg Arg Asp
1               5                   10                  15

(2) INFORMATION FOR SEQ ID NO:77:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: protein (v) FRAGMENT TYPE: N-terminal (xi) SEQUENCE DESCRIPTION:   SEQ ID NO:77: 71 KDA - HB:

Met Asn Leu Ile Glu Ala Lys Leu Gln Glu Asn Arg Asp Ala
1               5                   10

(2) INFORMATION FOR SEQ ID NO:78:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: protein (v) FRAGMENT TYPE: N-terminal (xi) SEQUENCE DESCRIPTION:   SEQ ID NO:78: 170 KDA - H9:

Met Leu Ser Thr Met Glu Lys Gln Leu Asn Glu Ser Gln Arg Asp
1               5                   10                  15
```

(2) INFORMATION FOR SEQ ID NO:79:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (v) FRAGMENT TYPE: N-terminal (xi) SEQUENCE DESCRIPTION: SEQ ID NO:79: 109 KDA - HM:

```
Met Leu Asp Ile Met Glu Lys Gln Leu Asn Glu Ser Glu Arg Asp
1               5                   10                  15
```

(2) INFORMATION FOR SEQ ID NO:80:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: protein (v) FRAGMENT TYPE: N-terminal (xi) SEQUENCE DESCRIPTION: SEQ ID NO:80: 170 KDA - WX-1:

```
Met Gln Asp Ser Arg Glu Val Ser
1               5
```

(2) INFORMATION FOR SEQ ID NO:81:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: protein (v) FRAGMENT TYPE: N-terminal (xi) SEQUENCE DESCRIPTION: SEQ ID NO:81: 69 KDA - H9:

```
Leu Arg Ser Ala Xxx Ser Ala Leu Thr Thr Leu Leu
1               5                   10
```

(2) INFORMATION FOR SEQ ID NO:82:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (v) FRAGMENT TYPE: N-terminal (xi) SEQUENCE DESCRIPTION: SEQ ID NO:82: 64 KDA - HP88:

```
Leu Lys Leu Ala Asp Asn Gly Tyr Phe Asn Glu Pro Leu Asn Val
1               5                   10                  15
```

(2) INFORMATION FOR SEQ ID NO:83:

(i) SEQUENCE CHARACTERISTICS:
        (A) LENGTH: 15 amino acids
        (B) TYPE: amino acid

```
            (C) STRANDEDNESS: single
            (D) TOPOLOGY: linear (ii) MOLECULE TYPE: protein (v) FRAGMENT TYPE: N-terminal (xi) SEQUENCE DESCRIPTION: SEQ ID NO:83: 70 KDA - NC-1:

Leu Lys Leu Ala Asp Asn Ser Tyr Phe Asn Glu Pro Leu Asn
1               5                   10                  15

(2) INFORMATION FOR SEQ ID NO:84:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: protein (v) FRAGMENT TYPE: N-terminal (xi) SEQUENCE DESCRIPTION: SEQ ID NO:84: 60 KDA - WIR:

Ser Lys Asp Glu Ser Lys Ala Asp Ser Gln Leu Val Tyr His Thr
1               5                   10                  15

(2) INFORMATION FOR SEQ ID NO:85:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: protein (v) FRAGMENT TYPE: N-terminal (xi) SEQUENCE DESCRIPTION: SEQ ID NO:85: 58 KDA - NC-1:

Met Lys Lys Arg Gly Leu Thr Thr Asn Ala Gly Ala Pro Val
1               5                   10

(2) INFORMATION FOR SEQ ID NO:86:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: protein (v) FRAGMENT TYPE: N-terminal (xi) SEQUENCE DESCRIPTION: SEQ ID NO:86: 60 KDA - WX-12:

Met Leu Asn Pro Ile Val Arg Lys Phe Glu Tyr Gly Glu His Thr
1               5                   10                  15

(2) INFORMATION FOR SEQ ID NO:87:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: protein (v) FRAGMENT TYPE: N-terminal
```

-continued

```
    (xi) SEQUENCE DESCRIPTION: SEQ ID NO:87: 60 KDA - HM:

Ala Glu Ile Tyr Asn Lys Asp Gly Asn Lys Leu Asp Leu Tyr Gly
1               5                   10                  15

(2) INFORMATION FOR SEQ ID NO:88:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (v) FRAGMENT TYPE: N-terminal (xi) SEQUENCE DESCRIPTION: SEQ ID NO:88: 140 KDA - HM:

Asn Leu Ile Glu Ala Thr Leu Glu Gln Asn Leu Arg Asp Ala
1               5                   10                  15
```

ANTAGONISTS OF HMG1 FOR TREATING INFLAMMATORY CONDITIONS

RELATED APPLICATIONS

This application is a continuation of U.S. application Ser. No. 10/210,747, filed Jul. 31, 2002, which is a continuation of U.S. application Ser. No. 09/503,632, filed Feb. 14, 2000, now issued as U.S. Pat. No. 6,468,533, which is a divisional of U.S. application Ser. No. 09/248,574, filed Feb. 11, 1999, now issued as U.S. Pat. No. 6,303,321. The entire teachings of the above applications are incorporated herein by reference.

TECHNICAL FIELD OF THE INVENTION

The present invention provides a pharmaceutical composition and method for treating diseases characterized by activation of an inflammatory cytokine cascade, particularly sepsis, including septic shock and ARDS (acute respiratory distress syndrome), comprising administering an effective amount of an antagonist to the high mobility group 1 protein (HMG1). The present invention further provides a diagnostic method for monitoring the severity of sepsis and related conditions, comprising measuring the serum concentration of HMG1 in a patient exhibiting symptoms of a disease characterized by activation of inflammatory cytokine cascade. Lastly, the present invention provides a pharmaceutical composition and method for effecting weight loss or treating obesity, comprising administering an effective amount of an HMG1 protein or a therapeutically active fragment of the gene product of an HMG1 gene.

BACKGROUND OF THE INVENTION

Sepsis is an often fatal clinical syndrome that develops after infection or injury. Sepsis is the most frequent cause of mortality in hospitalized patients. Experimental models of gram negative sepsis based on administration of bacterial endotoxin (lipopolysaccharide, LPS) have led to an improved understanding of the pathogenic mechanisms of lethal sepsis and conditions related to sepsis by virtue of the activation of a common underlying inflammatory cytokine cascade. This cascade of host-response mediators includes TNF, IL-1, PAF and other macrophage-derived factors that have been widely studied as acute, early mediators of eventual lethality in severe endotoxemia (Zhang and Trace), In The Cytokine Handbook, 3rd ed. Ed. Thompson (Academic Press Limited, USA). 515–547, 1998).

Unfortunately therapeutic approaches based on inhibiting these individual "early" mediators of endotoxemia have met with only limited success in large prospective clinical trials against sepsis in human patients. It is possible to infer from these disappointing results that later-appearing factors in the host response might critically determine pathogenesis and/or lethality, in sepsis and related disorders. Accordingly, there is a need to discover such putative "late" mediators necessary and/or sufficient for part or all of the extensive multisystem pathogenesis, or for the lethality, of severe endotoxemia, particularly as endotoxemia is representative of clinical sepsis and related clinical disorders.

HMG1 is a 30 kDa chromosomal nucleoprotein belonging to the burgeoning high mobility group (HMG) of non-histone chromatin-associated proteins. As a group, the HMG proteins recognize unique DNA structures and have been implicated in diverse cellular functions, including determination of nucleosome structure and stability, as well as in transcription and/or replication. The HMG proteins were first characterized by Johns and Goodwin as chromatin components with a high electrophoretic mobility in polyacrylamide gels (see in The HMG Chromosomal Proteins, E. W. Johns, Academic Press, London, 1982). Higher eukaryotes exhibit three families of HMG proteins: the HMG-1/-2 family, the HMG-14/-17 family and the HMG-I/-Y family. Although the families are distinguishable by size and DNA-binding properties, they are similar in their physical properties. HMG proteins are highly conserved across species, ubiquitously distributed and highly abundant, and are extractable from chromatin in 0.35 M NaCl and are soluble in 5% perchloric or trichloroacetic acid. Generally, HMG proteins are thought to bend DNA and facilitate binding of various transcription factors to their cognate sequences, including for instance, progesterone receptor estrogen receptor, HOX proteins, and Oct1, Oct2 and Oct6. Recently, it has become apparent that a large, highly diverse group of proteins including several transcription factors and other DNA-interacting proteins, contain one or more regions similar to HMG1, and this feature has come to be known as the HMG1 box or HMG1 domain. cDNAs coding for HMG1 have been cloned from human, rat, trout, hamster, pig and calf cells, and HMG1 is believed to be abundant in all vertebrate cell nuclei. The protein is highly conserved with interspecies sequence identities in the 80% range. In chromatin, HMG1 binds to linker DNA between nucleosomes and to a variety of non-β-DNA structures such as palindromes, cruciforms and stem-loop structures, as well as cisplatin-modified DNA. DNA binding by HMG1 is generally believed to be sequence insensitive. HMG1 is most frequently prepared from washed nuclei or chromatin, but the protein has also been detected in the cytoplasm. (Reviewed in Landsman and Bustin, BioEssays 15:539–546. 1993, Baxevanis and Landsman, Nucleic Acids Research 23:514–523,1995). To date, no link has been established between the HMG proteins and any clinical condition or disease.

HMG1 has been alternatively identified as a heparin-binding protein abundantly expressed in developing brain and dubbed "amphoterin" for its highly dipolar sequence, comprising two internal repeats of a positively charged domain of about 80 amino acids (the HMG1 box) and an acidic C-terminal domain containing a stretch of approximately 30 continuous glutamic or aspartic acid residues. Amphoterin/HMG1 has been localized to the outer surface of the plasma membranes of epithelial, and especially neuronal cells, where it has been specifically localized to the filipodia of neural cells. Inhibition studies have suggested that amphoterin/HMG1 is required for process (neurite) extension and amphoterin/HMG1 also may be involved in neuron-glia interactions (Merenmies et al., J. Biol. Chem. 266:16722–16729,1991; Merenmies et al., J. Biol. Chem. 266:16722–16729, 1991; Milev et al., J. Biol. Chem. 273: 6998–7005, 1998; and Salmivirta et al. Exp. Cell Res. 200:444–451, 1992). Amphoterin/HMG1 can be released from murine erythroleukemia cells after stimulation with the chemical induce, hexamethylenebisacetamide (Melloni et al., Biochem. Biophys. Res. Commun. 210:82–89, 1995). Previous study suggested that the gene product of the HMG1 gene functions as a differentiation enhancing factor by stimulating α-PKC (Melloni et al., Biochem. Biophys. Res. Commun. 210:82–89, 1995; and Melloni et al., FEBS Lett. 368:466–470, 1995).

The HMG1 gene product has been shown to interact with plasminogen and tissue-type plasminogen activator (t-PA) and effectively enhance plasmin generation at the cell surface, a system that is known to play a role in extracellular proteolysis during cell invasion and tissue remodeling. Amphoterin/HMG1 has also been shown to interact with the receptor of advanced glycosylation end products RAGE) (Mohan et al., *Biochem. Biophys. Res. Commun.* 182:689–696, 1992; Yamawaki et al., *J. Neurosci. Res.* 44:586–593, 1996; Salmivirta et al., *Exp. Cell Res.* 200: 444–451, 1992; and Vassalli et al., *J. Clin. Invest.* 88:1067–1072, 1991), (Redlitz and Plow, *Baillieres Clin. Haematol.* 8:313–327, 1995; and Parkkinen et al., *J. Biol. Chem.* 266:16730–16735, 1991).

There is a longstanding need in the art to discover improved agents that can prevent the cytokine-mediated inflammatory cascade and have therapeutic activity in a large variety of cytokine-mediated inflammatory diseases. The present invention was made during the course of investigative research to identify agents that mediate toxicity, pathogenesis and/or lethality in sepsis and other disorders related by a common activation of the inflammatory cytokine cascade.

Diseases and conditions mediated by the inflammatory cytokine cascade are numerous. Such conditions include the following grouped in disease categories:

Systemic Inflammatory Response Syndrome, which includes:
Sepsis syndrome
   Gram positive sepsis
   Gram negative sepsis
   Culture negative sepsis
   Fungal sepsis
   Neutropenic fever
   Urosepsis
Meningococcemia
Trauma hemorrhage
Hums
Ionizing radiation exposure
Acute pancreatitis
Adult respiratory distress syndrome (ARDS)

Reperfusion Injury, which includes
   Post-pump syndrome
   Ischemia-reperfusion injury Cardiovascular Disease, which includes
   Cardiac stun syndrome
   Myocardial infarction
   Congestive heart failure Infectious Disease, which includes
   HIV infection/HIV neuropathy
   Meningitis
   Hepatitis
   Septic arthritis
   Peritonitis
   Pneumonia Epiglottitis
   *E. coli* 0157:H7

Hemolytic uremic syndrome c/thrombolytic thrombocytopenic purpura
Malaria
Dengue hemorrhagic fever
Leishmaniasis
Toxic shock syndrome
*Streptococcal* myositis
Gas gangrene
*Mycobacterium* tuberculosis
*Mycobacterium avum intracellulare*
*Pneumocystis carim* pneumonia
Pelvic inflammatory disease
Orchitis/epidydimitis
*Legionella*
Lyme disease
Influenza A
Epstein-Barr virus
Viral associated hemiaphagocytic syndrome
Viral encephalitis/aseptic meningitis Obstetrics/Gynecology, including:
Premature labor
Miscarriage
Infertility Inflammatory Disease/Autoimmunity, which includes:
Rheumatoid arthritis/seronegative arthropathies
Osteoarthritis
Inflammatory bowel disease
Systemic lupus erythematosis
Iridoeyelitis/uveitistoptic neuritis
Idiopathic pulmonary fibrosis
Systemic vasculitis/Wegener's gramilomatosis
Sarcoidosis
Orchitis/vasectomy reversal procedures Allergic/Atopic Diseases, which includes:
Asthma
Allergic rhinitis
Eczema
Allergic contact dermatitis
Allergic conjunctivitis
Hypersensitivity pneumonitis Malignancy, which includes:
ALL
AML
CML
CLL
Hodgkin's disease, non-Hodgkin's lymphoma
Kaposi's sarcoma
Colorectal carcinoma
Nasopharyngeal carcinoma.
Malignant histiocytosis
Paraneoplastic sydrome/hypercalcemia of malignancy Transplants, including:
   Organ transplant rejection
   Graft-versus-host disease Cachexia Congenital, which includes:
Cystic fibrosis
   Familial hematophagocytic lymphohistiocytosis
   Sickle cell anemia Dermatologic, which includes:
   Psoriasis
   Alopecia Neurologic, which includes:
   Multiple sclerosis
   Migraine headache Renal, which includes:
   Nephrotic syndrome
   Hemodialysis
   Uremia Toxicity, which includes:
   OKT3 therapy
   Anti-CD3 therapy Cytokine therapy
Chemotherapy
Radiation therapy
Chronic salicylate intoxication Metabolic/Idiopathic, which includes:
Wilson's disease
Hemachromatosis
Alpha-1 antitrypsin deficiency
Diabetes
Hashimoto's thyroiditis
Osteoporosis
Hypothalamic-pituitary-adrenal axis evaluation
Primary biliary cirrhosis

SUMMARY OF THE INVENTION

The present invention provides a pharmaceutical composition for treating conditions (diseases) mediated by the inflammatory cytokine cascade, comprising an effective amount of an antagonist or inhibitor of HMG1. Preferably, the HMG1 antagonist is selected from the group consisting of antibodies that bind to an HMG1 protein, HMG1 gene antisense sequences and HMG1 receptor antagonists. The present invention provides a method for treating a condition mediated by the inflammatory cytokine cascade, comprising administering an effective amount of an HMG 1 antagonist. In another embodiment, the inventive method further comprises administering a second agent in combination with the HMG1 antagonist, wherein the second agent is an antagonist of an early sepsis mediator, such as TNF, IL-1α, IL-1β, MIF or IL-6. Most preferably, the second agent is an antibody to TNF or an IL-1 receptor antagonist (IL-1 ra).

The present invention further provides a diagnostic and prognostic method for monitoring the severity and predicting the likely clinical course of sepsis and related conditions for a patient exhibiting shock-like symptoms or at risk to exhibit symptoms associated with conditions mediated by the inflammatory cascade. The inventive diagnostic and prognostic method comprises measuring the concentration of HMG1 in a sample, preferably a serum sample, and comparing that concentration to a standard for HMG1 representative of a normal concentration range of HMG1 in a like sample, whereby higher levels of HMG1 are indicative of poor prognosis or the likelihood of toxic reactions. The diagnostic method may also be applied to other tissue or fluid compartments such as cerebrospinal fluid or urine. Lastly, the present invention provides a pharmaceutical composition and method for effecting weight loss or treating obesity, comprising administering an effective amount of HMG1 or a therapeutically active fragment thereof.

BRIEF DESCRIPTION OF THE DRAWINGS

FIG. 2 illustrates that HMG1 is a mediator of pathogenesis and lethality in endotoxemia.

FIG. 3 shows that HMG1 induced TNF release both in vitro (FIG. 3A) and in vivo (FIG. 3B). Specifically, FIG. 3A shows the mean±S.E.M. of the induced TNF response in two experiments (in triplicate).

FIG. 4 shows the mean±S.E.M. of net body weight change of three mice per group.

DETAILED DESCRIPTION OF THE INVENTION

Figure 1A:
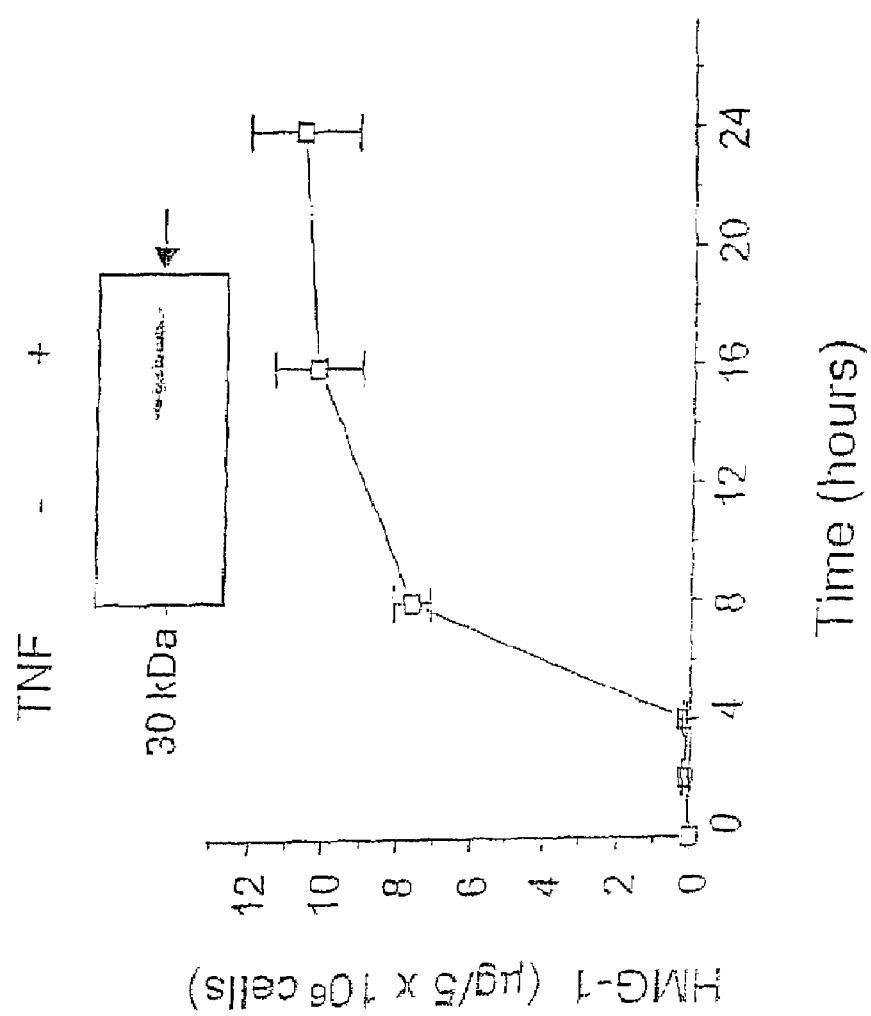
FIG. 1 shows two graphs that profile the induction of HMG1 release by LPS in vitro (FIG. 1A and in vivo (FIG. 1B). Specifically, FIG. 1A shows the accumulation of HMG1 in culture supernatants of macrophage RAW 264.7 cells after stimulation with LPS (100 ng/ml). The inset is a Western blot (using antibodies raised against recombinant HMG1) showing induction of HMG1 release from RAW 264.7 cells after induction with TNF.
FIG. 1B shows accumulation of HMG1in serum of LPS-treated mice. Serum from Balb/C mice was collected at various time points after LPS administration, and assayed for HMG1 by Western blotting using antibodies raised against recombinant HMG1.

The present invention is based upon the discovery and isolation of a highly inducible 30 kDa protein that is released by, and accumulates in media conditioned by, cultured murine macrophage-like cells (RAW 264.7) following stimulation with LPS, INF, or IL-1. A partial amino acid sequence of this isolated polypeptide was identical to the sequence of the HMG1 protein, also known as amphoterin, a protein not before linked to the pathogenesis of any disease. This information was used to clone a cDNA encoding HMG1, which sequence was expressed to provide recombinant protein, which protein was used to generate specific anti-HMG1 antibodies.

Therapeutic and diagnostic efficacy was determined in a series of predictive in vitro and in vivo experiments. The experiments are detailed in the Examples section. For example, following administration of endotoxin ($LD_{100}$) to mice, serum HMG1 levels increased later (at 16 h) than well-known "early" mediators of sepsis (such as TNF and IL-1) and plateau levels of HMG1 were maintained for 16 to 32 hours. Patients with lethal sepsis had high serum HMG1 levels, which were not detected in normal healthy volunteers. Moreover, acute experimental administration of rHMG1 to test animals, whether alone or in combination with sub-lethal amounts of LPS, caused marked pathological responses and even death. More distributed dosing schedules of lower amounts of rHMG1 led to significant weight loss in treated animals. These results give evidence that HMG1 is a mediator of endotoxemia and particularly a late mediator, as opposed to known "early" mediators such as TNF and IL-1. These data further show the importance of serum HMG1 as a marker for the severity or potential lethality of sepsis and related conditions.

In addition, treatment with anti-HMG1 antibodies provided full protection from $LD_{100}$ doses of LPS in mice. HMG1 is inducible bad TNF and IL-1β, and dose-dependently stimulates TNF release from huPBMCs. TNF is a marker of macrophage activation, so it is likely (with out limitation as to implied mechanisms or being bound by theory) that HMG1 promotes downstream re-activation of cytokine cascades which, in turn, mediates late pathogenesis and lethality in sepsis and related conditions involving activation of pro-inflammatory cytokine responses. Thus, HMG1 likely occupies a central role in mediating the inflammatory response to infection and injury, and antagonists of HMG1 will be of therapeutic benefit in sepsis and related conditions of inflammatory cascade activation. The appearance of HMG1 in the inflammatory cytokine cascade is suitable to propagate later phases of the host response and contribute to toxicity and lethality. The predictive data provided herein support the therapeutic efficacy of HMG1 antagonists and provide evidence in support of the aforementioned theory regarding mechanism of action. The in vivo treatment data showed the efficacy of HMG1 antagonists in general, and anti-HMG1 antibodies in particular, for treating conditions mediated by the inflammatory cytokine cascade in general and particularly sepsis conditions, including, for example, septic shock, sepsis syndrome or other "sepsis-like" conditions mediated by inflammatory cytokines. Further, the independent pathogenicity, and toxicity/lethality of HMG1 shows that HMG1 antagonists are particularly effective when co-administered with antagonists of "early" inflammatory mediators such as TNF, MIP, IL-1 and IL-6.

In summary, HMG1 is a cytokine mediator of inflammatory reactions because: 1) HMG1 is released from macrophages and pituicytes following stimulation with bacterial toxins or with pro-inflammatory cytokines (TNF or IL-1β); 2) HMG1 accumulates in serum of animals exposed to LPS and in patients with sepsis; and 3) HMG1-specific antibodies protect against mortality in a predictive lethal endotoxemia animal model of clinical sepsis and related conditions.

Pharmaceutical Composition and Method of Administration

The inventive pharmaceutical composition or inventive pharmaceutical combination can be administered to a patient either by itself (complex or combination) or in pharmaceutical compositions where it is mixed with suitable carriers and excipients. The inventive pharmaceutical composition or inventive pharmaceutical combination can be administered parentally, such as by intravenous injection or infusion, intraperitoneal injection, subcutaneous injection, or intramuscular injection. The inventive pharmaceutical composition or inventive pharmaceutical combination can be administered orally or rectally through appropriate formulation with carriers and excipients to form tablets, pills, capsules, liquids, gels, syrups, slurries, suspensions and the like. The inventive pharmaceutical composition or inventive pharmaceutical combination can be administered topically, such as by skill patch, to achieve consistent systemic levels of active agent. The inventive pharmaceutical composition or inventive pharmaceutical combination can be formulated into topical creams, skin or mucosal patches, liquids or gels suitable for topical application to skin or mucosal membrane surfaces. The inventive pharmaceutical composition or inventive pharmaceutical combination can be administered by inhaler to the respirator, tract for local or systemic treatment.

The dosage of the inventive pharmaceutical composition or inventive pharmaceutical combination of the present invention can be determined by those skilled in the art from this disclosure. The pharmaceutical composition or inventive pharmaceutical combination will contain an effective dosage (depending upon the route of administration and pharmacokinetics of the active agent) of the inventive pharmaceutical composition or inventive pharmaceutical combination and suitable pharmaceutical carriers and excipients, which are suitable for the particular route of administration of the formulation (i.e., oral, parenteral, topical or by inhalation). The active agent is mixed into the pharmaceutical formulation by means of mixing, dissolving granulating, dragee-making, emulsifying, encapsulating, entrapping or lyophilizing processes. The pharmaceutical formulations for parenteral administration include aqueous solutions of the active agent or combination in water-soluble form. Additionally, suspensions of the active agent may be prepared as oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxy,methyl cellulose, sorbitol, or dextran. The suspension may optionally contain stabilizers or agents to increase the solubility of the active agent or combination to allow for more concentrated solutions.

Pharmaceutical formulations for oral administration can be obtained by combining the active agent with solid excipients, such as sugars (e.g., lactose, sucrose, mannitol or sorbitol), cellulose preparations (e.g. starch, methyl cellulose, hydroxypropylmethyl cellulose, and sodium carboxymethyl cellulose), gelaten, gums, or polyvinylpyrrolidone. In addition, a disintegrating agent may be added, and a stabilizer may be added.

Antisense Oligomers

The present invention provides antisense oligomers having a sequence effective to inhibit or block the expression of the HMG1 gene or mRNA sequence. Antisense technology which uses specific-oligonucleotides to inhibit expression of target gene products is developing as a therapeutic modality for human disease. Several selection criteria are available to contribute to the optimization of antisense oligonucleotide antagonists. For example, it is advisable to choose sequences with 50% or more GC content. Preferred sequences span the AUG initiation codon of the target protein, but sites in the coding region and 5' UTR may perform equally well. Such sequences are generally about 18–30 nucleotides long and chosen to overlap the ATG initiation codon from the HMG1 cDNA sequence to inhibit protein expression. Longer oligomers are often found to inhibit the target to a greater extent, indicating that a preferred length is about 25 mer for the first oligonucleotides chosen as antisense reagents. Typically, three oligonucleotide sequences are chosen with regard to these criteria, and compared for antagonist activity to control oligonucleotide sequences, such as "reverse" oligonucleotides or those in which about ever, fourth base of the antisense sequence is randomized. Therefore, a preferred sequence for making antisense oligomer sequences to HMG1 is a 25 mer sequence chosen to overlap the ATG initiation codon (underlined) from the HMG1 cDNA sequence:

GAGGAAAAATAACTAAAC
        ATGGGCAAAGGAGATCCTAAGAAG [SEQ
        ID NO. 5]

and such preferred antisense sequences are used to construct antisense oligonucleotide agents (and suitable controls) for an in vitro comparison as antagonists of HMG1. These in vitro data are predictive of human clinical utility using antisense agents of comparable design.

HMG1-directed Antibodies

The antibodies disclosed herein may be polyclonal or monoclonal; may be from any of a number of human, non-human eukaryotic, cellular, fungal or bacterial sources; may be encoded by genomic or vector-borne coding sequences; and may be elicited against native or recombinant HMG1 or fragments thereof with or without the use of adjuvants, all according to a variety of methods and procedures well-known in the art for generating and producing antibodies. Generally, neutralizing antibodies against HMG1 (i.e., those that inhibit biological activities of HMG1 particularly with regard to its pro-inflammatory cytokine-like role) are preferred for therapeutic applications while non-neutralizing antibodies may be as suitable for diagnostic applications. Examples of such useful antibodies include but are not limited to polyclonal, monoclonal, chimeric, single-chain, and various human or humanized types of antibodies, as well as various fragments thereof such 95 Fab fragments and fragments produced from specialized expression systems.

Diagnostic Assay

The diagnostic assay provided here uses anti-HMG1 antibodies that can be either polycolonal or monoclonal or both. The diagnostic procedure can utilize standard antibody-based techniques for measuring concentrations of the gene product of HMG1 genes in a biological fluid. Preferred standard diagnostic procedures are ELISA assays and Western techniques.

EXAMPLE 1

Identification of HMG1 as a "Late" Mediator of Endotoxemia

This example provides the results of an experiment to identify and isolate later released macrophage-derived factors that play, a role in sepsis and in related conditions typified by inflammatory cytokine activity. The experiment reported in this example examined murine macrophage RAW 264.7 cell-conditioned media after stimulation of the cultures with TNF. Murine Macrophage RAW 264.7 cells were obtained from American Type Culture Collections (ATCC, Rockville, Md., USA), and proliferated in culture under DMEM supplemented with 10% fetal bovine serum and 1% glutamine. When confluency reached 70–80%, the medium was replaced by serum-free OPTI-MEM I medium and cultures were stimulated with pro-inflammatory cytokines (e.g. TNFα or IL-1) or bacterial endotoxin (LPS).

The proteins released from the above stimulated macrophage cultures were surveyed. Specifically, at different time points, cells and cell-conditioned media were separately collected by centrifugation (3000 rpm, 10 minutes). Proteins in the conditioned mediam were concentrated by ultrafiltration over Amicon membranes with Mr cutoff of 10 kDa (Amicon Inc., Beverly, Mass., USA), subsequently fractionated by SDS-PAGE, and stained with Coomassie blue (1.25% Coomassie Blue R250 in 30% methanol/10% acetic acid). After destaining with 30% methanol/7% acetic acid, protein(s) of interest (i.e., those that preferentially accumulated in conditioned media of stimulated cultures) was isolated by excision from the SDS-PAGE gel, and subjected to N-terminal sequencing analysis (Commonwealth Biotechnologies, Inc., Richmond, Va. USA).

Comparison of SDS-PAGE gel analysis of profiles of proteins accumulated in control (without TNFα stimulation) versus TNF-stimulated RAW 264.7 cells revealed a strongly inducible 30 kDa protein whose concentration in the cell-conditioned medium was significantly increased after stimulation for 16 hours. Amino acid sequence analysis of this isolated protein revealed its N-terminal sequence as Gly-Lys-Gly-Asp-Pro-Lys-Lys-Pro-Arg-Gly-Lys-Met-Ser-Ser [SEQ ID NO. 1]. A review of relevant gene databases found a 100% identity to the N-terminal amino acid sequence of HMG1.

These data identified HMG1 as a "late-appearing" product of LPS-stimulated macrophage cultures and therefore as a candidate pro-inflammatory mediator. This activity was confirmed by administration of recombinantly produced HMG1 and/or of anti-HMG1 antibodies in cellular and animal model systems that are predictive of human clinical conditions.

EXAMPLE 2

Cellular Sources of HMG1

This example shows which cell sources are capable of releasing HMG1 in response to TNF, IL-1 and/or LPS. Cells studied include $GH_3$ pituicytes, murine macrophage RAW 264.7 cell, pharmaceutical human primary peripheral blood mononuclear cells (huPBMCs), human primary T cells, rat adrenal PC-12 cells, and rat primary kidney cells (Table 1). The rat pituitary $GH_3$ cell line was obtained from American Type Culture Collection (ATCC, Rockville, Md., USA), and cultured in DEME supplemented with 10% fetal bovine serum and 1% glutamine. Human PBMCs and T cells were freshly isolated from whole blood of healthy donors and cultured in RPMI 1640 supplemented with 10% human serum as previously described (Zhang et al., *J. Exp. Med.* 185:1759–1768, 1997). When confluency reached 70–80%, the medium was replaced by serum-free OPTI-MEM I medium and cultures stimulated with proinflammatory cytokines (e.g., TNFα or IL-1) or bacterial endotoxin (LPS).

Although human T cell, rat adrenal (PC-12) cells, and rat primary kidney cells contained cell-associated HMG1 as demonstrated by Western blotting analysis of whole cell lysates using HMG1-specific antibodies (see example 4 below), HMG1 did not significantly accumulate in the medium of these cultures after stimulation with either TNF, IL-1β, or LPS (Table 1).

TABLE 1

Induced release of HMG1 from various types of cells.

| Cell Type | Stimulus | | |
|---|---|---|---|
| | TNF | IL-1β | LPS |
| Murine RAW 264.7 cells | Yes | Yes | Yes |
| Human PBMCs | Yes | Yes | Yes |
| Human primary T cells | No | No | No |
| Rat adrenal PC-12 cells | No | No | No |
| Rat pituitary GH₃ cells | Yes | Yes | No |
| Rat primary kidney cells | No | No | No |

Note: PBMCs, peripheral blood mononuclear cells.

TNF, IL-1β (minimal effective concentration=5 ng/ml for each) and bacterial endotoxin (LPS, minimal effective concentration=10 ng/ml) induced the release of HMG1 from human PBMCs in a time- and dose-dependent manner (Table 1). IFN-γ alone (0–200 U/ml) did not induce HMG1 release from any of the above cells, but when added in combination either with TNF or IL-1β, IFN-γ dose-dependently enhanced HMG1 release from macrophages, with a maximal 3-fold enhancement by IFN-γ at a concentration of 100 U/ml. The release of HMG1 was not due to cell death, because cell viability was unaffected by TNF, IL-1β, or LPS, as judged by Trypan blue exclusion (90–92±5% viable for control vs. 88–95±4% in the presence of 100 ng/ml TNF, IL-1β or LPS). The amount of HMG1 released by pituicytes and macrophages inversely correlated with the intracellular concentration of HMG1, as determined by Western blotting analysis, indicating that the released material is, in part, derived from pre-formed cell-associated HMG1 protein.

Figure 5:
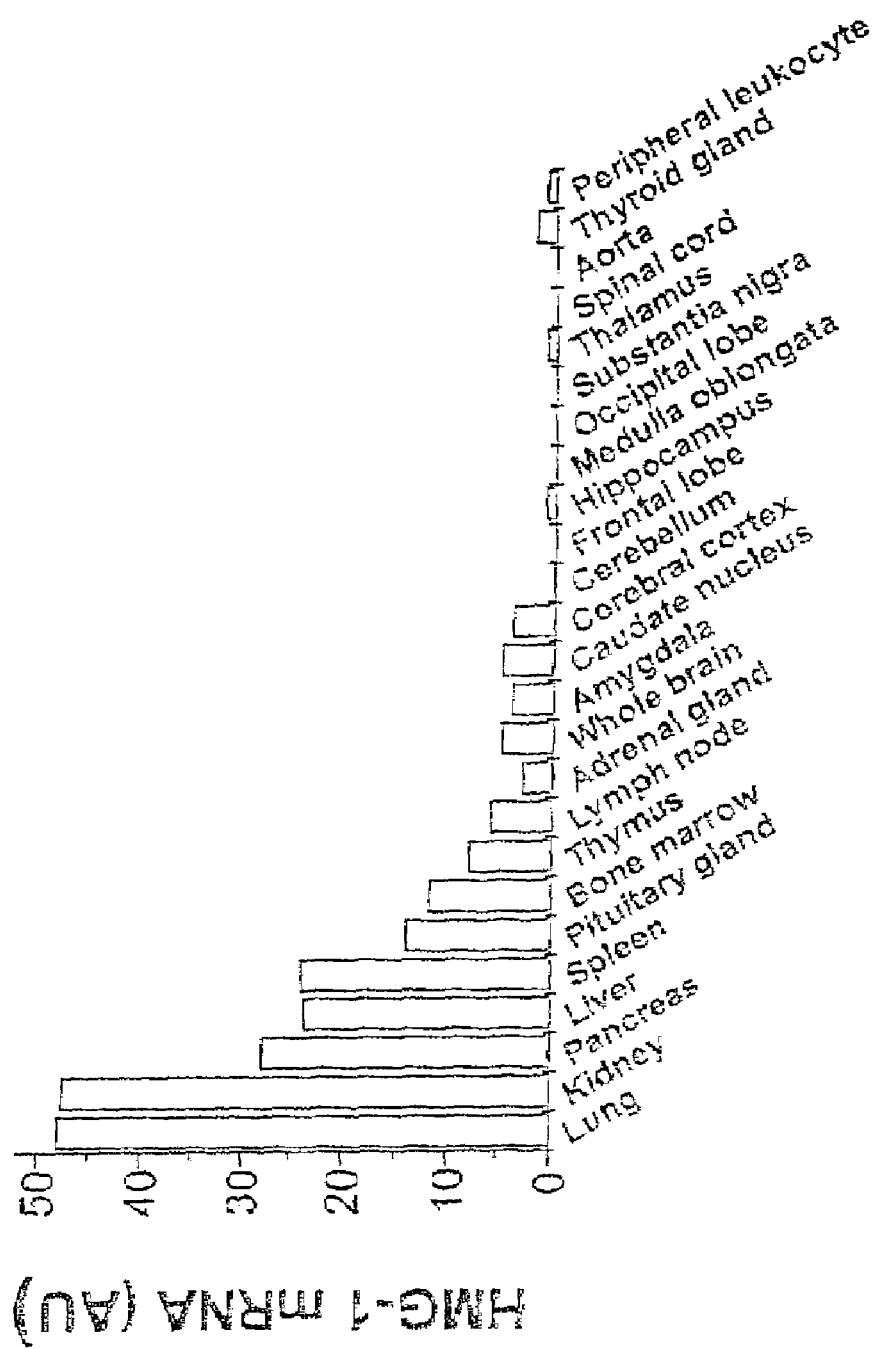
FIG. 5 shows the tissue distribution of HMG1 mRNA. Human RENA master blots containing poly(A)$^+$ RNA of various tissues (Clontech, Palo Alto, Calif., USA) were hybridized with a 0.6 lab digoxigenin-11-dUTP-labeled HMG1 cDNA probe synthesized by PCR using recombinant plasmid containing the HMG1 cDNA insert, all in accordance with methods well-known in the art. Briefly, hybridization was performed in a hybridization buffer (5×SSC/2% ) blocking reagent/0.1% SDS/50% formamide, Boehringer Mannheim, Indianapolis, Ind.) with a probe concentration of 10 ng/ml for 16 hours at 65° C. After hybridization, the filter was subjected to two washes of 0.5×SSC/0.1% SDS for 5 minutes, and two washes of 0.2×SSC/0.1% SDS for 10 minutes at room temperature. Signal was detected using anti-digoxigenin antibodies conjugated to phosphotase and detection reagents 4-nitrobluetetrazolium chloride (NBT) and 5-cromo-4-chloro-3-indolyl-phosphate (BCIP) (Boehringer-Mannheim) according to standard methods. The blots were scanned with a silver image scanner (Silverscanner II, Lacie Limited, Beaverton, Oreg.), and relative optical density (in arbitrary units, AU) was quantified using NIH 1.59 image software. Note that highest levels were observed in macrophage-rich tissues.

Potential sources of circulating HMG1 in vivo were assessed by hybridization of an HMG1-specific probe to mRNA prepared from various normal human tissues (blot substrate available from commercial sources), with the results summarized in FIG. 5. Several macrophage-rich tissues (lung, liver, kidney, pancreas and spleen) exhibited the most abundant HMG1 mRNA expression; less was observed in pituitary, bone marrow, thymus, lymph node and adrenal gland. In addition to providing information as to the relative tissue distribution of HMG1 expression, this study shows the practicality and utility of assaying for HMG1-specific nucleic acid sequences in tissue samples.

EXAMPLE 3

Recombinant HMG1 Administration, in Vitro and in Vivo

This example details procedures to produce HMG1 by well-known recombinant DNA technologies. The HMG1 open reading frame was amplified by PCR and subcloned into an expression vector (pCAL-n). Briefly, the 648-bp open reading frame of HMG1 cDNA was PCR amplified (94° C. 1', 56° C. 2', 72° C. 45", 30 cycles) from 5 ng Rat Brain Quick-Clone cDNA (Catalog #7150-1, Clontech, Palo Alto, Calif., USA) using primers containing the following sequences, 5'-CCC GC<u>GGATCC</u>A TCG AGG GAA GGA TGG GCA AAG GAG ATC CTA-3' [SEQ ID NO. 2], and 5'-CCC GC<u>AAGCTT</u>A TTC ATC ATC ATC ATC TTC T-3' [SEQ ID NO. 3]. The 680 bp PCR product (4 μg) was digested with Bam HI and Hind III, and cloned into the Bam HI/Hind III cloning sites of the pCAL-n vector (Stratagene, La Jolla, Calif., USA). The recombinant plasmid was transformed into *E. coli* BL21(DE3)pLysS (Novagen, Madison, Wis., USA), and positive clones were screened and confirmed by DNA sequencing on both strands using a Taq DyeDeoxy terminator cycle sequencing kit on the ABI 373A automated fluorescent sequencer (Applied Biosystels, Foster City, Calif., USA).

To express recombinant HMG1, positive clones were cultured at 37° C. with vigorous shaking, (250 rpm) until $OD_{600}$ reached 0.6, when IPTG (1 mM) was added. Twelve hours after IPTG induction, bacterial cells were harvested by centrifugation (6500 rpm, 15 minutes), and lysed by freeze-thaw cycles. The water-soluble fraction was collected after centrifugation (30 minutes, 12,000 rpm), and recombinant HMG1 was purified on a calmodulin-binding resin column as instructed by the manufacturer (Stratagene). Bacterial endotoxin was removed from the recombinant HMG1 by using Detoxi-Gel endotoxin-removing gel (Pierce, Rockford, Ill. USA, Cat. #20344), and residual LPS content was determined by the Limulus Amebocyte Lysate Test (LAL test, Cat. #50-648U, QCL-1000 Chromogenic LAL, Bio-Whittaker, Inc., Walkersville, Md., USA). Purified recombinant HMG1 was added to cultures of human peripheral blood mononuclear cells (HuPBMCs), and supernatants assayed for TNF by ELISA four hours after stimulation. The LPS-neutralizing agent polymyxin B (10 μg/ml) was added concurrently with recombinant HMG1 to eliminate the effect of any contaminating LPS on TNF release. Additionally recombinantly derived HMG1 was administered to test animals, with or without the additional endotoxemic challenge of exogenous LPS, to study the pathogenic potential of high levels of HMG1 in vivo (see FIGS. 2B and 2C). In some experiments, serum samples were secured from HMG1-treated animals to be assayed for TNF as detailed herein (see FIG. 1B).

The above procedure provides recombinant HMG1 as a fusion peptide comprising a 3.0 kDa calmodulin-binding domain and a thrombin cleavage site as an amino terminal extension in register with the HMG1 peptide sequence. In some experiments, the fusion tag was removed from an aliquot of the recombinant protein and the bioactivity of the full fusion protein was compared to the cleaved HMG1 peptide; no significant difference in bioactivity was noted and additional experiments (especially those requiring administration of recombinantly produced HMG1 to animals) typically were conducted with the (uncleaved) fusion protein.

Figure 3A:
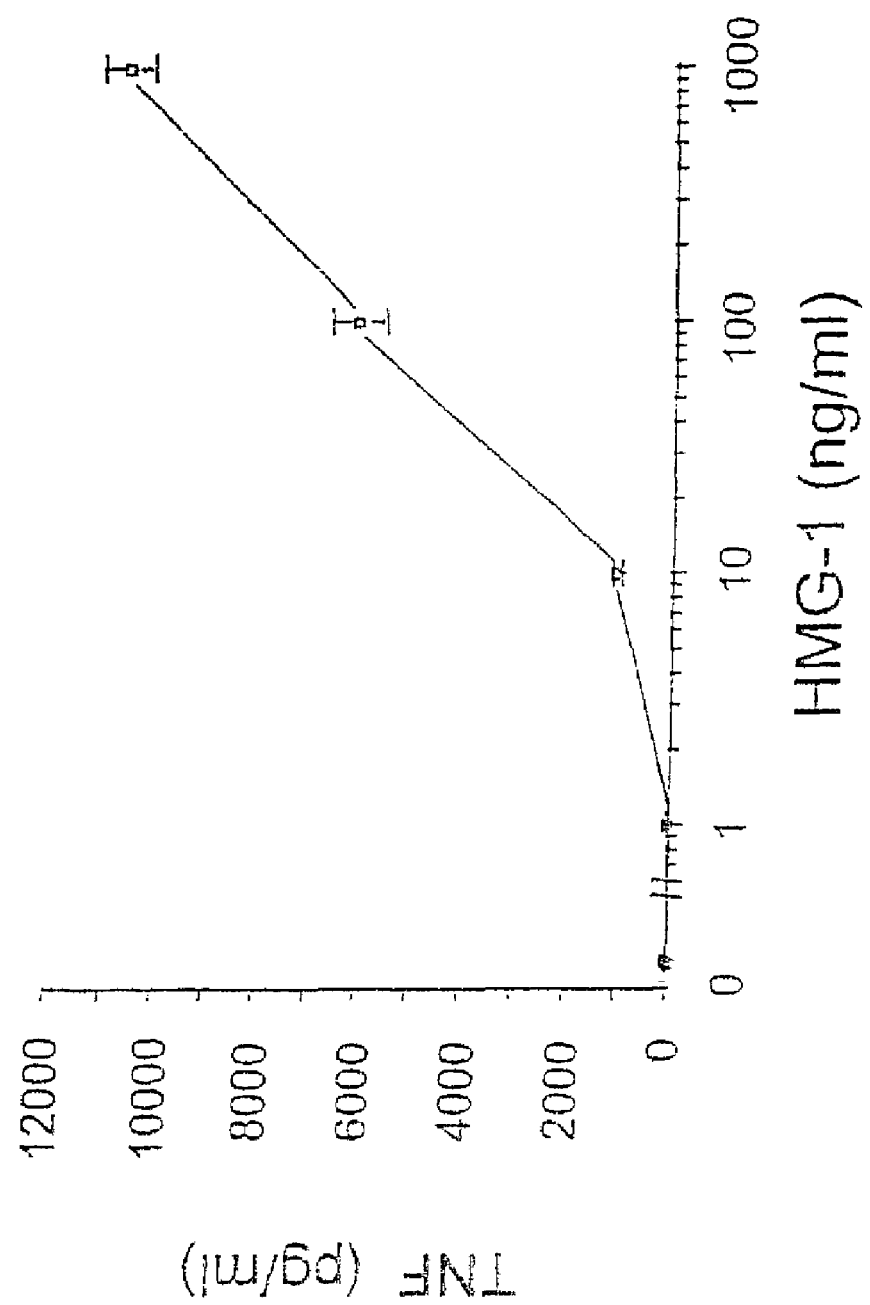
FIG. 3A shows that HMG1 induces TNF release from huPPBMCs in dose-dependent fashion. Freshly isolated huPBMC cultures were stimulated with purified recombinant HMG1 protein at the indicated doses, and culture media were sampled four hours later to be assayed for TNF according to known immunologic methods (ELISA).
Figure 3B:
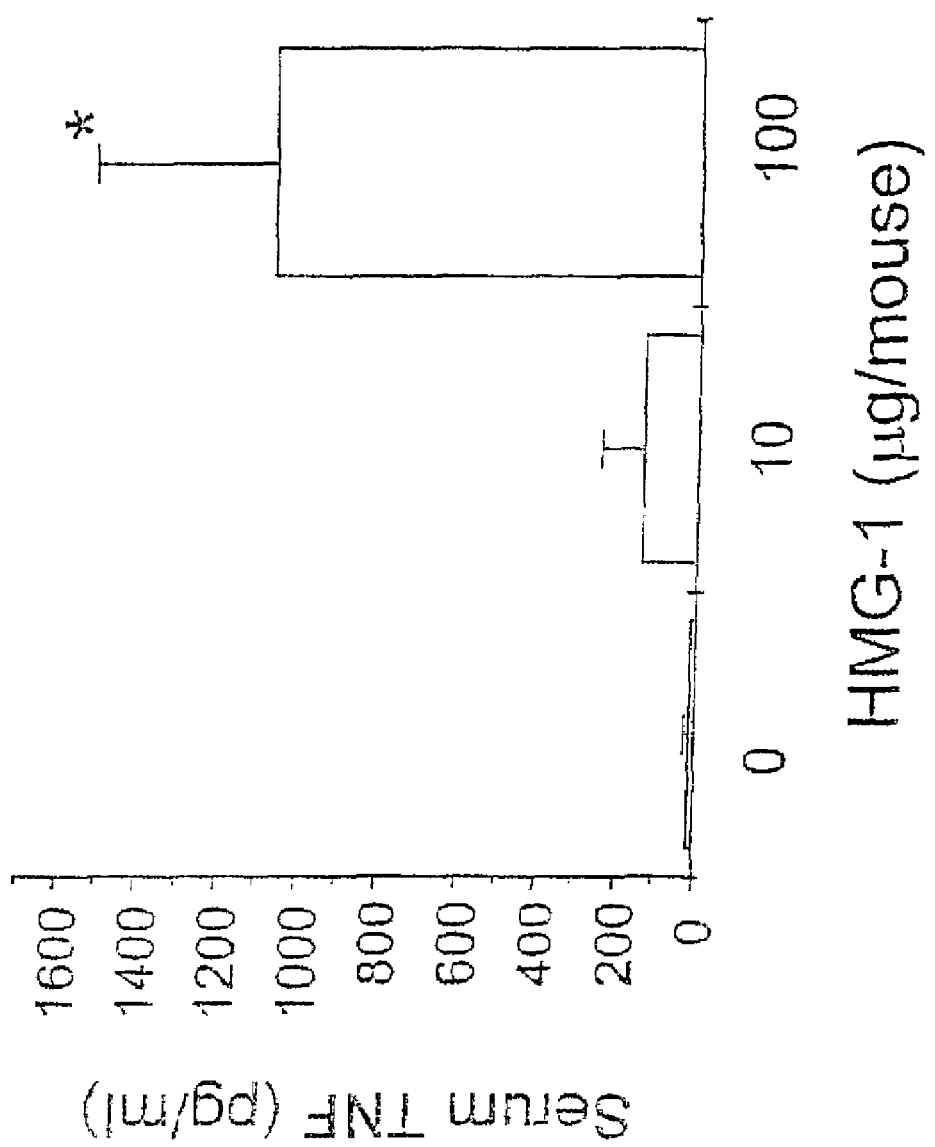
FIG. 3B shows that administration of HMG1 induced accumulation of TNF in serum of treated mice. Balb/C mice (20–23 g) were treated intraperitoneally with purified recombinant HMG1 at the indicated doses and blood samples were taken two hours later for assay of TNF by an L929 bioassay and (TNF levels expressed as mean±S.E.M., N=3).

As demonstrated in FIGS. 3A and 3B, in vitro or in vivo administration of recombinantly derived HMG1 induced a brisk TNF response, confirming the identification of HMG1 as a late-appearing LPS-induced macrophage-derived endogenous mediator with pro-inflammatory activity.

EXAMPLE 4

Anti-HMG1 Antibodies and Immunodetection

This example provides the results of experiments to generate and use polyclonal antibodies against HMG1. Briefly, polyclonal antibodies against an oligopeptide corresponding to the N-terminal amino acid sequence of HMG1, or against purified recombinant HMG1, were generated in rabbits according to standard procedures well known in the art. Briefly, eight copies of an oligopeptide with the sequence GKGDPKKPRGKMSSC [SEQ ID NO. 4] were anchored to radially branching lysine dendrites (small immunogenically inert core). These large macromolecules were injected three times both subcutaneously and intradermally (0.5–1.0 mg per injection) into rabbits at week 1, 2, and 4 after pre-bleed at Day 0. Two weeks after the last immunization, rabbits were bled and boosted intramuscularly with 1.0 mg of antigen followed by a second bleeding two weeks later. Alternatively, to produce polyclonal antibodies against recombinant HMG1, rabbits were immunized with recombinant HMG1 fusion peptide (100 μg per injection) following a similar protocol. Monoclonal antibodies reactive against HMG1 (i.e., that bind, and in some cases, neutralize or antagonize the biological activity of HMG1) are conveniently prepared according to methods well known in the art using the HMG1 antigens described herein or other HMG1 peptide fragments as immunogens. Such monoclonal-antibodies, and/or the hybridomas that produce them, are useful to produce various "humanized" antibodies reactive against HMG1 (all according to methods known in the art), which humanized antibodies are useful as taught herein.

HMG1-specific antibodies were used to measure by Western blotting analysis the inducible release of HMG 1 from RAW 264.7 cells after treatment with TNF or LPS (FIG. 1). Briefly, proteins were fractionated by SDS-PAGE on a 4–20% gradient gel, transferred to a PVDF membrane, and blotted with rabbit antiserum raised against either the N-terminal synthetic HMG1 antigen or against recombinant HMG1. The signal was detected using a ECL kit as instructed by the manufacturer (Amersham Life Science Inc., Arlington Heights, Ill., USA), and levels of HMG1 were determined by measuring optical intensity of bands on Western blots digitized for analysis using NIH 1.59 image software, with reference to a standard curve of purified recombinant HMG1.

Figure 1B:
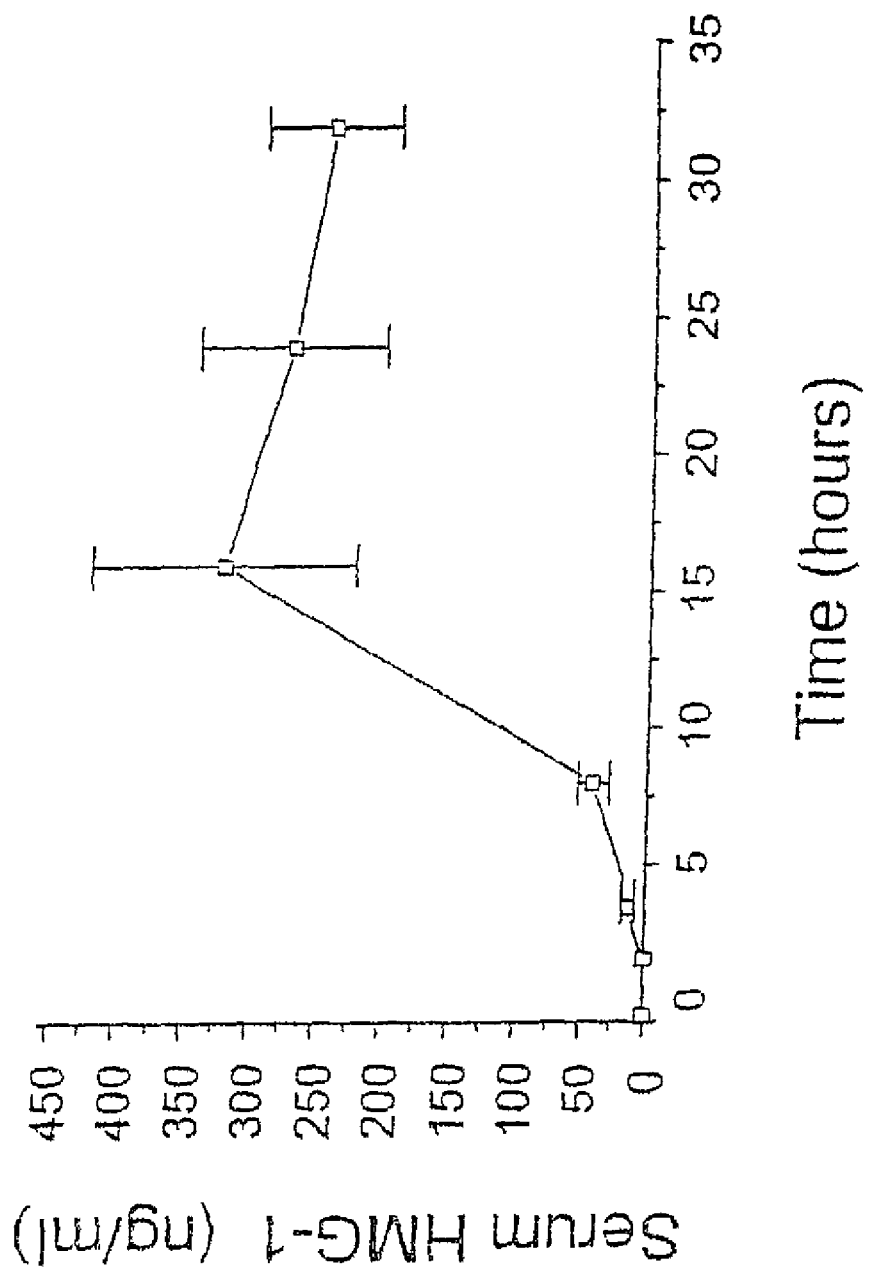

No HMG1 protein was detected in RAW 264.7 cells-conditioned medium in the absence of TNF or LPS treatment, but HMG1 accumulated in conditioned medium to high levels after such stimulation, reaching a plateau at 8–28 hours after stimulation (FIG. 1A). In summary, the data presented in Examples 1, 3 and in FIG. 1A show that the release of HMG1 from macrophages is stimulus-specific and time- and dose-dependent, with maximal accumulation observed within 8 hours after stimulation with TNF at concentrations as low as 5 ng/ml. It is well appreciated that sepsis, septic shock and related conditions may occur in humans in response to stimuli that differ qualitatively or quantitatively from the single large, lethal LPS bolus used in this predictive model. Nevertheless, experimental endotoxemia has been a valuable and predictive model system by which to identify critical components of the inflammatory cytokine cascade and by which to identify specific antagonists with predicted clinical utility. In this regard, HMG1 antagonists are perhaps more therapeutically attractive than TNF antagonists in view of the later appearance of HMG1 versus TIFF in the response to endotoxin.

EXAMPLE 5

Detection of HMG1 in In Vivo Animal Models

This example illustrates an in vivo experiment in rodents measuring serum HMG1 levels after administration of a sublethal dose of LPS ($LD_{50}$). Mice or rats were treated with LPS, and sera were collected at different time points, and assayed for levels of HMG1 by Western blotting analysis. The serum concentrations of HMG1 were estimated by measuring the optical band intensity with reference to a standard curve of purified HMG1. Serum levels increased significantly by 16 hours after LPS, and remained high for at least 32 hours (FIG. 1B), and were not detectable in vehicle-treated control animals. These data show that HMG1 represents a particularly attractive target for diagnosis of, and pharmaceutical intervention against sepsis and related disorders of cytokine toxicity because HMG1 is a late-appearing mediator in the inflammatory cytokine cascade.

EXAMPLE 6

Benefits of Protection Against HMG1

This example provides the results of a predictive is in vivo assay to measure therapeutic activity or antagonists of HMG1 in relation to treatment of sepsis and related conditions of cytokine-mediated toxicity. In this example, the HMG1 antagonist was an anti-HMG1 antibody preparation. Controls treated with pre-immune serum developed lethargy, piloerection, diarrhea, and succumbed to death within 48 hours. These clinical signs of endotoxemia were significantly prevented by administration of anti-HMG1 antibodies. Male Balb/C mice (6–7 weeks, 20–23 grams) were randomly grouped (10 animals per group) and pre-treated either with control pre-immune) or anti-HMG1 serum (as made in Example 4) 30 minutes before administration (intraperitoneally) of a lethal dose of LPS (50 mg/kg in 1×PBS). Other experimental groups received additional doses of anti-HMG1 serum at +12 or, +12, and +36 hours after LPS administration. Animals were observed for appearance and survival for at least two weeks.

Polyclonal antibodies against recombinant HMG1 were generated in rabbits, and anti serum was assayed for specificity and titer by ELISA and Western blotting procedures. The polyclonal antiserum immunospecifically recognized (bound to) recombinant HMG1 in Western blot analysis, for instance, and discriminated rHMG1 from other proteins in both crude bacterial lysates and as a purified protein that had been diluted into mouse serum. Using chemiluminescence-amplified detection methods in Western blotting analysis, polyclonal anti-HMG1 antiserum at dilutions up to 1:1000 was useful to detect as little as 50 pg rHMG1 protein. Administration of anti-HMG1 antiserum in the indicated (FIG. 2A) amounts at −0.5 (if one dose), −0.5 and 12 (if two doses), or −0.5, 12 and 36 (if three doses) hours relative to LPS challenge (at time 0) was protective against LPS-induced lethality, and repeated dosing schedules provided better protection.

Figure 2A:
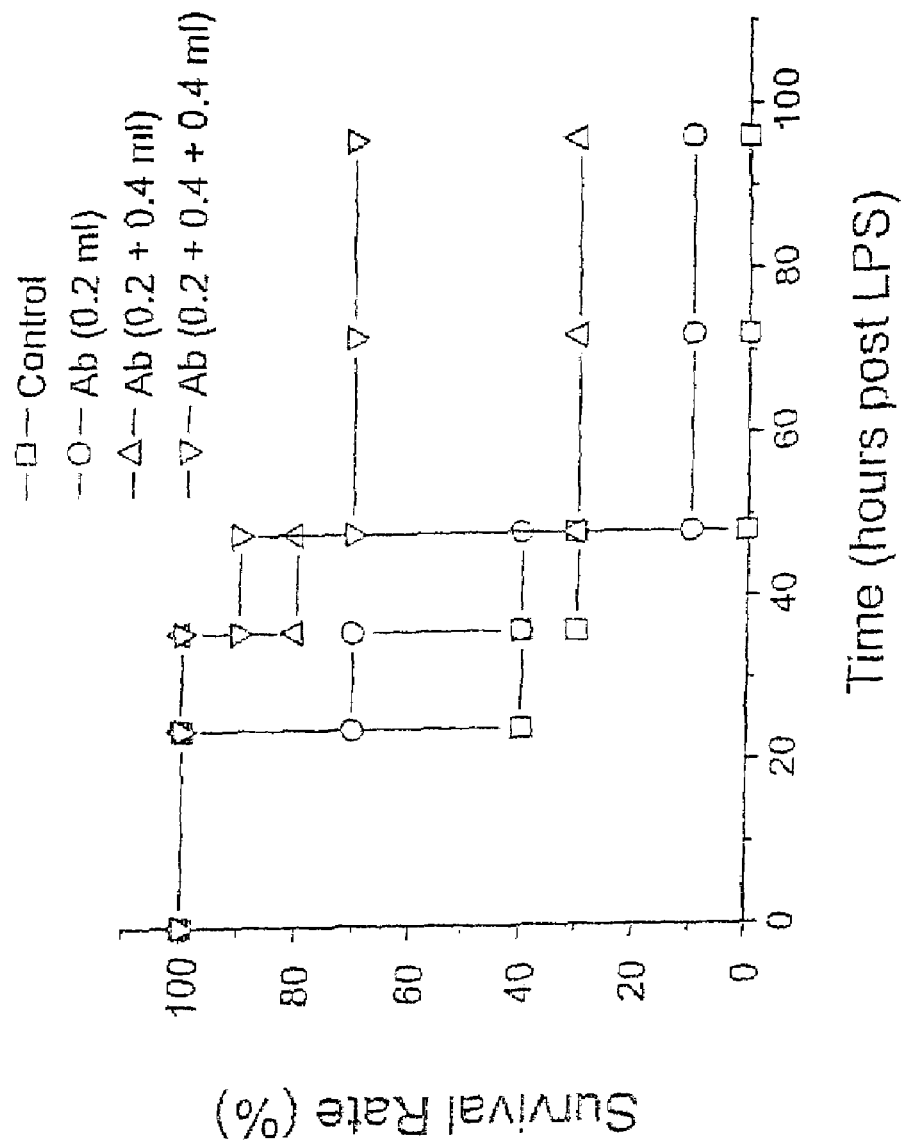
FIG. 2A shows the protective effect of anti-HMG1 antibodies against LPS lethality, tested in mice. Administration of anti-HMG1 antiserum in the indicated amounts at −0.5 (if one dose), −0.5 and 12 (if two doses), or −0.5, 12 and 36 (if three doses) hours relative to LPS challenge (at time 0) was protective against LPS-induced lethality, and repeated dosing schedules provided better protection.
Figure 2B:
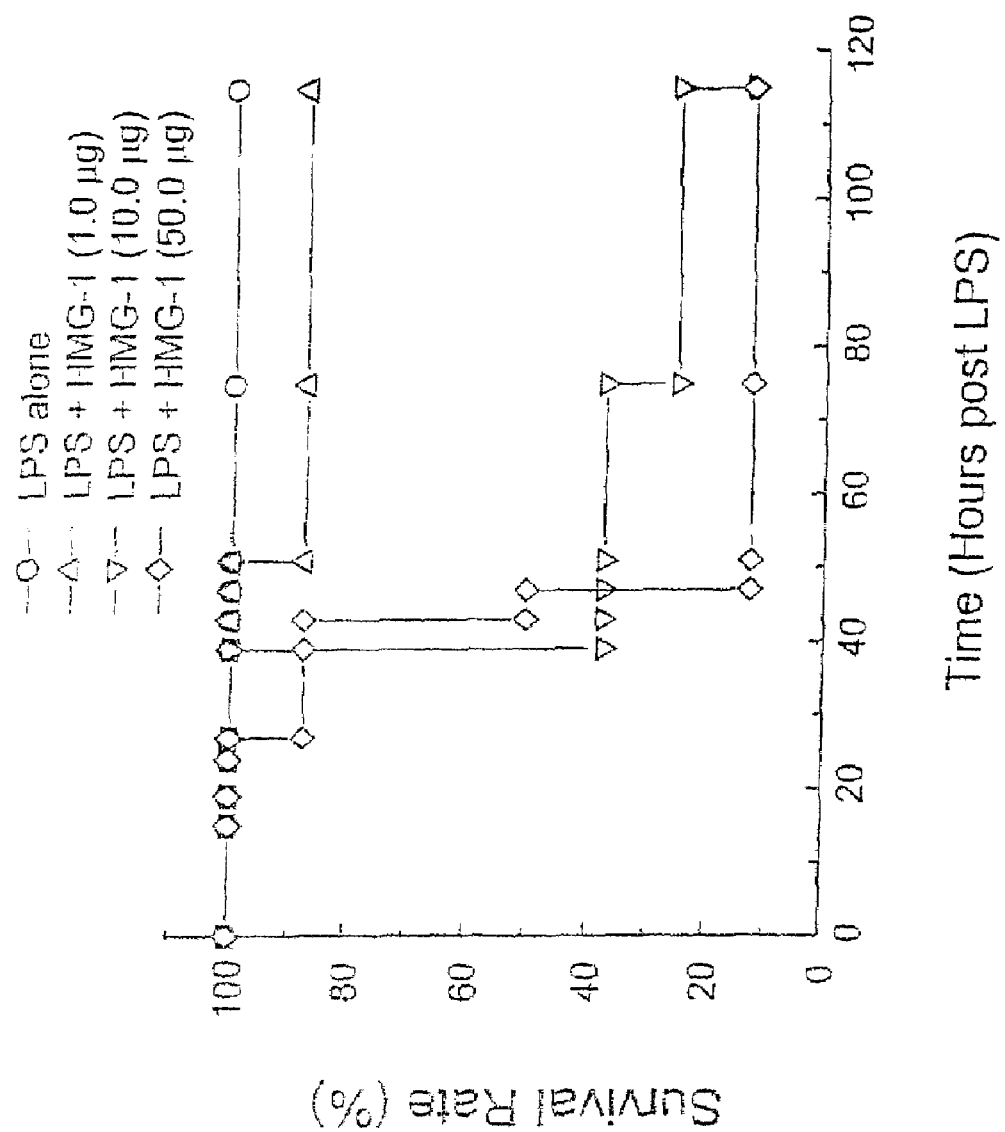
FIG. 2B illustrates that rHMG1 caused dose-dependent lethality in endotoxic mice. Male Balb/C mice (20–23 grams) were randomized in groups of ten to receive LPS (3.15 mg/kg; a non-lethal dose) alone or in combination with purified recombinant HMG1 protein. Administration of HMG1 at the indicated doses 2, 16, 28 and 40 hours after LPS challenge significantly increased the lethality of the underlying endotoxemia.

FIG. 2B illustrates that rHMG1 causes dose-dependent lethality in endotoxic mice. Male Balb/C mice (20–23 grams) were randomized in groups often to receive LPS (3.15 mg/kg; a non-lethal dose) alone or in combination with purified recombinant HMG1 protein. Administration of HMG1 at the indicated doses 2, 16, 28 and 40 hours after LPS challenge significantly increased the lethality of the underlying endotoxemia.

Figure 2C:
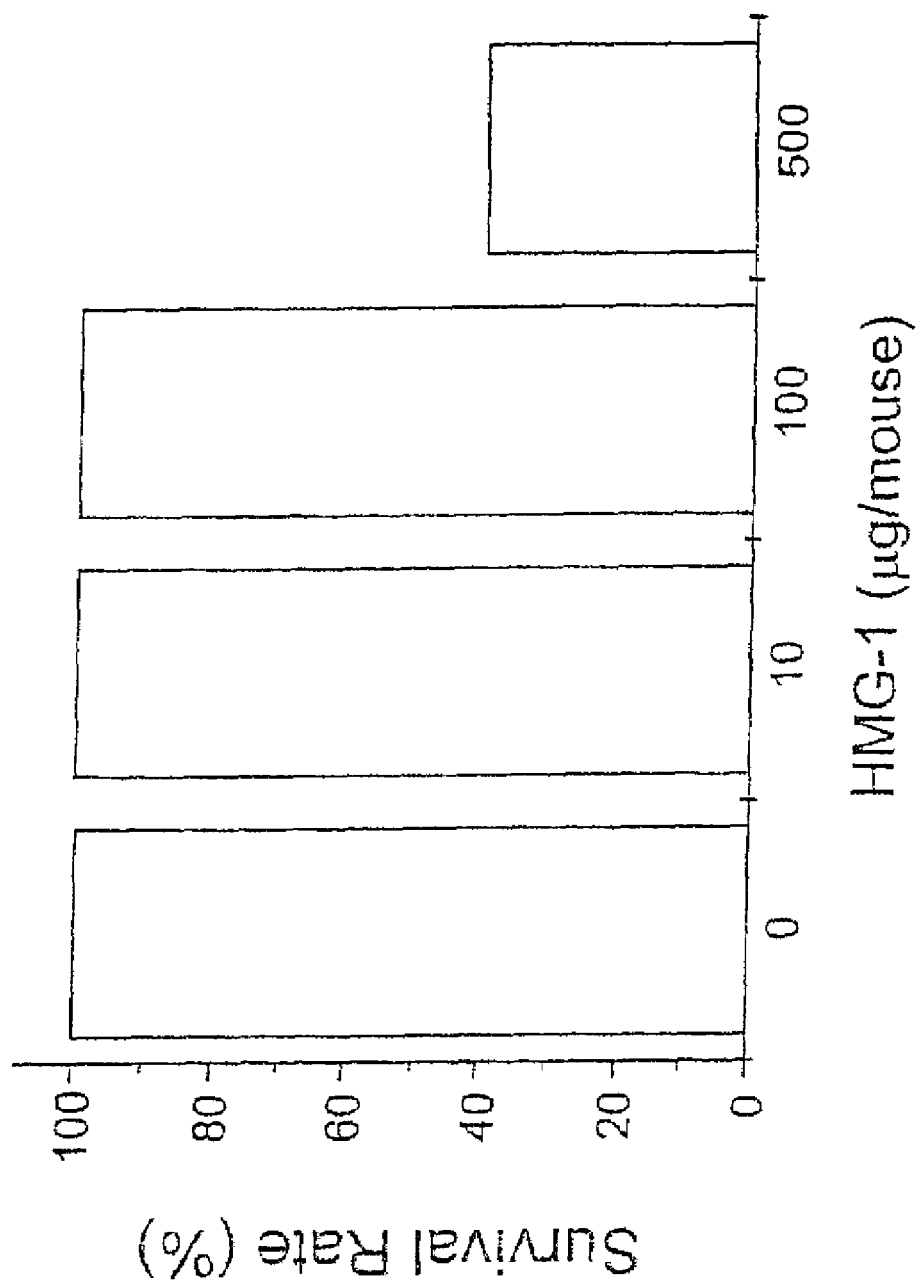
FIG. 2C illustrates independent lethal toxicity of HMG1 as a function of dose. Purified rHMG1 was administered to male Balb/C mice (five mice per treatment group) as a single i.p. bolus at the indicated dosage. Mice were observed for at least 48 hours, and 60% of mice treated with rHMG1 at a dose of 500 µg/mouse died within 24 hours of rHMG1 challenge, indicating a single dose $LD_{50}$ of less than 500 µg/mouse.

FIG. 2C illustrates the independent lethal toxicity of HMG1 as a function of dose. Purified rHMG1 was administered to male Balb/C mice (five mice per treatment group) as a single i.p. bolus at the indicated dosage. Mice were observed for at least 48 hours, and 60% of mice treated with rHMG1 at a dose of 500 μg/mouse died within 24 hours of rHMG1 challenge, indicating a single dose $LD_{50}$ of less than 500 μg/mouse.

The protection conferred by anti-HMG1 antibodies was specific, because administration of pre-immune serum, which showed no immunospecific reactivity to HMG1 on Western blots, did not spare subjects from LPS-mediated mortality (FIG. 2A). Moreover, HMG1-specific antibodies did not cross-react with other macrophage-derived cytokines (e.g. IL-1 and TNF), eliminating the possibility that antibodies conferred protection by binding and thereby neutralizing these mediators. Protection against sepsis, sepsis associated pathogenesis and sepsis-related diseases involving activation of pro-inflammatory cytokine cascades may be improved by combination therapy targeted against more than one component of the cytokine cascade. Antagonists of HMG1 in this regard can be combined with specific antagonists of TNF, IL-1, MIF and other inflammatory mediators, or with more broadly active antagonists of inflammatory responses that inhibit multiple components of the inflammatory cascade (e.g., aspirin, NSAIDS, anti-inflammatory steroids, etc.), to provide even more effective therapeutic modalities. Protection against LPS toxicity was antibody dose-related, and more frequent dosing with higher amounts of antibody reduced mortality by up to 70% (FIG. 2A). Mice were observed for at least 2 weeks in all experiments, and no late mortality occurred, indicating that anti-HMG1 antibody treatment confers lasting protection against LPS lethality, and does not merely delay the time of death.

EXAMPLE 7

HMG1 in Human Disease

This example provides data that establish an association between HMG1 and human sepsis, and thereby support an indication for using HMG1 antagonists generally and anti-HMG1 antibodies in particular in human sepsis and related conditions of cytokine toxicity. Serum HMG1 levels in normal healthy individuals and critically ill patients were measured using the polyclonal antibodies generated as in Example 4 in a Western blot format with reference to a standard curve of rHMG1 was not detectable in normal controls, but accumulated to high levels in critically ill patients with sepsis (Table 2).

TABLE 2

Serum appearance of HMG1 in sepsis patients.

| Patient (#) | Age (year) | HMG1 (ng/ml) | Diagnosis | Outcome |
|---|---|---|---|---|
| 1 | 27 | <d.l. | Normal | Healthy |
| 2 | 34 | <d.l. | Normal | Healthy |
| 3 | 35 | <d.l. | Normal | Healthy |
| 4 | 36 | <d.l. | Normal | Healthy |
| 5 | 61 | <d.l. | Normal | Healthy |
| 6 | 31 | <d.l. | Normal | Healthy |
| 7 | 55 | 10 | Sepsis, anastomotic leak | Recovered |

TABLE 2-continued

Serum appearance of HMG1 in sepsis patients.

| Patient (#) | Age (year) | HMG1 (ng/ml) | Diagnosis | Outcome |
|---|---|---|---|---|
| 8 | 70 | 7–20 | Sepsis, colonic perforation | Recovered |
| 9 | 44 | 10–60 | Sepsis, MOF, spinal reconstruction | Died |
| 10 | 60 | >120 | Sepsis, MOF, perforated gastric ulcer | Died |
| 11 | 47 | >120 | Sepsis, MOF, pneumonia | Died |

Note: <d.l.—below detection limit; MOF—Multiple Organ Failure.

These data show that elevated serum HMG1 levels are observed in patients with sepsis, and the highest levels of serum HMG1 are observed in lethal cases (Table 2). These data further indicate the therapeutic importance of HMG1 antagonists in sepsis and also provide evidence for the diagnostic utility of an assay for sepsis and severity (i.e., potential lethality) of sepsis by measuring serum concentrations of HMG1. This diagnostic assay is also useful for diagnosing the severity of allied conditions involving activation of the inflammatory cytokine cascade.

Figure 6:
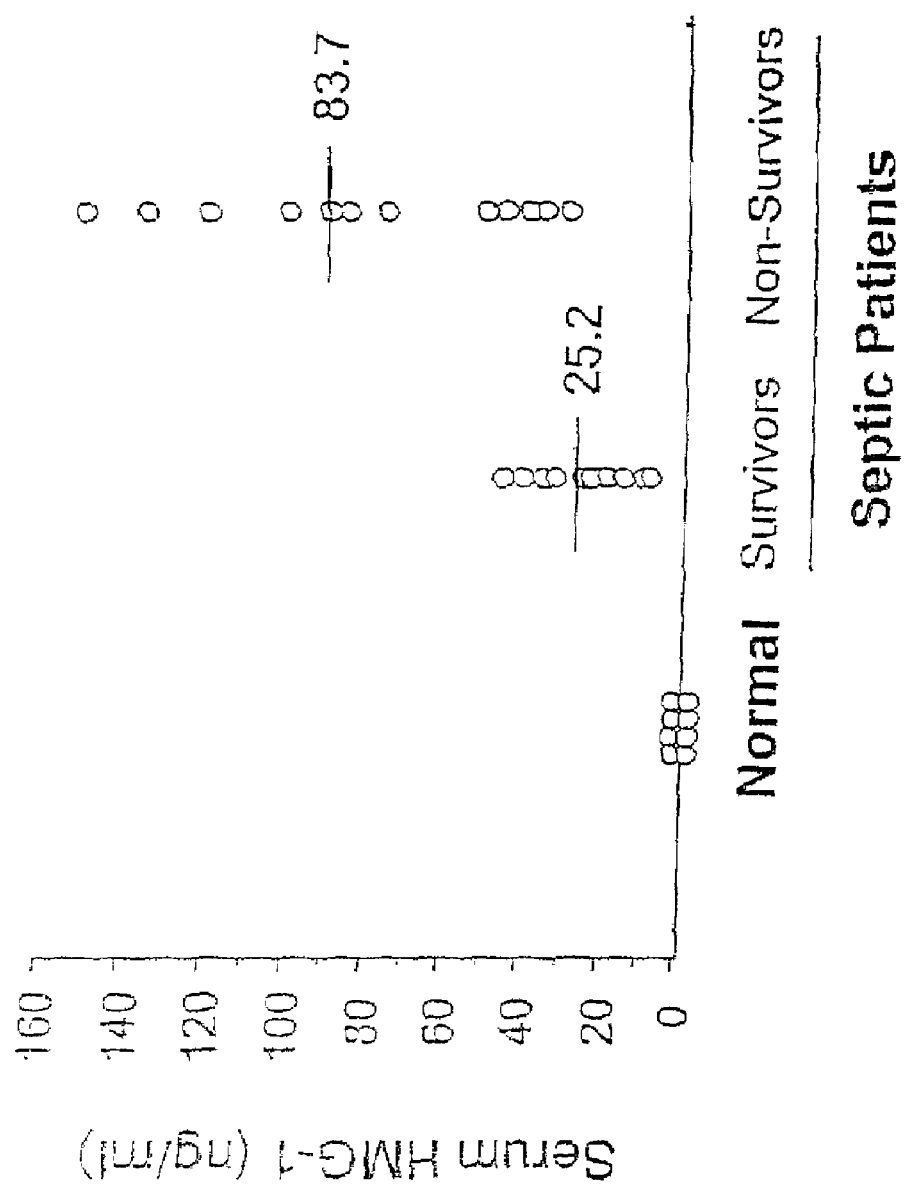
FIG. 6 shows, in comparison to a group of normal control subjects, increased human serum HMG1 levels as detected in hospitalized human subjects with sepsis, wherein the septic patients have been further categorized as to whether the patient died or survived.

Additional subjects were screened for serum HMG1 levels in association with lethal versus non-lethal sepsis, with results (cumulative with Table 2) as described in FIG. 6. The data summarized in FIG. 6 represent serum samples obtained from eight healthy subjects and twenty-five septic patients infected with Gram positive [*Bacillus fragilis* (1 patient), *Enterococcus facecalis* (1 patient), *Streptococcus pneumonia* (4 patients), *Listeria monocytogenes* (1 patient), or *Staphylococcus aureus* (2 patients)], Gram negative [*Escherichia coli* (7 patients), *Klebsiella pneumonia* (1 patient), *Acinetobacter calcoaceticus* (1 patient), *Pseudomonas aeruginosa* (1 patient), *Fusobacterium nucleatum* (1 patient), *Citrobacter freundii* (1 patient)], or unidentified pathogens (5 patients). Serum was fractionated by SDS-PAGE gel electrophoresis, and HMG1 levels were determined by Western blotting analysis with reference to standard curves of purified rHMG1 diluted in normal human serum. The detection limit by Western blotting analysis is 50 pg. Note that HMG1 is not detectable in normal controls, but significantly increased in septic patients. The average level of HMG1 in serum=of non-surviving septic patients (N=13 patients, mean HMG1 level=83.7±22.3 ng/ml) is significantly higher than in survivors (NT=12, mean HMG1 level=25.2±15.1 ng/ml, P<0.05). These data provide direct evidence of the utility of screening tissue (including, without limitation blood or serum) samples for HMG1 sequences (protein or nucleic acid) as a diagnostic and prognostic indicator of the presence of sepsis and related disorders of cytokine activation and of the severity and likely clinical course of such diseases and conditions.

EXAMPLE 8

HMG1 Induces Pro-inflammatory Mediators and Weight Loss

The present results provide evidence that HMG1 is a late released mediator element of the inflammatory cytokine cascade. Addition of recombinant HMG1 to primary human peripheral blood mononuclear cells led to the dose-dependent induction of TNF within four hours after stimulation (FIG. 3A). This stimulation by recombinant HMG1 of TNF release by HuPBMCs was not due to LPS contamination because: (i) purified recombinant HMG1 was not contaminated by LPS as judged by an LAL endotoxin assay; ii) addition of the LPS-neutralizing agent polymyxin B did not affect HMG1-induced TNF release; and iii) proteolytic cleavage of recombinant HMG1 preparations with trypsin completely abolished the TNF release activity for the PBMC cultures. HMG1 stimulation also induced macrophages to release nitric oxide (NO)

To confirm that HMG1 induced serum TNF release in vivo, purified recombinant HMG1 was administered intraperitoneally to Balb/C mice, and blood samples were collected to be assayed for TNF by the L929 assay. As shown in FIG. 3B, TNF was not detectable in serum of control animals, but was significantly increased two hours after administration of recombinant HMG1 protein.

Figure 4:
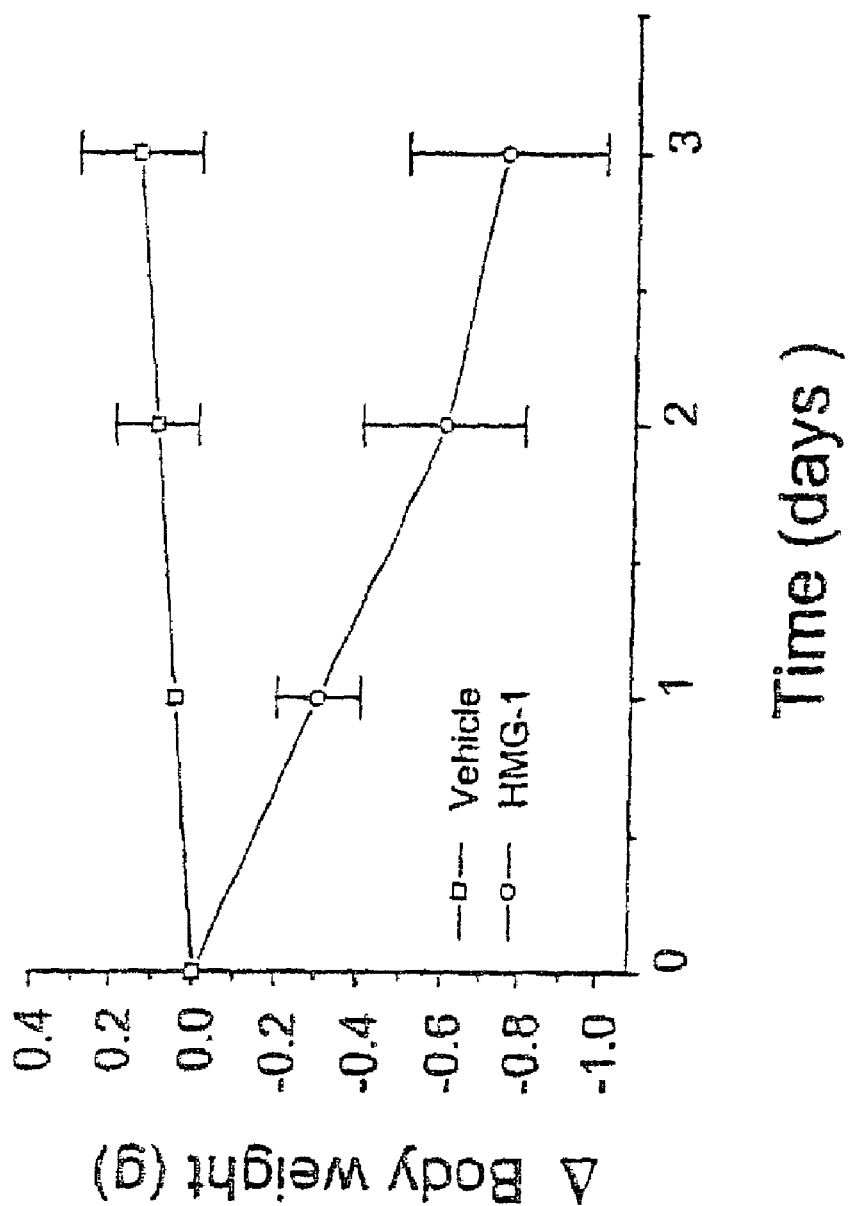
FIG. 4 shows that HMG1 caused body weight loss in mice. Purified HMG1 was administered intraperitoneally to mice at 100 µg/mouse/day for three days, and body weight was monitored.

Repetitive administration of recombinant gene product of the HMG1 gene (100 μg/mouse/day) caused significant body weight loss (FIG. 4) in mice. Without limitation on as to mechanism and without being bound by theory, these data are consistent with the hypothesis that HMG1 acts as a feed-forward stimulator of the pro-inflammatory cascade under both in vitro and in vivo conditions. These in vivo data in a predictive model of weight loss also provide predictive evidence that a pharmaceutical formulation comprising HMG1 or a therapeutically active fragment thereof is an effective weight loss therapy.

EXAMPLE 9

In Vivo Sources of HMG1

Serum HMG1 levels in hypophysectomized versus control rats also were measured by quantitation of Western blot intensities as described above. There were significantly higher HMG1 levels within 12 hours after endotoxic challenge (LPS at 1.0 mg/kg) in hypophysectomized rats (approx. 75 ng/ml) as compared to controls (approx. 25 ng/ml). These results indicate that pituicytes are not the major source of serum HMG1 levels and that macrophages may play a quantitatively more important role.

We claim:

1. A method for diagnosing a condition characterized by activation of the inflammatory cytokine cascade in a mammalian subject, comprising measuring the concentration of HMG1 in a test sample from the subject, and comparing that concentration to a standard for HMG1 representative of a normal range of HMG1 in a like sample, wherein a level of HMG1 in the test sample higher than the standard indicates a diagnosis of a condition characterized by activation of the inflammatory cytokine cascade.

2. The method of claim 1, wherein the condition is arthritis.

3. The method of claim 1, wherein the condition is systemic lupus erythematosis.

4. The method of claim 1, wherein the sample is a blood or serum sample.

5. The method of claim 1, wherein the mammalian subject is human.

6. The method of claim 1, wherein the concentration of HMG1 is measured using an antibody that binds an HMG1 protein.

7. A prognostic method for monitoring the severity and predicting the likely clinical course of a mammalian subject having a condition characterized by activation of the inflammatory cytokine cascade, comprising measuring the concentration of HMG1 in a test sample from the subject, and comparing that concentration to a standard for HMG1 representative of a normal range of HMG1 in a like sample, wherein the magnitude of the difference between the level of HMG1 in the test sample and the standard positively correlates with the severity of the condition characterized by activation of the inflammatory cytokine cascade and with a poor prognosis of the condition.

8. The method of claim 7, wherein the condition is arthritis.

9. The method of claim 7, wherein the condition is systemic lupus erythematosis.

10. The method of claim 7, wherein the sample is a blood or serum sample.

11. The method of claim 7, wherein the mammalian subject is human.

12. The method of claim 7, wherein the concentration of HMG1 is measured using an antibody that binds an HMG1 protein.

13. A method for diagnosing rheumatoid arthritis in a mammalian subject, comprising measuring the concentration of HMG1 in a test sample from the subject, and comparing that concentration to a standard for HMG1 representative of a normal range of HMG1 in a like sample, wherein a level of HMG1 in the test sample higher than the standard indicates a diagnosis of rheumatoid arthritis.

14. The method of claim 13, wherein the sample is a blood or serum sample.

15. The method of claim 13, wherein the mammalian subject is human.

16. The method of claim 13, wherein the concentration of HMG1 is measured using an antibody that binds an HMG1 protein.

17. A prognostic method for monitoring the severity and predicting the likely clinical course of a mammalian subject having rheumatoid arthritis comprising measuring the concentration of HMG1 in a test sample from the subject, and comparing that concentration to a standard for HMG1 representative of a normal range of HMG1 in a Like sample, wherein the magnitude of the difference between the level of HMG1 in the test sample and the standard positively correlates with the severity of arthritis and with a poor prognosis of rheumatoid arthritis.

18. The method of claim 17, wherein the sample is a blood or serum sample.

19. The method of claim 17, wherein the mammalian subject is human.

20. The method of claim 17, wherein the concentration of HMG1 is measured using an antibody that binds an HMG1 protein.

21. The method of claim 1, wherein the condition is trauma hemorrhage.

22. The method of claim 7, wherein the condition is trauma hemorrhage.

23. The method of claim 1, wherein the condition is malaria.

24. The method of claim 7, wherein the condition is malaria.

* * * * *